United States Patent
Takahashi

(10) Patent No.: US 12,098,128 B2
(45) Date of Patent: Sep. 24, 2024

(54) COMPOUND, AND ORGANIC ELECTROLUMINESCENCE DEVICE AND ELECTRONIC APPARATUS USING THE SAME

(71) Applicant: IDEMITSU KOSAN CO.,LTD., Tokyo (JP)

(72) Inventor: Ryota Takahashi, Sodegaura (JP)

(73) Assignee: IDEMITSU KOSAN CO., LTD., Tokyo (JP)

(*) Notice: Subject to any disclaimer, the term of this patent is extended or adjusted under 35 U.S.C. 154(b) by 749 days.

(21) Appl. No.: 17/183,682

(22) Filed: Feb. 24, 2021

(65) Prior Publication Data
US 2021/0355085 A1   Nov. 18, 2021

(30) Foreign Application Priority Data

Feb. 27, 2020 (JP) .................... 2020-031927

(51) Int. Cl.
*C07D 209/86* (2006.01)
*H01L 51/00* (2006.01)
(Continued)

(52) U.S. Cl.
CPC ........... *C07D 209/86* (2013.01); *H10K 85/40* (2023.02); *H10K 85/615* (2023.02);
(Continued)

(58) Field of Classification Search
None
See application file for complete search history.

(56) References Cited

U.S. PATENT DOCUMENTS

2014/0319507 A1   10/2014 Yamamoto et al.
2021/0057650 A1*  2/2021 Kim .................... C07D 409/14

FOREIGN PATENT DOCUMENTS

WO   WO-2013077344 A1 *  5/2013 ........... C07D 487/06
WO   WO-2019194617 A1 * 10/2019

* cited by examiner

*Primary Examiner* — Jay Yang
(74) *Attorney, Agent, or Firm* — Foley & Lardner LLP

(57) ABSTRACT

A compound represented by the following formula (1):

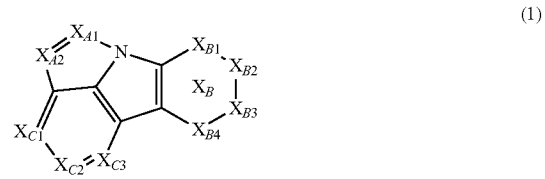

(1)

wherein in the formula (1), a ring $X_B$ is a six-membered hydrocarbon ring or a six-membered heterocyclic ring having one or two nitrogen atoms; one or more sets of adjacent two of $X_{B1}$ to $X_{B4}$ are fused with a substituted or unsubstituted hydrocarbon ring including 5 to 50 ring carbon atoms, or a substituted or unsubstituted heterocyclic ring including 5 to 50 ring atoms; one or more sets of adjacent two of $X_{C1}$ to $X_{C3}$ are fused with a substituted or unsubstituted hydrocarbon ring including 5 to 50 ring carbon atoms or a substituted or unsubstituted heterocyclic ring including 5 to 50 ring atoms.

21 Claims, 1 Drawing Sheet

(51) Int. Cl.
    *H10K 85/40*    (2023.01)
    *H10K 85/60*    (2023.01)
    *H10K 50/11*    (2023.01)
    *H10K 101/10*    (2023.01)

(52) U.S. Cl.
    CPC ..... *H10K 85/6572* (2023.02); *H10K 85/6574* (2023.02); *H10K 50/11* (2023.02); *H10K 2101/10* (2023.02)

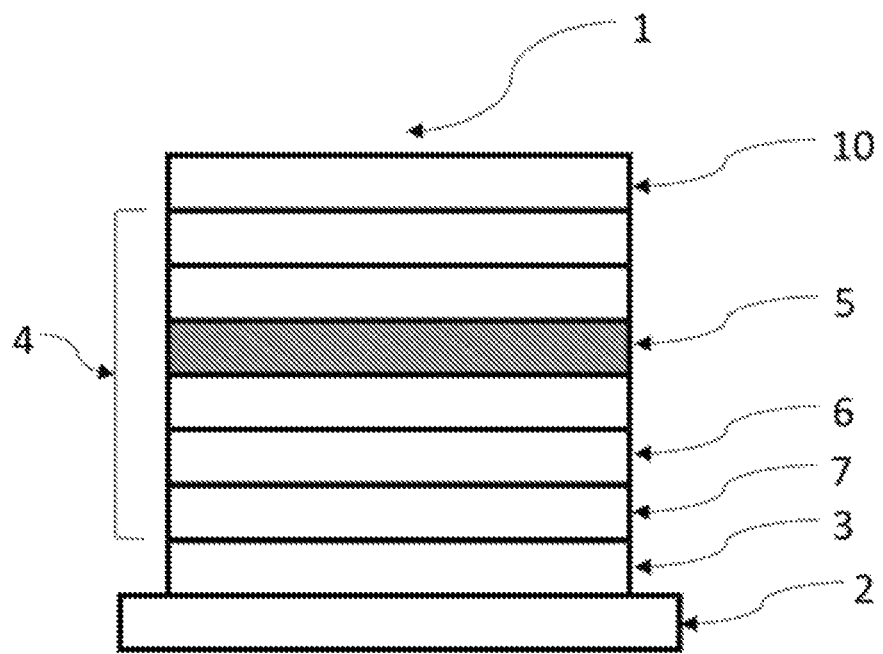

COMPOUND, AND ORGANIC ELECTROLUMINESCENCE DEVICE AND ELECTRONIC APPARATUS USING THE SAME

TECHNICAL FIELD

The invention relates to a novel compound, an organic electroluminescence device using the same, and an electronic apparatus.

BACKGROUND ART

When voltage is applied to an organic electroluminescence device (hereinafter, referred to as an organic EL device), holes and electrons are injected into an emitting layer from an anode and a cathode, respectively. Then, thus injected holes and electrons are recombined in the emitting layer, and excitons are formed therein.

The organic EL device includes the emitting layer between the anode and the cathode. Further, the organic EL device has a stacked structure including an organic layer such as a hole-injecting layer, a hole-transporting layer, an electron-injecting layer, and an electron-transporting layer in several cases.

Patent Document 1 discloses a compound used as a material for an organic electroluminescence device.

RELATED ART DOCUMENTS

Patent Documents

[Patent Document 1] WO 2013/077344 A1

SUMMARY OF THE INVENTION

It is an object of the invention to provide a novel compound useful as a material for an organic EL device, an organic EL device using the novel compound, and an electronic apparatus using the organic EL device.

According to the invention, there is provided the following compound, organic electroluminescence device, and electronic apparatus 1. A compound represented by the following formula (1):

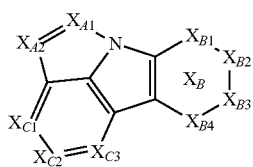

(1)

wherein in the formula (1), $X_{A1}$ and $X_{A2}$ are fused with a substituted or unsubstituted aliphatic hydrocarbon ring including 5 to 50 ring carbon atoms or a substituted or unsubstituted non-aromatic heterocyclic ring including 5 to 50 ring atoms, or are not fused with the ring;

$X_{A1}$ and $X_{A2}$ which are not involved in the fusion of the ring are independently
CH,
$C(R_a)$, or
N;

a ring $X_B$ is a six-membered hydrocarbon ring or a six-membered heterocyclic ring having one or two nitrogen atoms;

one or more sets of adjacent two of $X_{B1}$ to $X_{B4}$ are fused with
a substituted or unsubstituted hydrocarbon ring including 5 to 50 ring carbon atoms, or
a substituted or unsubstituted heterocyclic ring including 5 to 50 ring atoms;

$X_{B1}$ to $X_{B4}$ which are not involved in the fusion of the ring are independently
CH,
$C(R_a)$,
$C(R_a)_2$,
N, or
$N(R_a)$;

one or more sets of adjacent two of $X_{C1}$ to $X_{C3}$ are fused with a substituted or unsubstituted hydrocarbon ring including 5 to 50 ring carbon atoms or a substituted or unsubstituted heterocyclic ring including 5 to 50 ring atoms $X_{C1}$ or $X_{C3}$ which is not involved in the fusion of the ring is
CH,
$C(R_a)$, or
N;

$R_a$ is a substituent;

when a plurality of $R_a$'s are present, the plurality of $R_a$'s may be the same as or different from each other; and adjacent two or more $R_a$'s form a substituted or unsubstituted, saturated or unsaturated ring by bonding with each other, or do not form the ring.

2. A material for an organic electroluminescence device, which comprises the compound according to 1.

3. An organic electroluminescence device comprising: a cathode, an anode,
one or two or more organic layers disposed between the cathode and the anode, wherein
at least one of the organic layers comprises the compound according to 1.

4. An electronic apparatus, wherein the organic electroluminescence device according to 3 is comprised.

Advantageous Effects of the Invention

According to the invention, a novel compound useful as a material for an organic EL device, an organic EL device using the novel compound, and an electronic apparatus using the organic EL device can be provided.

BRIEF DESCRIPTION OF THE DRAWINGS

The FIGURE shows the schematic configuration of an organic EL device according to one embodiment of the invention.

MODE FOR CARRYING OUT THE INVENTION

Definition

In this specification, a hydrogen atom includes its isotopes different in the number of neutrons, namely, a protium, a deuterium and a tritium.

In this specification, at a bondable position in a chemical formula where a symbol such as "R", or "D" representing a deuterium atom is not indicated, a hydrogen atom, that is, a protium atom, a deuterium atom or a tritium atom is bonded.

In this specification, the number of ring carbon atoms represents the number of carbon atoms forming a subject ring itself among the carbon atoms of a compound having a structure in which atoms are bonded in a ring form (for example, a monocyclic compound, a fused ring compound, a cross-linked compound, a carbocyclic compound, or a heterocyclic compound). When the subject ring is substituted by a substituent, the carbon contained in the substituent is not included in the number of ring carbon atoms. The same shall apply to "the number of ring carbon atoms" described below, unless otherwise specified. For example, a benzene ring has 6 ring carbon atoms, a naphthalene ring includes 10 ring carbon atoms, a pyridine ring includes 5 ring carbon atoms, and a furan ring includes 4 ring carbon atoms. Further, for example, a 9,9-diphenylfluorenyl group includes 13 ring carbon atoms, and a 9,9'-spirobifluorenyl group includes 25 ring carbon atoms.

When a benzene ring is substituted by, for example, an alkyl group as a substituent, the number of carbon atoms of the alkyl group is not included in the number of ring carbon atoms of the benzene ring. Therefore, the number of ring carbon atoms of the benzene ring substituted by the alkyl group is 6. When a naphthalene ring is substituted by, for example, an alkyl group as a substituent, the number of carbon atoms of the alkyl group is not included in the number of ring carbon atoms of the naphthalene ring. Therefore, the number of ring carbon atoms of the naphthalene ring substituted by the alkyl group is 10.

In this specification, the number of ring atoms represents the number of atoms forming a subject ring itself among the atoms of a compound having a structure in which atoms are bonded in a ring form (for example, the structure includes a monocyclic ring, a fused ring and a ring assembly) (for example, a monocyclic compound, a fused ring compound, a cross-linked compound, a carbocyclic compound and a heterocyclic compound). The number of ring atoms does not include atoms which do not form the ring (for example, a hydrogen atom which terminates a bond of the atoms forming the ring), or atoms contained in a substituent when the ring is substituted by the substituent. The same shall apply to "the number of ring atoms" described below, unless otherwise specified. For example, the number of atoms of a pyridine ring is 6, the number of atoms of a quinazoline ring is 10, and the number of atoms of a furan ring is 5. For example, hydrogen atoms bonded to a pyridine ring and atoms constituting a substituent substituted on the pyridine ring are not included in the number of ring atoms of the pyridine ring. Therefore, the number of ring atoms of a pyridine ring with which a hydrogen atom or a substituent is bonded is 6. For example, hydrogen atoms and atoms constituting a substituent which are bonded with a quinazoline ring is not included in the number of ring atoms of the quinazoline ring. Therefore, the number of ring atoms of a quinazoline ring with which a hydrogen atom or a substituent is bonded is 10.

In this specification, "XX to YY carbon atoms" in the expression "a substituted or unsubstituted ZZ group including XX to YY carbon atoms" represents the number of carbon atoms in the case where the ZZ group is unsubstituted by a substituent, and does not include the number of carbon atoms of a substituent in the case where the ZZ group is substituted by the substituent. Here, "YY" is larger than "XX", and "XX" means an integer of 1 or more and "YY" means an integer of 2 or more.

In this specification, "XX to YY atoms" in the expression "a substituted or unsubstituted ZZ group including XX to YY atoms" represents the number of atoms in the case where the ZZ group is unsubstituted by a substituent, and does not include the number of atoms of a substituent in the case where the ZZ group is substituted by the substituent. Here, "YY" is larger than "XX", and "XX" means an integer of 1 or more and "YY" means an integer of 2 or more.

In this specification, the unsubstituted ZZ group represents the case where the "substituted or unsubstituted ZZ group" is a "ZZ group unsubstituted by a substituent", and the substituted ZZ group represents the case where the "substituted or unsubstituted ZZ group" is a "ZZ group substituted by a substituent".

In this specification, a term "unsubstituted" in the case of "a substituted or unsubstituted ZZ group" means that hydrogen atoms in the ZZ group are not substituted by a substituent. Hydrogen atoms in a term "unsubstituted ZZ group" are a protium atom, a deuterium atom, or a tritium atom.

In this specification, a term "substituted" in the case of "a substituted or unsubstituted ZZ group" means that one or more hydrogen atoms in the ZZ group are substituted by a substituent. Similarly, a term "substituted" in the case of "a BB group substituted by an AA group" means that one or more hydrogen atoms in the BB group are substituted by the AA group.

"Substituent as described in this specification"

Hereinafter, the substituent described in this specification will be explained.

The number of ring carbon atoms of the "unsubstituted aryl group" described in this specification is 6 to 50, preferably 6 to 30, and more preferably 6 to 18, unless otherwise specified.

The number of ring atoms of the "unsubstituted heterocyclic group" described in this specification is 5 to 50, preferably 5 to 30, and more preferably 5 to 18, unless otherwise specified.

The number of carbon atoms of the "unsubstituted alkyl group" described in this specification is 1 to 50, preferably 1 to 20, and more preferably 1 to 6, unless otherwise specified.

The number of carbon atoms of the "unsubstituted alkenyl group" described in this specification is 2 to 50, preferably 2 to 20, and more preferably 2 to 6, unless otherwise specified.

The number of carbon atoms of the "unsubstituted alkynyl group" described in this specification is 2 to 50, preferably 2 to 20, and more preferably 2 to 6, unless otherwise specified.

The number of ring carbon atoms of the "unsubstituted cycloalkyl group" described in this specification is 3 to 50, preferably 3 to 20, and more preferably 3 to 6, unless otherwise specified.

The number of ring carbon atoms of the "unsubstituted arylene group" described in this specification is 6 to 50, preferably 6 to 30, and more preferably 6 to 18, unless otherwise specified.

The number of ring atoms of the "unsubstituted divalent heterocyclic group" described in this specification is 5 to 50, preferably 5 to 30, and more preferably 5 to 18, unless otherwise specified.

The number of carbon atoms of the "unsubstituted alkylene group" described in this specification is 1 to 50, preferably 1 to 20, and more preferably 1 to 6, unless otherwise specified.

"Substituted or unsubstituted aryl group"

Specific examples of the "substituted or unsubstituted aryl group" described in this specification (specific example group G1) include the following unsubstituted aryl groups (specific example group G1A), substituted aryl groups (specific example group G1B), and the like. (Here, the unsubstituted aryl group refers to the case where the "substituted or unsubstituted aryl group" is an "aryl group unsubstituted by a substituent", and the substituted aryl group refers to the case where the "substituted or unsubstituted aryl group" is an "aryl group substituted by a substituent"). In this specification, in the case where simply referred as an "aryl group", it includes both a "unsubstituted aryl group" and a "substituted aryl group."

The "substituted aryl group" means a group in which one or more hydrogen atoms of the "unsubstituted aryl group" are substituted by a substituent. Specific examples of the "substituted aryl group" include, for example, groups in which one or more hydrogen atoms of the "unsubstituted aryl group" of the following specific example group G1A are substituted by a substituent, the substituted aryl groups of the following specific example group G1B, and the like. It should be noted that the examples of the "unsubstituted aryl group" and the examples of the "substituted aryl group" enumerated in this specification are mere examples, and the "substituted aryl group" described in this specification also includes a group in which a hydrogen atom bonded with a carbon atom of the aryl group itself in the "substituted aryl group" of the following specific group G1B is further substituted by a substituent, and a group in which a hydrogen atom of a substituent in the "substituted aryl group" of the following specific group G1B is further substituted by a substituent.

Unsubstituted aryl group (specific example group G1A):
a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group,
a benzanthryl group,
a phenanthryl group,
a benzophenanthryl group,
a phenalenyl group,
a pyrenyl group,
a chrysenyl group,
a benzochrysenyl group,
a triphenylenyl group,
a benzotriphenylenyl group,
a tetracenyl group,
a pentacenyl group,
a fluorenyl group,
a 9,9'-spirobifluorenyl group,
a benzofluorenyl group,
a dibenzofluorenyl group,
a fluoranthenyl group,
a benzofluoranthenyl group,
a perylenyl group, and
a monovalent aryl group derived by removing one hydrogen atom from the ring structures represented by any of the following general formulas (TEMP-1) to (TEMP-15).

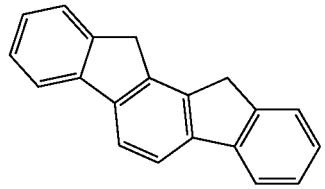

(TEMP-1)

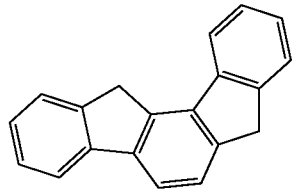

(TEMP-2)

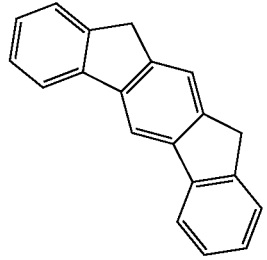

(TEMP-3)

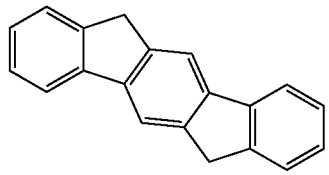

(TEMP-4)

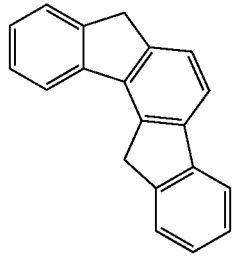

(TEMP-5)

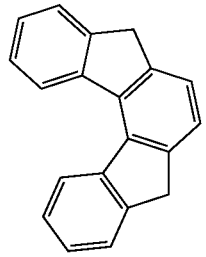

(TEMP-6)

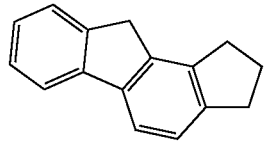

(TEMP-7)

-continued

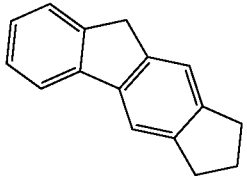
(TEMP-8)

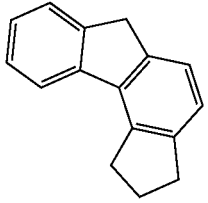
(TEMP-9)

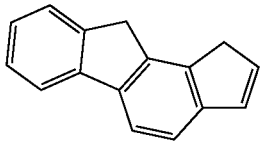
(TEMP-10)

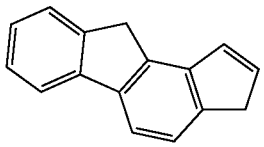
(TEMP-11)

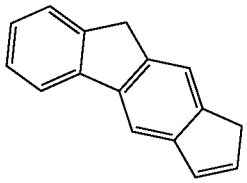
(TEMP-12)

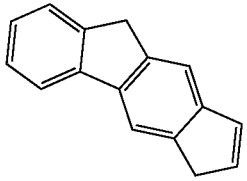
(TEMP-13)

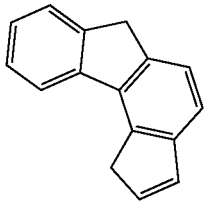
(TEMP-14)

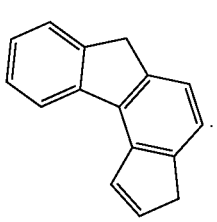
(TEMP-15)

Substituted aryl group (specific example group G1B):
an o-tolyl group,
a m-tolyl group,
a p-tolyl group,
a p-xylyl group,
a m-xylyl group,
an o-xylyl group,
a p-isopropylphenyl group,
a m-isopropylphenyl group,
an o-isopropylphenyl group,
a p-t-butylphenyl group,
a m-t-butylphenyl group,
an o-t-butylphenyl group,
a 3,4,5-trimethylphenyl group,
a 9,9-dimethylfluorenyl group,
a 9,9-diphenylfluorenyl group,
a 9,9-bis(4-methylphenyl)fluorenyl group,
a 9,9-bis(4-isopropylphenyl)fluorenyl group,
a 9,9-bis(4-t-butylphenyl)fluorenyl group,
a cyanophenyl group,
a tiphenylsilylphenyl group,
a trimethylsilylphenyl group,
a phenylnaphthyl group,
a naphthylphenyl group, and
a group in which one or more hydrogen atoms of a monovalent group derived from the ring structures represented by any of the general formulas (TEMP-1) to (TEMP-15) are substituted by a substituent.

"Substituted or unsubstituted heterocyclic group"

The "heterocyclic group" described in this specification is a ring group having at least one hetero atom in the ring atom. Specific examples of the hetero atom include a nitrogen atom, an oxygen atom, a sulfur atom, a silicon atom, a phosphorus atom, and a boron atom.

The "heterocyclic group" in this specification is a monocyclic group or a fused ring group.

The "heterocyclic group" in this specification is an aromatic heterocyclic group or a non-aromatic heterocyclic group.

Specific examples of the "substituted or unsubstituted heterocyclic group" (specific example group G2) described in this specification include the following unsubstituted heterocyclic group (specific example group G2A), the following substituted heterocyclic group (specific example group G2B), and the like. (Here, the unsubstituted heterocyclic group refers to the case where the "substituted or unsubstituted heterocyclic group" is a "heterocyclic group unsubstituted by a substituent", and the substituted heterocyclic group refers to the case where the "substituted or unsubstituted heterocyclic group" is a "heterocyclic group substituted by a substituent"). In this specification, in the case where simply referred as a "heterocyclic group", it includes both the "unsubstituted heterocyclic group" and the "substituted heterocyclic group."

The "substituted heterocyclic group" means a group in which one or more hydrogen atom of the "unsubstituted heterocyclic group" are substituted by a substituent. Specific examples of the "substituted heterocyclic group" include a group in which a hydrogen atom of "unsubstituted heterocyclic group" of the following specific example group G2A is substituted by a substituent, the substituted heterocyclic groups of the following specific example group G2B, and the like. It should be noted that the examples of the "unsubstituted heterocyclic group" and the examples of the "substituted heterocyclic group" enumerated in this specification are mere examples, and the "substituted heterocyclic group" described in this specification includes groups in which hydrogen atom bonded with a ring atom of the heterocydic group itself in the "substituted heterocyclic group" of the specific example group G2B is further substituted by a substituent, and a group in which hydrogen atom of a substituent in the "substituted heterocyclic group" of the specific example group G2B is further substituted by a substituent.

Specific example group G2A includes, for example, the following unsubstituted heterocyclic group containing a nitrogen atom (specific example group G2A1), the following unsubstituted heterocyclic group containing an oxygen atom (specific example group G2A2), the following unsubstituted heterocyclic group containing a sulfur atom (specific example group G2A3), and the monovalent heterocyclic group derived by removing one hydrogen atom from the ring structures represented by any of the following general formulas (TEMP-16) to (TEMP-33) (specific example group G2A4).

Specific example group G2B includes, for example, the following substituted heterocyclic group containing a nitrogen atom (specific example group G2B1), the following substituted heterocyclic group containing an oxygen atom (specific example group G2B2), the following substituted heterocyclic group containing a sulfur atom (specific example group G2B3), and the following group in which one or more hydrogen atoms of the monovalent heterocyclic group derived from the ring structures represented by any of the following general formulas (TEMP-16) to (TEMP-33) are substituted by a substituent (specific example group G2B4).

Unsubstituted heterocyclic group containing a nitrogen atom (specific example group G2A1):
  a pyrrolyl group,
  an imidazolyl group,
  a pyrazolyl group,
  a triazolyl group,
  a tetrazolyl group,
  an oxazolyl group,
  an isoxazolyl group,
  an oxadiazolyl group,
  a thiazolyl group,
  an isothiazolyl group,
  a thiadiazolyl group,
  a pyridyl group,
  a pyridazinyl group,
  a pyrimidinyl group,
  a pyrazinyl group,
  a triazinyl group,
  an indolyl group,
  an isoindolyl group,
  an indolizinyl group,
  a quinolizinyl group,
  a quinolyl group,
  an isoquinolyl group,
  a cinnolyl group,
  a phthalazinyl group,
  a quinazolinyl group,
  a quinoxalinyl group,
  a benzimidazolyl group,
  an indazolyl group,
  a phenanthrolinyl group,
  a phenanthridinyl group,
  an acridinyl group,
  a phenazinyl group,
  a carbazolyl group,
  a benzocarbazolyl group,
  a morpholino group,
  a phenoxazinyl group,
  a phenothiazinyl group,
  an azacarbazolyl group, and
  a diazacarbazolyl group.

Unsubstituted heterocyclic group containing an oxygen atom (specific example group G2A2):
  a furyl group,
  an oxazolyl group,
  an isoxazolyl group,
  an oxadiazolyl group,
  a xanthenyl group,
  a benzofuranyl group,
  an isobenzofuranyl group,
  a dibenzofuranyl group,
  a naphthobenzofuranyl group,
  a benzoxazolyl group,
  a benzisoxazolyl group,
  a phenoxazinyl group,
  a morpholino group,
  a dinaphthofuranyl group,
  an azadibenzofuranyl group,
  a diazadibenzofuranyl group,
  an azanaphthobenzofuranyl group, and
  a diazanaphthobenzofuranyl group.

Unsubstituted heterocyclic group containing a sulfur atom (specific example group G2A3):
  a thienyl group,
  a thiazolyl group,
  an isothiazolyl group,
  a thiadiazolyl group,
  a benzothiophenyl group (benzothienyl group),
  an isobenzothiophenyl group (isobenzothienyl group),
  a dibenzothiophenyl group (dibenzothienyl group),
  a naphthobenzothiophenyl group (naphthobenzothienyl group),
  a benzothiazolyl group,
  a benzisothiazolyl group,
  a phenothiazinyl group,
  a dinaphthothiophenyl group (dinaphthothienyl group),
  an azadibenzothiophenyl group (azadibenzothienyl group),
  a diazadibenzothiophenyl group (diazadibenzothienyl group),
  an azanaphthobenzothiophenyl group (azanaphthobenzothienyl group), and
  a diazanaphthobenzothiophenyl group (diazanaphthobenzothienyl group).

Monovalent heterocyclic group derived by removing one hydrogen atom from the ring structures represented by any of the following general formulas (TEMP-16) to (TEMP-33) (specific example group G2A4):

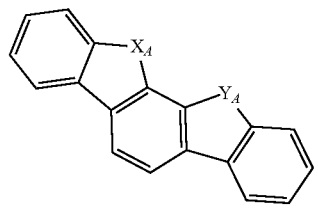

(TEMP-16)

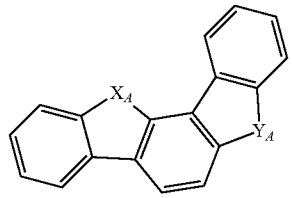

(TEMP-17)

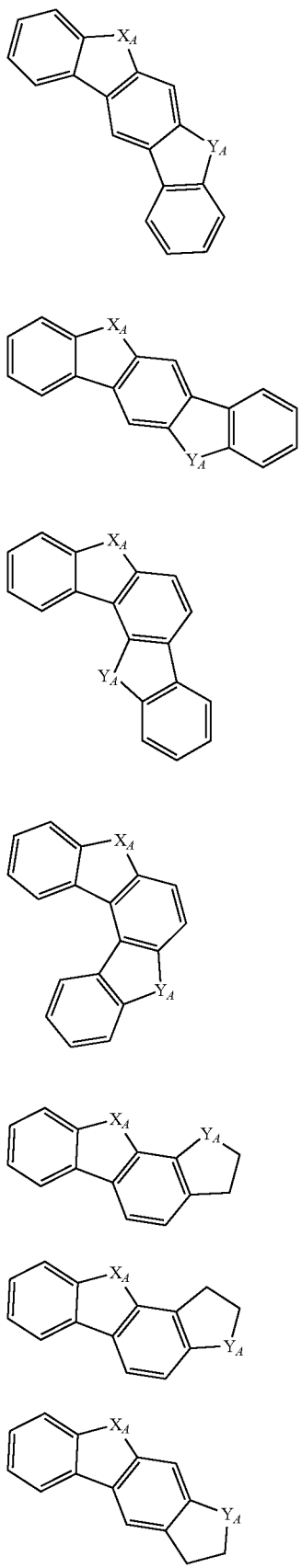
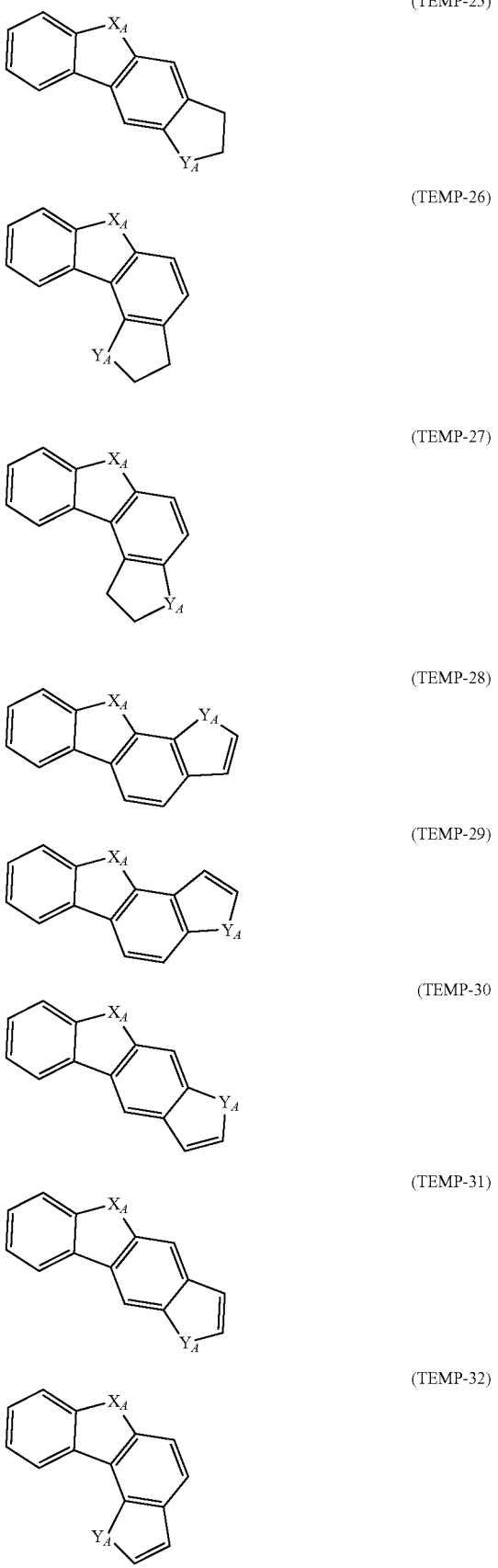

-continued

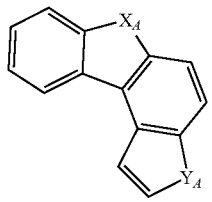

(TEMP-33)

In the general formulas (TEMP-16) to (TEMP-33), $X_A$ and $Y_A$ are independently an oxygen atom, a sulfur atom, NH, or $CH_2$. Provided that at least one of $X_A$ and $Y_A$ is an oxygen atom, a sulfur atom, or NH. In the general formulas (TEMP-16) to (TEMP-33), when at least one of $X_A$ and $Y_A$ is NH or $CH_2$, the monovalent heterocyclic group derived from the ring structures represented by any of the general formulas (TEMP-16) to (TEMP-33) includes a monovalent group derived by removing one hydrogen atom from these NH or $CH_2$.

Substituted heterocyclic group containing a nitrogen atom (specific example group G2B1):
  a (9-phenyl)carbazolyl group,
  a (9-biphenylyl)carbazolyl group,
  a (9-phenyl)phenylcarbazolyl group,
  a (9-naphthyl)carbazolyl group,
  a diphenylcarbazol-9-yl group,
  a phenylcarbazol-9-yl group,
  a methylbenzimidazolyl group,
  an ethylbenzimidazolyl group,
  a phenyltriazinyl group,
  a biphenylyltriazinyl group,
  a diphenyltriazinyl group,
  a phenylquinazolinyl group, and
  a biphenylylquinazolinyl group.

Substituted heterocyclic group containing an oxygen atom (specific example group G2B2):
  a phenyldibenzofuranyl group,
  a methyldibenzofuranyl group,
  a t-butyldibenzofuranyl group, and
  a monovalent residue of spiro[9H-xanthene-9,9'-[9H]fluorene].

Substituted heterocyclic group containing a sulfur atom (specific example group G2B3):
  a phenyldibenzothiophenyl group,
  a methyldibenzothiophenyl group,
  a t-butyldibenzothiophenyl group, and
  a monovalent residue of spiro[9H-thioxanthene-9,9'-[9H]fluorene].

Group in which one or more hydrogen atoms of the monovalent heterocyclic group derived from the ring structures represented by any of the following general formulas (TEMP-16) to (TEMP-33) are substituted by a substituent (specific example group G2B4):

The "one or more hydrogen atoms of the monovalent heterocyclic group" means one or more hydrogen atoms selected from hydrogen atoms bonded with ring carbon atoms of the monovalent heterocyclic group, a hydrogen atom bonded with a nitrogen atom when at least one of $X_A$ and $Y_A$ is NH, and hydrogen atoms of a methylene group when one of $X_A$ and $Y_A$ is $CH_2$.

"Substituted or unsubstituted alkyl group"

Specific examples of the "substituted or unsubstituted alkyl group" (specific example group G3) described in this specification include the following unsubstituted alkyl groups (specific example group G3A) and the following substituted alkyl groups (specific example group G3B). (Here, the unsubstituted alkyl group refers to the case where the "substituted or unsubstituted alkyl group" is an "alkyl group unsubstituted by a substituent", and the substituted alkyl group refers to the case where the "substituted or unsubstituted alkyl group" is an "alkyl group substituted by a substituent"). In this specification, in the case where simply referred as an "alkyl group" includes both the "unsubstituted alkyl group" and the "substituted alkyl group."

The "substituted alkyl group" means a group in which one or more hydrogen atoms in the "unsubstituted alkyl group" are substituted by a substituent. Specific examples of the "substituted alkyl group" include groups in which one or more hydrogen atoms in the following "unsubstituted alkyl group" (specific example group G3A) are substituted by a substituent, the following substituted alkyl group (specific example group G3B), and the like. In this specification, the alkyl group in the "unsubstituted alkyl group" means a linear alkyl group. Thus, the "unsubstituted alkyl group" includes a straight-chain "unsubstituted alkyl group" and a branched-chain "unsubstituted alkyl group". It should be noted that the examples of the "unsubstituted alkyl group" and the examples of the "substituted alkyl group" enumerated in this specification are mere examples, and the "substituted alkyl group" described in this specification includes a group in which hydrogen atom of the alkyl group itself in the "substituted alkyl group" of the specific example group G3B is further substituted by a substituent, and a group in which hydrogen atom of a substituent in the "substituted alkyl group" of the specific example group G3B is further substituted by a substituent.

Unsubstituted alkyl group (specific example group G3A):
  a methyl group,
  an ethyl group,
  a n-propyl group,
  an isopropyl group,
  a n-butyl group,
  an isobutyl group,
  a s-butyl group, and
  a t-butyl group.

Substituted alkyl group (specific example group G3B):
  a heptafluoropropyl group (including isomers),
  a pentafluoroethyl group,
  a 2,2,2-trifluoroethyl group, and
  a trifluoromethyl group.

"Substituted or unsubstituted alkenyl group"

Specific examples of the "substituted or unsubstituted alkenyl group" described in this specification (specific example group G4) include the following unsubstituted alkenyl group (specific example group G4A), the following substituted alkenyl group (specific example group G4B), and the like. (Here, the unsubstituted alkenyl group refers to the case where the "substituted or unsubstituted alkenyl group" is an "alkenyl group unsubstituted by a substituent", and the "substituted alkenyl group" refers to the case where the "substituted or unsubstituted alkenyl group" is a "alkenyl group substituted by a substituent."). In this specification, in the case where simply referred as an "alkenyl group" includes both the "unsubstituted alkenyl group" and the "substituted alkenyl group."

The "substituted alkenyl group" means a group in which one or more hydrogen atoms in the "unsubstituted alkenyl group" are substituted by a substituent. Specific examples of the "substituted alkenyl group" include a group in which the following "unsubstituted alkenyl group" (specific example group G4A) has a substituent, the following substituted alkenyl group (specific example group G4B), and the like. It should be noted that the examples of the "unsubstituted alkenyl group" and the examples of the "substituted alkenyl group" enumerated in this specification are mere examples, and the "substituted alkenyl group" described in this specification includes a group in which a hydrogen atom of the alkenyl group itself in the "substituted alkenyl group" of the specific example group G4B is further substituted by a substituent, and a group in which a hydrogen atom of a substituent in the "substituted alkenyl group" of the specific example group G4B is further substituted by a substituent.

Unsubstituted alkenyl group (specific example group G4A):
 a vinyl group,
 an allyl group,
 a 1-butenyl group,
 a 2-butenyl group, and
 a 3-butenyl group.

Substituted alkenyl group (specific example group G4B):
 a 1,3-butanedienyl group,
 a 1-methylvinyl group,
 a 1-methylallyl group,
 a 1,1-dimethylallyl group,
 a 2-methylally group, and
 a 1,2-dimethylallyl group.

"Substituted or unsubstituted alkynyl group"

Specific examples of the "substituted or unsubstituted alkynyl group" described in this specification (specific example group G5) include the following unsubstituted alkynyl group (specific example group G5A) and the like. (Here, the unsubstituted alkynyl group refers to the case where the "substituted or unsubstituted alkynyl group" is an "alkynyl group unsubstituted by a substituent"). In this specification, in the case where simply referred as an "alkynyl group" includes both the "unsubstituted alkynyl group" and the "substituted alkynyl group."

The "substituted alkynyl group" means a group in which one or more hydrogen atoms in the "unsubstituted alkynyl group" are substituted by a substituent. Specific examples of the "substituted alkynyl group" include a group in which one or more hydrogen atoms in the following "unsubstituted alkynyl group" (specific example group G5A) are substituted by a substituent, and the like.

Unsubstituted alkynyl group (specific example group G5A):
 an ethynyl group.

"Substituted or Unsubstituted Cycloalkyl Group"

Specific examples of the "substituted or unsubstituted cycloalkyl group" described in this specification (specific example group G6) include the following unsubstituted cycloalkyl group (specific example group G6A), the following substituted cycloalkyl group (specific example group G6B), and the like. (Here, the unsubstituted cycloalkyl group refers to the case where the "substituted or unsubstituted cycloalkyl group" is a "cycloalkyl group unsubstituted by a substituent", and the substituted cycloalkyl group refers to the case where the "substituted or unsubstituted cycloalkyl group" is a "cycloalkyl group substituted by a substituent"). In this specification, in the case where simply referred as a "cycloalkyl group" includes both the "unsubstituted cycloalkyl group" and the "substituted cycloalkyl group."

The "substituted cycloalkyl group" means a group in which one or more hydrogen atoms in the "unsubstituted cycloalkyl group" are substituted by a substituent. Specific examples of the "substituted cycloalkyl group" include a group in which one or more hydrogen atoms in the following "unsubstituted cycloalkyl group" (specific example group G6A) are substituted by a substituent, and examples of the following substituted cycloalkyl group (specific example group G6B), and the like. It should be noted that the examples of the "unsubstituted cycloalkyl group" and the examples of the "substituted cycloalkyl group" enumerated in this specification are mere examples, and the "substituted cycloalkyl group" in this specification includes a group in which one or more hydrogen atoms bonded with the carbon atom of the cycloalkyl group itself in the "substituted cycloalkyl group" of the specific example group G6B are substituted by a substituent, and a group in which a hydrogen atom of a substituent in the "substituted cycloalkyl group" of specific example group G6B is further substituted by a substituent.

Unsubstituted cycloalkyl group (specific example group G6A):
 a cyclopropyl group,
 a cyclobutyl group,
 a cyclopentyl group,
 a cyclohexyl group,
 a 1-adamantyl group,
 a 2-adamantyl group,
 a 1-norbornyl group, and
 a 2-norbornyl group.

Substituted cycloalkyl group (specific example group G6B):
 a 4-methylcyclohexyl group.

"Group represented by —Si($R_{901}$)($R_{902}$)($R_{903}$)"

Specific examples of the group represented by —Si($R_{901}$)($R_{902}$)($R_{903}$) described in this specification (specific example group G7) include:
 —Si(G1)(G1)(G1),
 —Si(G1)(G2)(G2),
 —Si(G1)(G1)(G2),
 —Si(G2)(G2)(G2),
 —Si(G3)(G3)(G3), and
 —Si(G6)(G6)(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

Plural G1's in —Si(G1)(G1)(G1) are the same or different.

Plural G2's in —Si(G1)(G2)(G2) are the same or different.

Plural G1's in —Si(G1)(G1)(G2) are the same or different.

Plural G2's in —Si(G2)(G2)(G2) are be the same or different.

Plural G3's in —Si(G3)(G3)(G3) are the same or different.

Plural G6's in —Si(G6)(G6)(G6) are be the same or different.

"Group represented by —O—($R_{904}$)"

Specific examples of the group represented by —O—($R_{904}$) in this specification (specific example group G8) include:
 —O(G1),
 —O(G2),
 —O(G3), and
 —O(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

"Group represented by —S—($R_{905}$)"

Specific examples of the group represented by —S—($R_{905}$) in this specification (specific example group G9) include:

—S(G1),
—S(G2),
—S(G3), and
—S(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

"Group represented by —N($R_{906}$)($R_{907}$)"

Specific examples of the group represented by —N($R_{906}$)($R_{907}$) in this specification (specific example group G10) include:

—N(G1)(G1),
—N(G2)(G2),
—N(G1)(G2),
—N(G3)(G3), and
—N(G6)(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

Plural G1's in —N(G1)(G1) are the same or different.
Plural G2's in —N(G2)(G2) are the same or different.
Plural G3's in —N(G3)(G3) are the same or different.
Plural G6's in —N(G6)(G6) are the same or different.

"Halogen atom"

Specific examples of the "halogen atom" described in this specification (specific example group G11) include a fluorine atom, a chlorine atom, a bromine atom, an iodine atom, and the like.

"Substituted or unsubstituted fluoroalkyl group"

The "substituted or unsubstituted fluoroalkyl group" described in this specification is a group in which at least one hydrogen atom bonded with a carbon atom constituting the alkyl group in the "substituted or unsubstituted alkyl group" is substituted by a fluorine atom, and includes a group in which all hydrogen atoms bonded with a carbon atom constituting the alkyl group in the "substituted or unsubstituted alkyl group" are substituted by a fluorine atom (a perfluoro group). The number of carbon atoms of the "unsubstituted fluoroalkyl group" is 1 to 50, preferably 1 to 30, more preferably 1 to 18, unless otherwise specified in this specification. The "substituted fluoroalkyl group" means a group in which one or more hydrogen atoms of the "fluoroalkyl group" are substituted by a substituent. The "substituted fluoroalkyl group" described in this specification also includes a group in which one or more hydrogen atoms bonded with a carbon atom of the alkyl chains in the "substituted fluoroalkyl group" are further substituted by a substituent, and a group in which one or more hydrogen atom of a substituent in the "substituted fluoroalkyl group" are further substituted by a substituent. Specific examples of the "unsubstituted fluoroalkyl group" include a group in which one or more hydrogen atoms in the "alkyl group" (specific group G3) are substituted by a fluorine atom, and the like.

"Substituted or unsubstituted haloalkyl group"

The "substituted or unsubstituted haloalkyl group" described in this specification is a group in which at least one hydrogen atom bonded with a carbon atom constituting the alkyl group in the "substituted or unsubstituted alkyl group" is substituted by a halogen atom, and also includes a group in which all hydrogen atoms bonded with a carbon atom constituting the alkyl group in the "substituted or unsubstituted alkyl group" are substituted by a halogen atom. The number of carbon atoms of the "unsubstituted haloalkyl group" is 1 to 50, preferably 1 to 30, more preferably 1 to 18, unless otherwise specified in this specification. The "substituted haloalkyl group" means a group in which one or more hydrogen atoms of the "haloalkyl group" are substituted by a substituent. The "substituted haloalkyl group" described in this specification also includes a group in which one or more hydrogen atoms bonded with a carbon atom of the alkyl chain in the "substituted haloalkyl group" are further substituted by a substituent, and a group in which one or more hydrogen atoms of a substituent in the "substituted haloalkyl group" are further substituted by a substituent. Specific examples of the "unsubstituted haloalkyl group" include a group in which one or more hydrogen atoms in the "alkyl group" (specific example group G3) are substituted by a halogen atom, and the like. A haloalkyl group is sometimes referred to as an alkyl halide group.

"Substituted or unsubstituted alkoxy group" Specific examples of the "substituted or unsubstituted alkoxy group" described in this specification include a group represented by —O(G3), wherein G3 is the "substituted or unsubstituted alkyl group" described in the specific example group G3. The number of carbon atoms of the "unsubstituted alkoxy group" is 1 to 50, preferably 1 to 30, more preferably 1 to 18, unless otherwise specified in this specification.

"Substituted or unsubstituted alkylthio group" Specific examples of the "substituted or unsubstituted alkylthio group" described in this specification include a group represented by —S(G3), wherein G3 is the "substituted or unsubstituted alkyl group" described in the specific example group G3. The number of carbon atoms of the "unsubstituted alkylthio group" is 1 to 50, preferably 1 to 30, more preferably 1 to 18, unless otherwise specified in this specification.

"Substituted or unsubstituted aryloxy group" Specific examples of the "substituted or unsubstituted aryloxy group" described in this specification include a group represented by —O(G1), wherein G1 is the "substituted or unsubstituted aryl group" described in the specific example group G1. The number of ring carbon atoms of the "unsubstituted aryloxy group" is 6 to 50, preferably 6 to 30, more preferably 6 to 18, unless otherwise specified in this specification.

"Substituted or unsubstituted arylthio group" Specific examples of the "substituted or unsubstituted arylthio group" described in this specification include a group represented by —S(G1), wherein G1 is a "substituted or unsubstituted aryl group" described in the specific example group G1. The number of ring carbon atoms of the "unsubstituted arylthio group" is 6 to 50, preferably 6 to 30, more preferably 6 to 18, unless otherwise specified in this specification.

"Substituted or unsubstituted trialkylsilyl group" Specific examples of the "trialkylsilyl group" described in this specification include a group represented by —Si(G3)(G3)(G3), where G3 is the "substituted or unsubstituted alkyl group" described in the specific example group G3. Plural G3's in —Si(G3)(G3)(G3) are the same or different. The number of carbon atoms in each alkyl group of the "trialkylsilyl group" is 1 to 50, preferably 1 to 20, more preferably 1 to 6, unless otherwise specified in this specification.

"Substituted or unsubstituted aralkyl group"

Specific examples of the "substituted or unsubstituted aralkyl group" described in this specification is a group represented by -(G3)-(G1), wherein G3 is the "substituted or unsubstituted alkyl group" described in the specific example group G3, and G1 is the "substituted or unsubstituted aryl group" described in the specific example group G1. Therefore, the "aralkyl group" is a group in which a hydrogen atom of the "alkyl group" is substituted by an "aryl group" as a substituent, and is one form of the "substituted alkyl group." The "unsubstituted aralkyl group" is the "unsubstituted alkyl group" substituted by the "unsubstituted aryl group", and the number of carbon atoms of the "unsubstituted aralkyl group" is 7 to 50, preferably 7 to 30, more preferably 7 to 18, unless otherwise specified in this specification.

Specific examples of the "substituted or unsubstituted aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, and the like.

Unless otherwise specified in this specification, examples of the substituted or unsubstituted aryl group described in this specification preferably include a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, 9,9-dimethylfluorenyl group, 9,9-diphenylfluorenyl group, and the like.

Unless otherwise specified in this specification, examples of the substituted or unsubstituted heterocyclic groups described in this specification preferably include a pyridyl group, a pyrimidinyl group, a triazinyl group, a quinolyl group, an isoquinolyl group, a quinazolinyl group, a benzimidazolyl group, a phenanthrolinyl group, a carbazolyl group (a 1-carbazolyl group, a 2-carbazolyl group, a 3-carbazolyl group, a 4-carbazolyl group, or a 9-carbazolyl group), a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group (a (9-phenyl)carbazol-1-yl group, a (9-phenyl)carbazol-2-yl group, a (9-phenyl)carbazol-3-yl group, or a (9-phenyl)carbazol-4-yl group), a (9-biphenylyl)carbazolyl group, a (9-phenyl)phenylcarbazolyl group, a diphenylcarbazol-9-yl group, a phenylcarbazol-9-yl group, a phenyltriazinyl group, a biphenylyltriazinyl group, a diphenyltriazinyl group, a phenyldibenzofuranyl group, a phenyldibenzothiophenyl group, and the like.

In this specification, the carbazolyl group is specifically any of the following groups, unless otherwise specified in this specification.

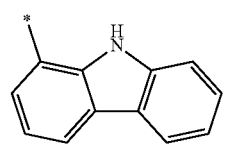
(TEMP-Cz1)

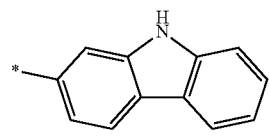
(TEMP-Cz2)

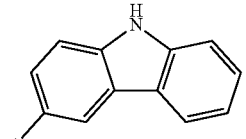
(TEMP-Cz3)

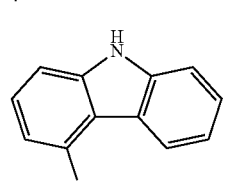
(TEMP-Cz4)

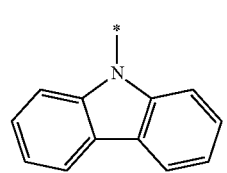
(TEMP-Cz5)

In this specification, the (9-phenyl)carbazolyl group is specifically any of the following groups, unless otherwise specified in this specification.

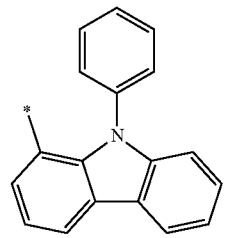
(TEMP-Cz6)

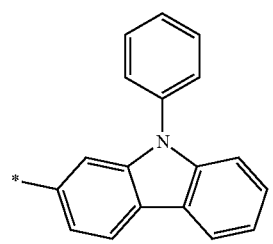
(TEMP-Cz7)

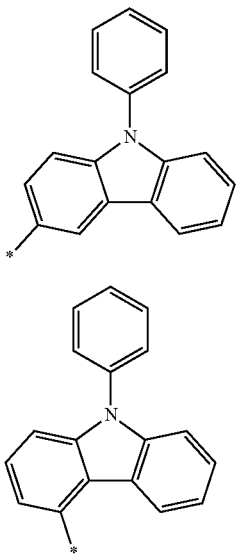

In the general formulas (TEMP-Cz1) to (TEMP-Cz9), * represents a bonding position.

In this specification, the dibenzofuranyl group and the dibenzothiophenyl group are specifically any of the following groups, unless otherwise specified in this specification.

In the general formulas (TEMP-34) to (TEMP-41), * represents a bonding position.

The substituted or unsubstituted alkyl group described in this specification is preferably a methyl group, an ethyl group, a propyl group, an isopropyl group, a n-butyl group, an isobutyl group, a t-butyl group, or the like, unless otherwise specified in this specification.

"Substituted or unsubstituted arylene group"

The "substituted or unsubstituted arylene group" described in this specification is a divalent group derived by removing one hydrogen atom on the aryl ring of the "substituted or unsubstituted aryl group", unless otherwise specified. Specific examples of the "substituted or unsubstituted arylene group" (specific example group G12) include a divalent group derived by removing one hydrogen atom on the aryl ring of the "substituted or unsubstituted aryl group" described in the specific example group G1, and the like.

"Substituted or unsubstituted divalent heterocyclic group"

The "substituted or unsubstituted divalent heterocyclic group" described in this specification is a divalent group derived by removing one hydrogen atom on the heterocyclic ring of the "substituted or unsubstituted heterocyclic group", unless otherwise specified. Specific examples of the "substituted or unsubstituted divalent heterocyclic group" (specific example group G13) include a divalent group derived by removing one hydrogen atom on the heterocyclic ring of the "substituted or unsubstituted heterocyclic group" described in the specific example group G2, and the like.

"Substituted or unsubstituted alkylene group"

The "substituted or unsubstituted alkylene group" described in this specification is a divalent group derived by removing one hydrogen atom on the alkyl chain of the "substituted or unsubstituted alkyl group", unless otherwise specified. Specific examples of the "substituted or unsubstituted alkylene group" (specific example group G14) include a divalent group derived by removing one hydrogen atom on the alkyl chain of the "substituted or unsubstituted alkyl group" described in the specific example group G3, and the like.

The substituted or unsubstituted arylene group described in this specification is preferably any group of the following general formulas (TEMP-42) to (TEMP-68), unless otherwise specified in this specification.

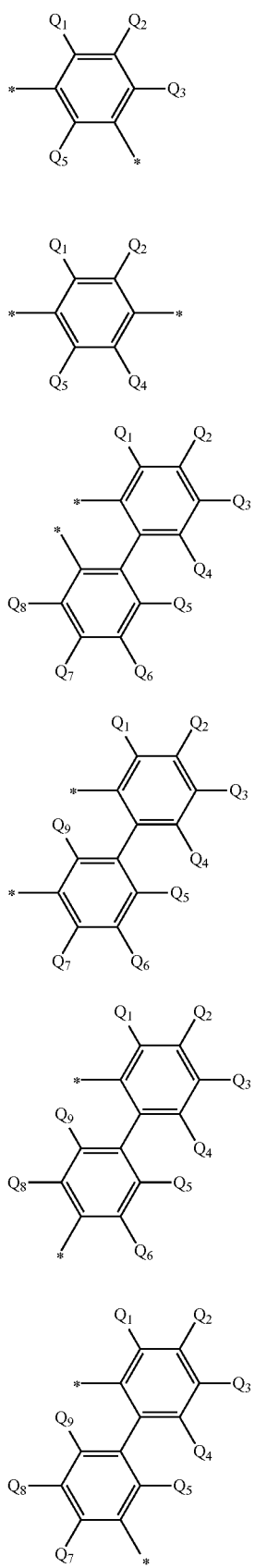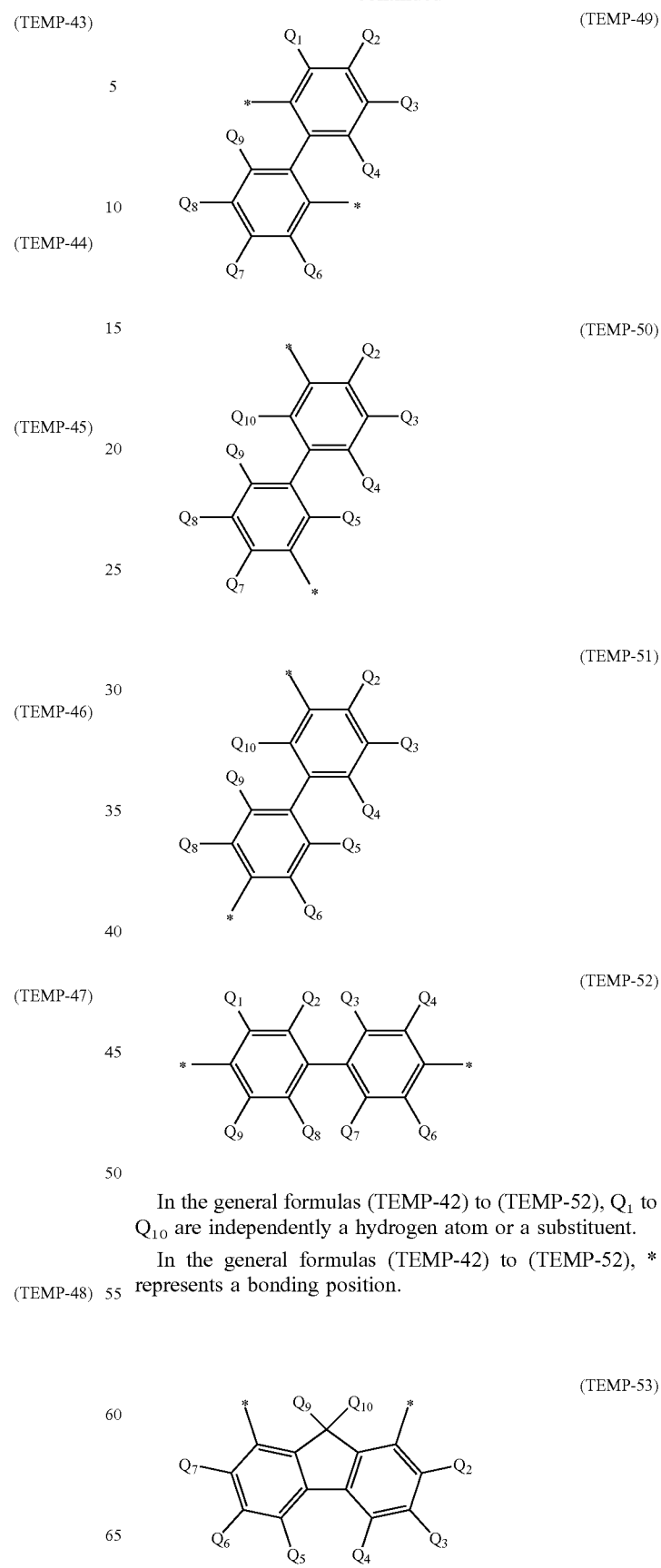
In the general formulas (TEMP-42) to (TEMP-52), $Q_1$ to $Q_{10}$ are independently a hydrogen atom or a substituent.
In the general formulas (TEMP-42) to (TEMP-52), * represents a bonding position.

(TEMP-54)
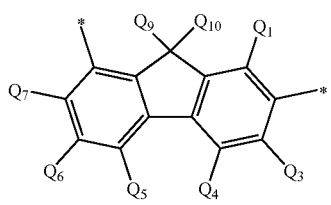
(TEMP-55)
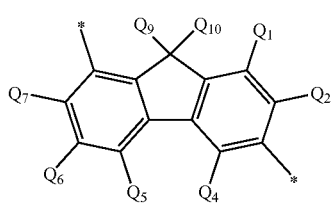
(TEMP-56)
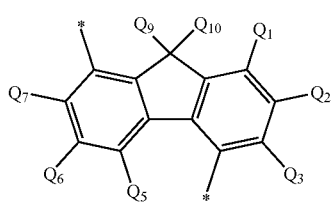
(TEMP-57)
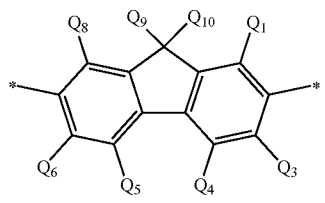
(TEMP-58)
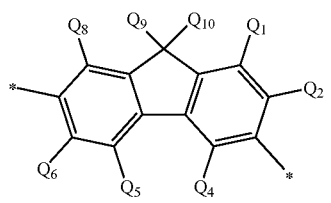
(TEMP-59)
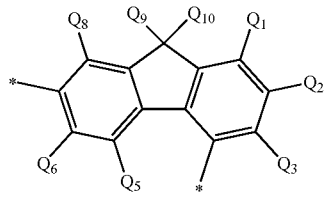
(TEMP-60)
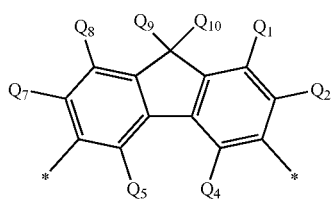
(TEMP-61)
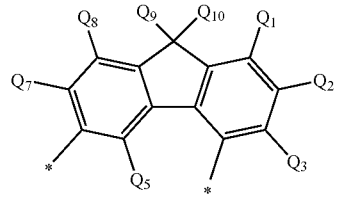
(TEMP-62)
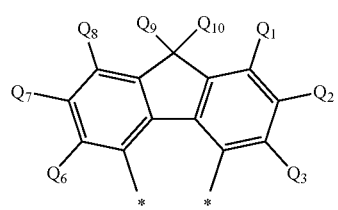
In the general formulas (TEMP-53) to (TEMP-62), $Q_1$ to $Q_{10}$ are independently a hydrogen atom or a substituent.
$Q_9$ and $Q_{10}$ may be bonded with each other via a single bond to form a ring.
In the general formulas (TEMP-53) to (TEMP-62), * represents a bonding position.
(TEMP-63)
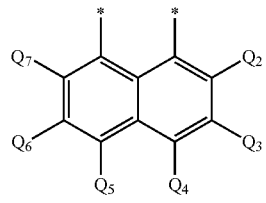
(TEMP-64)
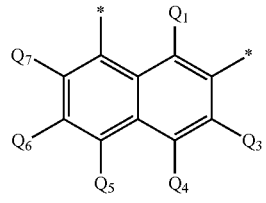
(TEMP-65)
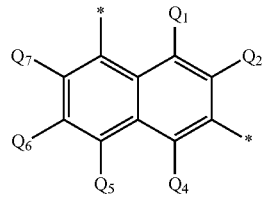
(TEMP-66)
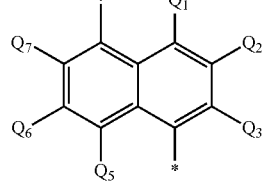

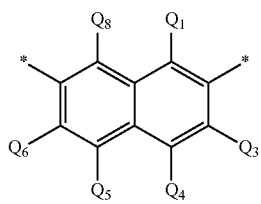
(TEMP-67)

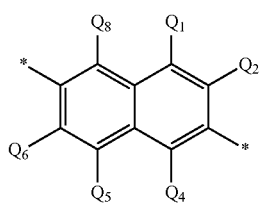
(TEMP-68)

In the general formulas (TEMP-63) to (TEMP-68), $Q_1$ to $Q_8$ are independently a hydrogen atom or a substituent.

In the general formulas (TEMP-63) to (TEMP-68), * represents a bonding position.

The substituted or unsubstituted divalent heterocyclic group described in this specification is preferably any group of the following general formulas (TEMP-69) to (TEMP-102), unless otherwise specified in this specification.

(TEMP-69)

(TEMP-70)

(TEMP-71)

(TEMP-72)

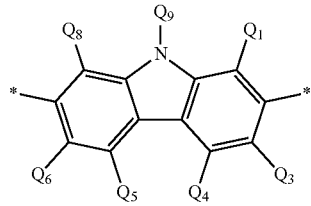
(TEMP-73)

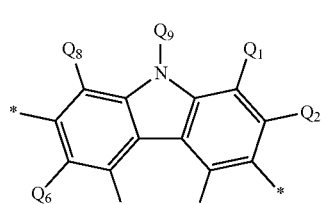
(TEMP-74)

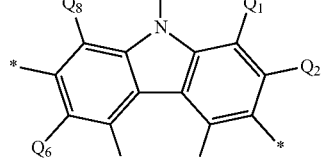
(TEMP-75)

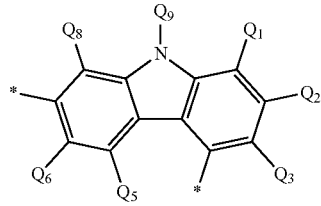
(TEMP-76)

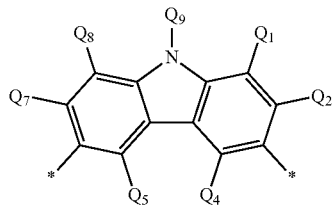
(TEMP-77)

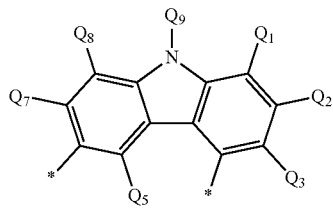
(TEMP-78)

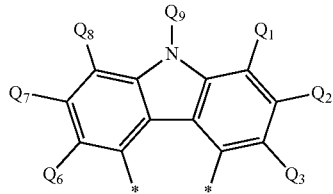
(TEMP-79)

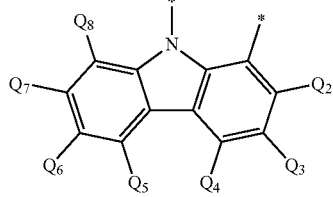

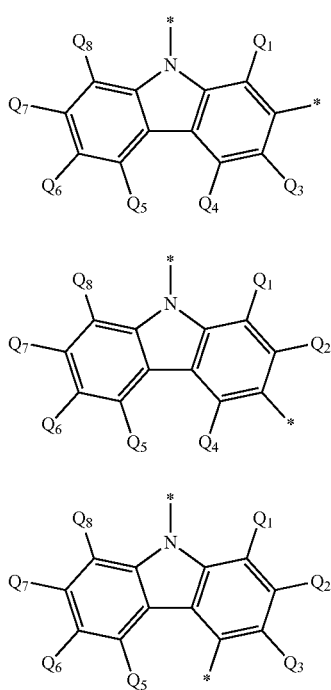
In the general formulas (TEMP-69) to (TEMP-82), $Q_1$ to $Q_9$ are independently a hydrogen atom or a substituent.
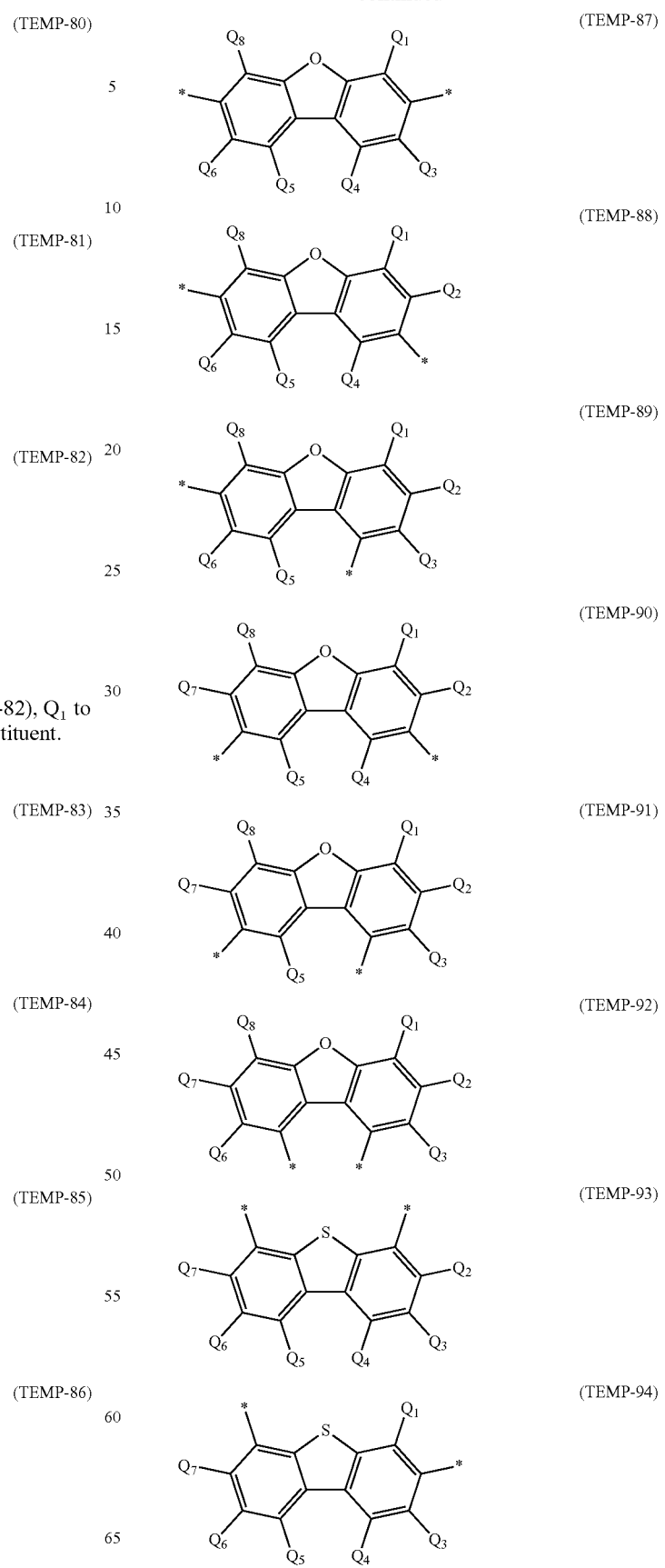

-continued

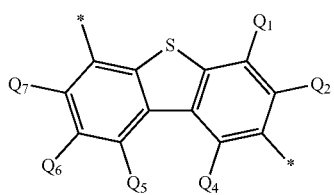
(TEMP-95)

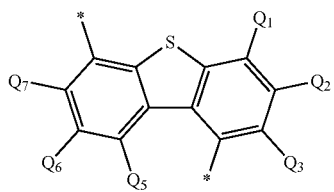
(TEMP-96)

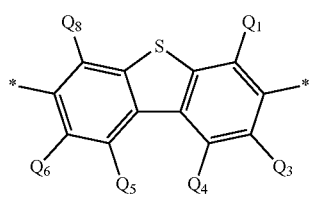
(TEMP-97)

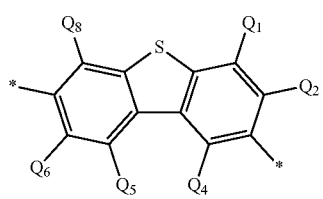
(TEMP-98)

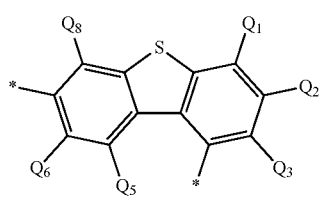
(TEMP-99)

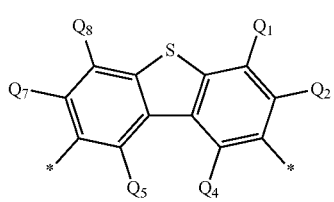
(TEMP-100)

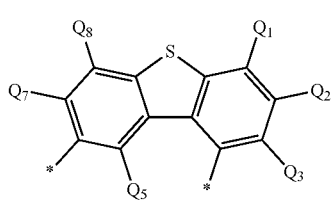
(TEMP-101)

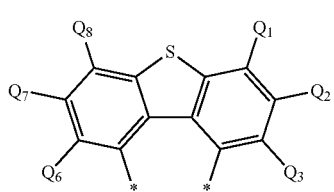
(TEMP-102)

In the general formulas (TEMP-83) to (TEMP-102), $Q_1$ to $Q_8$ are independently a hydrogen atom or a substituent.

The above is the explanation of the "Substituent described in this specification."

"The case where bonded with each other to form a ring"

In this specification, the case where "one or more sets of adjacent two or more form a substituted or unsubstituted monocycle by bonding with each other, form a substituted or unsubstituted fused ring by bonding with each other, or do not bond with each other" means the case where "one or more sets of adjacent two or more form a substituted or unsubstituted monocycle by bonding with each other"; the case where "one or more sets of adjacent two or more form a substituted or unsubstituted fused ring by bonding with each other"; and the case where "one or more sets of adjacent two or more do not bond with each other."

The case where "one or more sets of adjacent two or more form a substituted or unsubstituted monocycle by bonding with each other" and the case where "one or more sets of adjacent two or more form a substituted or unsubstituted fused ring by bonding with each other" in this specification (these cases may be collectively referred to as "the case where forming a ring by bonding with each other") will be described below The case of an anthracene compound represented by the following general formula (TEMP-103) in which the mother skeleton is an anthracene ring will be described as an example.

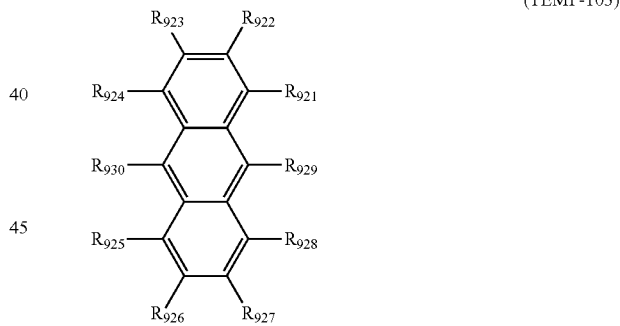
(TEMP-103)

For example, in the case where "one or more sets of adjacent two or more among $R_{921}$ to $R_{930}$ form a ring by bonding with each other", the one sets of adjacent two includes a pair of $R_{921}$ and $R_{922}$, a pair of $R_{922}$ and $R_{923}$, a pair of $R_{923}$ and $R_{924}$, a pair of $R_{924}$ and $R_{930}$, a pair of $R_{930}$ and $R_{925}$, a pair of $R_{925}$ and $R_{926}$, a pair of $R_{926}$ and $R_{927}$, a pair of $R_{927}$ and $R_{928}$, a pair of $R_{928}$ and $R_{929}$, and a pair of $R_{929}$ and $R_{921}$.

The "one or more sets" means that two or more sets of the adjacent two or more sets may form a ring at the same time. For example, $R_{921}$ and $R_{922}$ form a ring $Q_A$ by bonding with each other, and at the same, time $R_{925}$ and $R_{926}$ form a ring $Q_B$ by bonding with each other, the anthracene compound represented by the general formula (TEMP-103) is represented by the following general formula (TEMP-104).

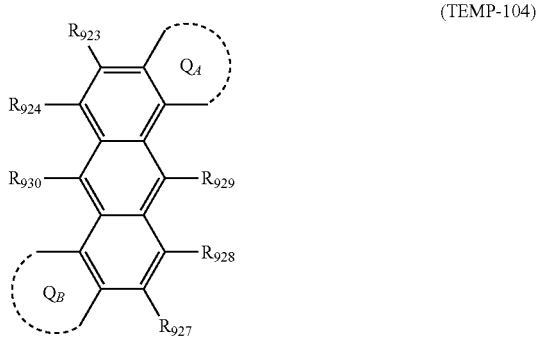

(TEMP-104)

The case where the "pair of adjacent two or more" form a ring includes not only the case where the pair of adjacent "two" is bonded with as in the above-mentioned examples, but also the case where the pair of adjacent "three or more" are bonded with each other. For example, it means the case where $R_{921}$ and $R_{922}$ form a ring $Q_A$ by bonding with each other, and $R_{922}$ and $R_{923}$ form a ring $Q_C$ by bonding with each other, and adjacent three ($R_{921}$, $R_{922}$ and $R_{923}$) form rings by bonding with each other and together fused to the anthracene mother skeleton. In this case, the anthracene compound represented by the general formula (TEMP-103) is represented by the following general formula (TEMP-105). In the following general formula (TEMP-105), the ring $Q_A$ and the ring $Q_C$ share $R_{922}$.

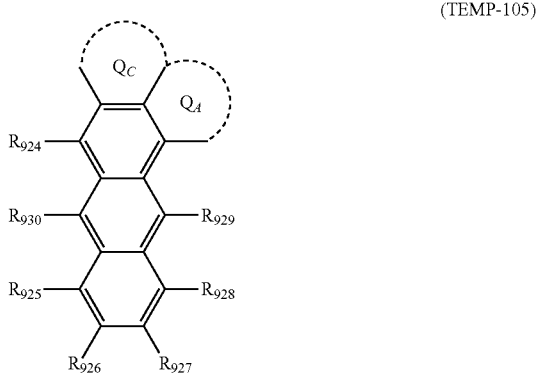

(TEMP-105)

The "monocycle" or "fused ring" formed may be a saturated ring or an unsaturated ring, as a structure of the formed ring alone. Even when the "one pair of adjacent two" forms a "monocycle" or a "fused ring", the "monocycle" or the "fused ring" may form a saturated ring or an unsaturated ring. For example, the ring $Q_A$ and the ring $Q_B$ formed in the general formula (TEMP-104) are independently a "monocycle" or a "fused ring." The ring $Q_A$ and the ring $Q_C$ formed in the general formula (TEMP-105) are "fused ring." The ring $Q_A$ and ring $Q_C$ of the general formula (TEMP-105) are fused ring by fusing the ring $Q_A$ and the ring $Q_C$ together. When the ring $Q_A$ of the general formula (TMEP-104) is a benzene ring, the ring $Q_A$ is a monocycle. When the ring $Q_A$ of the general formula (TMEP-104) is a naphthalene ring, the ring $Q_A$ is a fused ring.

The "unsaturated ring" means an aromatic hydrocarbon ring or an aromatic heterocyclic ring. The "saturated ring" means an aliphatic hydrocarbon ring, or a non-aromatic heterocyclic ring.

Specific examples of the aromatic hydrocarbon ring include a structure in which the group listed as a specific example in the specific example group G1 is terminated by a hydrogen atom.

Specific examples of the aromatic heterocyclic ring include a structure in which the aromatic heterocyclic group listed as a specific example in the example group G2 is terminated by a hydrogen atom.

Specific examples of the aliphatic hydrocarbon ring include a structure in which the group listed as a specific example in the specific example group G6 is terminated by a hydrogen atom.

The term "to form a ring" means forming a ring only with plural atoms of the mother skeleton, or with plural atoms of the mother skeleton and one or more arbitrary elements in addition. For example, the ring $Q_A$ shown in the general formula (TEMP-104), which is formed by bonding $R_{921}$ and $R_{922}$ with each other, is a ring formed from the carbon atom of the anthracene skeleton with which $R_{921}$ is bonded, the carbon atom of the anthracene skeleton with which $R_{922}$ is bonded, and one or more arbitrary elements. For example, in the case where the ring $Q_A$ is formed with $R_{921}$ and $R_{922}$, when a monocyclic unsaturated ring is formed with the carbon atom of the anthracene skeleton with which $R_{921}$ is bonded, the carbon atom of the anthracene skeleton with which $R_{922}$ is bonded, and four carbon atoms, the ring formed with $R_{921}$ and $R_{922}$ is a benzene ring.

Here, the "arbitrary element" is preferably at least one element selected from the group consisting of a carbon element, a nitrogen element, an oxygen element, and a sulfur element, unless otherwise specified in this specification. In the arbitrary element (for example, a carbon element or a nitrogen element), a bond which does not form a ring may be terminated with a hydrogen atom or the like, or may be substituted with "arbitrary substituent" described below. When an arbitrary element other than a carbon element is contained, the ring formed is a heterocyclic ring.

The number of "one or more arbitrary element(s)" constituting a monocycle or a fused ring is preferably 2 or more and 15 or less, more preferably 3 or more and 12 or less, and still more preferably 3 or more and 5 or less, unless otherwise specified in this specification.

The "monocycle" is preferable among the "monocycle" and the "fused ring", unless otherwise specified in this specification.

The "unsaturated ring" is preferable among the "saturated ring" and the "unsaturated ring", unless otherwise specified in this specification.

Unless otherwise specified in this specification, the "monocycle" is preferably a benzene ring.

Unless otherwise specified in this specification, the "unsaturated ring" is preferably a benzene ring.

Unless otherwise specified in this specification, when "one or more sets of adjacent two or more" are "bonded with each other to form a substituted or unsubstituted monocycle" or "bonded with each other to form a substituted or unsubstituted fused ring", this specification, one or more sets of adjacent two or more are preferably bonded with each other to form a substituted or unsubstituted "unsaturated ring" from plural atoms of the mother skeleton and one or more and 15 or less elements which is at least one kind selected from a carbon elements, a nitrogen element, an oxygen element, and a sulfur element.

The substituent in the case where the above-mentioned "monocycle" or "fused ring" has a substituent is, for example, an "arbitrary substituent" described below. Specific examples of the substituent which the above-mentioned "monocycle" or "fused ring" has the substituent described above in the "Substituent described in this specification" section.

The substituent in the case where the above-mentioned "saturated ring" or "unsaturated ring" has a substituent is, for example, an "arbitrary substituent" described below. Specific examples of the substituent which the above-mentioned "monocycle" or "fused ring" has the substituent described above in the "Substituent described in this specification" section.

The foregoing describes the case where "one or more sets of adjacent two or more form a substituted or unsubstituted monocycle by bonding with each other" and the case where "one or more sets of adjacent two or more form a substituted or unsubstituted fused ring by bonding with each other" (the case where "forming a ring by bonding with each other").

Substituent in the case of "substituted or unsubstituted"

In one embodiment in this specification, the substituent (in this specification, sometimes referred to as an "arbitrary substituent") in the case of "substituted or unsubstituted" is, for example, a group selected from the group consisting of:
- an unsubstituted alkyl group including 1 to 50 carbon atoms,
- an unsubstituted alkenyl group including 2 to 50 carbon atoms,
- an unsubstituted alkynyl group including 2 to 50 carbon atoms,
- an unsubstituted cycloalkyl group including 3 to 50 ring carbon atoms,
- —Si($R_{901}$)($R_{902}$)($R_{903}$),
- —O—($R_{904}$),
- —S—($R_{905}$),
- —N($R_{906}$)($R_{907}$),
- a halogen atom, a cyano group, a nitro group,
- an unsubstituted aryl group including 6 to 50 ring carbon atoms, and
- an unsubstituted heterocyclic group including 5 to 50 ring atoms, wherein, $R_{901}$ to $R_{907}$ are independently
a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted heterocyclic group including 5 to 50 ring atoms.

When two or more $R_{901}$'s are present, the two or more $R_{901}$'s may be the same or different.
When two or more $R_{902}$'s are present, the two or more $R_{902}$'s may be the same or different.
When two or more $R_{903}$'s are present, the two or more $R_{903}$'s may be the same or different.
When two or more $R_{904}$'s are present, the two or more $R_{904}$'s may be the same or different.
When two or more $R_{905}$'s are present, the two or more $R_{905}$'s may be the same or different.
When two or more $R_{906}$'s are present, the two or more $R_{906}$'s may be the same or different.
When two or more $R_{907}$'s are present, the two or more $R_{907}$'s may be the same or different.

In one embodiment, the substituent in the case of "substituted or unsubstituted" is a group selected from the group consisting of:
an alkyl group including 1 to 50 carbon atoms,
an aryl group including 6 to 50 ring carbon atoms, and
a heterocyclic group including 5 to 50 ring atoms.

In one embodiment, the substituent in the case of "substituted or unsubstituted" is a group selected from the group consisting of:
an alkyl group including 1 to 18 carbon atoms,
an aryl group including 6 to 18 ring carbon atoms, and
a heterocyclic group including 5 to 18 ring atoms.

Specific examples of each of the arbitrary substituents include specific examples of substituent described in the section "Substituent described in this specification" above.

Unless otherwise specified in this specification, adjacent arbitrary substituents may form a "saturated ring" or an "unsaturated ring", preferably form a substituted or unsubstituted saturated 5-membered ring, a substituted or unsubstituted saturated 6-membered ring, a substituted or unsubstituted unsaturated 5-membered ring, or a substituted or unsubstituted unsaturated 6-membered ring, more preferably form a benzene ring.

Unless otherwise specified in this specification, the arbitrary substituent may further have a substituent. The substituent which the arbitrary substituent further has is the same as that of the above-mentioned arbitrary substituent.

In this specification, the numerical range represented by "AA to BB" means the range including the numerical value AA described on the front side of "AA to BB" as the lower limit and the numerical value BB described on the rear side of "AA to BB" as the upper limit.

[Compound]

The compound, which is an aspect of the invention, is a compound represented by the following formula (1).

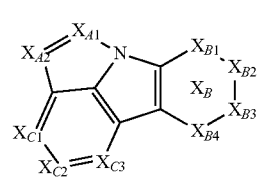

(1)

In the formula (1), $X_{A1}$ and $X_{A2}$ are fused with a substituted or unsubstituted aliphatic hydrocarbon ring including 5 to 50 ring carbon atoms or a substituted or unsubstituted non-aromatic heterocyclic ring including 5 to 50 ring atoms, or are not fused with the ring.

$X_{A1}$ and $X_{A2}$ which are not involved in the fusion of the ring are independently
CH,
C($R_a$), or
N.

A ring $X_B$ is a six-membered hydrocarbon ring or a six-membered heterocyclic ring having one or two nitrogen atoms.

$X_{B1}$ to $X_{B4}$ are atoms constituting the ring $X_B$.

One or more sets of adjacent two of $X_{B1}$ to $X_{B4}$ are fused with
a substituted or unsubstituted hydrocarbon ring including 5 to 50 ring carbon atoms, or
a substituted or unsubstituted heterocyclic ring including 5 to 50 ring atoms.

$X_{B1}$ to $X_{B4}$ which are not involved in the fusion of the ring are independently
CH,
C($R_a$),
C($R_a$)$_2$,
N, or
N($R_a$).

One or more sets of adjacent two of $X_{C1}$ to $X_{C3}$ are fused with a substituted or unsubstituted hydrocarbon ring including 5 to 50 ring carbon atoms or a substituted or unsubstituted heterocyclic ring including 5 to 50 ring atoms.

$X_{C1}$ or $X_{C3}$ which is not involved in the fusion of the ring is
CH,
$C(R_a)$, or
N.

$R_a$ is a substituent.

When a plurality of $R_a$'s are present, the plurality of $R_a$'s may be the same as or different from each other.

Adjacent two or more $R_a$'s form a substituted or unsubstituted, saturated or unsaturated ring by bonding with each other, or do not form the ring.

The compound represented by the formula (1) is useful as a material for an organic electroluminescence device.

The compound represented by the formula (1) (hereinafter, sometimes referred to as compound (1)) is useful as an emitting material of the organic EL device, and particularly, is useful as a dopant material of an emitting layer of the organic EL device.

The compound (1) has an effect of prolonging the lifetime of the organic electroluminescence device fabricated using the same.

The compound (1) is described below.

$X_{A1}$ and $X_{A2}$ are fused with a substituted or unsubstituted aliphatic hydrocarbon ring including 5 to 50 ring carbon atoms, or a substituted or unsubstituted non-aromatic heterocyclic ring including 5 to 50 ring atoms, or are not fused with the ring.

In the case where $X_{A1}$ and $X_{A2}$ are fused with the ring, examples of the "aliphatic hydrocarbon ring" include saturated aliphatic hydrocarbon rings or unsaturated aliphatic hydrocarbon rings.

Examples of the "saturated aliphatic hydrocarbon ring" including 5 to 50 ring carbon atoms include monocyclic rings such as cyclopentane, cyclohexane, cycloheptane, cyclononane, cycodecane, cycoundecane, and cyclododecane; fused rings such as bicycloundecane and decahydronaphthalene (decalin); and spirocyclic compounds.

Examples of the "unsaturated aliphatic hydrocarbon ring" include monocyclic alkenes such as cyclopentene and cyclohexene, and bicyclic alkenes such as norbornene and norbomadiene.

The terms of the "non-aromatic heterocyclic ring" means a monocyclic ring not exhibiting aromaticity, or a bicyclic or more polycyclic fused ring not exhibiting aromaticity, which has one or more selected from hetero atoms such as O, S, and N as the ring atom. The non-aromatic bicyclic or more polycyclic heterocyclic ring includes those not exhibiting aromaticity in which the "aromatic hydrocarbon ring", the "aliphatic hydrocarbon ring", and/or the "aromatic heterocyclic ring" is fused to a non-aromatic monocyclic heterocyclic ring or a non-aromatic bicyclic or more polycyclic ring. In addition, the "non-aromatic heterocyclic ring" also includes cross-linked rings, and spiro rings.

Examples of the non-aromatic monocyclic heterocyclic ring including 5 to 50 ring atoms include, for example, pyrrolidine, pyrroline, imidazolidine, imidazoline, pyrazolidine, pyrazoline, piperidine, piperazine, morpholine, thiomorpholine, dihydropyridine, tetrahydropyridine, tetrahydrofuran, tetrahydropyran, dihydrothiazole, tetrahydrothiazole, tetrahydroisothiazole, dihydrooxazine, hexahydroazepine, tetrahydrodiazepine, tetrahydropyridazine, hexahydropyrimidine, dioxolane, dioxazine, aziridine, dioxolane, oxepane, thiolane, thiin, thiazine, and the like.

Examples of the non-aromatic bicyclic or more polycyclic heterocyclic ring including 5 to 50 ring atoms include indoline, isoindoline, chromane, isochromane, and the like.

In one embodiment, $X_{A1}$ and $X_{A2}$ are fused with a substituted or unsubstituted aliphatic hydrocarbon ring including 5 to 30, preferably 5 to 20, more preferably 5 to 10 ring carbon atoms, or a substituted or unsubstituted non-aromatic heterocyclic ring including 5 to 30, preferably 5 to 20, more preferably 5 to 10 ring atoms, or are not fused with the ring.

In one embodiment, $X_{A1}$ and $X_{A2}$ are fused with a substituted or unsubstituted aliphatic hydrocarbon ring including 5 to 30, preferably 5 to 20, more preferably 5 to 10 ring carbon atoms, or are not fused with the ring.

In one embodiment, the compound represented by the formula (1) is a compound represented by the following formula (2A-1) or (2A-2).

(2A-1)

(2A-2)

In the formulas (2A-1) and (2A-2), $X_{A2}$, the ring $X_B$, $X_{B1}$ to $X_{B4}$, $X_{C1}$ to $X_{C3}$, and $R_a$ are as defined in the formula (1).

In the formula (2A-2),
a ring $X_A$ is a five-membered or six-membered aliphatic hydrocarbon ring, or a five-membered or six-membered non-aromatic heterocyclic ring having one or two nitrogen atoms.

$X_{A11}$ to $X_{A14}$ are atoms constituting the ring $X_A$ or single bonds.

$X_{A11}$ to $X_{A14}$ are independently
a single bond,
$CH_2$,
$CH(R_a)$,
$C(R_a)_2$,
NH, or
$N(R_a)$.

Provided that 0 or 1 of $X_{A11}$ to $X_{A14}$ is a single bond.

Adjacent two or more $R_a$'s form a substituted or unsubstituted, saturated or unsaturated ring by bonding with each other, or do not form the ring.

In one embodiment, at least one of $X_{A1}$ and $X_{A2}$ in the formula (1) is $C(R_a)$ and, the other is CH or N. That is, in one embodiment, the compound represented by the formula (1) is the compound represented by the formula (2A-1).

In one embodiment, the ring $X_A$ in the formula (2A-2) is a five-membered aliphatic hydrocarbon ring or a five-membered non-aromatic heterocyclic ring.

In one embodiment, the ring $X_B$ in the formula (1) is a benzene ring, or a six-membered aromatic heterocyclic ring having one or two nitrogen atoms.

Examples of the "six-membered aromatic heterocyclic ring having one or two nitrogen atoms" include pyridine, pyridadine (1,2-diazine), pyrimidine (1,3-diazine), and pyrazine (1,4-diazine) described below

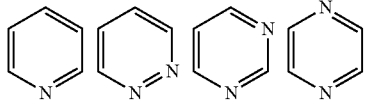

In one embodiment, the ring $X_B$ in the formula (1) is a benzene ring.

In one embodiment, one set of $X_{B1}$ and $X_{B2}$, $X_{B2}$ and $X_{B3}$, and $X_{B3}$ and $X_{B4}$ in the formula (1) is fused with a substituted or unsubstituted hydrocarbon ring including 5 to 50 ring carbon atoms, or a substituted or unsubstituted heterocyclic ring including 5 to 50 ring atoms.

In one embodiment, one set of $X_{B1}$ and $X_{B2}$, $X_{B2}$ and $X_{B3}$, and $X_{B3}$ and $X_{B4}$ in the formula (1) is fused with a substituted or unsubstituted hydrocarbon ring including 5 to 30, preferably 5 to 20, more preferably 5 to 10 ring carbon atoms, or a substituted or unsubstituted heterocyclic ring including 5 to 30, preferably 5 to 20, more preferably 5 to 10 ring atoms.

In one embodiment, $X_{B2}$ and $X_{B3}$ in the formula (1) are fused with a substituted or unsubstituted hydrocarbon ring including 5 to 50 ring carbon atoms, or a substituted or unsubstituted heterocyclic ring including 5 to 50 ring atoms.

In one embodiment, $X_{B2}$ and $X_{B3}$ in the formula (1) are fused with a substituted or unsubstituted hydrocarbon ring including 5 to 30, preferably 5 to 20, more preferably 5 to 10 ring carbon atoms, or a substituted or unsubstituted heterocyclic ring including 5 to 30, preferably 5 to 20, more preferably 5 to 10 ring atoms.

In one embodiment, the ring fused with the ring $X_B$ in the formula (1) includes a partial structure represented by any one of the following formulas (b1) to (b3).

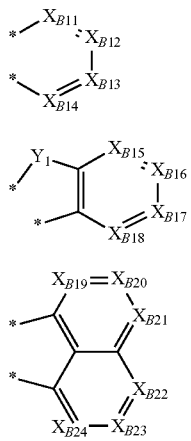

In the formulas (b1) to (b3), two *'s are respectively bonded with one set of $X_{B1}$ and $X_{B2}$, $X_{B2}$ and $X_{B3}$, and $X_{B3}$ and $X_{B4}$ in the formula (1).

$Y_1$ is
O,
S,
NH,
$N(R_a)$, or
$C(R_a)_2$.

$X_{B11}$ to $X_{B24}$ are independently
CH,
$C(R_a)$, or
N.

$R_a$ is a substituent.

When a plurality of $R_a$'s are present, the plurality of $R_a$'s may be the same as or different from each other.

Adjacent two or more $R_a$'s form a substituted or unsubstituted, saturated or unsaturated ring by bonding with each other, or do not form the ring.

In one embodiment, one set of $X_{B1}$ and $X_{B2}$, $X_{B2}$ and $X_{B3}$, and $X_{B3}$ and $X_{B4}$ in the formula (1) is fused with the partial structure represented by any one of the formulas (b1) to (b3).

In one embodiment, the partial structure represented by the formula (b2) is a partial structure represented by any one of the following formulas (b2-1) to (b2-5).

In the formulas (b2-1) to (b2-5), *, $X_{B15}$ to $X_{B18}$, and $R_a$ are as defined in the formula (b2).

$X_{B25}$ and $X_{B26}$ are independently
CH,
$C(R_a)$, or
N.

In one embodiment, one set of $X_{B1}$ and $X_{B2}$, $X_{B2}$ and $X_{B3}$, and $X_{B3}$ and $X_{B4}$ in the formula (1) is fused with the partial structure represented by any one of the formulas (b2-1) to (b2-5).

In one embodiment, the partial structure represented by the formula (b2-5) is a partial structure represented by any one of the following formulas (b2-5-1) to (b2-5-4).

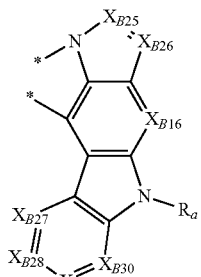
(b2-5-1)

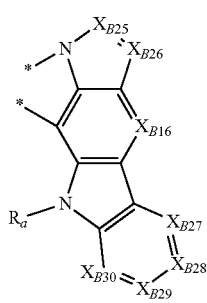
(b2-5-2)

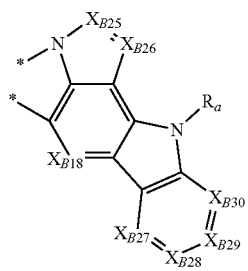
(b2-5-3)

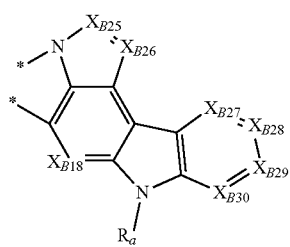
(b2-5-4)

In the formulas (b2-5-1) to (b2-5-4), *, $X_{B16}$, $X_{B18}$, $X_{B25}$, $X_{B26}$, and $R_a$ are as defined in the formula (b2-5); and $X_{B27}$ to $X_{B30}$ are independently
CH,
C($R_a$), or
N.

In one embodiment, one set of $X_{B1}$ and $X_{B2}$, $X_{B2}$ and $X_{B3}$, and $X_{B3}$ and $X_{B4}$ in the formula (1) is fused with the partial structure represented by any one of the formulas (b2-5-1) to (b2-5-4).

In one embodiment, the compound represented by the formula (1) is a compound represented by any one of the following formulas (3B-1) to (3B-3).

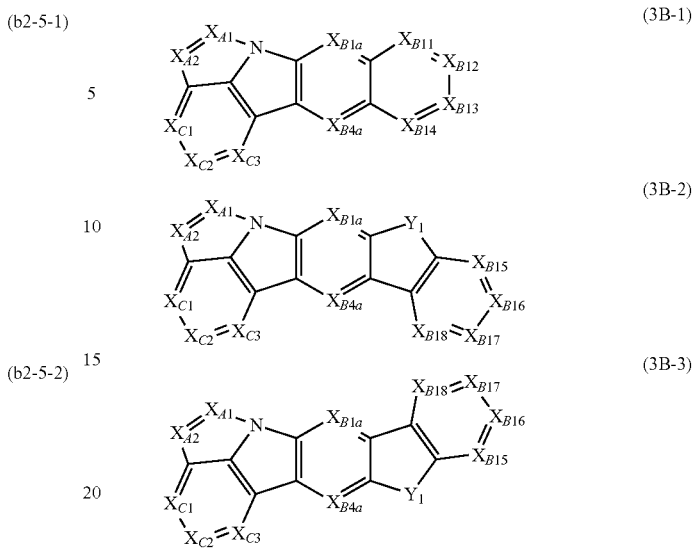
(3B-1)

(3B-2)

(3B-3)

In the formulas (3B-1) to (3B-3), $X_{A1}$, $X_{A2}$, and $X_{C1}$ to $X_{C3}$ are as defined in the formula (1).

$X_{B1a}$ and $X_{B4a}$ are independently
CH,
C($R_a$), or
N.

$Y_1$ is
O,
S,
NH,
N($R_a$),
$CH_2$,
CH($R_a$), or
C($R_a$)$_2$.

$X_{B11}$ to $X_{B18}$ are independently
CH,
C($R_a$), or
N.

$R_a$ is a substituent.

When a plurality of $R_a$'s are present, the plurality of $R_a$'s may be the same as or different from each other.

Adjacent two or more $R_a$'s form a substituted or unsubstituted, saturated or unsaturated ring by bonding with each other, or do not form the ring.

In one embodiment, the compound represented by the formula (3B-2) is a compound represented by any one of the following formulas (3B-2-1) to (3B-2-5).

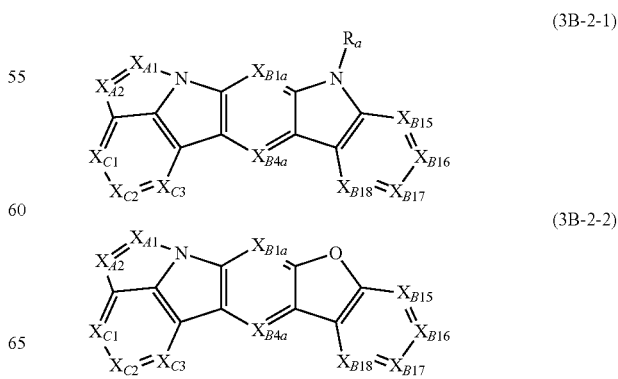
(3B-2-1)

(3B-2-2)

(3B-2-3)

(3B-2-4)

(3B-2-5)

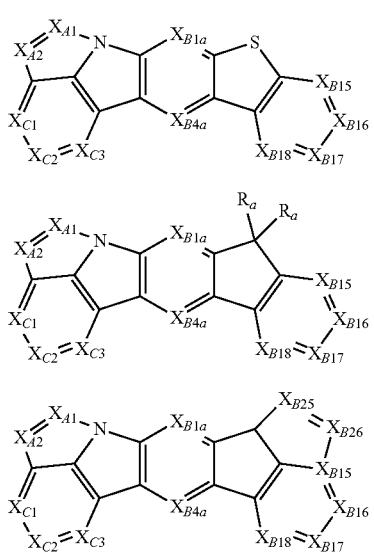

(c1)

(c2)

(c3)

(c4)

In the formulas (3B-2-1) to (3B-2-5), $X_{A1}$, $X_{A2}$, $X_{C1}$ to $X_{C3}$, $X_{B15}$ to $X_{B18}$, $X_{B1a}$, $X_{B4a}$, and $R_a$ are as defined in the formula (3B-2).

$X_{B25}$ and $X_{B2}$ are independently

CH, $C(R_a)$, or

N.

$R_a$ is a substituent.

When a plurality of $R_a$'s are present, the plurality of $R_a$'s may be the same as or different from each other.

Adjacent two or more $R_a$'s form a substituted or unsubstituted, saturated or unsaturated ring by bonding with each other, or do not form the ring.

In one embodiment, the compound represented by the formula (1) is a compound represented by the formula (3B-2-5).

In one embodiment, one set of $X_{C1}$ and $X_{C2}$, and $X_{C2}$ and $X_{C3}$ in the formula (1) is fused with a substituted or unsubstituted hydrocarbon ring including 5 to 50 ring carbon atoms, or a substituted or unsubstituted heterocyclic ring including 5 to 50 ring atoms.

Here, the "hydrocarbon ring" includes aliphatic hydrocarbon rings and aromatic hydrocarbon rings, and the "heterocyclic ring" includes non-aromatic heterocyclic rings and aromatic heterocyclic rings. Specific examples of the "aliphatic hydrocarbon ring" and the "non-aromatic heterocyclic ring" are as defined above. Specific examples of the "aromatic hydrocarbon ring" and "aromatic heterocyclic ring" are as described in [Definitions] above.

In one embodiment, one set of $X_{C1}$ and $X_{C2}$, and $X_{C2}$ and $X_{C3}$ in the formula (1) is fused with a substituted or unsubstituted hydrocarbon ring including 5 to 30, preferably 5 to 20, more preferably 5 to 10 ring carbon atoms, or a substituted or unsubstituted heterocyclic ring including 5 to 30, preferably 5 to 20, more preferably 5 to 10 ring atoms.

In one embodiment, the ring fused with one set of $X_{C1}$ and $X_{C2}$, and $X_{C2}$ and $X_{C3}$ in the formula (1) includes a partial structure represented by any one of the following formulas (c1) to (c4).

In the formulas (c1) to (c4), two *'s are respectively bonded with one set of $X_{C1}$ and $X_{C2}$, and $X_{C2}$ and $X_{C3}$ in the formula (1).

$Y_2$ is

O,

S,

NH, $N(R_a)$, or $C(R_a)_2$.

$X_{C11}$ to $X_{C18}$ and $X_{C24}$ to $X_{C26}$ are independently

CH, $C(R_a)$, or

N.

$X_{C21}$ is $CH_2$, $CH(R_a)$, $C(R_a)_2$,

NH, or $N(R_a)$.

$X_{C22}$ and $X_{C23}$ are independently

CH, $C(R_a)$,

N,

NH, or $N(R_a)$.

$R_a$ is a substituent.

When a plurality of $R_a$'s are present, the plurality of $R_a$'s may be the same as or different from each other.

Adjacent two or more $R_a$'s form a substituted or unsubstituted, saturated or unsaturated ring by bonding with each other, or do not form the ring.

In one embodiment, the ring fused with one set of $X_{C1}$ and $X_{C2}$, and $X_{C2}$ and $X_{C3}$ in the formula (1) includes a partial structure represented by the formula (c2).

In one embodiment, the ring fused with $X_{C2}$ and $X_{C3}$ in the formula (1) includes a partial structure represented by the formula (c2).

In one embodiment, the partial structure represented by the formula (c2) is a partial structure represented by any one of the following formulas (c2-1) to (c2-4).

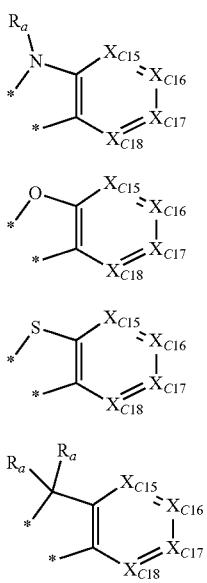

(c2-1)

(c2-2)

(c2-3)

(c2-4)

In the formulas (c2-1) to (c2-4), *, $X_{C15}$ to $X_{C18}$, and $R_a$ are as defined in the formula (c2).

In one embodiment, the partial structure represented by the formula (c2) is a partial structure represented by the formula (c2-1).

In one embodiment, the ring fused with $X_{C2}$ and $X_{C3}$ in the formula (1) includes a partial structure represented by the formula (c2-1).

In one embodiment, the compound represented by the formula (1) is a compound represented by any one of the following formulas (4C-1) to (4C-5).

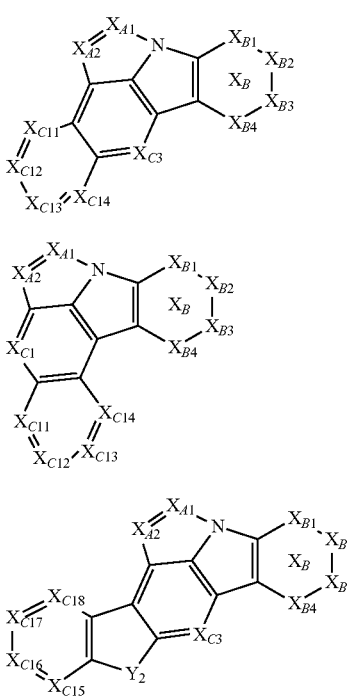

(4C-1)

(4C-2)

(4C-3)

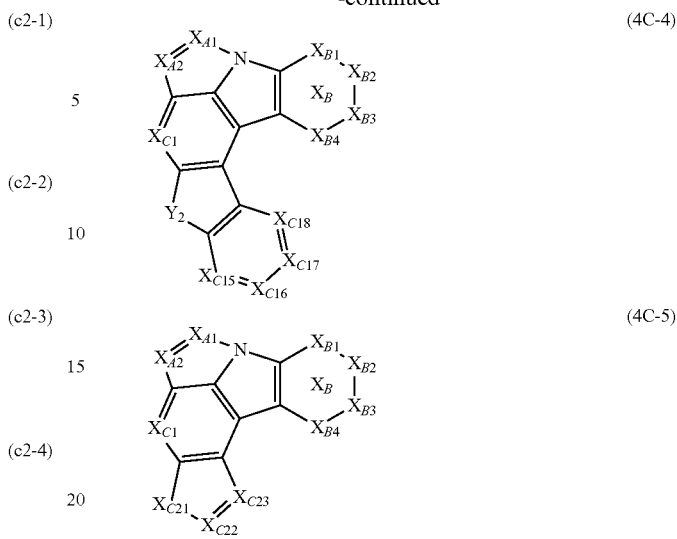

(4C-4)

(4C-5)

In the formulas (4C-1) to (4C-5), $X_{A1}$, $X_{A2}$, the ring $X_B$, $X_{B1}$ to $X_{B4}$, $X_{C1}$, and $X_{C3}$ are as defined in the formula (1).

$Y_2$ is

O,

S,

NH, $N(R_a)$, $CH_2$, $CH(R_a)$, or $C(R_a)_2$.

$X_{C11}$ to $X_{C18}$ and $X_{C21}$ to $X_{C23}$ are independently

CH, $C(R_a)$, or

N.

$R_a$ is a substituent.

When a plurality of $R_a$'s are present, the plurality of $R_a$'s may be the same as or different from each other.

Adjacent two or more $R_a$'s form a substituted or unsubstituted, saturated or unsaturated ring by bonding with each other, or do not form the ring.

In one embodiment, the compound represented by the formula (1) is the compound represented by the formula (4C-4).

In one embodiment, the compound represented by the formula (4C-4) is a compound represented by any one of the following formulas (4C-4-1) to (4C-4-4).

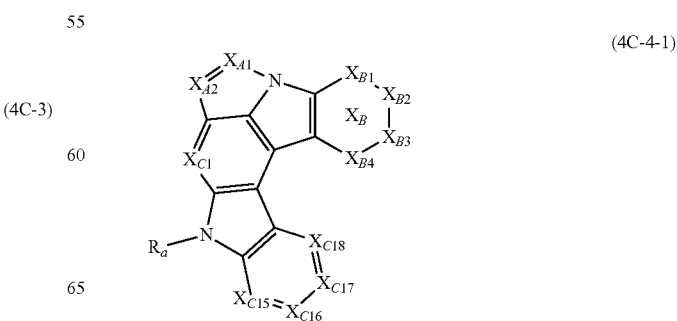

(4C-4-1)

(4C-4-2)

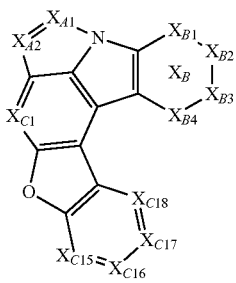

(4C-4-3)

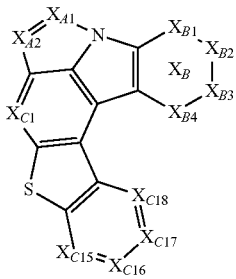

(4C-4-4)

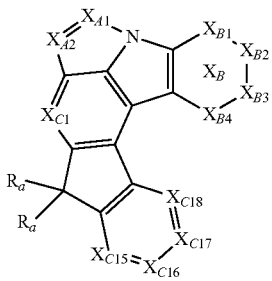

In the formulas (4C-4-1) to (4C-4-4), $X_{A1}$, $X_{A2}$, the ring $X_B$, $X_{B1}$ to $X_{B4}$, $X_{C15}$ to $X_{C18}$, and $X_{C1}$ are as defined in the formula (4C-4).

$R_a$ is a substituent.

When a plurality of $R_a$'s are present, the plurality of $R_a$'s may be the same as or different from each other.

Adjacent two or more $R_a$'s form a substituted or unsubstituted, saturated or unsaturated ring by bonding with each other, or do not form the ring.

In one embodiment, the compound represented by the formula (1) is the compound represented by the formula (4C-4-1).

In one embodiment, the compound represented by the formula (1) is a compound represented by the following formula (1-1).

(1-1)

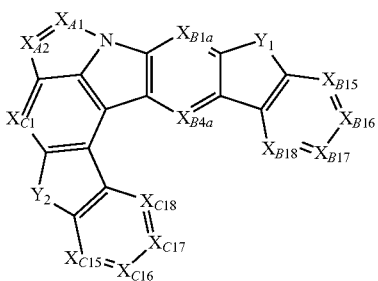

In the formula (1-1), $X_{A1}$, $X_{A2}$, and $X_{C1}$ are as defined in the formula (1).

$X_{B1a}$, $X_{B4a}$, $X_{B15}$ to $X_{B18}$, and $X_{C15}$ to $X_{C18}$ are independently

CH, $C(R_a)$, or

N.

$Y_1$ and $Y_2$ are independently

O,

S,

NH, $N(R_a)$, $CH_2$, $CH(R_a)$, or $C(R_a)_2$.

$R_a$ is a substituent.

When a plurality of $R_a$'s are present, the plurality of $R_a$'s may be the same as or different from each other.

Adjacent two or more $R_a$'s form a substituted or unsubstituted, saturated or unsaturated ring by bonding with each other, or do not form the ring.

In one embodiment, the compound represented by the formula (1-1) is a compound represented by any one of the following formulas (1-1-1) to (1-1-5).

(1-1-1)

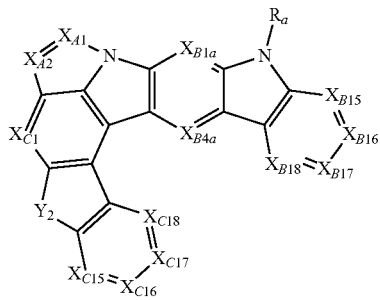

(1-1-2)

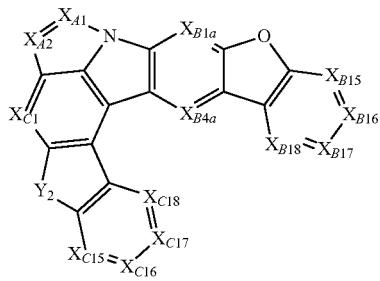

(1-1-3)

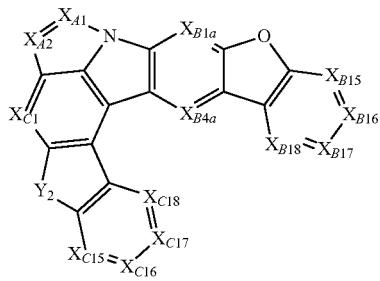

(1-1-4)

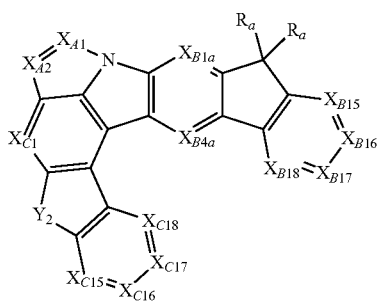

(1-1-5)

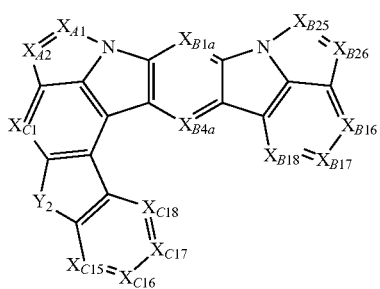

In the formulas (1-1-1) to (1-1-5), $X_{A1}$, $X_{A2}$, $X_{B1a}$, $X_{B4a}$, $X_{B15}$ to $X_{B18}$, $X_{C1}$, $X_{C15}$ to $X_{C18}$, $Y_2$, and $R_a$ are as defined in the formula (1-1).

$X_{B25}$ and $X_{B26}$ are independently
CH,
$C(R_a)$, or
N.

In one embodiment, the compound represented by the formula (1-1) is the compound represented by the formula (1-1-5).

In one embodiment, the compound represented by the formula (1-1-5) is a compound represented by the following formula (1-1-5a).

(1-1-5a)

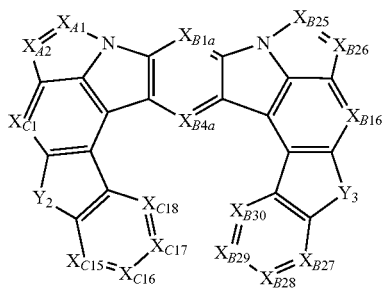

In the formula (1-1-5a), $X_{A1}$, $X_{A2}$, $X_{B1a}$, $X_{B4a}$, $X_{B16}$, $X_{C1}$, $X_{C15}$ to $X_{C18}$, $X_{B25}$, $X_{B26}$, and $Y_2$ are as defined in the formula (1-1-5).

$Y_3$ is
O,
S,
NH,
$N(R_a)$, or
$C(R_a)_2$.

$X_{B27}$ to $X_{B30}$ are independently
CH,
$C(R_a)$, or
N.

$R_a$ is a substituent.
When a plurality of $R_a$'s are present, the plurality of $R_a$'s may be the same as or different from each other.
Adjacent two or more $R_a$'s form a substituted or unsubstituted, saturated or unsaturated ring by bonding with each other, or do not form the ring.

In one embodiment, the substituent $R_a$ in the formula (1) is selected from the group consisting of a halogen atom, a cyano group, a nitro group,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
—S—($R_{905}$),
—N($R_{906}$)($R_{907}$),
a substituted or unsubstituted aryl group including 6 to 50 ring carbon atoms, and
a substituted or unsubstituted monovalent heterocyclic group including 5 to 50 ring atoms.

$R_{901}$ to $R_{907}$ are independently
a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted monovalent heterocyclic group including 5 to 50 ring atoms. When two or more of each of $R_{901}$ to $R_{907}$ are present, the two or more of each of $R_{901}$ to $R_{907}$ may be the same as or different from each other.

In one embodiment, the substituent $R_a$ in the formula (1) is selected from the group consisting of a halogen atom, a cyano group, a nitro group,
a substituted or unsubstituted alkyl group including 1 to 30, preferably 1 to 20, more preferably 1 to 10 carbon atoms,
a substituted or unsubstituted alkenyl group including 2 to 30, preferably 2 to 20, more preferably 2 to 10 carbon atoms,
a substituted or unsubstituted alkynyl group including 2 to 30, preferably 2 to 20, more preferably 2 to 10 carbon atoms,
a substituted or unsubstituted cycloalkyl group including 3 to 30, preferably 3 to 20, more preferably 3 to 10 ring carbon atoms,
—Si($R_{901}$)($R_{902}$)($R_{903}$),
—O—($R_{904}$),
—S—($R_{905}$),
—N($R_{906}$)($R_{907}$),
a substituted or unsubstituted aryl group including 6 to 30, preferably 6 to 20, more preferably 6 to 14 ring carbon atoms, and
a substituted or unsubstituted monovalent heterocyclic group including 5 to 30, preferably 5 to 20, more preferably 5 to 14 ring atoms.

In one embodiment, $R_{901}$ to $R_{907}$ are independently
a hydrogen atom,
a substituted or unsubstituted alkyl group including 1 to 30, preferably 1 to 20, more preferably 1 to 10 carbon atoms,
a substituted or unsubstituted cycloalkyl group including 3 to 30, preferably 3 to 20, more preferably 3 to 10 ring carbon atoms, a substituted or unsubstituted aryl group including 6 to 30, preferably 6 to 20, more preferably 6 to 14 ring carbon atoms, or a substituted or unsubstituted monovalent heterocyclic group including 5 to 30, preferably 5 to 20, more preferably 5 to 14 ring atoms. When two or more of each of $R_{901}$ to $R_{907}$ are present, the two or more of each of $R_{901}$ to $R_{907}$ may be the same as or different from each other.

In one embodiment, the substituent $R_a$ in the formula (1) is selected from the group consisting of a halogen atom, a cyano group, a nitro group, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, and a substituted or unsubstituted monovalent heterocyclic group including 5 to 50 ring atoms.

In one embodiment, the substituent $R_a$ in the formula (1) is selected from the group consisting of a halogen atom, a cyano group, a nitro group, a substituted or unsubstituted alkyl group including 1 to 30, preferably 1 to 20, more preferably 1 to 10 carbon atoms, a substituted or unsubstituted cycloalkyl group including 3 to 30, preferably 3 to 20, more preferably 3 to 10 ring carbon atoms, a substituted or unsubstituted aryl group including 6 to 30, preferably 6 to 20, more preferably 6 to 14 ring carbon atoms, and a substituted or unsubstituted monovalent heterocyclic group including 5 to 30, preferably 5 to 20, more preferably 5 to 14 ring atoms.

In one embodiment, $R_a$ is selected from the group consisting of a halogen atom (a fluorine atom, an iodine atom, etc.), a cyano group, a nitro group, an alkyl group including 1 to 5 carbon atoms (alkyl groups such as a methyl group, an ethyl group, an isopropyl group, a t-butyl group, etc.), a substituted alkyl group including 1 to 5 carbon atoms (fluoroalkyl groups such as a trifluoromethyl group), an aryl group including 6 to 14 ring carbon atoms (a phenyl group, a naphthyl group, a fluorenyl group, an anthryl group, a phenanthryl group, etc.), a monovalent heterocyclic group including 5 to 14 ring atoms, and —Si($R_{901}$)($R_{902}$)($R_{903}$) (such as a trimethylsilyl group, etc.)

In one embodiment, the compound represented by the formula (1) may have a deuterium atom as a hydrogen atom.

The above atoms and groups are as detailed in [Definition] of this specification.

Specific examples of the compound represented by the formula (1) will be described below, but these are merely examples, and the compound represented by the formula (1) is not limited to the following specific examples. In the following specific examples, "D" represents a deuterium atom.

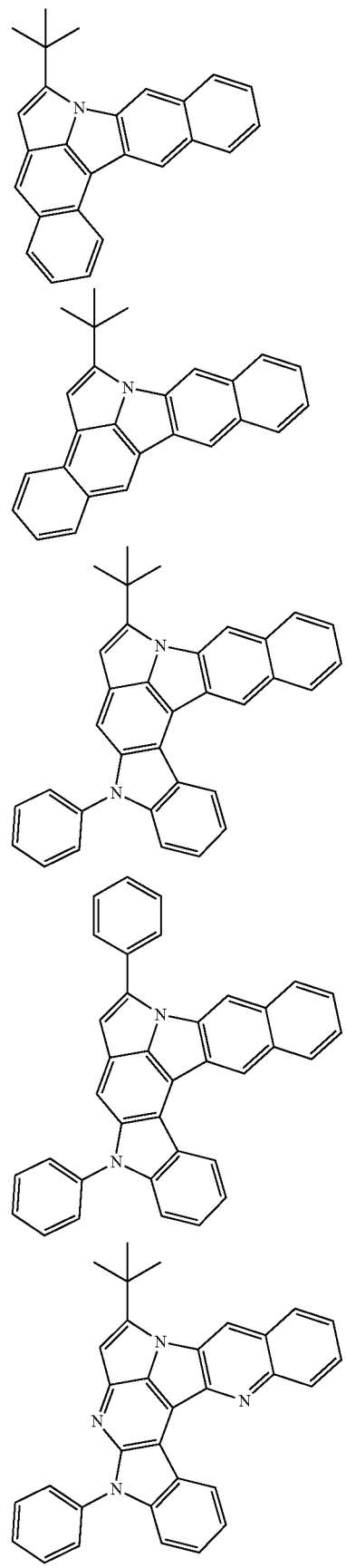

53
-continued
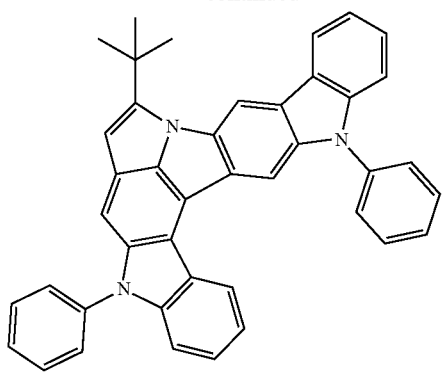
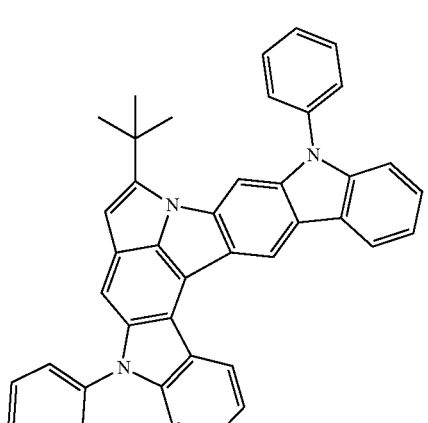
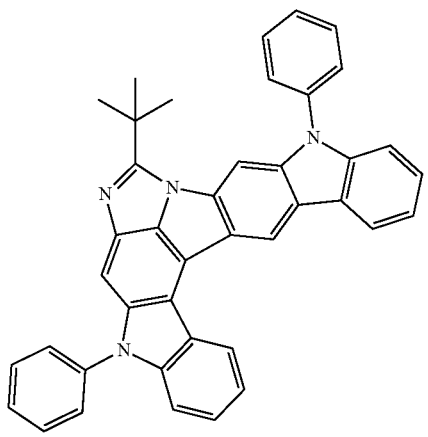
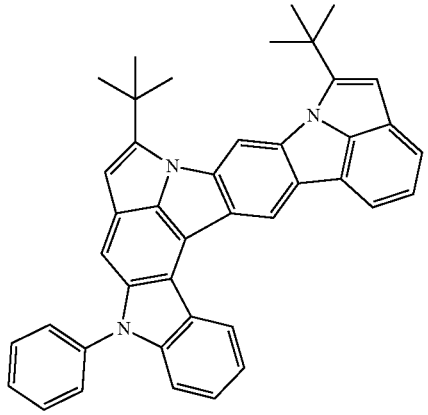
54
-continued
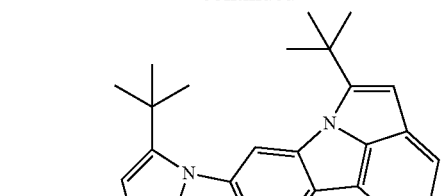
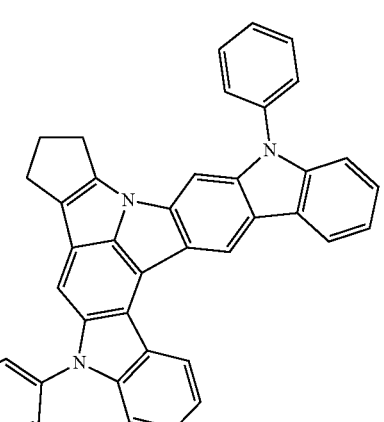
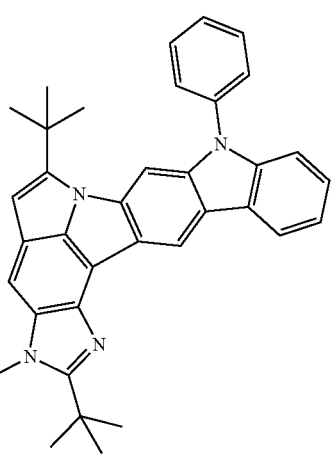
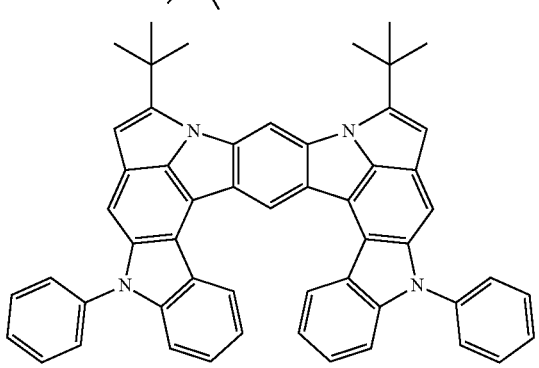

55
-continued
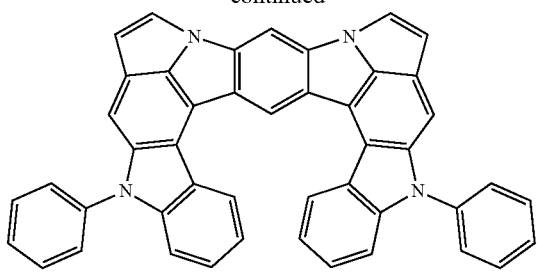
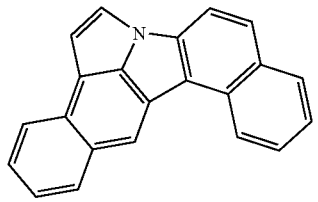
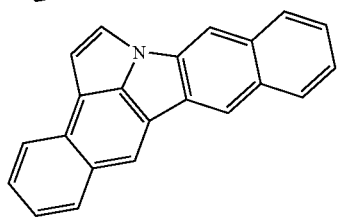
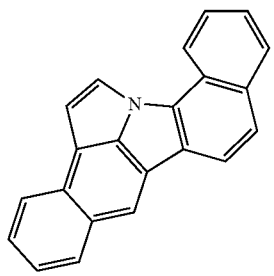
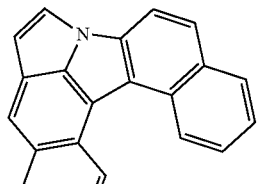
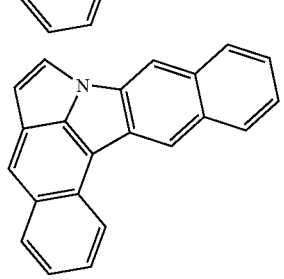
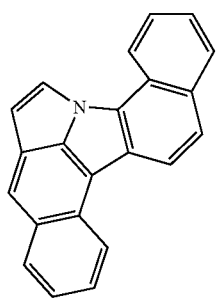
56
-continued
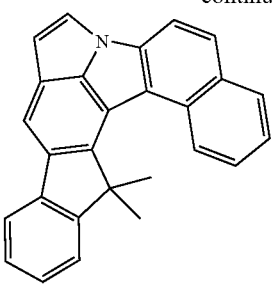
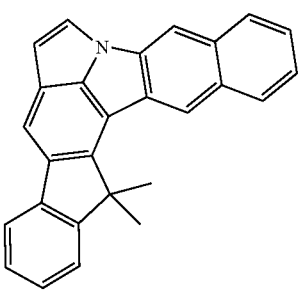
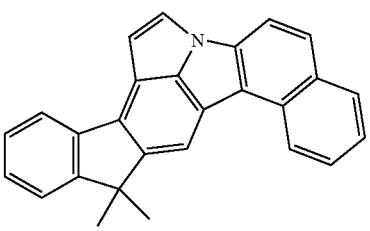
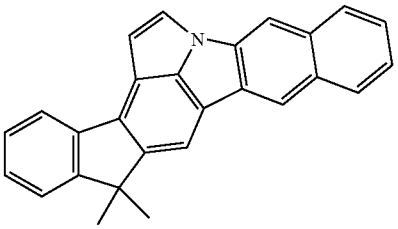
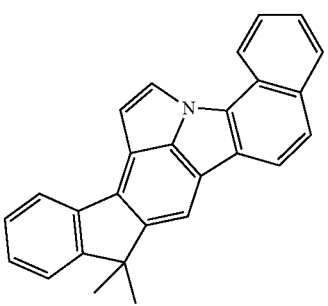
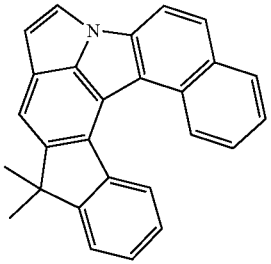

57
-continued
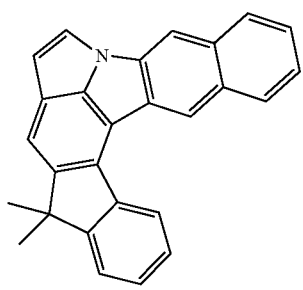
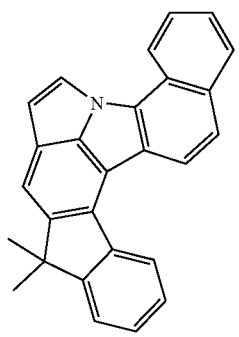
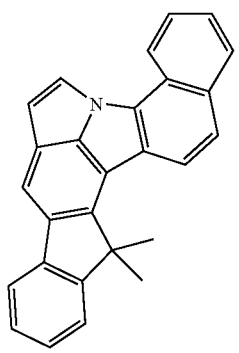
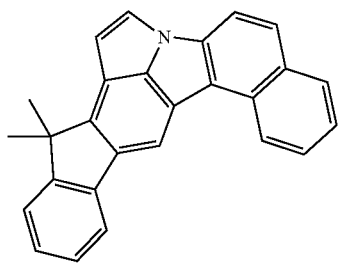
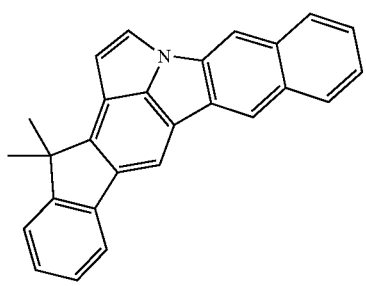
58
-continued
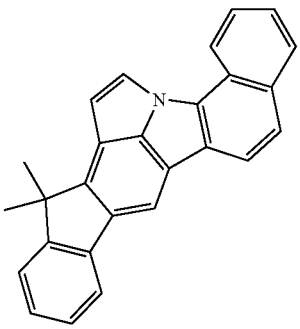
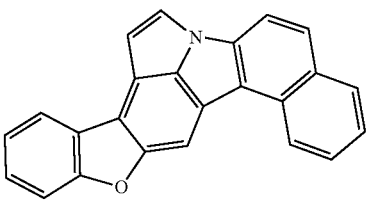
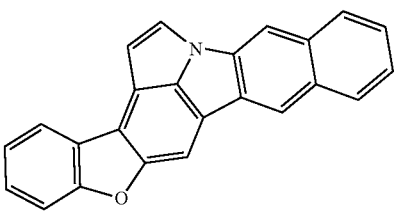
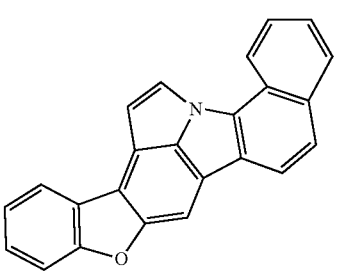
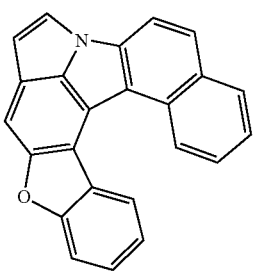
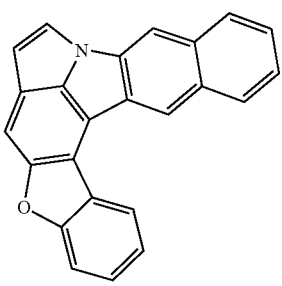

-continued
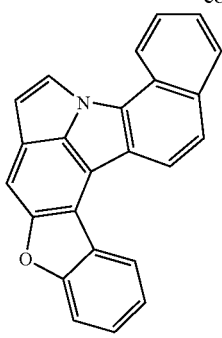
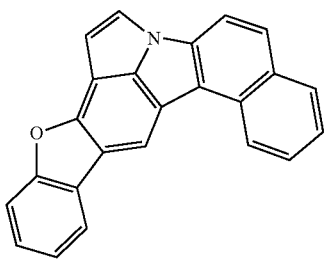
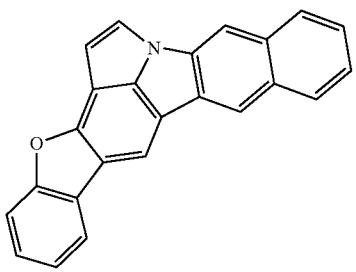
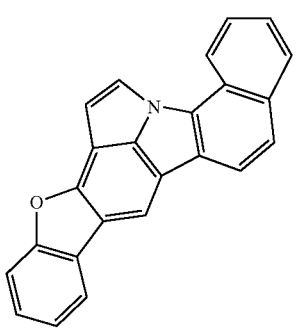
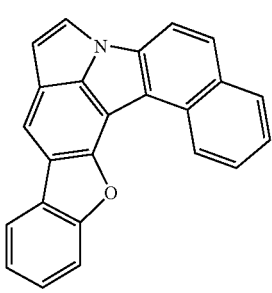
-continued
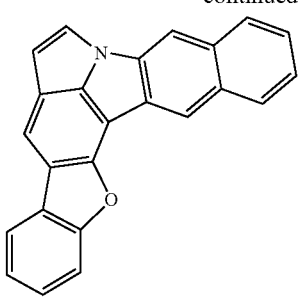
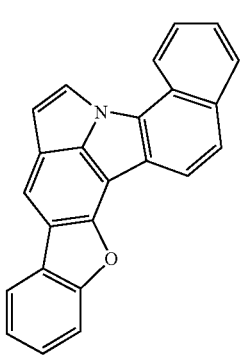
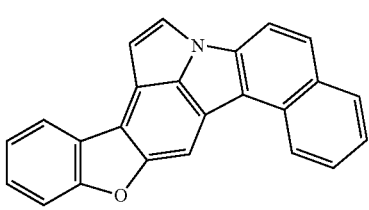
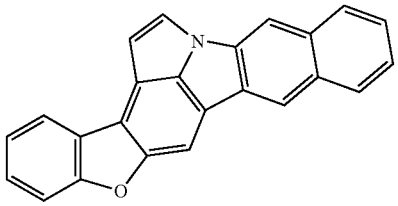
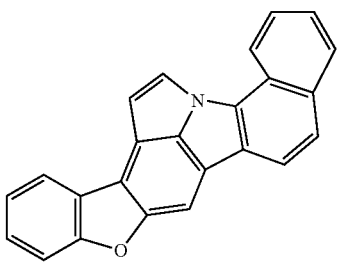
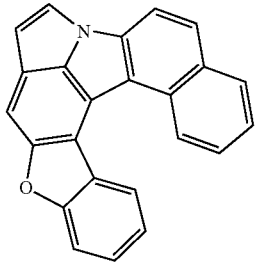

61
-continued
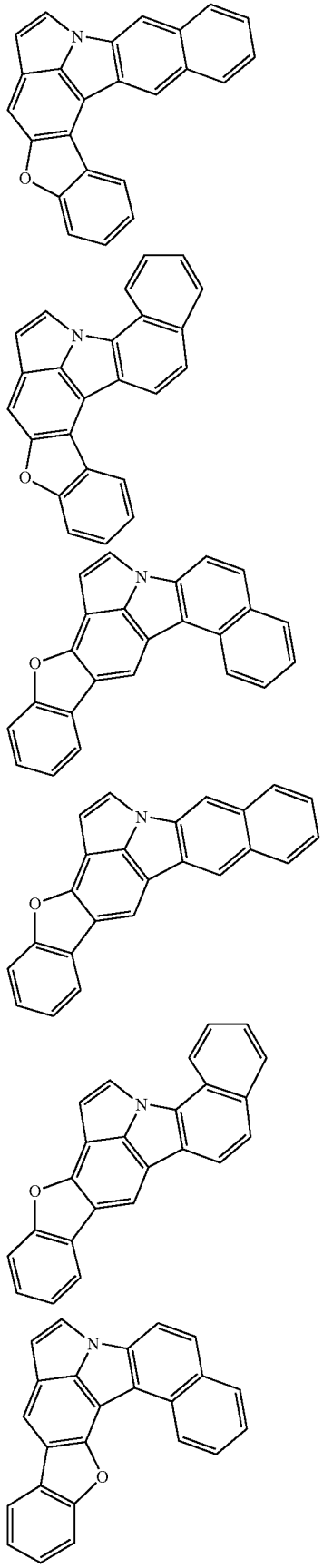
62
-continued
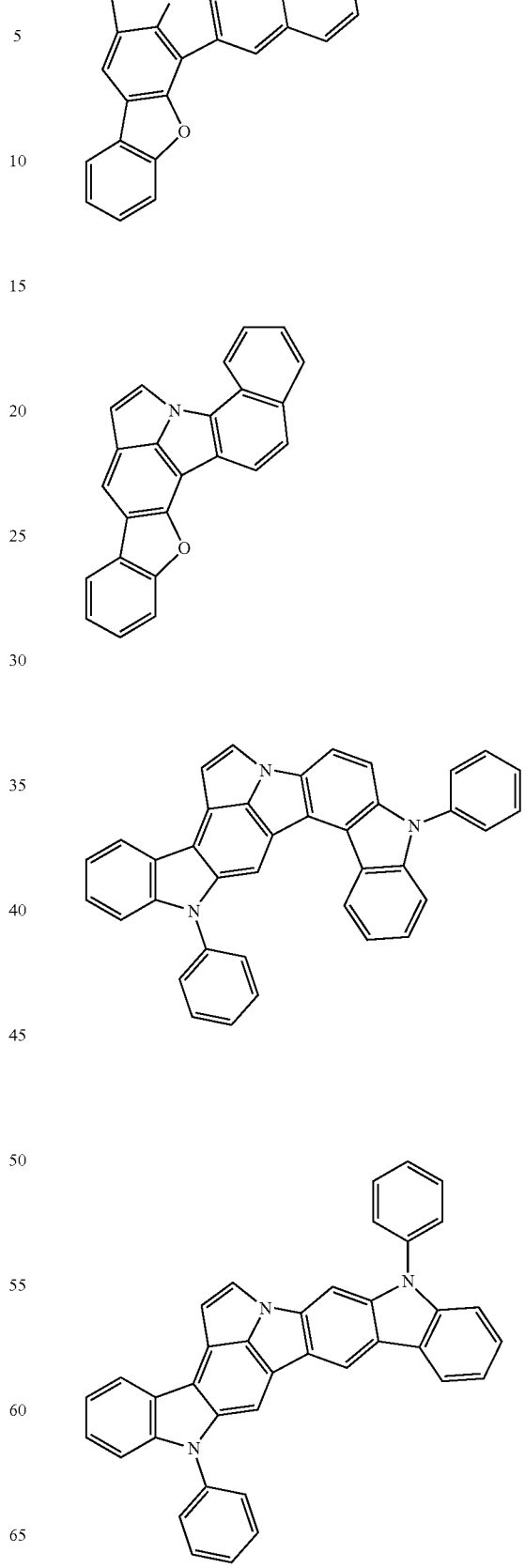

-continued
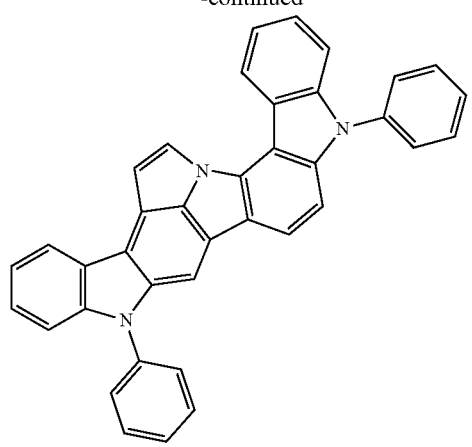
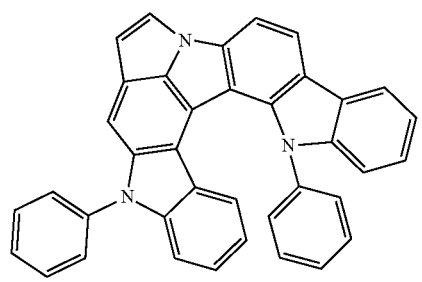
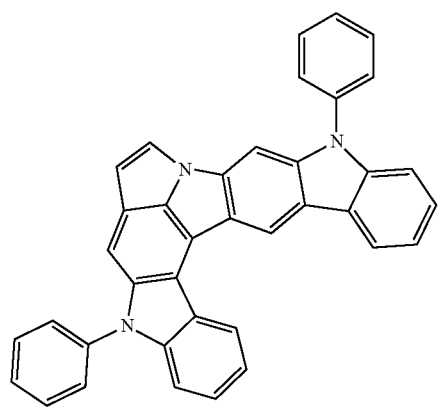
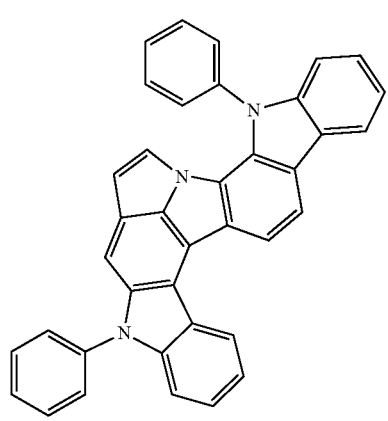
-continued
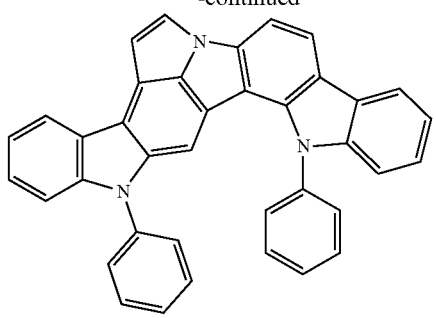
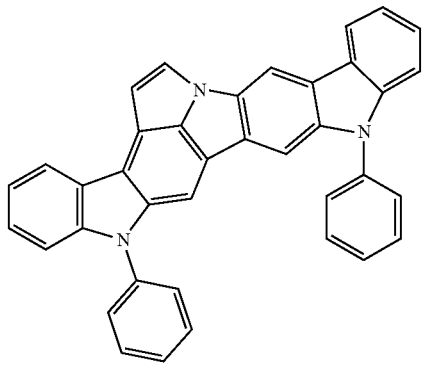
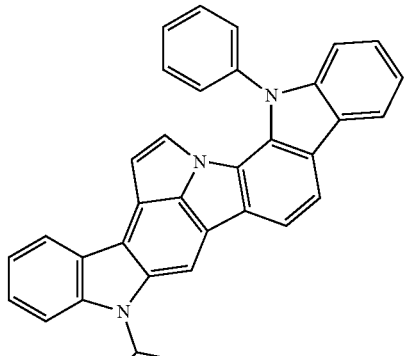
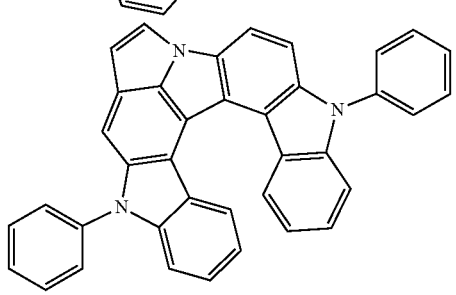
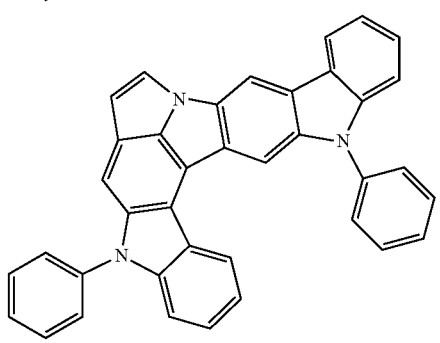

-continued
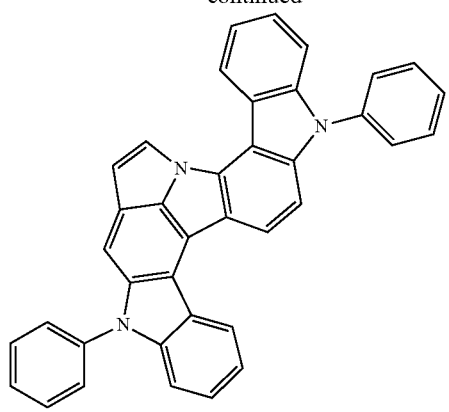
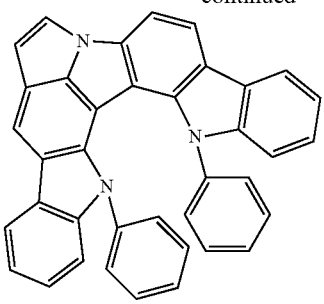
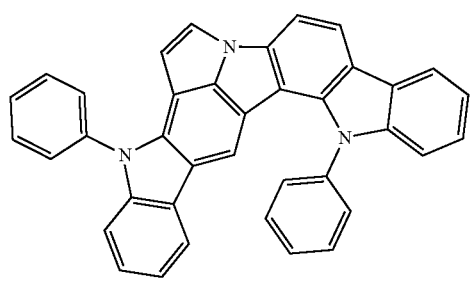
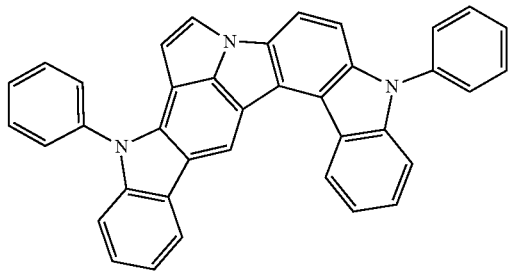
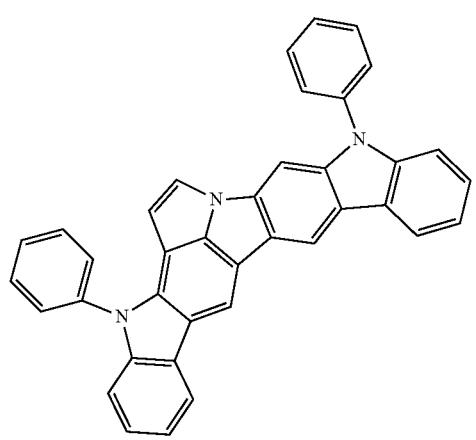
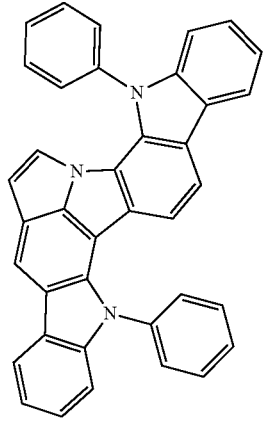
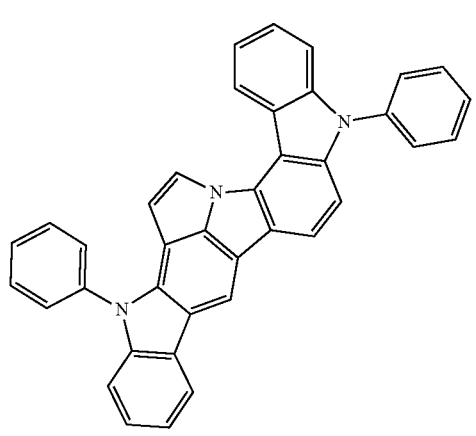
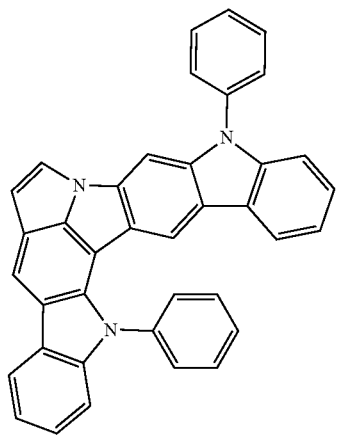

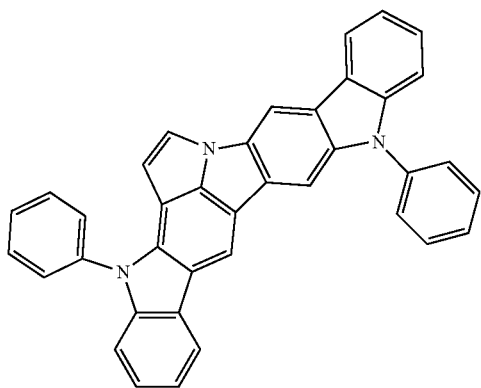
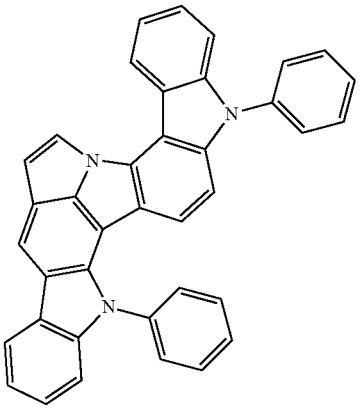
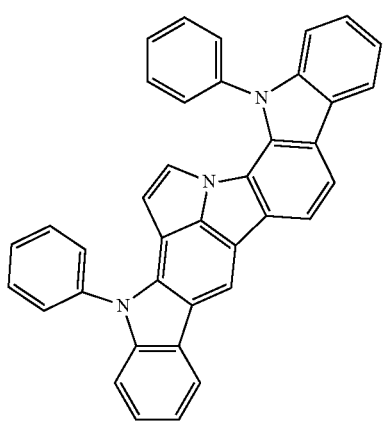
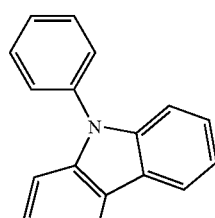
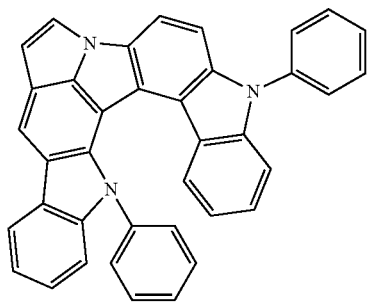
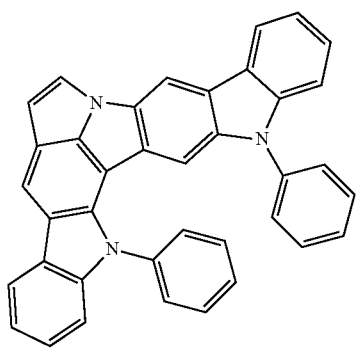
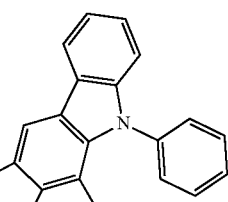

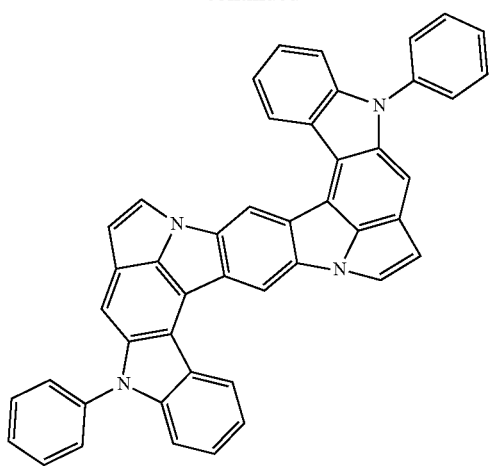
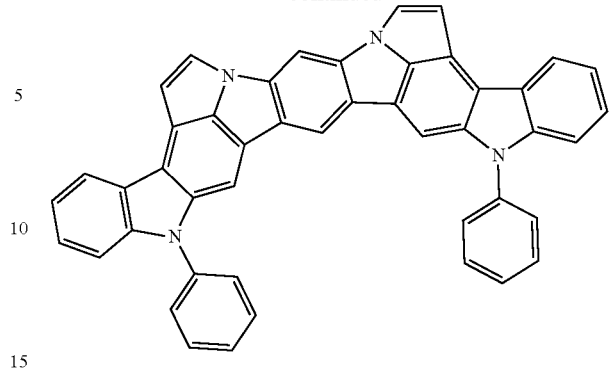
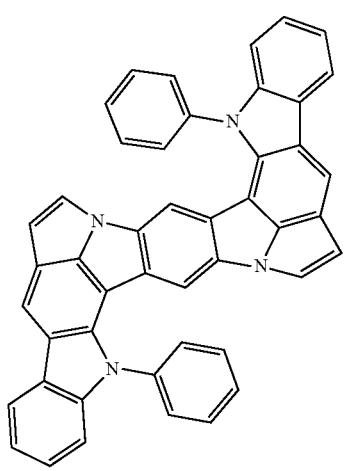
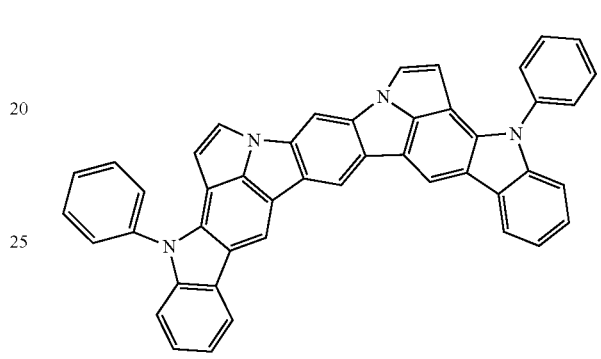
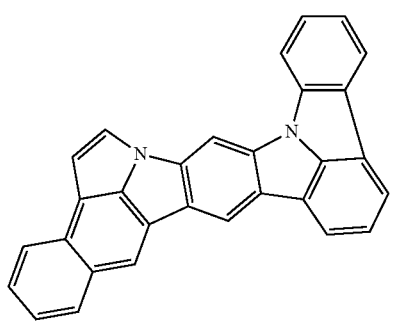
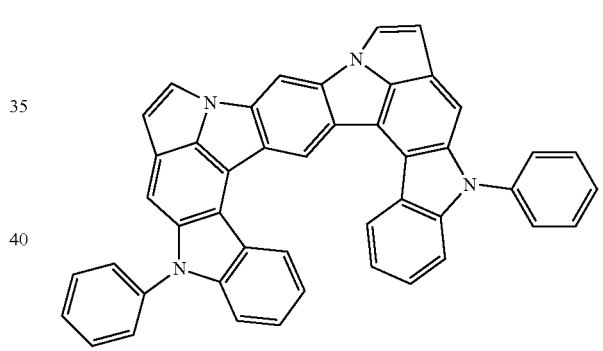
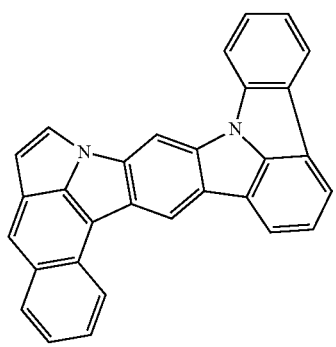
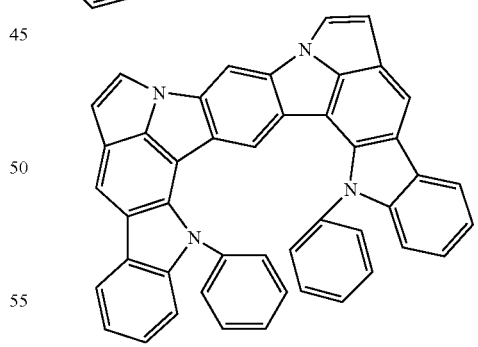
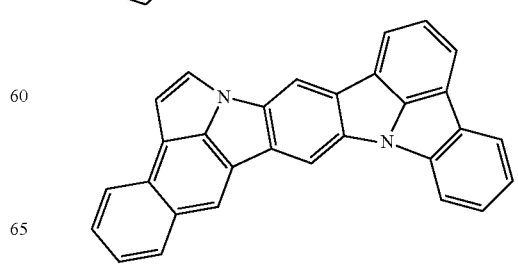

71
-continued
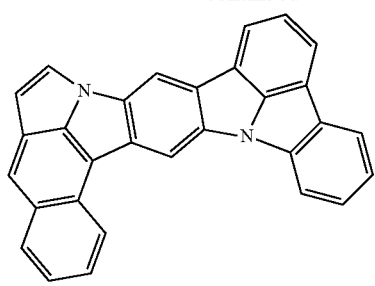
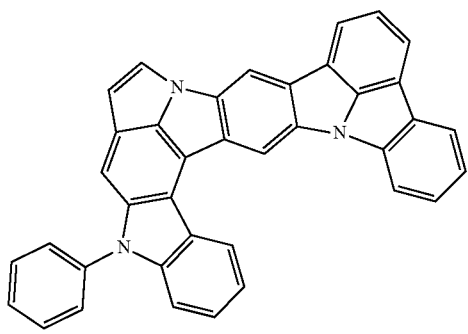
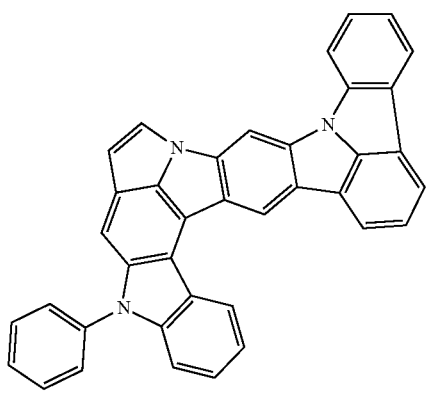
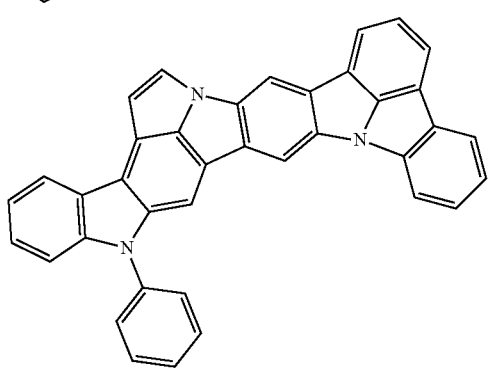
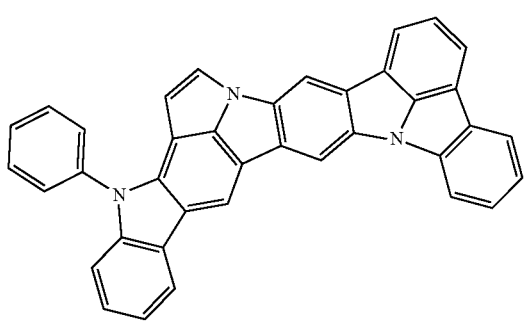
72
-continued
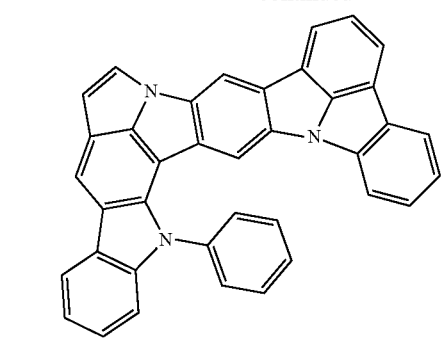
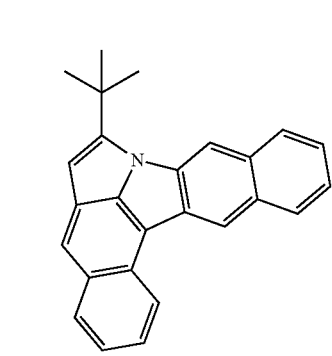
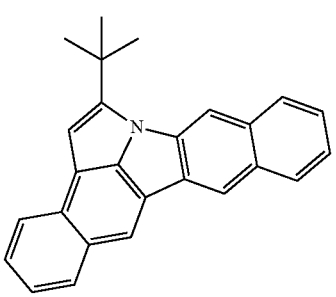
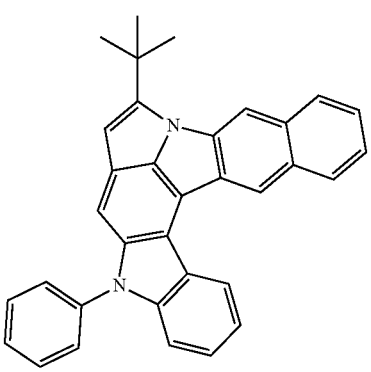
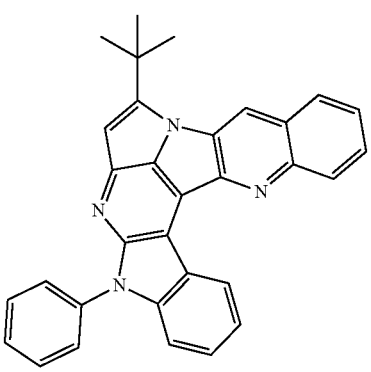

73
-continued
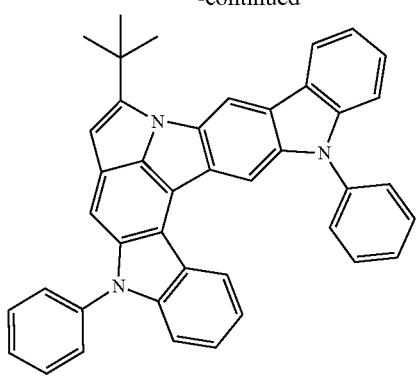
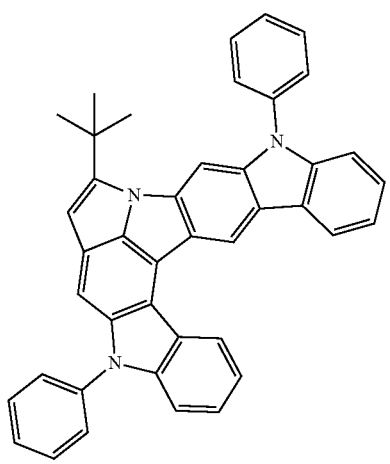
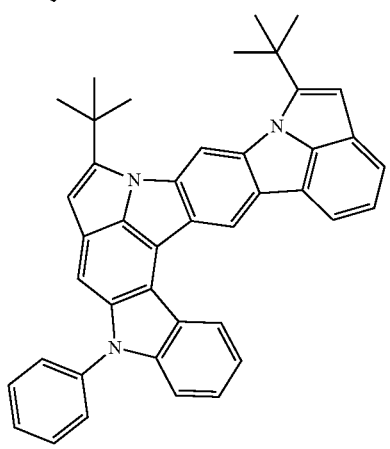
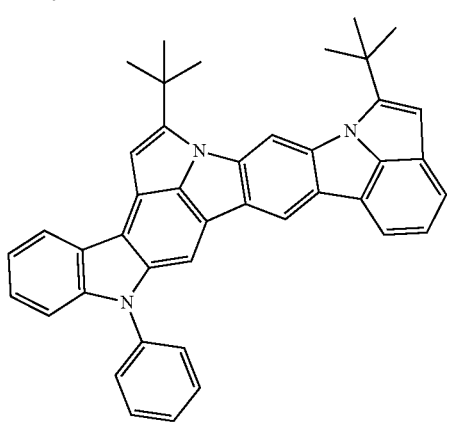
74
-continued
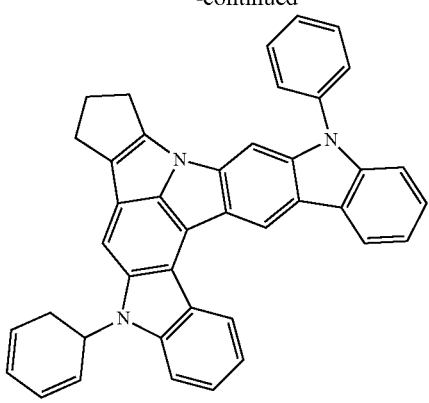
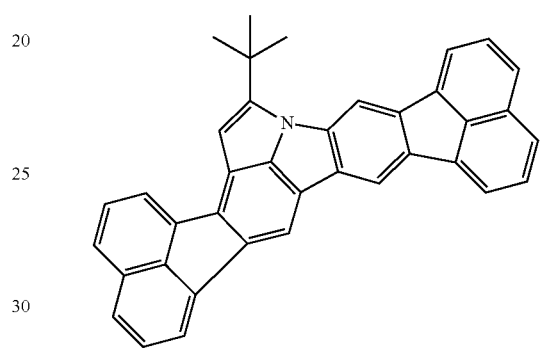
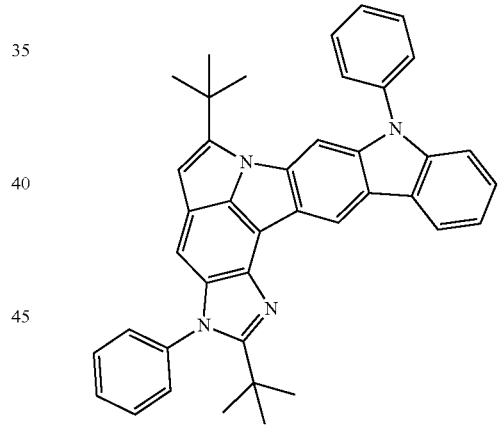
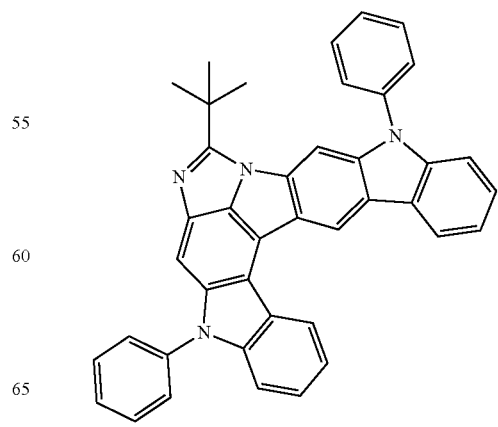

75
-continued
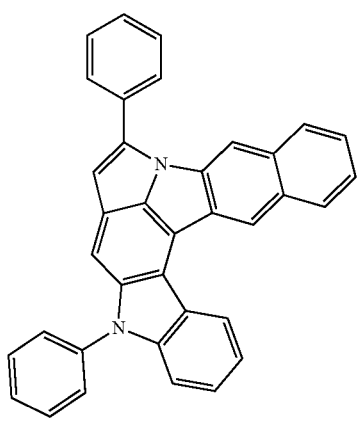
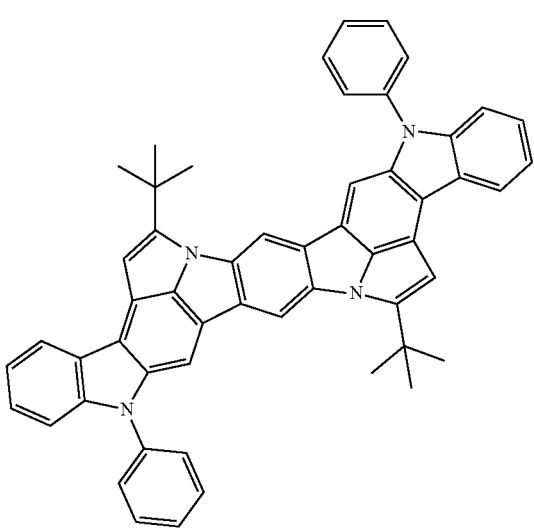
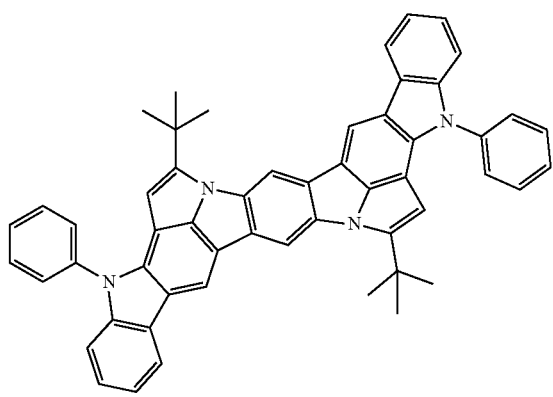
76
-continued
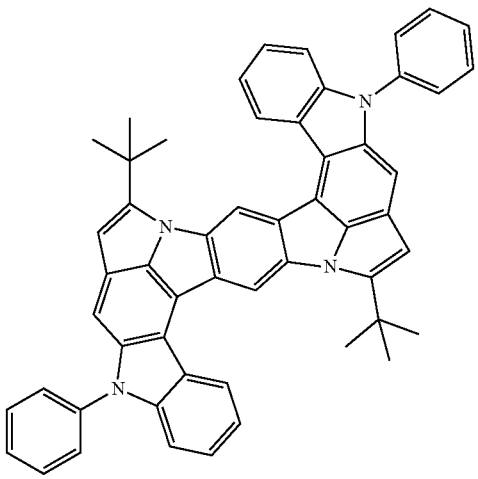
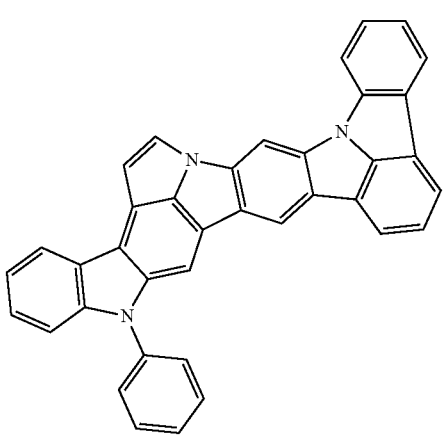

77
-continued
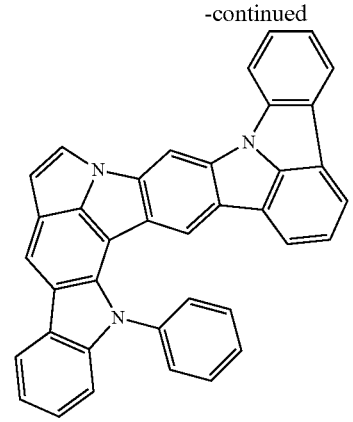
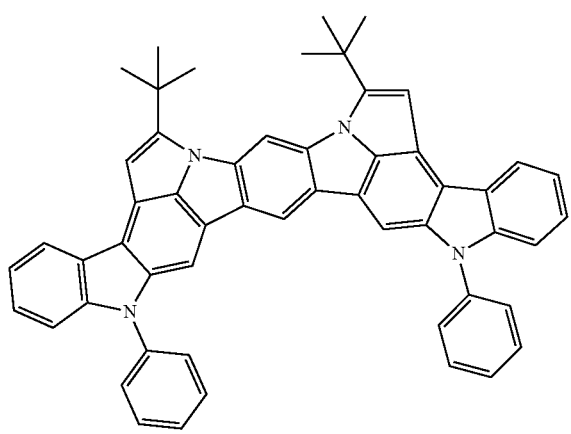
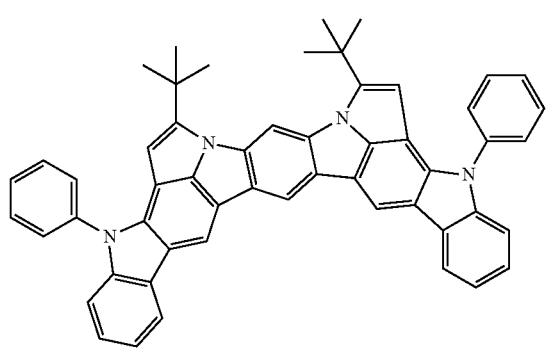
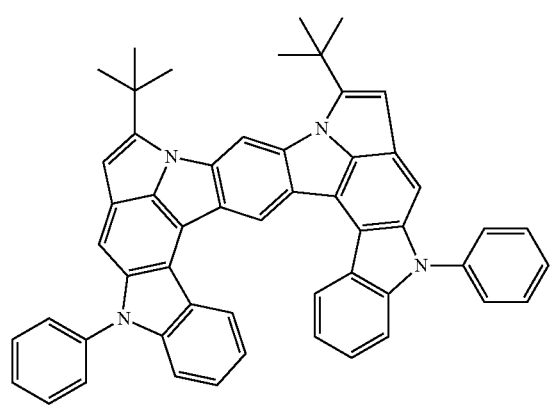
78
-continued
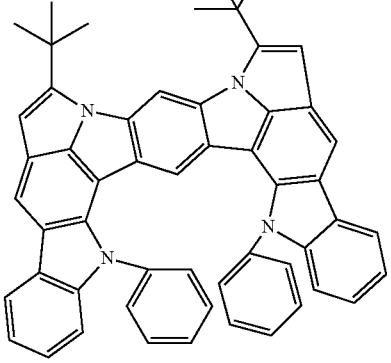
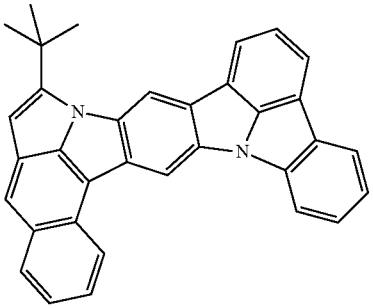
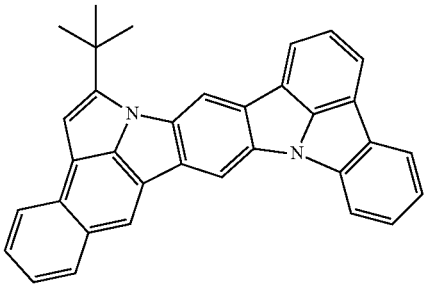
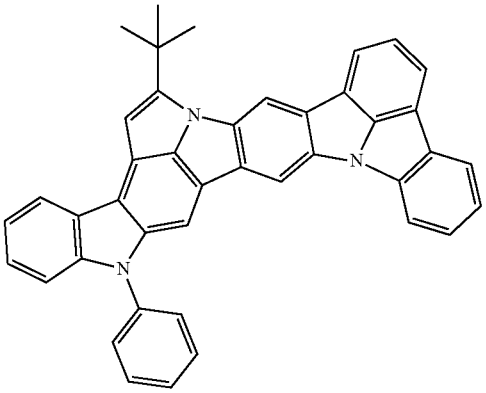
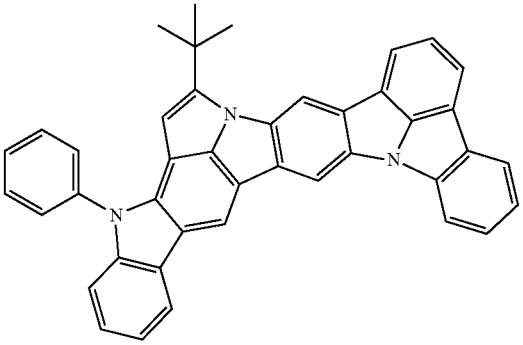

79
-continued
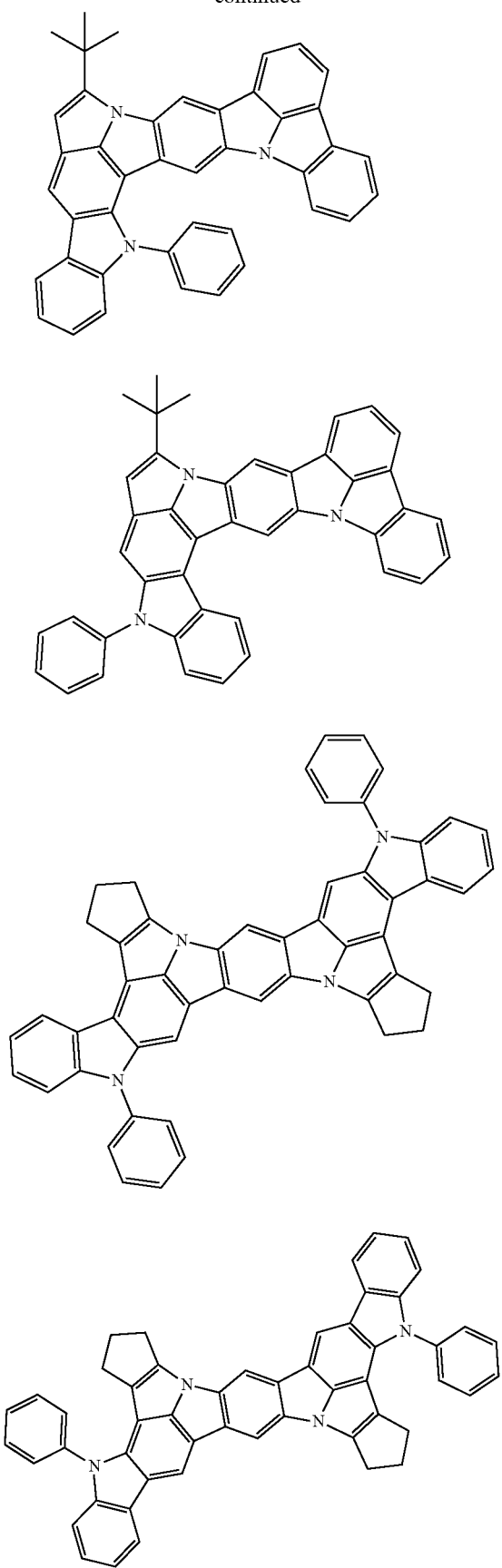
80
-continued
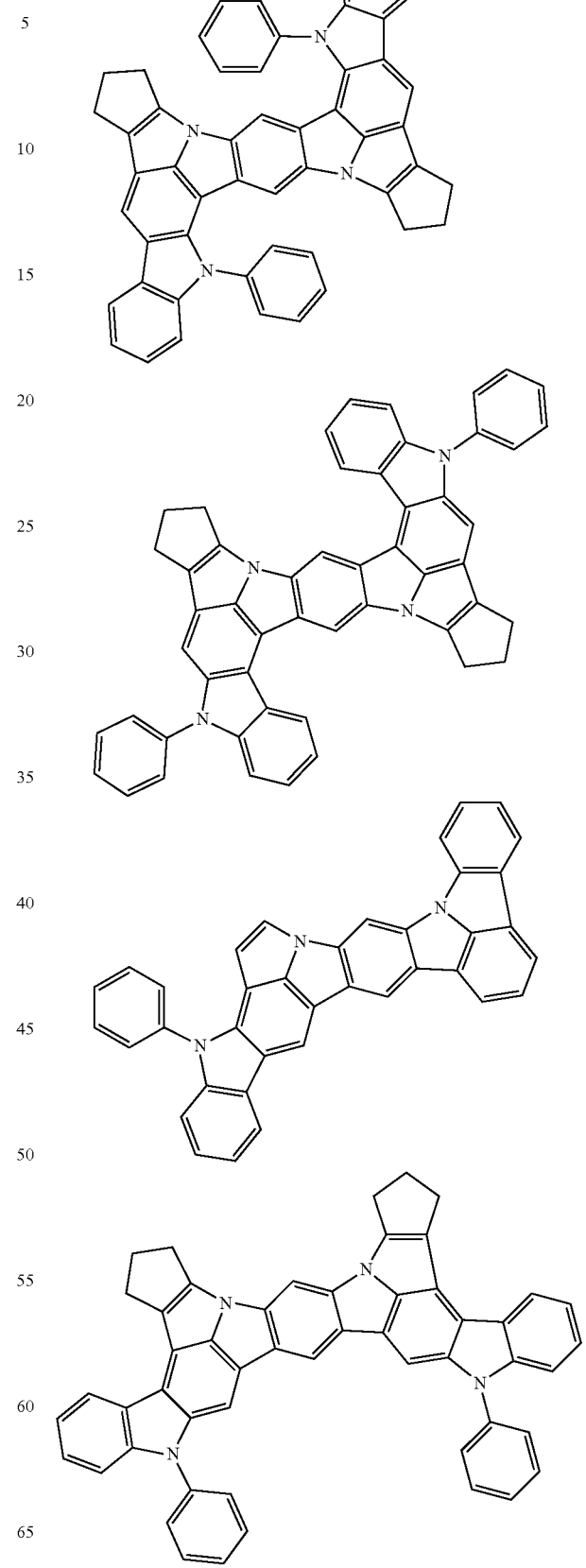

-continued
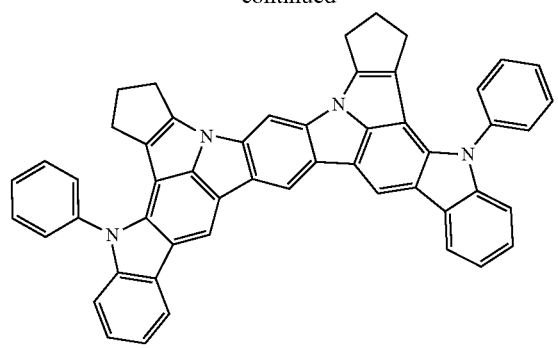
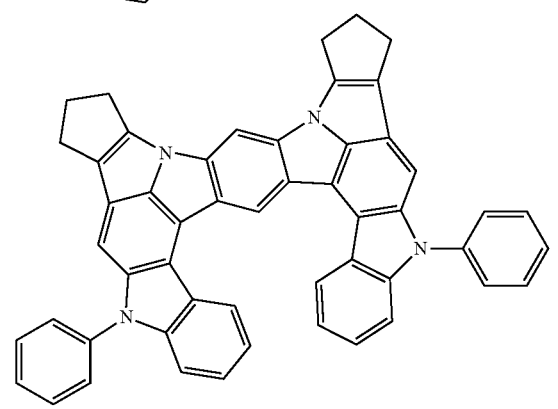
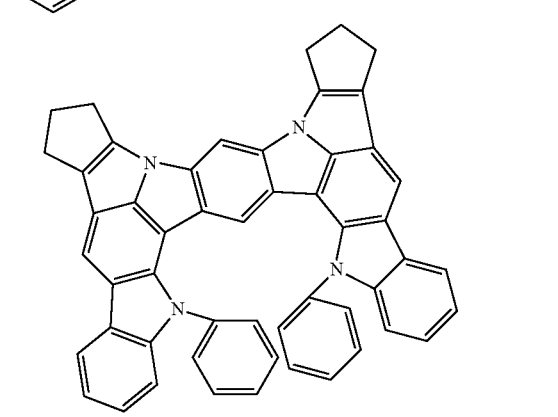
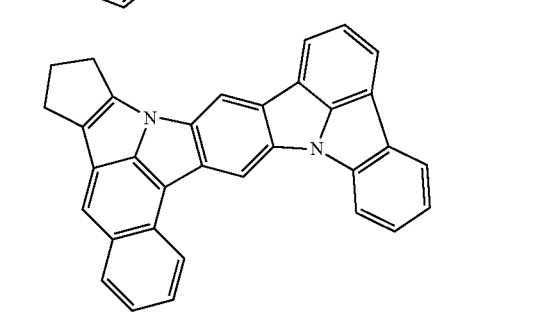
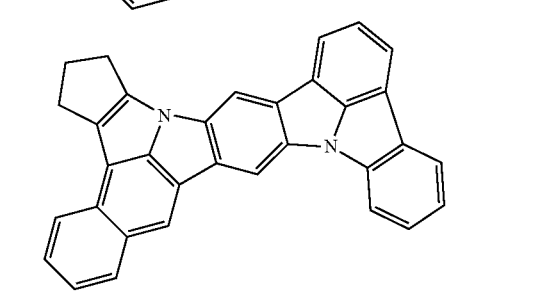
-continued
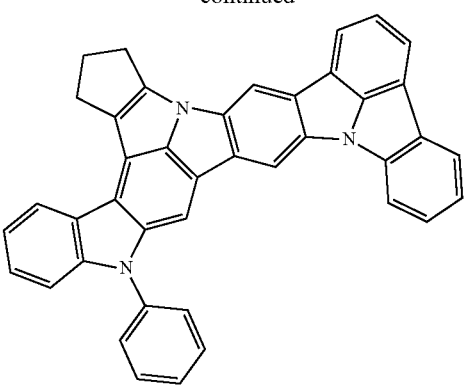
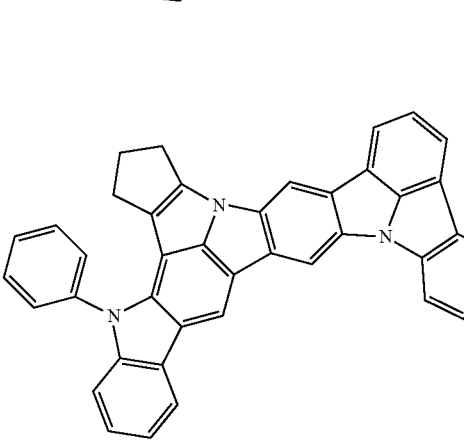
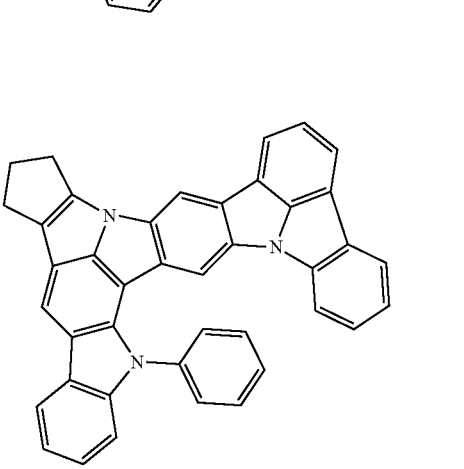
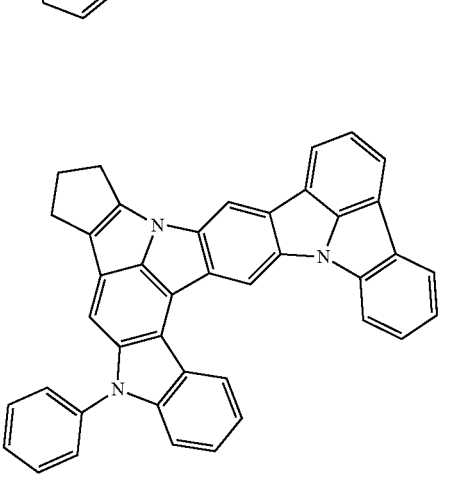

83
-continued
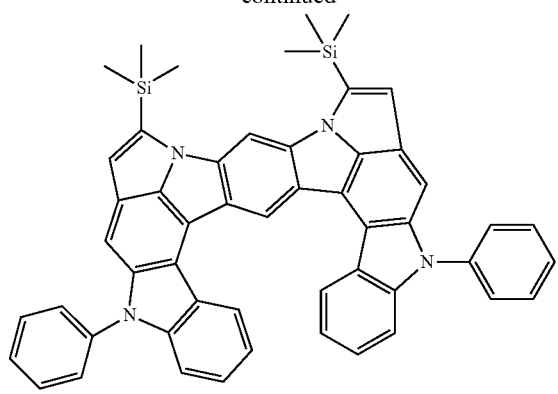
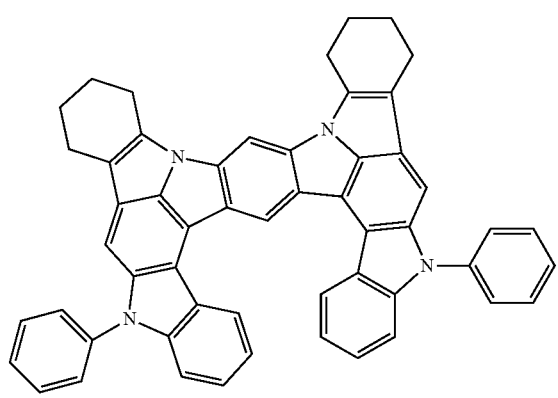
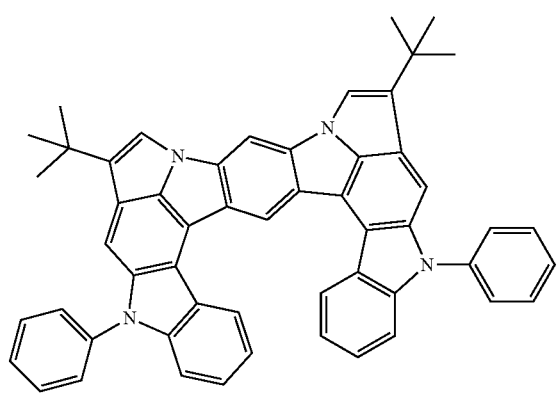
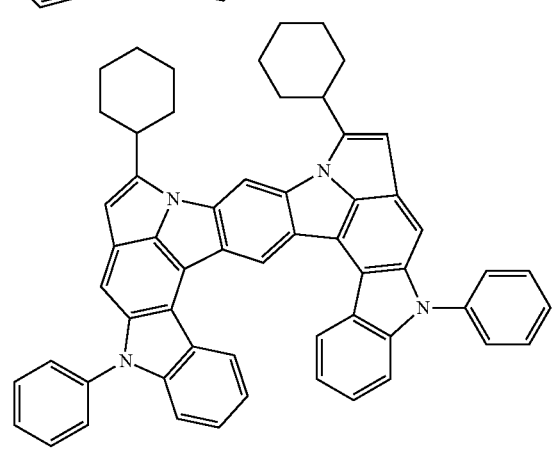
84
-continued
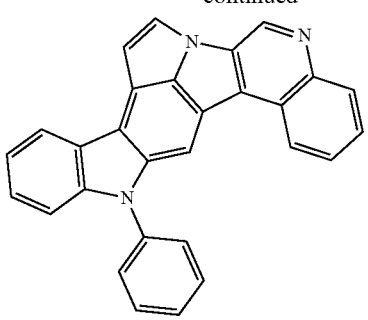
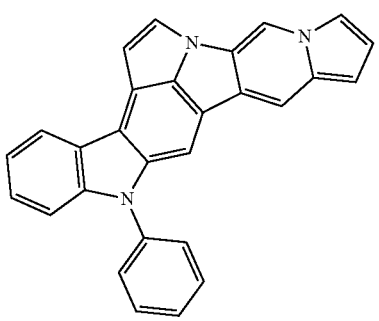
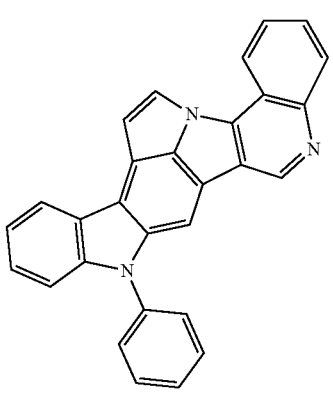
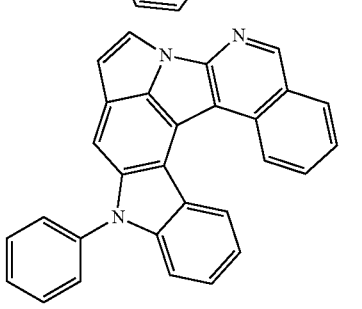
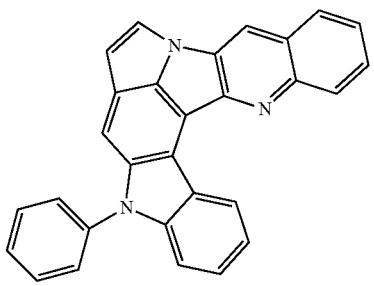

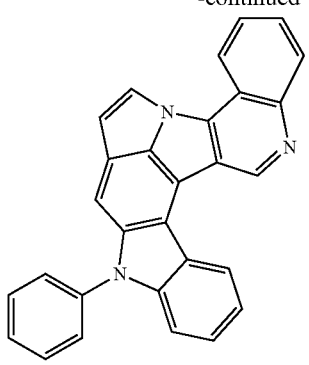
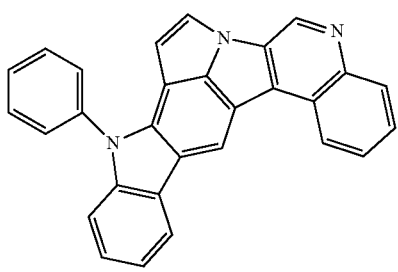
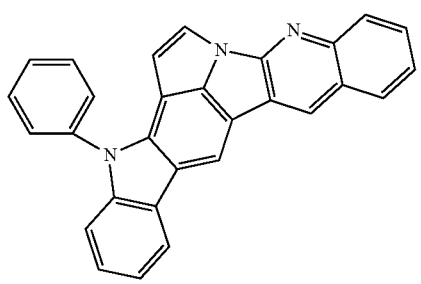
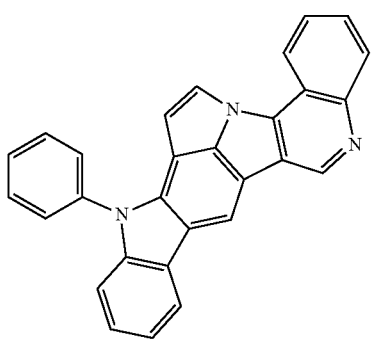
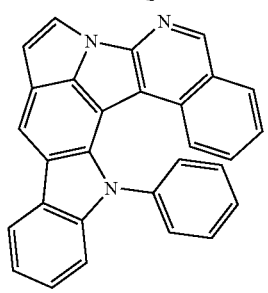
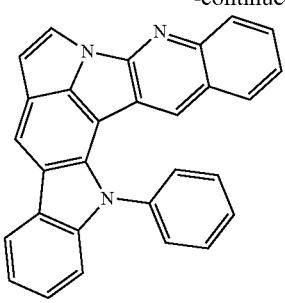
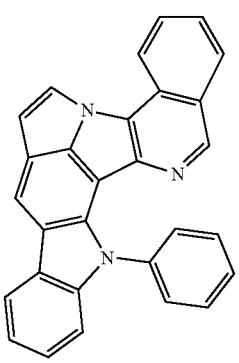
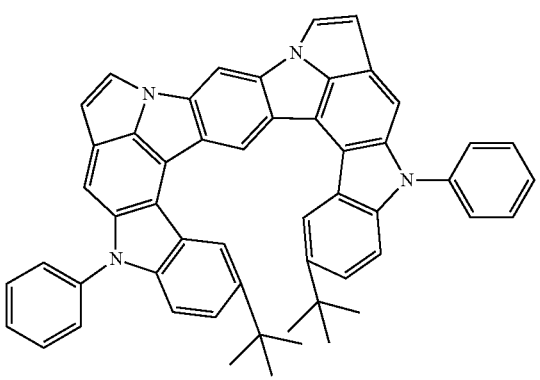
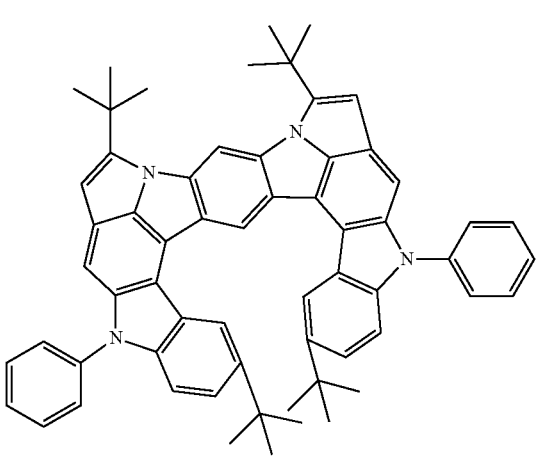

87
-continued
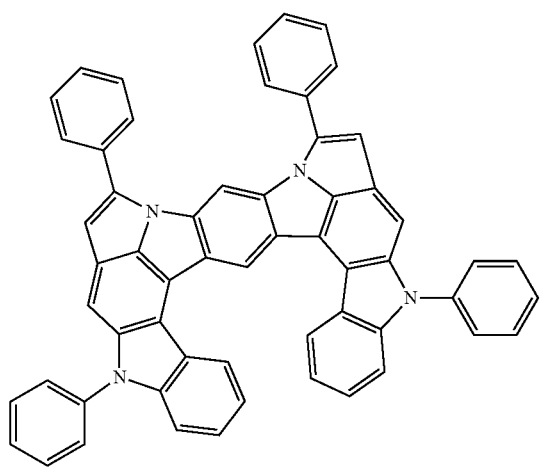
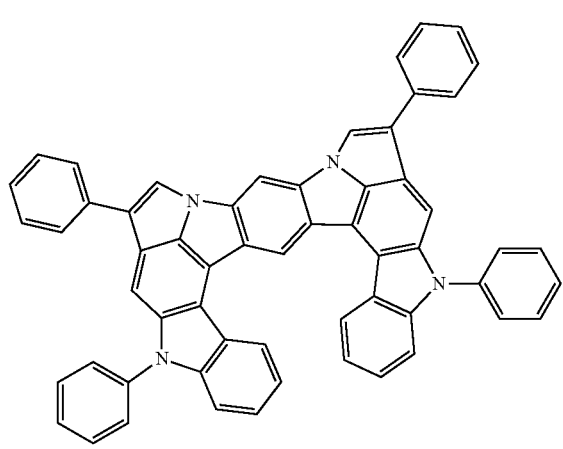
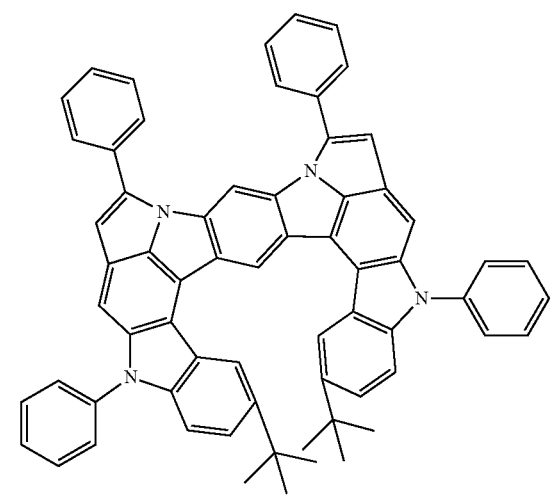
88
-continued
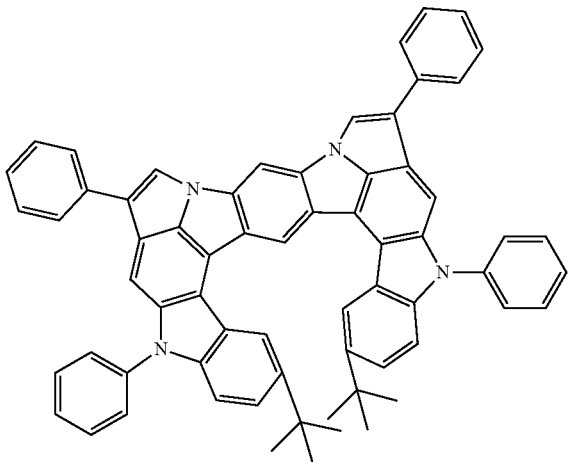
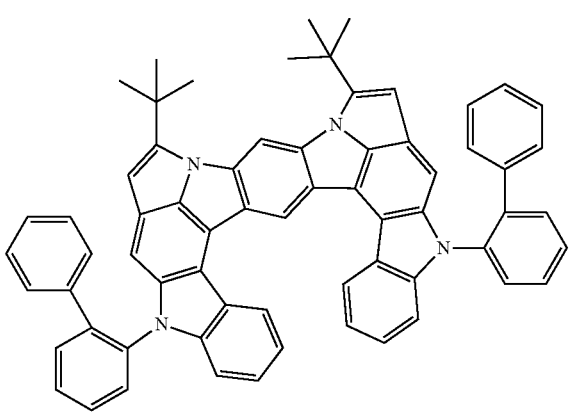
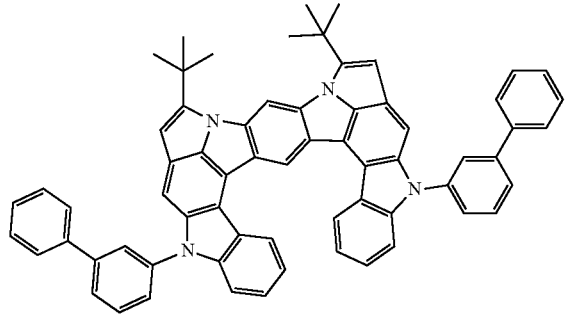
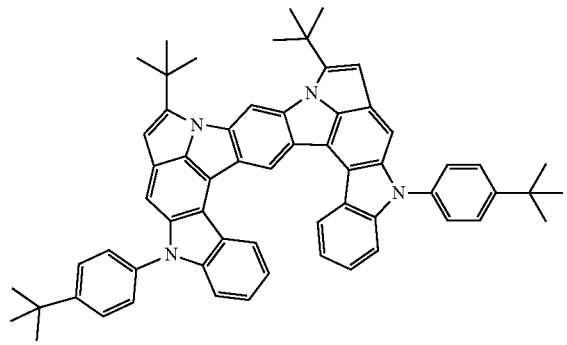

89
-continued
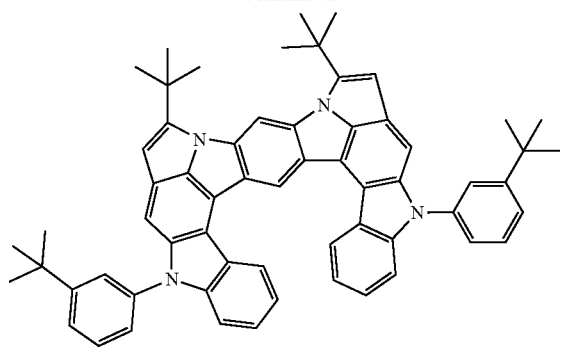
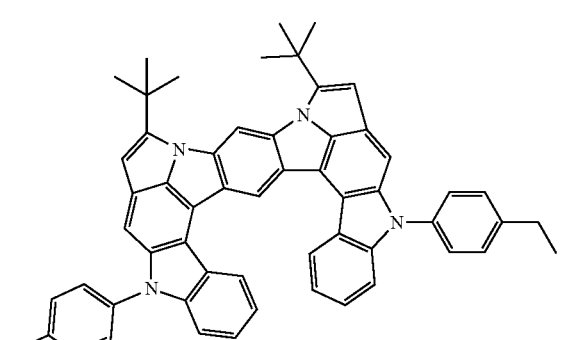
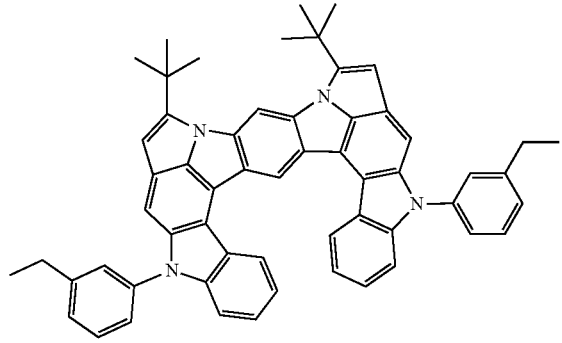
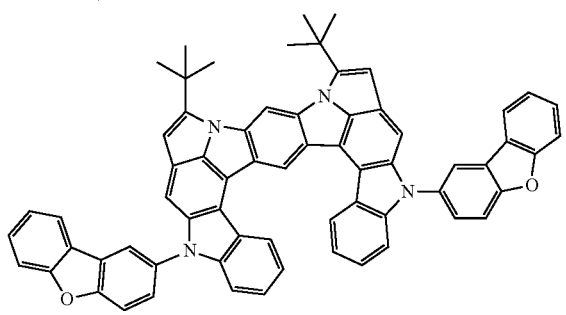
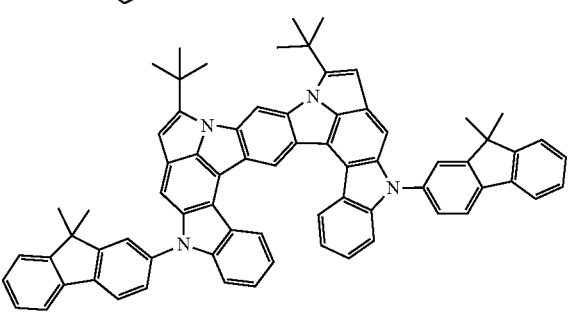
90
-continued
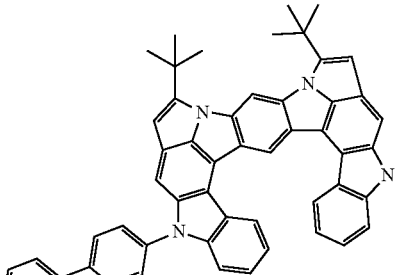
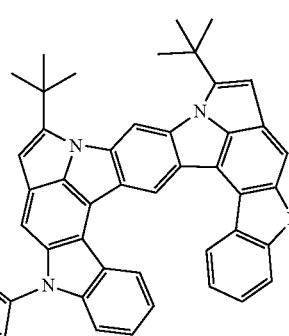
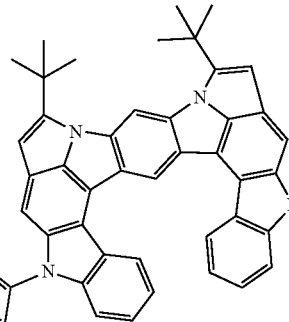
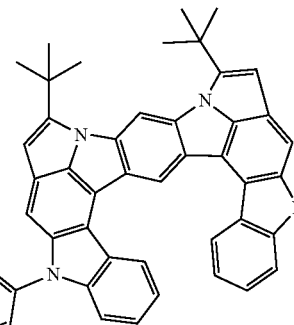
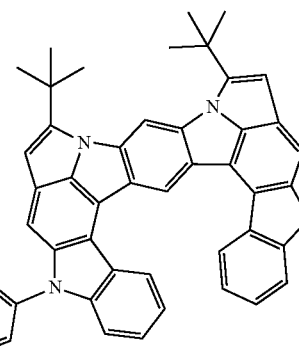

91
-continued
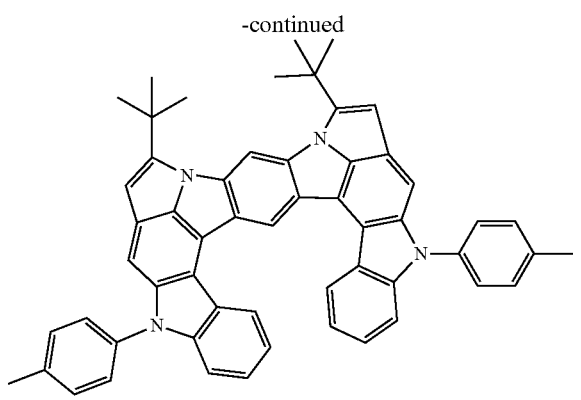
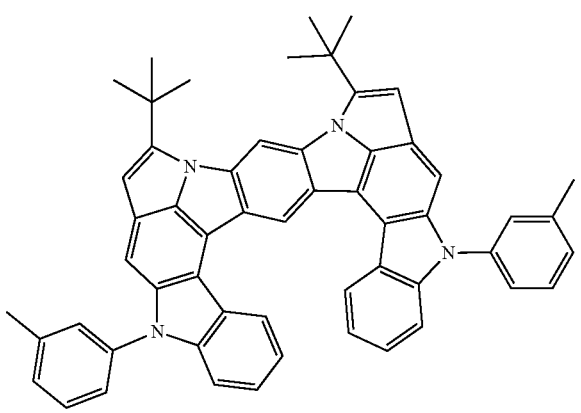
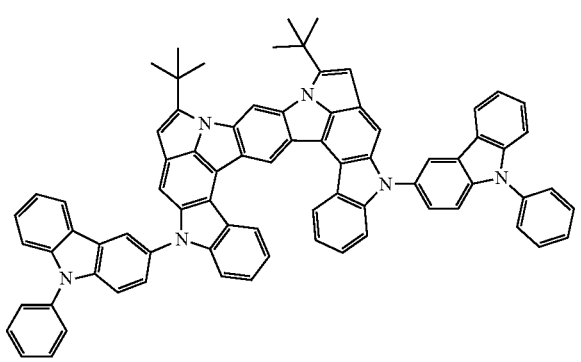
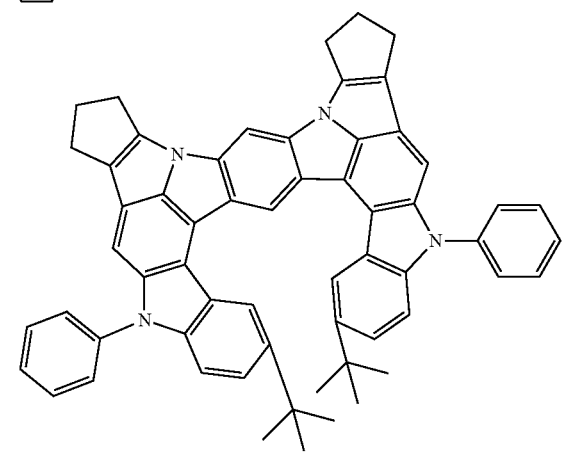
92
-continued
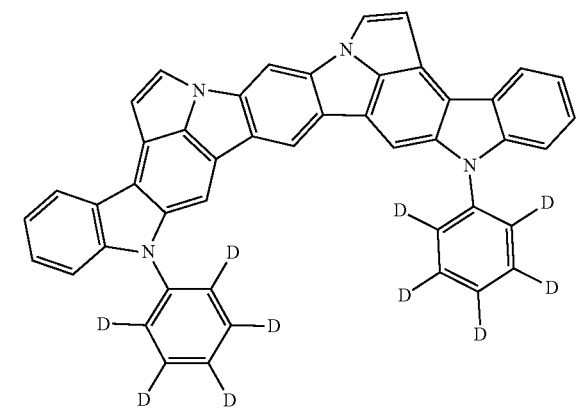
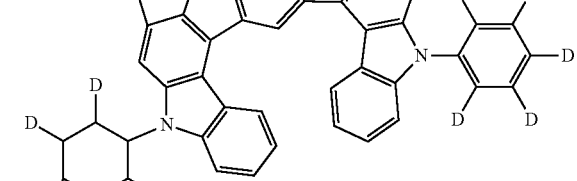
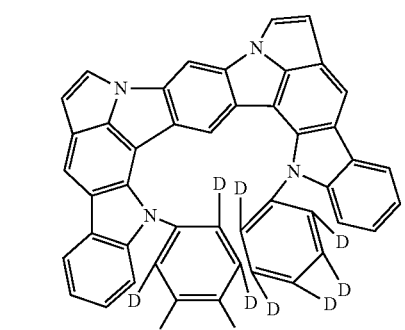
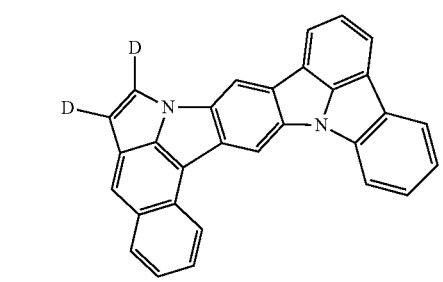

-continued

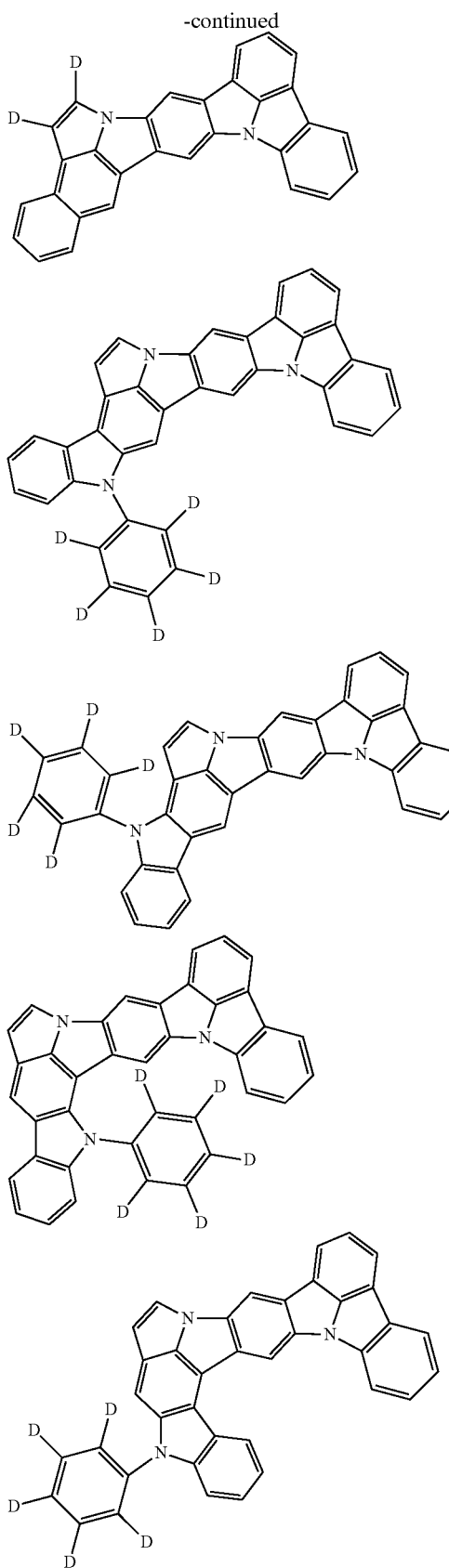

The compound represented by the formula (1) can be synthesized by following the method in Examples described later with the use of known alternative reaction or raw materials, in accordance with an intended product.

[Material for Organic Electroluminescence Device]

The material for an organic electroluminescence device according to an aspect of the invention contains the compound represented by the formula (1).

The compound (1) can be used as a material for an organic EL device to increase the lifetime of the resulting device.

In one embodiment, the material for an organic EL device is used as an emitting material for an organic EL device.

In one embodiment, the material for an organic EL device is used as a dopant material for an emitting layer of the organic EL device.

The material for an organic EL device of an aspect of the invention may consist of the compound (1), or may contain the compound (1) and a substances (a compound or a material) different from the compound (1).

[Organic Electroluminescence Device]

The organic EL device according to an aspect of the invention includes a cathode;

an anode; and one or two or more organic layers disposed between the cathode and the anode, wherein at least one layer of the organic layers contains the compound represented by the formula (1).

The organic EL device with long lifetime can be obtained by containing the compound (1) in the organic layer.

Schematic configuration of the organic EL device of an aspect of the invention will be explained by referring to the FIGURE.

The organic EL device 1 includes a substrate 2, an anode 3, a cathode 10, and an organic layer 4 between the anode 3 and the cathode 10, and the organic layer 4 includes an emitting layer 5. A first layer (hole-transporting layer) 6 is provided between the anode 3 and the emitting layer 5. In one embodiment, a hole-injecting layer 7 may further be provided between the anode 3 and the first layer (hole-transporting layer) 6. An electron-injecting layer and an electron-transporting layer (not shown in the FIGURE) may be formed between the emitting layer 5 and the cathode 10. An electron-blocking layer (not shown in the FIGURE) may be provided on the anode 3 side of the emitting layer 5, and a hole-blocking layer (not shown in the FIGURE) may be provided on the cathode 10 side of the emitting layer 5. Due to such a configuration, electrons and holes are confined in the emitting layer 5, whereby efficiency of the formation of excitons in the emitting layer 5 can be further enhanced.

In one embodiment, the organic layer includes an emitting layer, and the emitting layer contains the compound represented by the formula (1).

In one embodiment, the organic layer contains a second compound which is not the same as the compound.

In one embodiment, the second compound is a heterocyclic compound or a fused aromatic compound.

In one embodiment, the second compound is a compound selected from anthracene derivatives.

In one embodiment, the second compound is a compound represented by the following formula (10).

<Compound Represented by the Formula (10)>

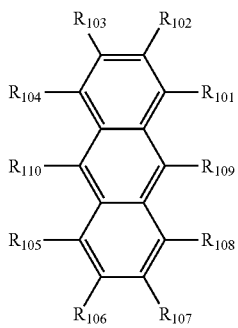

(10)

In the formula (10),
one or more sets of adjacent two or more of $R_{101}$ to $R_{110}$ form a substituted or unsubstituted, saturated or unsaturated ring by bonding with each other, or do not form the substituted or unsubstituted, saturated or unsaturated ring.

$R_{101}$ to $R_{110}$ which do not form the substituted or unsubstituted, saturated or unsaturated ring are independently
a hydrogen atom,
a substituent R, or
a group represented by the following formula (11):

-$L_{101}$-$Ar_{101}$ (11)

In the formula (11),
$L_{101}$ is
a single bond,
a substituted or unsubstituted arylene group including 6 to 50 ring carbon atoms, or
a substituted or unsubstituted divalent heterocyclic group including 5 to 50 ring atoms.
$Ar_{101}$ is
a substituted or unsubstituted aryl group including 6 to 50 ring carbon atoms, or
a substituted or unsubstituted monovalent heterocyclic group including 5 to 50 ring atoms.
the substituent R is
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms.
When two or more of the substituent R's are present, the two or more of the substituent R's may be the same as or different from each other.
$R_{901}$ to $R_{907}$ are independently
a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted monovalent heterocyclic group including 5 to 50 ring atoms.
When two or more of each of $R_{901}$ to $R_{907}$ are present, the two or more of each of $R_{901}$ to $R_{907}$ may be the same as or different from each other.
Provided that at least one of $R_{101}$ to $R_{110}$ which do not form the substituted or unsubstituted, saturated or unsaturated ring is a group represented by the formula (11). When two or more of the groups represented by the formula (11) are present, each of two or more of the groups represented by the formula (11) may be the same as or different from each other.
The compound represented by the formula (10) may have a deuterium atom as a hydrogen atom.
In one embodiment, at least one $Ar_{101}$ in the formula (10) is a substituted or unsubstituted aryl group including 6 to 50 ring carbon atoms.
In one embodiment, at least one $Ar_{101}$ in the formula (10) is a substituted or unsubstituted monovalent heterocyclic group including 5 to 50 ring atoms.
In one embodiment, all of $Ar_{101}$'s in the formula (10) are a substituted or unsubstituted aryl group including 6 to 50 ring carbon atoms. The plurality of $Ar_{101}$'s may be the same as or different from each other.
In one embodiment, one of $Ar_{101}$ in the formula (10) is a substituted or unsubstituted monovalent heterocyclic group including 5 to 50 ring atoms, and the remaining $Ar_{101}$ is a substituted or unsubstituted aryl group including 6 to 50 ring carbon atoms. The plurality of $Ar_{101}$'s may be the same as or different from each other.
In one embodiment, at least one $L_{101}$ in the formula (10) is a single bond.
In one embodiment, all of $L_{101}$'s in the formula (10) are single bonds.
In one embodiment, at least one $L_{101}$ in the formula (10) is a substituted or unsubstituted arylene group including 6 to 50 ring carbon atoms.
In one embodiment, at least one $L_{101}$ in the formula (10) is a substituted or unsubstituted phenylene group or a substituted or unsubstituted naphthyl group.
In one embodiment, the group represented by -$L_{101}$-$Ar_{101}$ in the formula (10) is selected from the group consisting of
a substituted or unsubstituted phenyl group,
a substituted or unsubstituted naphthyl group,
a substituted or unsubstituted biphenyl group,
a substituted or unsubstituted phenanthrenyl group,
a substituted or unsubstituted benzophenanthrenyl group,
a substituted or unsubstituted fluorenyl group,
a substituted or unsubstituted benzofluorenyl group,
a substituted or unsubstituted dibenzofuranyl group,
a substituted or unsubstituted naphthobenzofuranyl group,
a substituted or unsubstituted dibenzothiophenyl group, and
a substituted or unsubstituted carbazolyl group.
In one embodiment, the substituent R in the formula (10) are independently
a substituted or unsubstituted alkyl group including 1 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
—S—($R_{905}$),
—N($R_{906}$)($R_{907}$), a halogen atom, a cyano group, a nitro group, or a substituted or unsubstituted aryl group including 6 to 50 ring carbon atoms.

$R_{901}$ to $R_{907}$ are as defined in the formula (10).

In one embodiment, the substituent in the case of "substituted or unsubstituted" in the formula (10) are independently a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group including 6 to 50 ring carbon atoms, or a substituted or unsubstituted monovalent heterocyclic group including 5 to 50 ring atoms.

$R_{901}$ to $R_{907}$ are as defined in the formula (10).

In one embodiment, the substituent in the case of "substituted or unsubstituted" in the formula (10) are independently a substituted or unsubstituted alkyl group including 1 to 50 carbon atoms, a substituted or unsubstituted cycloalkyl group including 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, or a substituted or unsubstituted aryl group including 6 to 50 ring carbon atoms.

$R_{901}$ to $R_{907}$ are as defined in the formula (10).

In one embodiment, the substituent in the case of "substituted or unsubstituted" in the formula (10) is selected from the group consisting of an alkyl group including 1 to 18 carbon atoms, an aryl group including 6 to 18 ring carbon atoms, and a monovalent heterocyclic group including 5 to 18 ring atoms.

In one embodiment, the substituent in the case of "substituted or unsubstituted" in the formula (10) is an alkyl group including 1 to 5 carbon atoms.

In one embodiment, the compound represented by the formula (10) is a compound represented by the following formula (20).

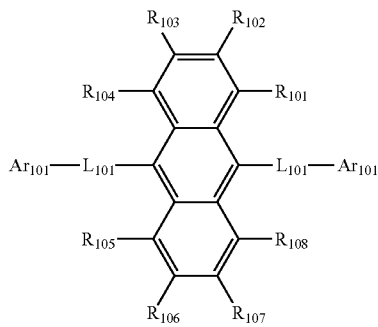

(20)

In the formula (20), $R_{101}$ to $R_{108}$, $L_{101}$, and $Ar_{101}$ are as defined in the formula (10).

The compound represented by the formula (20) may have a deuterium atom as a hydrogen atom.

In other words, in one embodiment, the compound represented by the formula (10) or the formula (20) has at least the two groups represented by the formula (11).

In one embodiment, the compound represented by the formula (10) or the formula (20) has the two or three groups represented by the formula (11).

In one embodiment, $R_{101}$ to $R_{110}$ in the formula (10) and $R_{101}$ to $R_{108}$ in the formula (20) do not form the substituted or unsubstituted, saturated or unsaturated ring.

In one embodiment, $R_{101}$ to $R_{110}$ in the formula (10) and $R_{101}$ to $R_{108}$ in the (20) are hydrogen atoms.

In one embodiment, the compound represented by the formula (20) is a compound represented by the following formula (30).

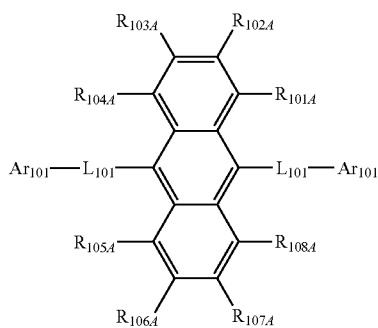

(30)

In the formula (30), $L_{101}$ and $Ar_{101}$ are as defined in the formula (10).

Adjacent two of $R_{101A}$ to $R_{108A}$ do not form a substituted or unsubstituted, saturated or unsaturated ring.

$R_{101A}$ to $R_{103A}$ are independently a hydrogen atom, or a substituent R.

The substituent R is as defined in the formula (10).

In other words, the compound represented by the formula (30) is a compound having the two groups represented by the formula (11).

The compound represented by the formula (30) has substantially only protium atoms as hydrogen atoms.

Note that "having substantially only protium atoms" means the case where the ratio of protium compound based on the total moles of the compound having only protium atoms as hydrogen atoms (protium compound) and the compound having the same structure as the former and having a deuterium atom as a hydrogen atom (deuterium compound), is 90 mol % or more, 95 mol % or more, or 99 mol % or more.

In one embodiment, the compound represented by the formula (30) is a compound represented by the following formula (31).

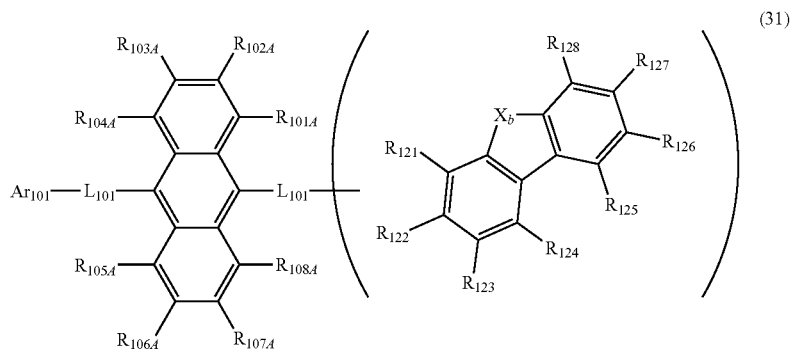

(31)

In the formula (31), $L_{101}$ and $Ar_{101}$ are as defined in the formula (10).

$R_{101A}$ to $R_{108A}$ are as defined in the formula (30) above.

$X_b$ is O, S, $N(R_{131})$, or $C(R_{132})(R_{133})$.

One of $R_{121}$ to $R_{128}$ and $R_{131}$ to $R_{133}$ is a single bond which bonds with $L_{101}$.

One or more sets of adjacent two or more of $R_{121}$ to $R_{128}$ which are not a single bond which bonds with $L_{101}$ form a substituted or unsubstituted, saturated or unsaturated ring by bonding with each other, or do not form the substituted or unsubstituted, saturated or unsaturated ring.

$R_{121}$ to $R_{128}$ which are not a single bond which bonds with $L_{101}$ and do not form the substituted or unsubstituted, saturated or unsaturated ring are independently
a hydrogen atom, or
a substituent R.

The substituent R is as defined in the formula (10).

$R_{131}$ to $R_{133}$ which are not a single bond which bonds with $L_{101}$ are independently
a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted monovalent heterocyclic group including 5 to 50 ring atoms.

When two or more of each of $R_{131}$ to $R_{133}$ are present, the two or more of each of $R_{131}$ to $R_{133}$ may be the same as or different from each other.

In one embodiment, the compound represented by the formula (31) is a compound represented by the following formula (32).

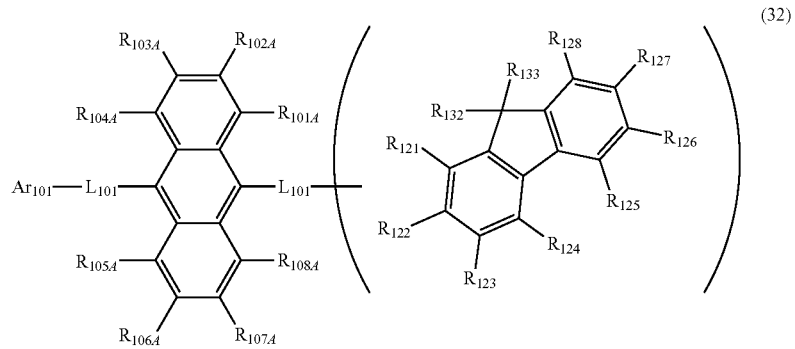

(32)

In the formula (32), $R_{101A}$ to $R_{108A}$, $L_{101}$, $Ar_{101}$, $R_{121}$ to $R_{128}$, $R_{132}$, and $R_{133}$ are as defined in the formula (31).

In one embodiment, the compound represented by the formula (31) is a compound represented by the following formula (33).

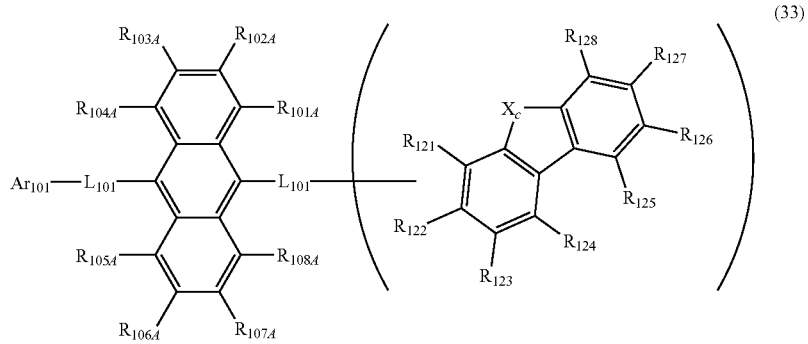

(33)

In the formula (33), $R_{101A}$ to $R_{108A}$, $L_{101}$, $Ar_{101}$, and $R_{121}$ to $R_{128}$ are as defined in the formula (31).

$X_c$ is O, S, or $NR_{131}$.

$R_{131}$ is as defined in the formula (31).

In one embodiment, the compound represented by the formula (31) is a compound represented by the following formula (34).

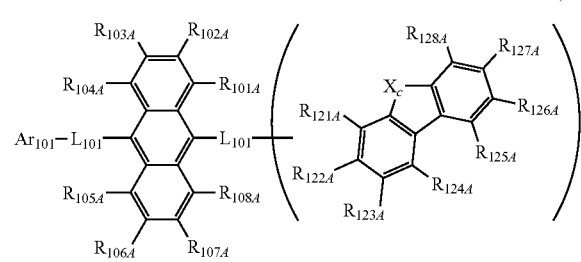

(34)

In the formula (34), $R_{101A}$ to $R_{108A}$, $L_{101}$, and $Ar_{101}$ are as defined in the formula (31).

$X_c$ is O, S, or $NR_{131}$.

$R_{131}$ is as defined in the formula (31).

One of $R_{121A}$ to $R_{128A}$ is a single bond which bonds with $L_{101}$.

One or more sets of adjacent two or more of $R_{121A}$ to $R_{128A}$ which are not a single bond which bonds with $L_{101}$ do not form a substituted or unsubstituted, saturated or unsaturated ring.

$R_{121A}$ to $R_{128A}$ which are not a single bond which bonds with $L_{101}$ are independently a hydrogen atom, or a substituent R.

The substituent R is as defined in the formula (10).

In one embodiment, the compound represented by the formula (31) is a compound represented by the following formula (35).

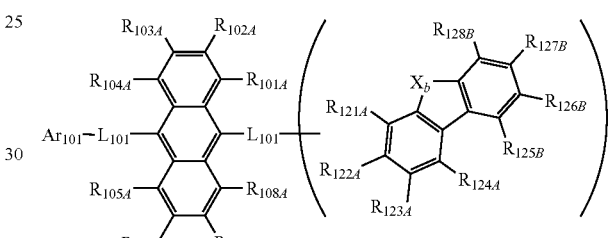

(35)

In the formula (35), $R_{101A}$ to $R_{108A}$, $L_{101}$, $Ar_{101}$, and X are as defined in the formula (31).

One or more sets of adjacent two or more of $R_{121A}$ to $R_{124A}$ do not form a substituted or unsubstituted, saturated or unsaturated ring by bonding with each other.

Any one set of $R_{125B}$ and $R_{126B}$, $R_{126B}$ and $R_{127B}$, and $R_{127B}$ and $R_{128B}$ form a ring represented by the following formula (35a) or (35b) by bonding with each other.

(35a)

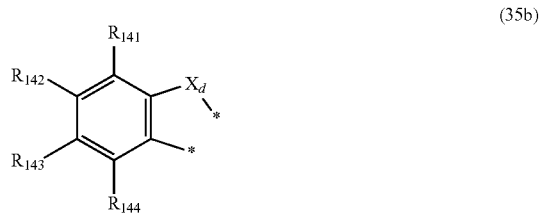

(35b)

In the formulas (35a) and (35b), two *'s are respectively bonded with any one set of $R_{125B}$ and $R_{R126B}$, $R_{126B}$ and $R_{127B}$, and $R_{127B}$ and $R_{128B}$.

$R_{141}$ to $R_{144}$ are independently
a hydrogen atom, or
a substituent R.

The substituent R is as defined in the formula (10).

$X_d$ is O or S.

One of $R_{121A}$ to $R_{124A}$ $R_{125B}$ to $R_{128B}$ which do not form the ring represented by the formula (35a) or (35b), and $R_{141}$ to $R_{144}$ is a single bond which bonds with $L_{101}$.

$R_{121A}$ to $R_{124A}$ which are not a single bond which bonds with $L_{101}$ and $R_{125B}$ to $R_{128B}$ which are not a single bond which bonds with $L_{101}$ and do not form the ring represented by the formula (35a) or (35b) are independently
a hydrogen atom, or
a substituent R.

The substituent R is as defined in the formula (10).

In one embodiment, the compound represented by the formula (35) is a compound represented by the following formula (36).

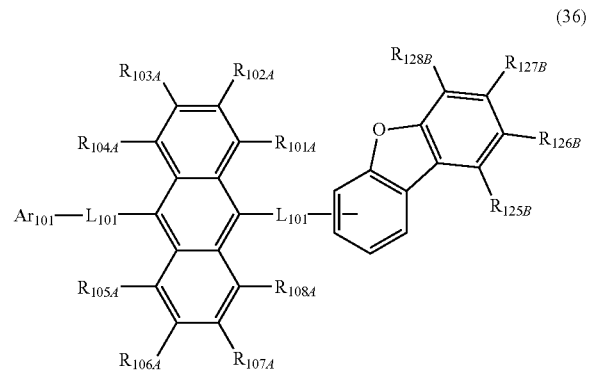

(36)

In the formula (36), $R_{101A}$ to $R_{108A}$, $L_{101}$, $Ar_{101}$, and $R_{125B}$ to $R_{128B}$ are as defined in the formula (35).

In one embodiment, the compound represented by the formula (34) is a compound represented by the following formula (37).

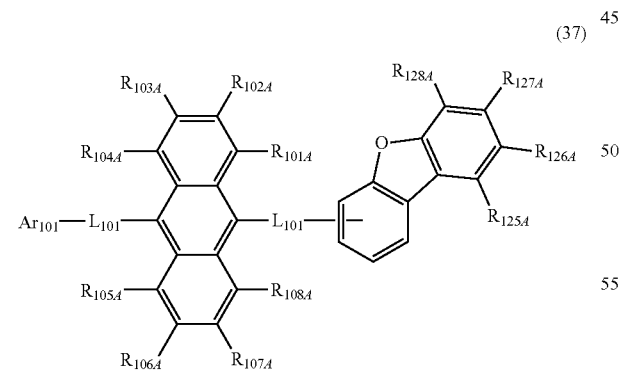

(37)

In the formula (37), $R_{101A}$ to $R_{108A}$, $R_{125A}$ to $R_{128A}$, $L_{101}$, and $Ar_{101}$ are as defined in the formula (34).

In one embodiment, $R_{101A}$ to $R_{108A}$ in the formulas (30) to (37) are hydrogen atoms.

In one embodiment, the compound represented by the formula (10) is a compound represented by the following formula (40).

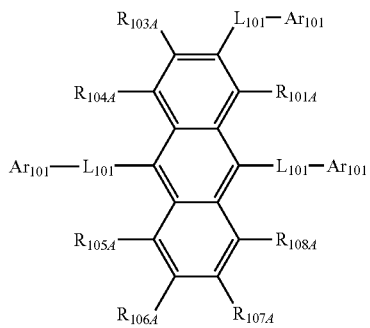

(40)

In the formula (40), $L_{101}$ and $Ar_{101}$ are as defined in the formula (10).

One or more sets of adjacent two or more of $R_{101A}$ and $R_{103A}$ to $R_{108A}$ form a substituted or unsubstituted, saturated or unsaturated ring by bonding with each other, or do not form the substituted or unsubstituted, saturated or unsaturated ring.

$R_{101A}$ and $R_{103A}$ to $R_{108A}$ which do not form the substituted or unsubstituted, saturated or unsaturated ring are independently
a hydrogen atom, or
a substituent R.

The substituent R is as defined in the formula (10).

In other words, the compound represented by the formula (40) is a compound having the three groups represented by the formula (11). The compound represented by the formula (40) has substantially only protium atoms as hydrogen atoms.

In one embodiment, the compound represented by the formula (40) is a compound represented by the following formula (41).

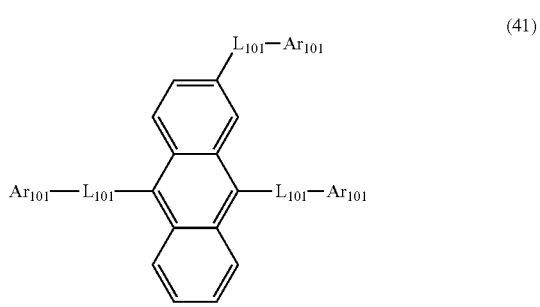

(41)

In the formula (41), $L_{101}$ and $Ar_{101}$ are as defined in the formula (40).

In one embodiment, the compound represented by the formula (40) is a compound represented by any one of the following formulas (42-1) to (42-3).

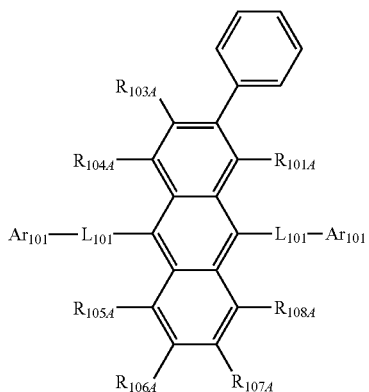
(42-1)

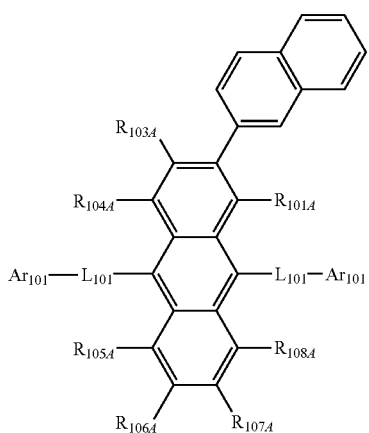
(42-2)

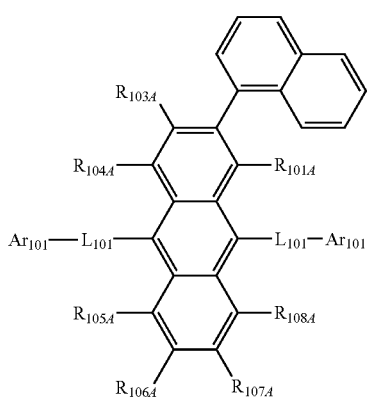
(42-3)

In the formula (42-1) to (42-3), $R_{101A}$ to $R_{108A}$, $L_{101}$, and $Ar_{101}$ are as defined in the formula (40).

In one embodiment, the compound represented by the formulas (42-1) to (42-3) is a compound represented by any one of the following formulas (43-1) to (43-3).

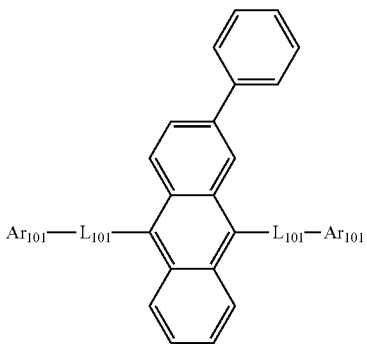
(43-1)

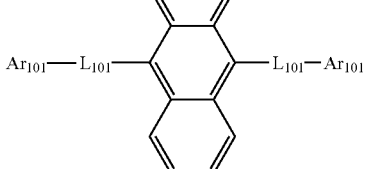
(43-2)

(43-3)

In the formulas (43-1) to (43-3), $L_{101}$ and $Ar_{101}$ are as defined in the formula (40).

In one embodiment, the group represented by -$L_{101}$-$Ar_{101}$ in the formulas (40), (41), (42-1) to (42-3), and (43-1) to (43-3) is selected from the group consisting of
a substituted or unsubstituted phenyl group,
a substituted or unsubstituted naphthyl group,
a substituted or unsubstituted biphenyl group,
a substituted or unsubstituted phenanthrenyl group,
a substituted or unsubstituted benzophenanthrenyl group,
a substituted or unsubstituted fluorenyl group,
a substituted or unsubstituted benzofluorenyl group,
a substituted or unsubstituted dibenzofuranyl group,
a substituted or unsubstituted naphthobenzofuranyl group,
a substituted or unsubstituted dibenzothiophenyl group, and
a substituted or unsubstituted carbazolyl group.

In one embodiment, the compound represented by the formula (10) or the formula (20) include a compound in which at least one of the hydrogen atoms possessed by these compounds is a deuterium atom.

In one embodiment, at least one of $R_{101}$ to $R_{108}$ which are hydrogen atoms, hydrogen atoms possessed by $R_{101}$ to $R_{108}$, which are the substituent R, hydrogen atoms possessed by $L_{101}$, hydrogen atoms possessed by the substituent of $L_{101}$, hydrogen atoms possessed by $Ar_{101}$, and hydrogen atoms possessed by the substituent of $Ar_{101}$ in the formula (20) is a deuterium atom.

The compounds represented by each of the formulas (30) to (37) include a compound in which at least one of the hydrogen atoms possessed by these compounds is a deuterium atom.

In one embodiment, at least one of the hydrogen atoms which bonds with the carbon atoms constituting the anthracene skeleton in the compounds represented by each of the formulas (30) to (37) is a deuterium atom.

In one embodiment, the compound represented by the formula (30) is a compound represented by the following formula (30D).

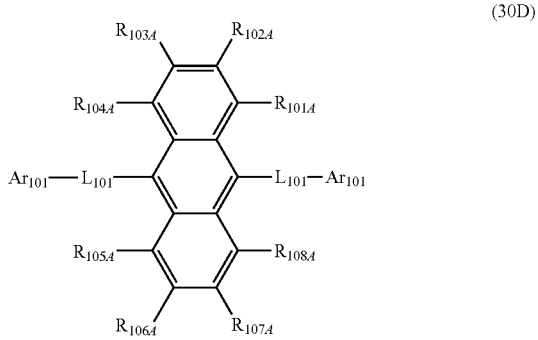

(30D)

In the formula (30D), $R_{101A}$ to $R_{108A}$, $L_{101}$, and $Ar_{101}$ are as defined in the formula (30).

Provided that at least one of:

$R_{101A}$ to $R_{110A}$, which are hydrogen atoms, hydrogen atoms possessed by $R_{101A}$ to $R_{110A}$, which are the substituent R, hydrogen atoms possessed by $L_{101}$, hydrogen atoms possessed by the substituent of $L_{101}$, hydrogen atoms possessed by $Ar_{101}$, and hydrogen atoms possessed by the substituent of $Ar_{101}$ is a deuterium atom.

In other words, the compound represented by the formula (30D) is a compound in which at least one of the hydrogen atoms possessed by the compound represented by the formula (30) is a deuterium atom.

In one embodiment, at least one of $R_{101A}$ to $R_{108A}$, which is a hydrogen atom, in the formula (30D) is a deuterium atom.

In one embodiment, the compound represented by the formula (30D) is a compound represented by the following formula (31D).

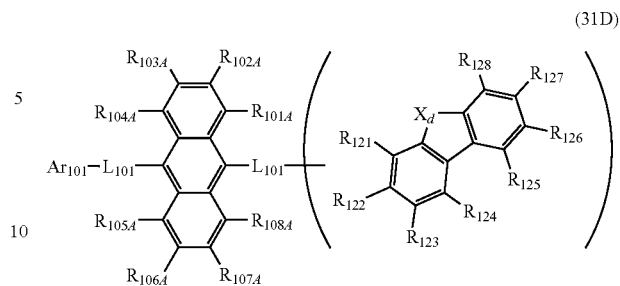

(31D)

In the formula (31D), $R_{101A}$ to $R_{108A}$, $L_{101}$, and $Ar_{101}$ are as defined in the formula (30D).

$X_d$ is O or S.

One of $R_{121}$ to $R_{128}$ is a single bond which bonds with $L_{101}$.

One or more sets of adjacent two or more of $R_{121}$ to $R_{128}$ which are not a single bond which bonds with $L_{101}$ form a substituted or unsubstituted, saturated or unsaturated ring or do not form a substituted or unsubstituted by bonding with each other, saturated or unsaturated ring.

$R_{121}$ to $R_{128}$ which are not a single bond which bonds with $L_{101}$ and do not form the substituted or unsubstituted, saturated or unsaturated ring are independently a hydrogen atom, or a substituent R.

The substituent R is as defined in the formula (10).

Provided that at least one of:

$R_{101A}$ to $R_{110A}$ which are hydrogen atoms, hydrogen atoms possessed by $R_{101A}$ to $R_{110A}$, which are the substituent R, hydrogen atoms possessed by $L_{101}$, hydrogen atoms possessed by the substituent of $L_{101}$, hydrogen atoms possessed by $Ar_{101}$, hydrogen atoms possessed by the substituent of $Ar_{101}$, $R_{121}$ to $R_{128}$ which are hydrogen atoms, and hydrogen atoms possessed by $R_{121}$ to $R_{128}$, which are the substituent R is a deuterium atom.

In one embodiment, the compound represented by the formula (31D) is a compound represented by the following formula (32D).

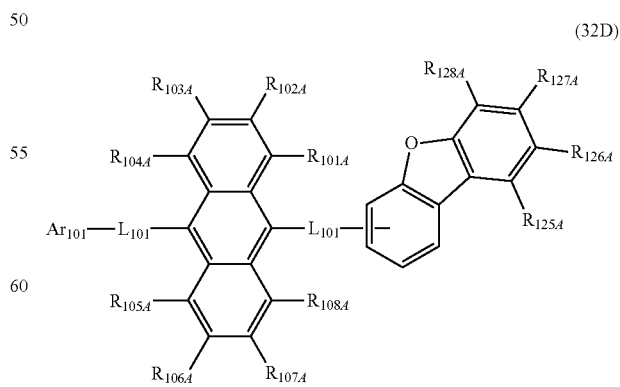

(32D)

In the formula (32D), $R_{101A}$ to $R_{108A}$, $R_{125A}$ to $R_{128A}$, $L_{101}$, and $Ar_{101}$ are as defined in the formula (31D).

Provided that at least one of
$R_{101A}$ to $R_{108A}$, which are hydrogen atoms,
hydrogen atoms possessed by $R_{101A}$ to $R_{108A}$ which are the substituent R,
$R_{125A}$ to $R_{128A}$ which are hydrogen atoms,
hydrogen atoms possessed by $R_{125A}$ to $R_{128A}$, which are the substituent R,
hydrogen atoms which bonds with the carbon atoms constituting the dibenzofuran skeleton in the formula (32D),
hydrogen atoms possessed by $L_{101}$,
hydrogen atoms possessed by the substituent of $L_{101}$,
hydrogen atoms possessed by $Ar_{101}$, and
hydrogen atoms possessed by the substituent of $Ar_{101}$
is a deuterium atom.

In one embodiment, the compound represented by the formula (32D) is a compound represented by the following formula (32D-1) or (32D-2).

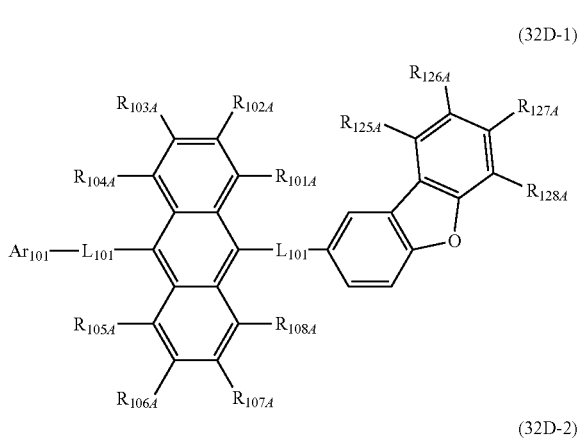

(32D-1)

(32D-2)

In the formulas (32D-1) and (32D-2), $R_{101A}$ to $R_{108A}$, $R_{125A}$ to $R_{128A}$, $L_{101}$, and $Ar_{101}$ are as defined in the formula (32D).

Provided that at least one of
$R_{101A}$ to $R_{108A}$ which are hydrogen atoms,
hydrogen atoms possessed by $R_{101A}$ to $R_{108A}$, which are the substituent R,
$R_{125A}$ to $R_{128A}$ which are hydrogen atoms,
hydrogen atoms possessed by $R_{125A}$ to $R_{128A}$, which are the substituent R,
hydrogen atoms which bonds with the carbon atom constituting the dibenzofuran skeleton in the formula (32D-1) or (32D-2),
hydrogen atoms possessed by $L_{101}$,
hydrogen atoms possessed by the substituent of $L_{101}$,
hydrogen atoms possessed by $Ar_{101}$, and
hydrogen atoms possessed by the substituent of $Ar_{101}$
is a deuterium atom.

In one embodiment, at least one of the hydrogen atoms possessed by the compounds represented by each of the formulas (40), (41), (42-1) to (42-3), and (43-1) to (43-3) is a deuterium atom.

In one embodiment, at least one of the hydrogen atoms which bond with the carbon atoms constituting the anthracene skeleton in the compound represented by the formula (41) ($R_{101A}$ to $R_{108A}$, which are hydrogen atoms) is a deuterium atom.

In one embodiment, the compound represented by the formula (40) is a compound represented by the following formula (40D).

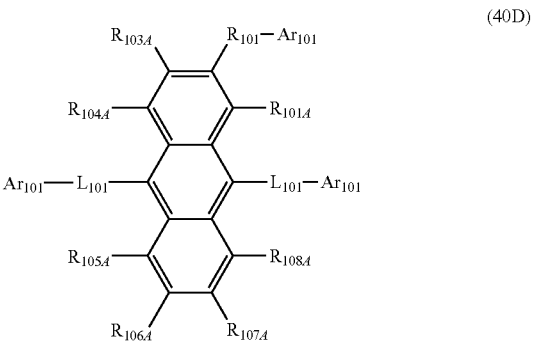

(40D)

In the formula (40D), $L_{101}$ and $Ar_{101}$ are as defined in the formula (10).

One or more sets of adjacent two or more of $R_{101A}$ and $R_{103A}$ to $R_{108A}$ do not form a substituted or unsubstituted, saturated or unsaturated ring.

$R_{101A}$ and $R_{103A}$ to $R_{108A}$ are independently
a hydrogen atom, or
a substituent R.

The substituent R is as defined in the formula (10).
Provided that at least one of:
$R_{101A}$ and $R_{103A}$ to $R_{108A}$, which are hydrogen atoms,
hydrogen atoms possessed by $R_{101A}$ and $R_{103A}$ to $R_{108A}$, which are the substituent R,
hydrogen atoms possessed by $L_{101}$,
hydrogen atoms possessed by the substituent of $L_{101}$,
hydrogen atoms possessed by $Ar_{101}$, and
hydrogen atoms possessed by the substituent of $Ar_{101}$
is a deuterium atom.

In one embodiment, at least one of $R_{101A}$ and $R_{103A}$ to $R_{108A}$ in the formula (40D) is a deuterium atom.

In one embodiment, the compound represented by the formula (40D) is a compound represented by the following formula (41D).

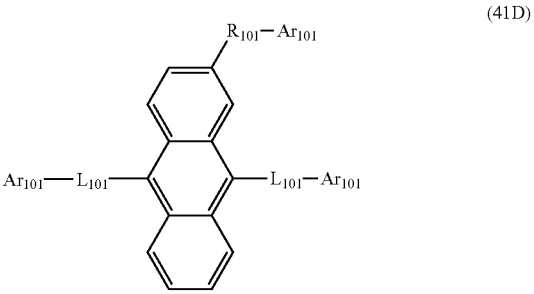

(41D)

In the formula (41D), $L_{101}$ and $Ar_{101}$ are as defined in the formula (40D).

Provided that in the formula (41D), at least one of
hydrogen atoms which bond with the carbon atoms constituting the anthracene skeleton,
hydrogen atoms possessed by $L_{101}$,
hydrogen atoms possessed by the substituent of $L_{101}$,
hydrogen atoms possessed by $Ar_{101}$, and
hydrogen atoms possessed by the substituent of $Ar_{101}$ is a deuterium atom.

In one embodiment, the compound represented by the formula (40D) is a compound represented by any one of the following formulas (42D-1) to (42D-3).

(42D-1)

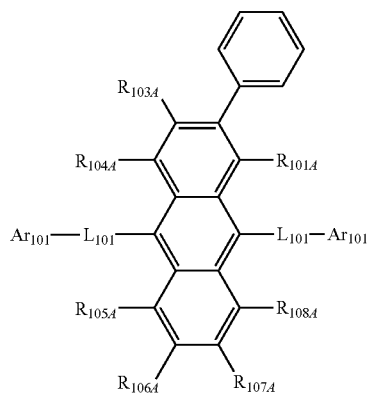

(42D-2)

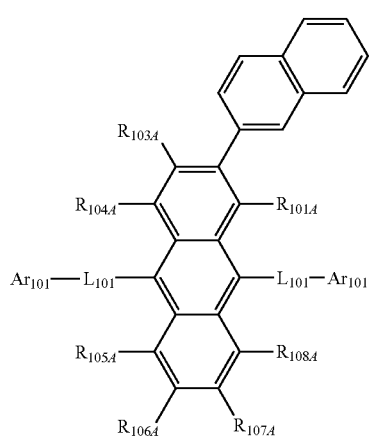

(42D-3)

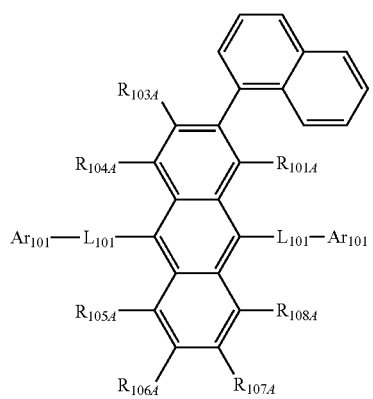

In the formulas (42D-1) to (42D-3), $R_{101A}$ to $R_{108A}$, $L_{101}$, and $Ar_{101}$ are as defined in the formula (40D).

Provided that in the formula (42D-1), at least one of:
$R_{101A}$ and $R_{103A}$ to $R_{108A}$, which are hydrogen atoms,
hydrogen atoms possessed by $R_{101A}$ and $R_{103A}$ to $R_{108A}$, which are the substituent R,
hydrogen atoms possessed by $L_{101}$,
hydrogen atoms possessed by the substituent of $L_{101}$,
hydrogen atoms possessed by $Ar_{101}$,
hydrogen atoms possessed by the substituent of $Ar_{101}$, and
hydrogen atoms which bond with the carbon atoms constituting the phenyl group in the formula (42D-1) is a deuterium atom.

In the formula (42D-2), at least one of:
$R_{101A}$ and $R_{103A}$ to $R_{108A}$, which are hydrogen atoms,
hydrogen atoms possessed by $R_{101A}$ and $R_{103A}$ to $R_{108A}$, which are the substituent R,
hydrogen atoms possessed by $L_{101}$,
hydrogen atoms possessed by the substituent of $L_{101}$,
hydrogen atoms possessed by $Ar_{101}$,
hydrogen atoms possessed by the substituent of $Ar_{101}$, and
hydrogen atoms which bond with the carbon atoms constituting the naphthyl group in the formula (42D-2) is a deuterium atom.

In the formula (42D-3), at least one of:
$R_{101A}$ and $R_{103A}$ to $R_{108A}$, which are hydrogen atoms,
hydrogen atoms possessed by $R_{101A}$ and $R_{103A}$ to $R_{108A}$, which are the substituent R,
hydrogen atoms possessed by $L_{101}$,
hydrogen atoms possessed by the substituent of $L_{101}$,
hydrogen atoms possessed by $Ar_{101}$,
hydrogen atoms possessed by the substituent of $Ar_{101}$, and
hydrogen atoms which bond with the carbon atoms constituting the naphthyl group in the formula (42D-3) is a deuterium atom.

In one embodiment, the compounds represented by each of the formulas (42D-1) to (42D-3) are compounds represented by each of the following formulas (43D-1) to (43D-3).

(43D-1)

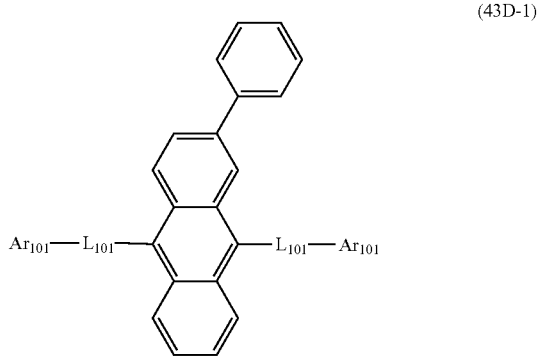

(43D-2)

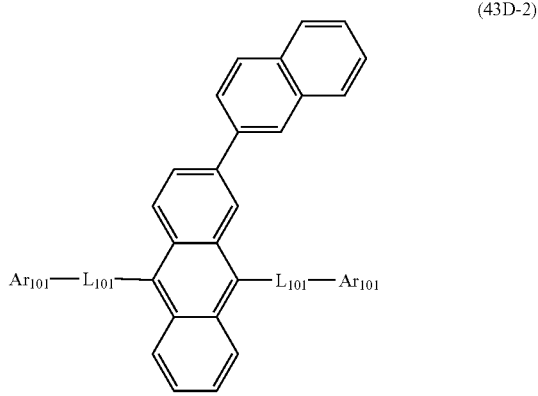

(43D-3)

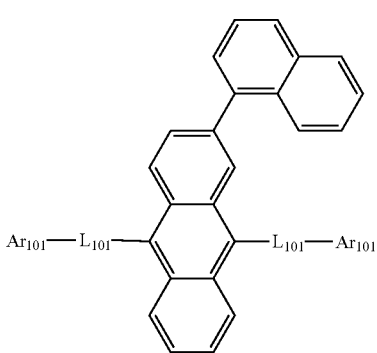

In the formulas (43D-1) to (43D-3), $L_{101}$ and $Ar_{101}$ are as defined in the formula (40D).

Provided that at least one of hydrogen atoms which bond with the carbon atoms constituting the anthracene skeleton in the formula (43D-1),
hydrogen atoms possessed by $L_{101}$,
hydrogen atoms possessed by the substituent of $L_{101}$,
hydrogen atoms possessed by $Ar_{101}$,
hydrogen atoms possessed by the substituent of $Ar_{101}$, and
hydrogen atoms which bond with the carbon atoms constituting the phenyl group in the formula (43D-1) is a deuterium atom.

At least one of hydrogen atoms which bond with the carbon atoms constituting the anthracene skeleton in the formula (43D-2),
hydrogen atoms possessed by $L_{101}$,
hydrogen atoms possessed by the substituent of $L_{101}$,
hydrogen atoms possessed by $Ar_{101}$,
hydrogen atoms possessed by the substituent of $Ar_{101}$, and
hydrogen atoms which bond with the carbon atoms constituting the naphthyl group in the formula (43D-2) is a deuterium atom.

At least one of hydrogen atoms which bond with the carbon atoms constituting the anthracene skeleton in the formula (43D-3),
hydrogen atoms possessed by $L_{101}$,
hydrogen atoms possessed by the substituent of $L_{101}$,
hydrogen atoms possessed by $Ar_{101}$,
hydrogen atoms possessed by the substituent of $Ar_{101}$, and
hydrogen atoms which bond with the carbon atoms constituting the naphthyl group in the formula (43D-3) is a deuterium atom.

In one embodiment, in the compound represented by the formula (20), at least one $Ar_{101}$ is a monovalent group having a structure represented by the following formula (50).

(50)

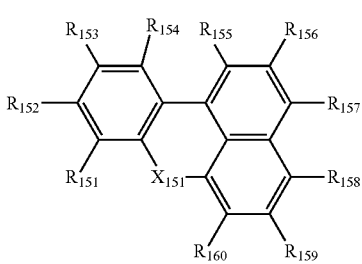

In the formula (50),
$X_{151}$ is O, S, or $C(R_{161})(R_{162})$.
One of $R_{151}$ to $R_{160}$ is a single bond which bonds with $L_{101}$.

One or more sets of adjacent two or more of $R_{151}$ to $R_{154}$ and one or more sets of adjacent two or more of $R_{155}$ to $R_{160}$, which are not a single bond which bonds with $L_{101}$, form a substituted or unsubstituted, saturated or unsaturated ring by bonding with each other, or do not form a substituted or unsubstituted, saturated or unsaturated ring.

$R_{161}$ and $R_{162}$ form a substituted or unsubstituted, saturated or unsaturated ring by bonding with each other, or do not form a substituted or unsubstituted, saturated or unsaturated ring.

$R_{161}$ and $R_{162}$ which do not form the substituted or unsubstituted, saturated or unsaturated ring, and $R_{151}$ to $R_{160}$ which are not a single bond which bonds with $L_{101}$ and do not form the substituted or unsubstituted, saturated or unsaturated ring are independently a hydrogen atom or a substituent R.

The substituent R is as defined in the formula (10).

$Ar_{101}$, which is not a monovalent group having the structure represented by the formula (50) is
a substituted or unsubstituted aryl group including 6 to 50 ring carbon atoms, or
a substituted or unsubstituted divalent heterocyclic group including 5 to 50 ring atoms.

The position to be the single bond which bonds with $L_{101}$ in the formula (50) is not particularly limited.

In one embodiment, one of $R_{151}$ to $R_{160}$ in the formula (50) is a single bond which bonds with $L_{101}$.

In one embodiment, $Ar_{101}$ is a monovalent group represented by the following formula (50-$R_{152}$), (50-$R_{153}$), (50-$R_{154}$), (50-$R_{157}$), or (50-$R_{158}$).

(50-$R_{152}$)

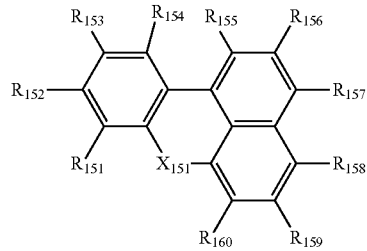

(50-$R_{153}$)

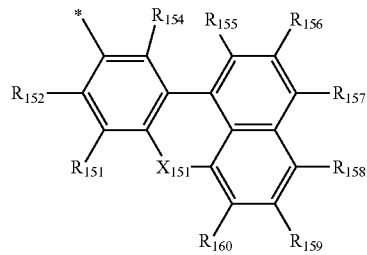

(50-$R_{154}$)

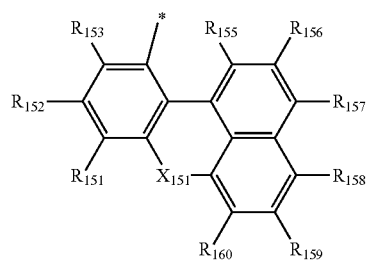

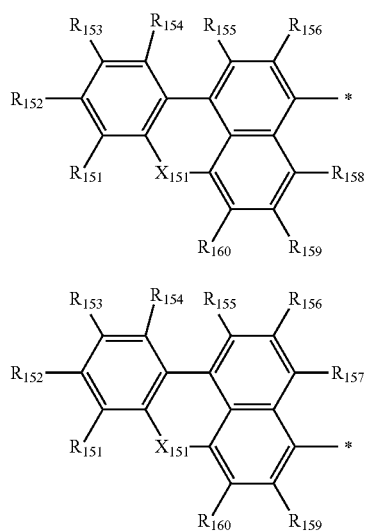

In the formulas (50-R$_{152}$), (50-R$_{153}$), (50-R$_{154}$), (50-R$_{157}$), and (50-R$_{158}$), X$_{151}$, R$_{151}$ to R$_{160}$ are as defined in the formula (50).

* is a single bond which bonds with L$_{101}$.

Specific examples of the compound represented by the formula (10) include the following compounds. The compound represented by the formula (10) is not limited to these specific examples. In the following specific examples, "Me" represents a methyl group, and "D" represents a deuterium atom

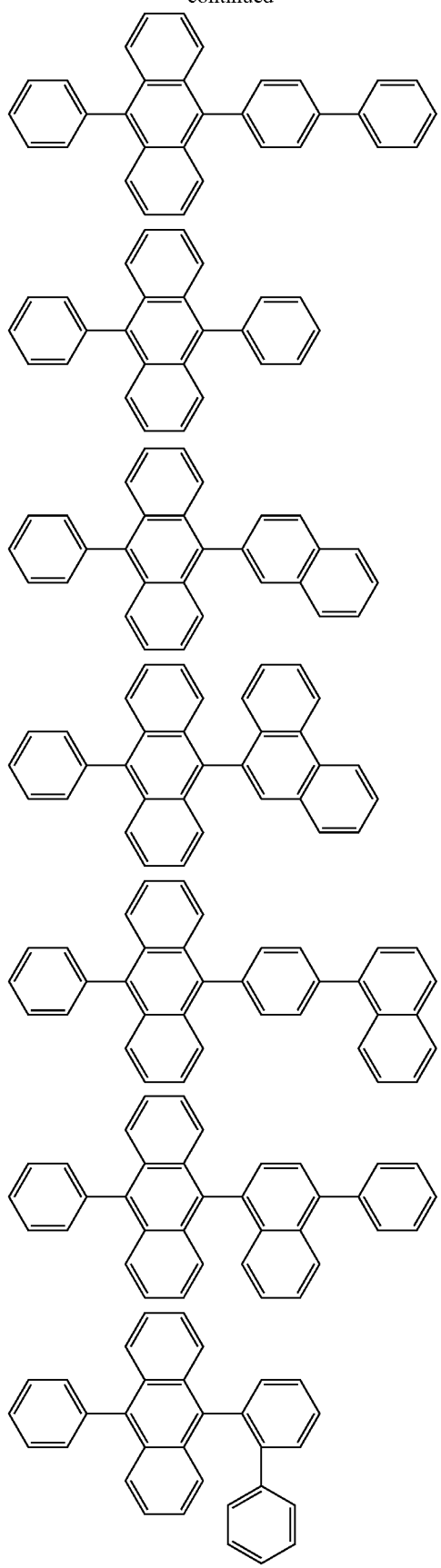

117
-continued
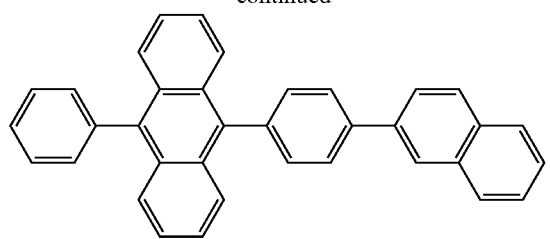
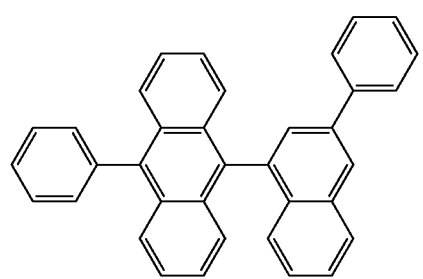
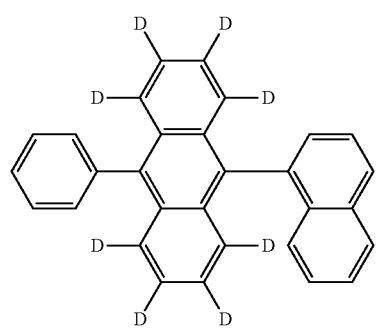
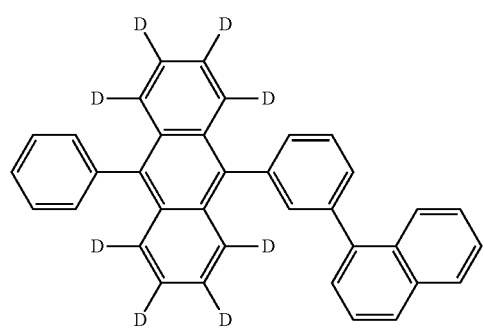
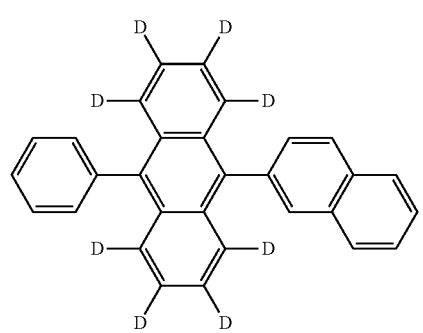
118
-continued
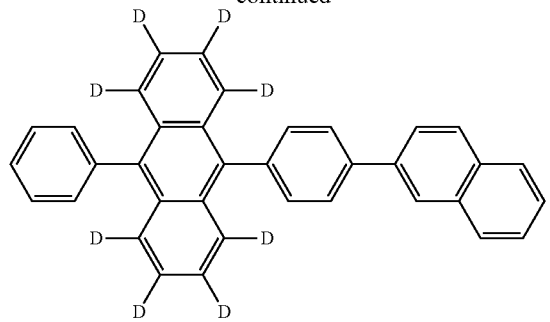
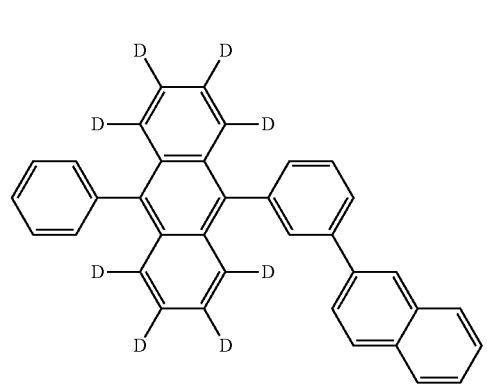
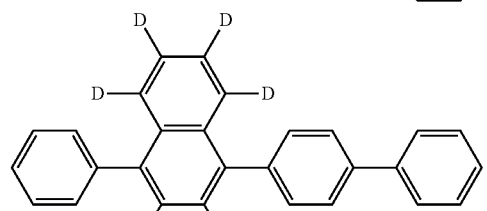
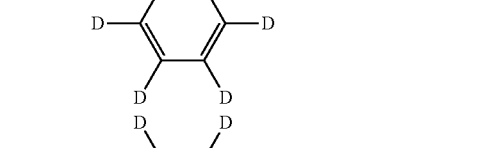
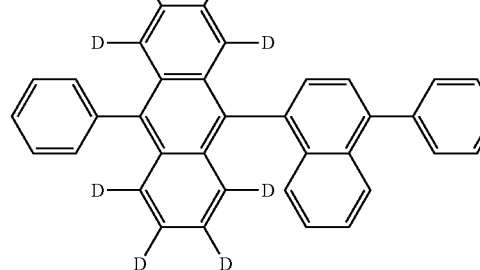
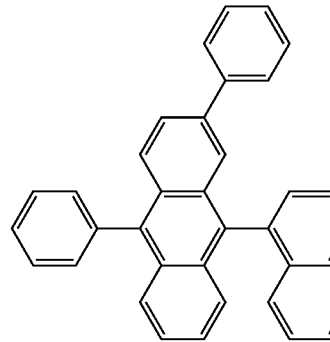

119
-continued
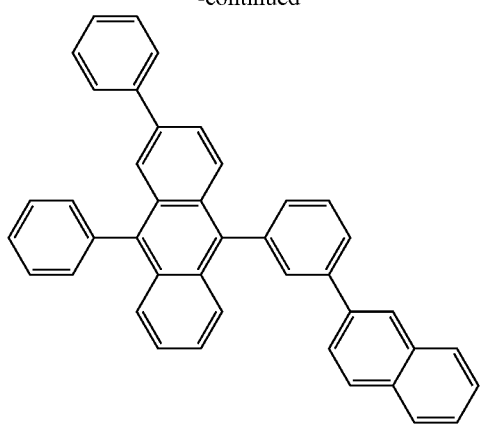
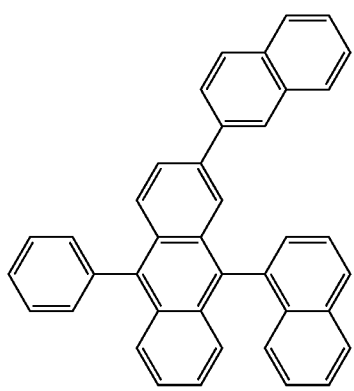
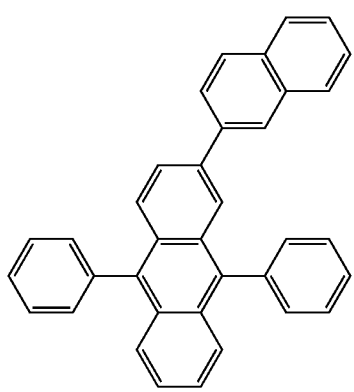
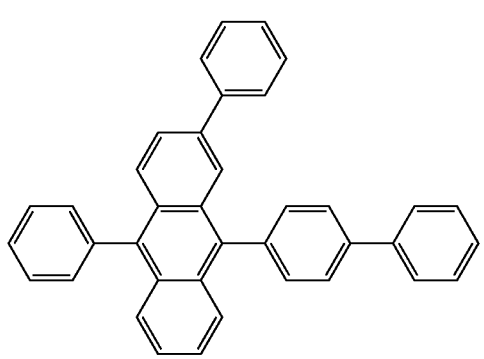
120
-continued
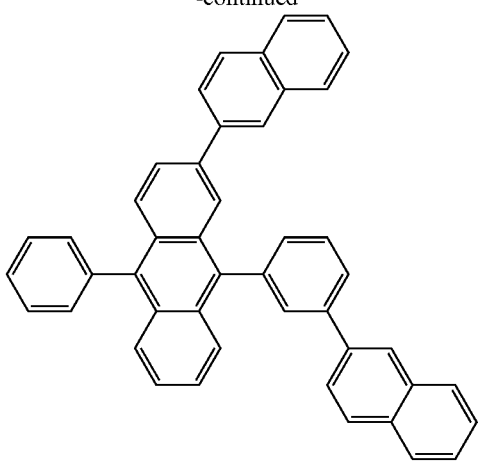
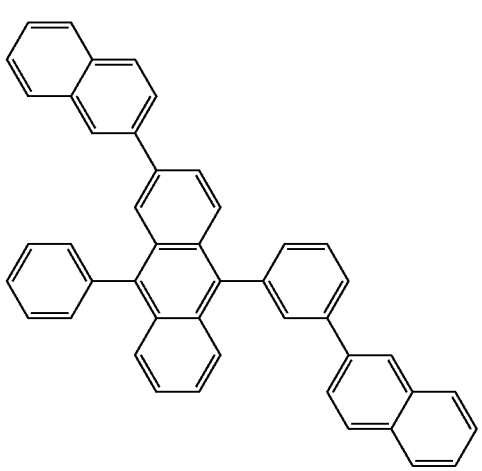
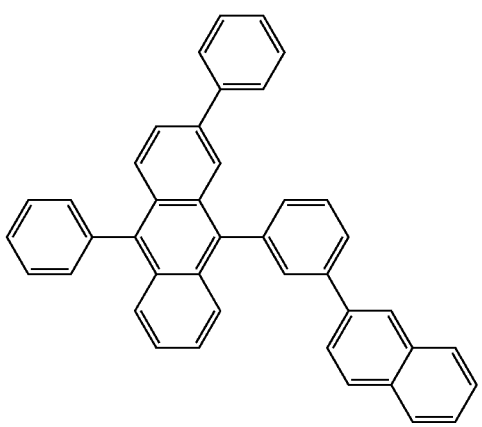
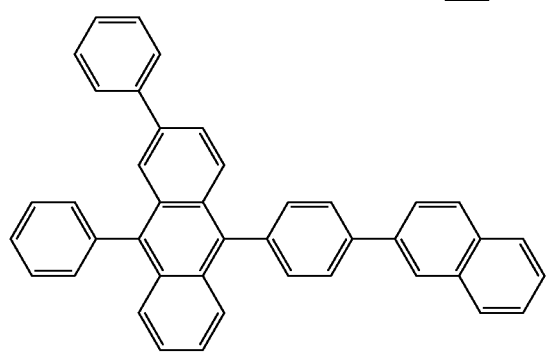

121
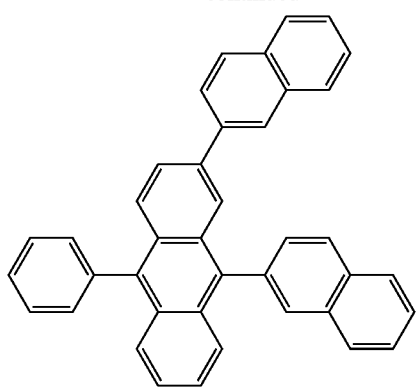
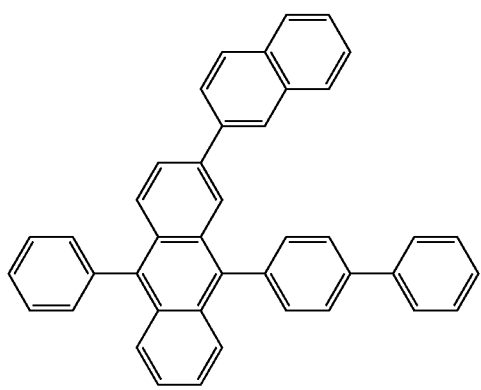
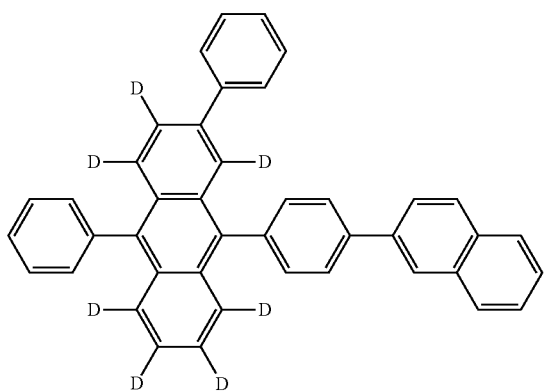
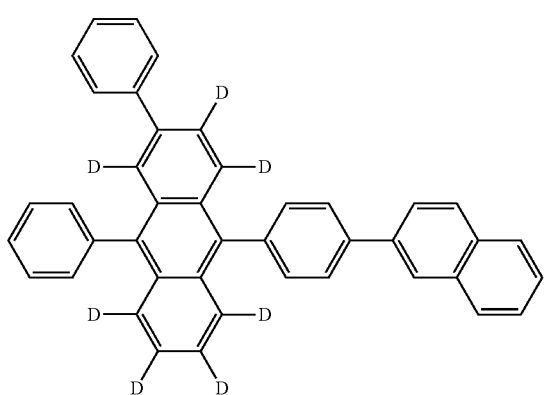
122
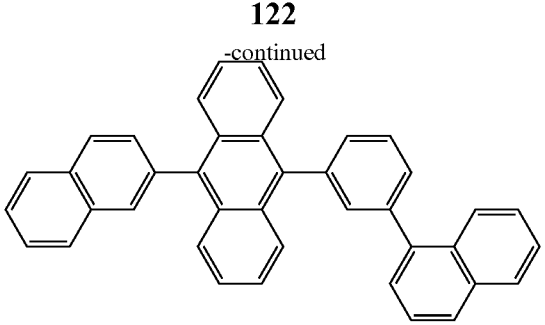
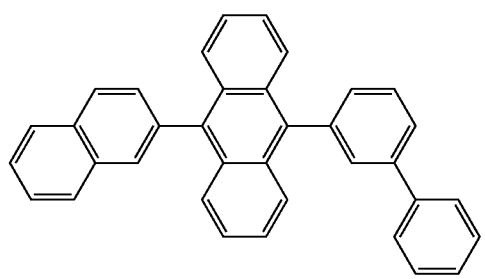
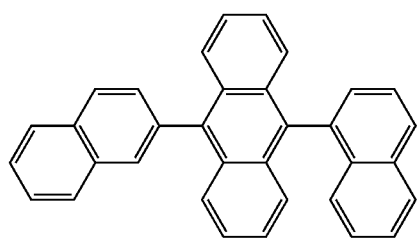
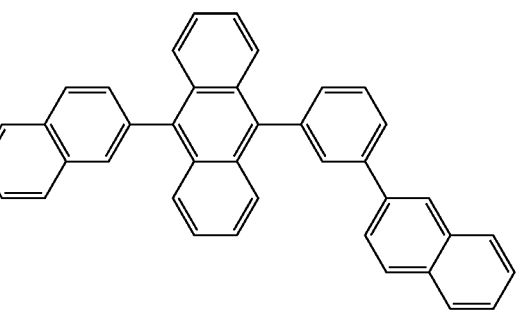
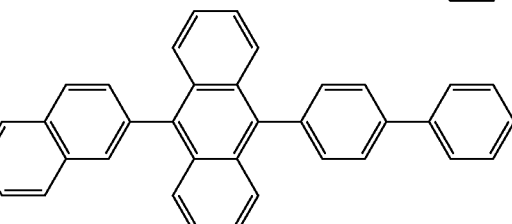
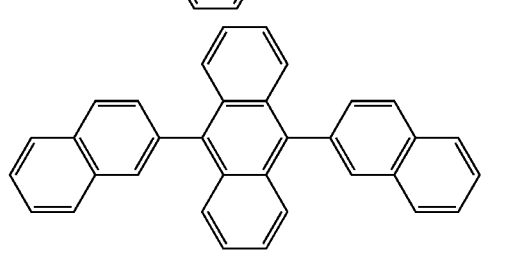

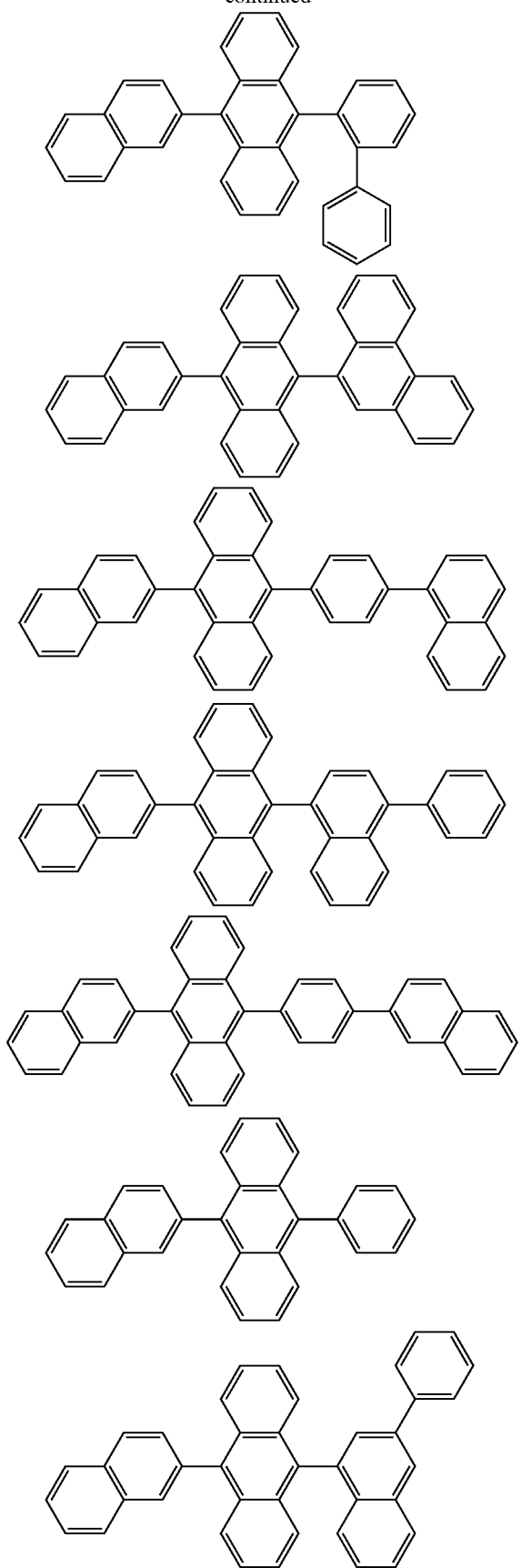

125
-continued
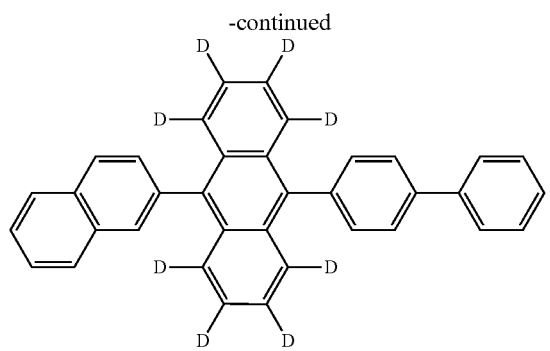
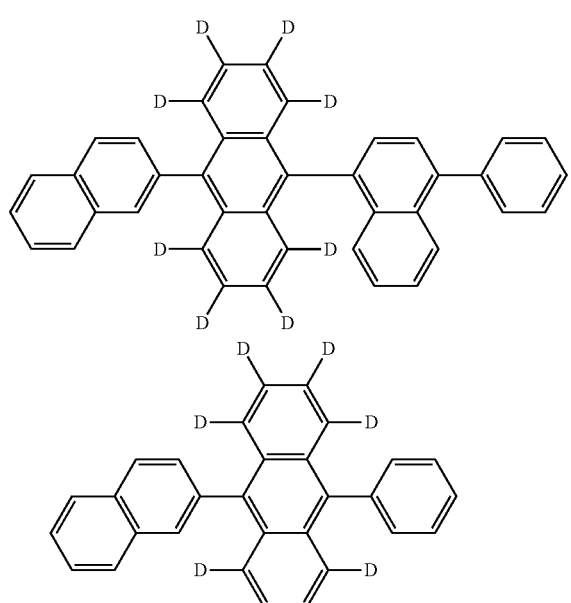
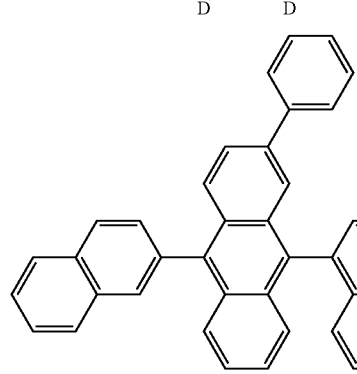
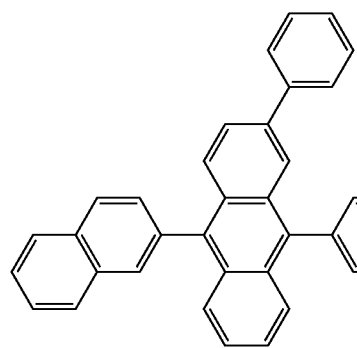
126
-continued
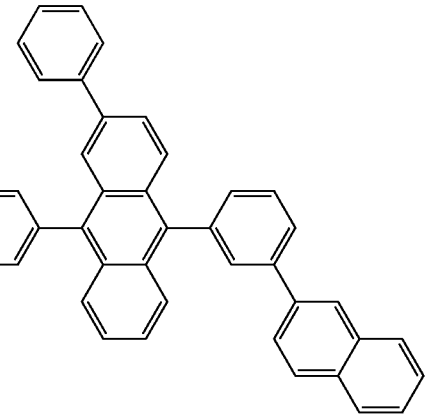
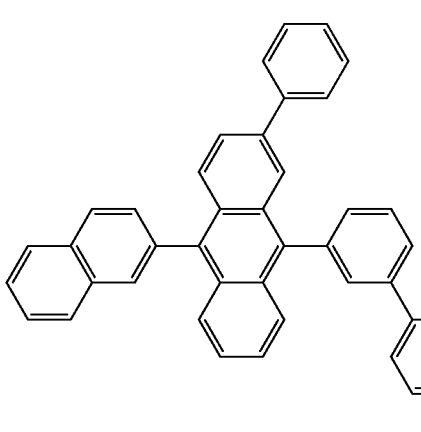
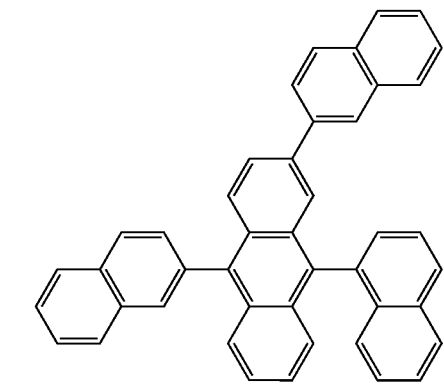
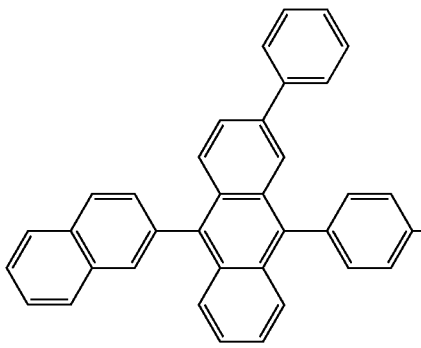

-continued
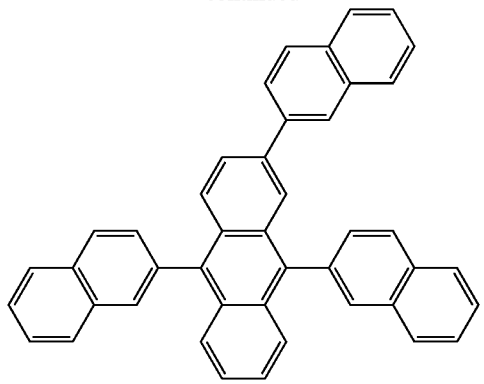
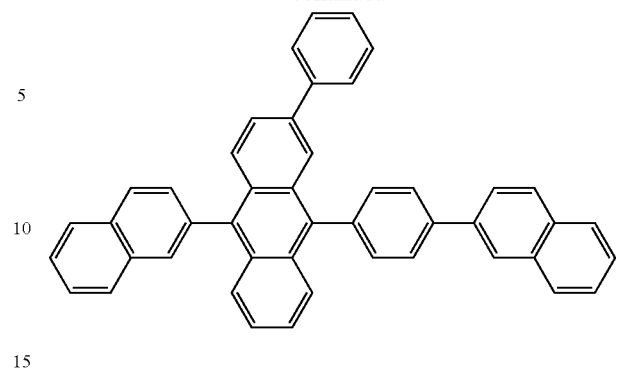
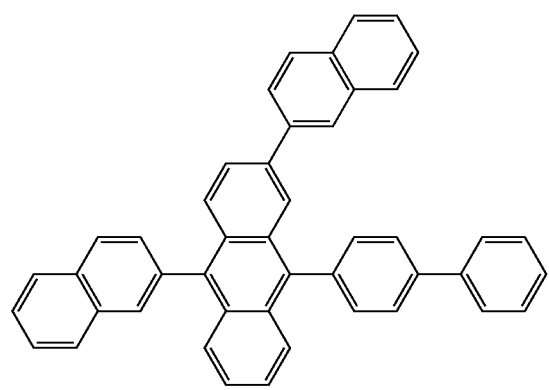
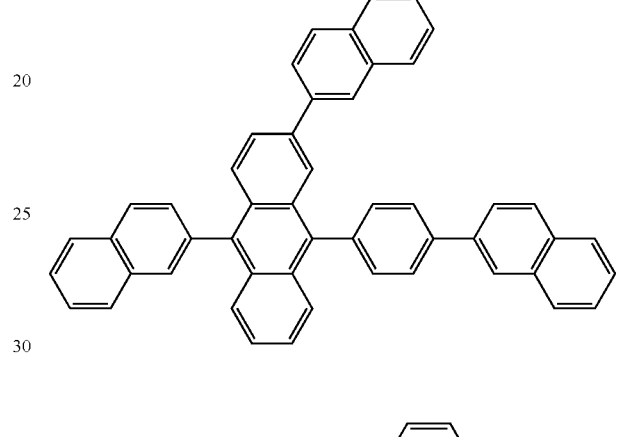
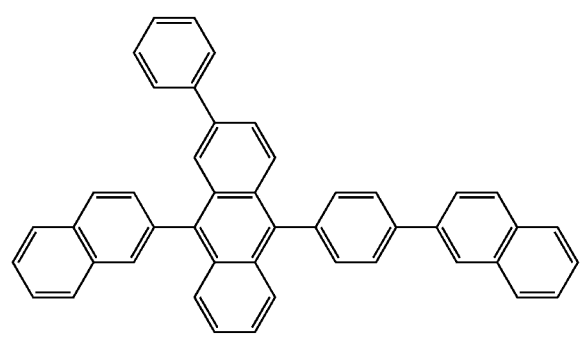
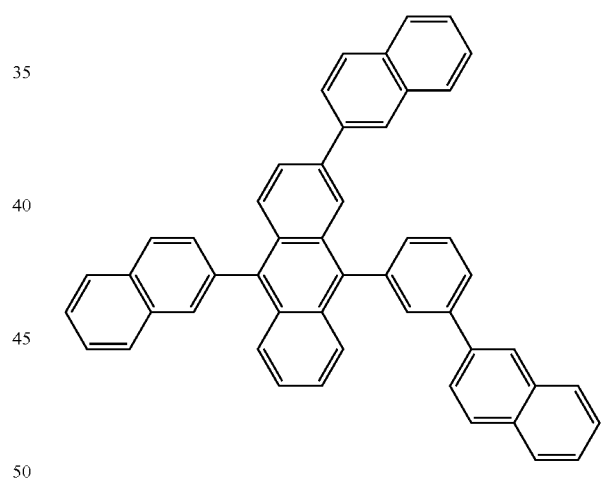
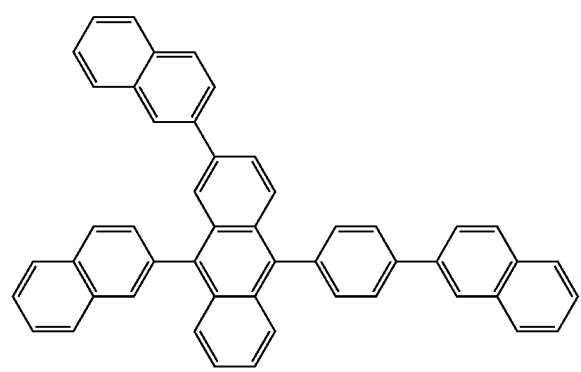
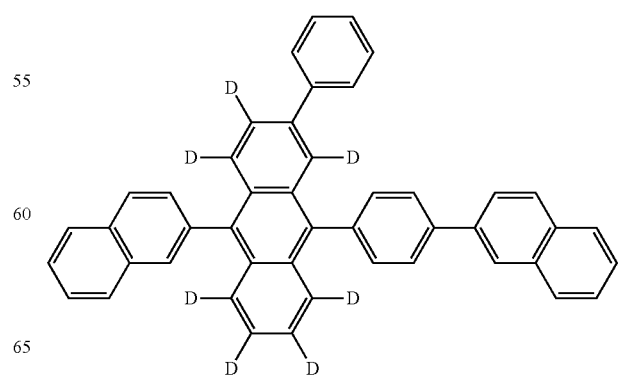

-continued
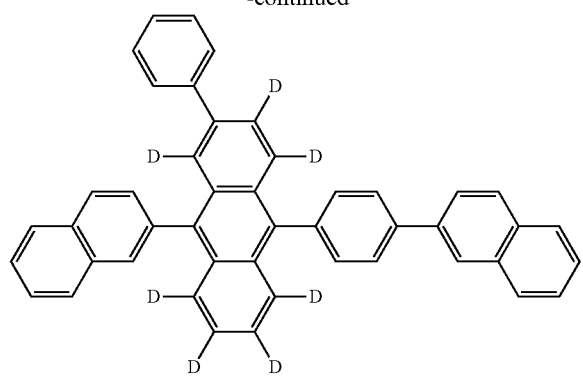
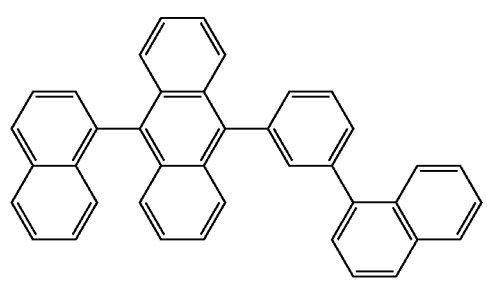
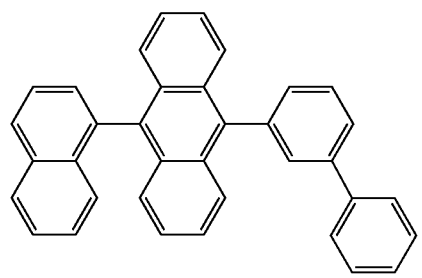
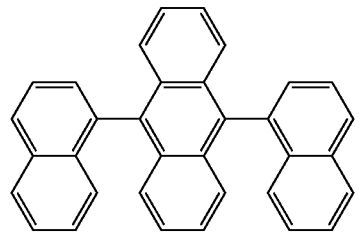
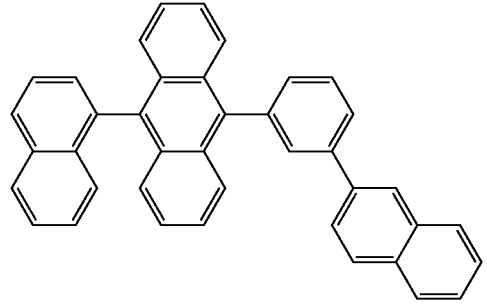
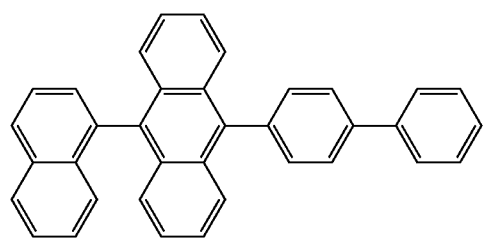
-continued
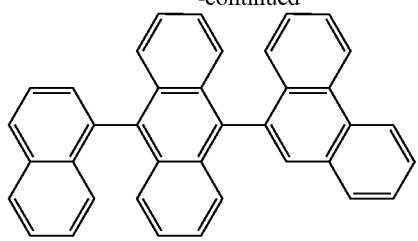
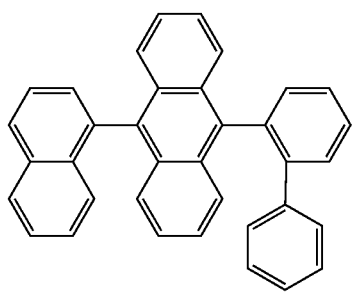
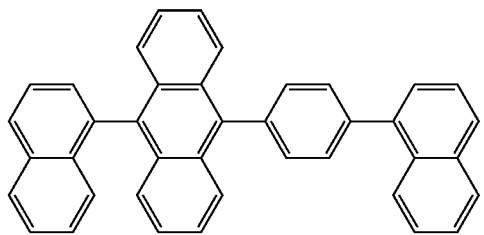
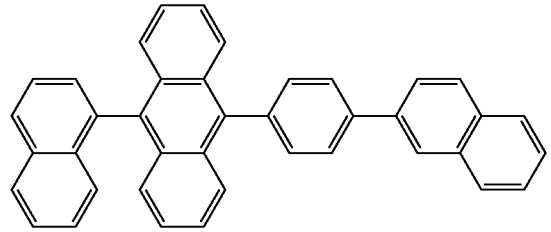
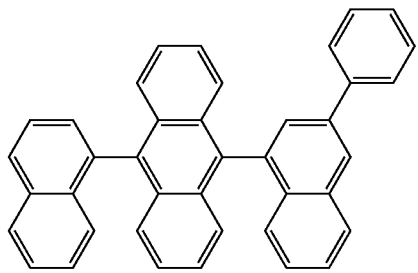
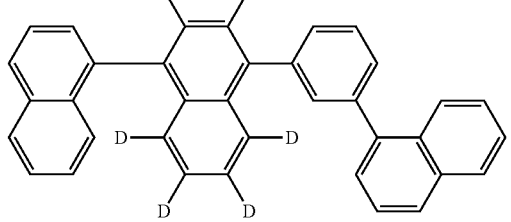

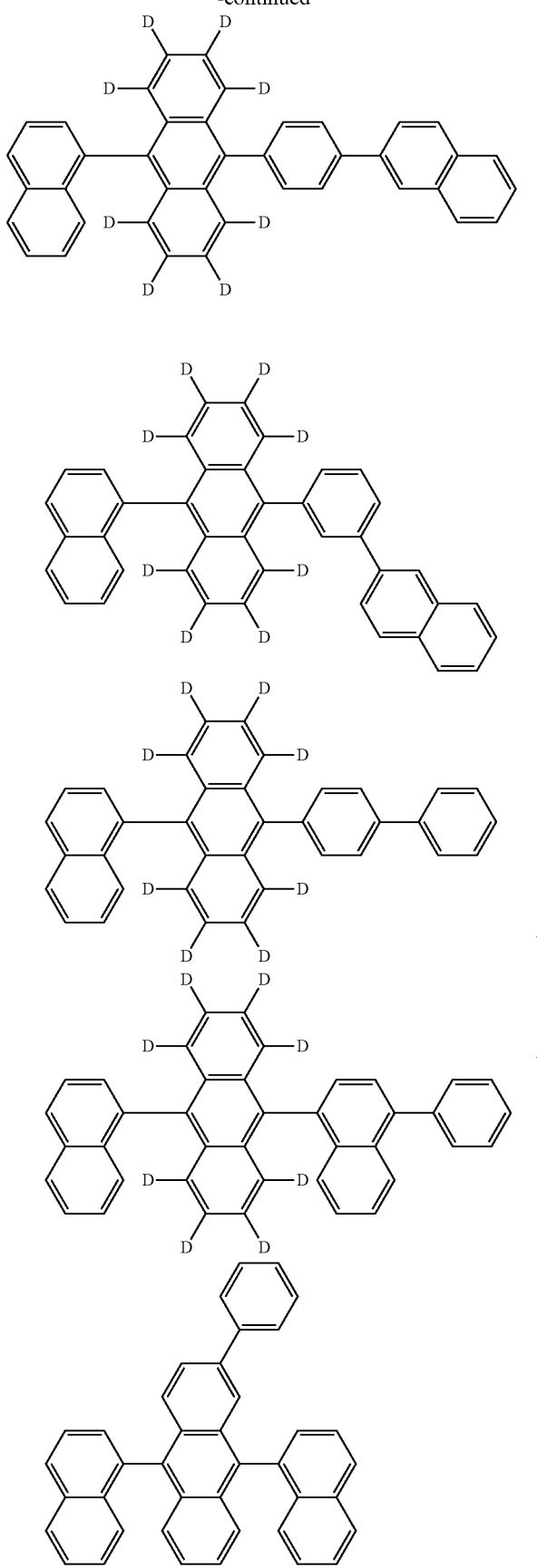

133
-continued
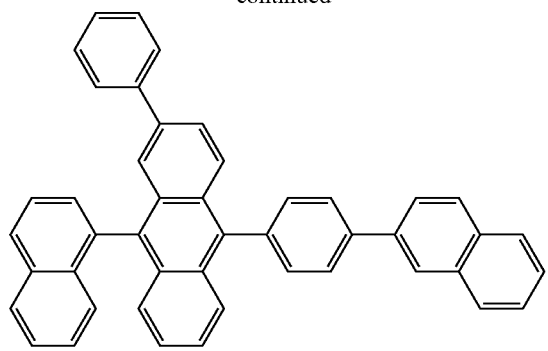
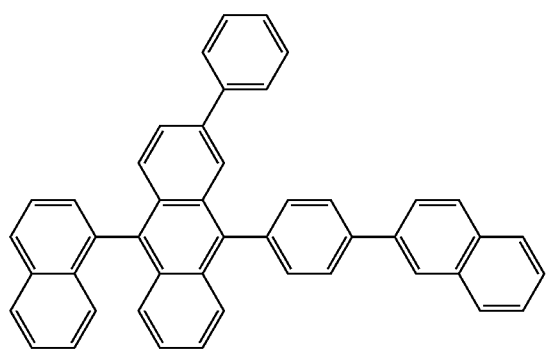
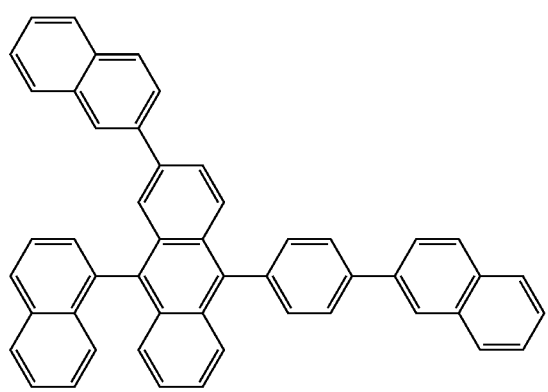
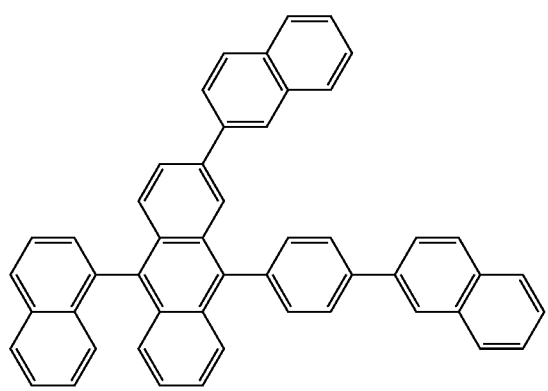
134
-continued
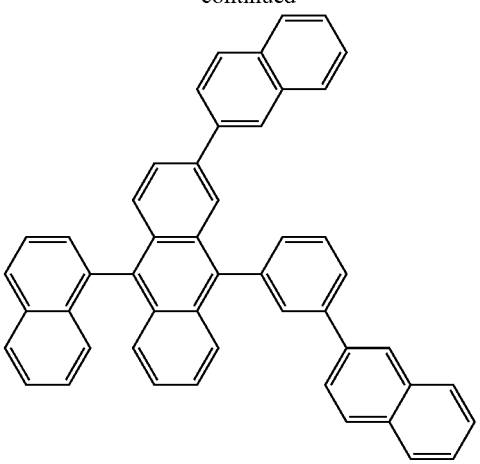
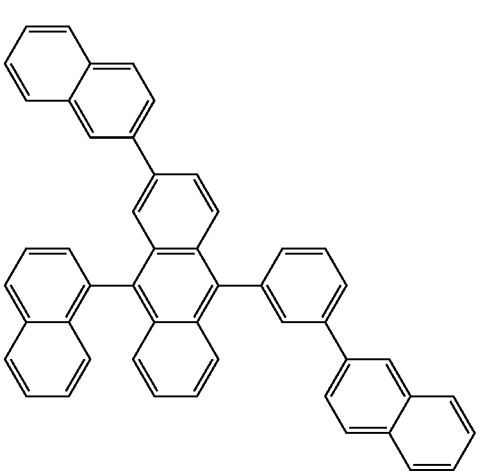
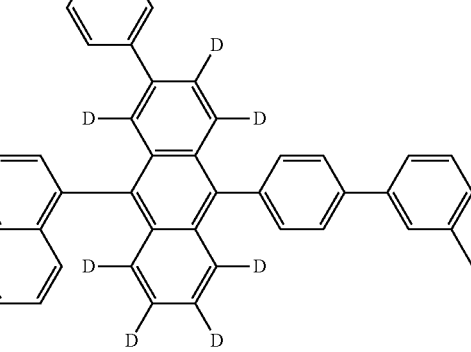

135
-continued
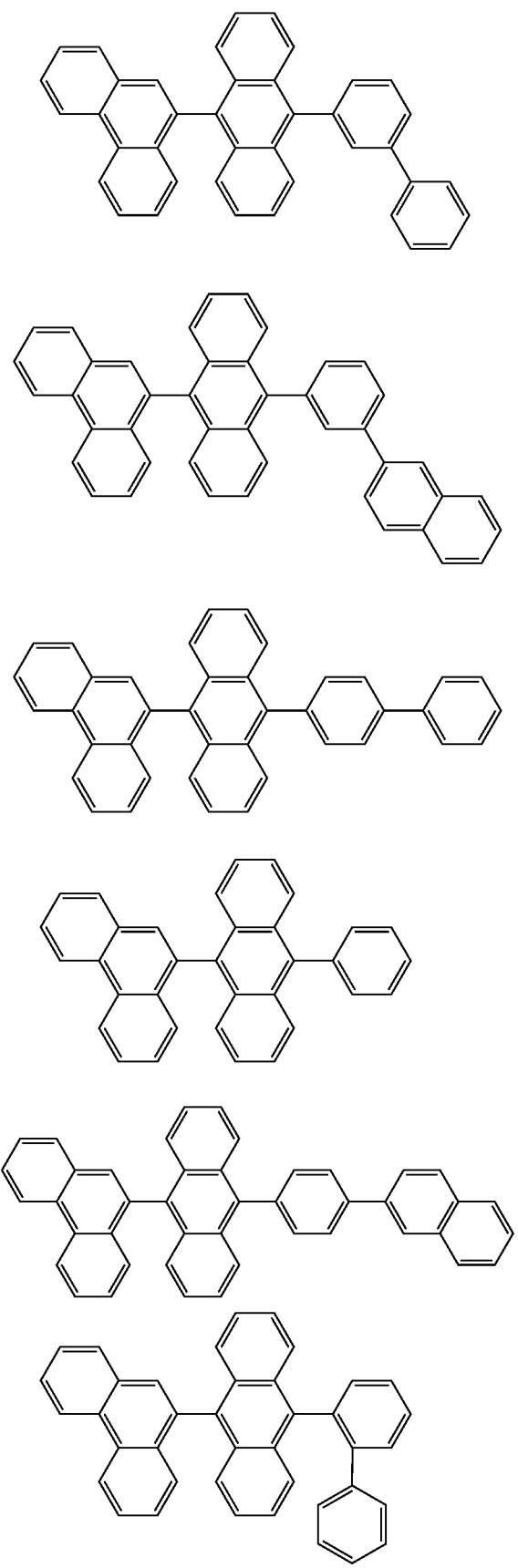
136
-continued
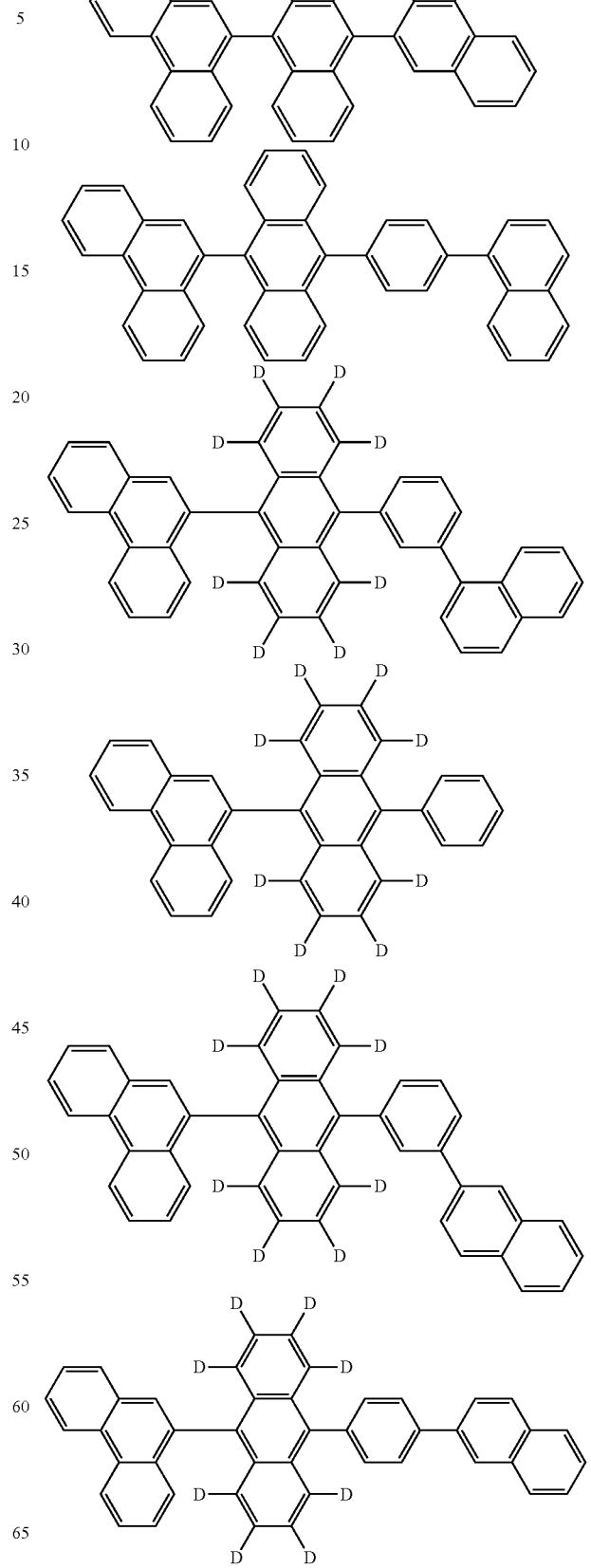

-continued
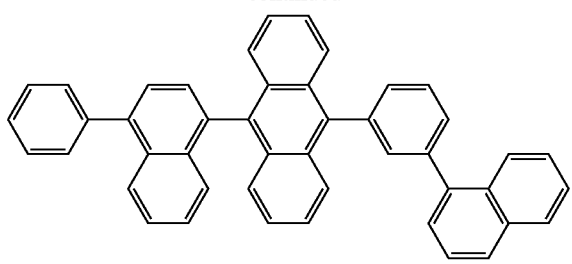
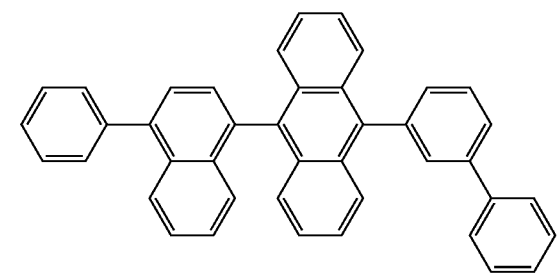
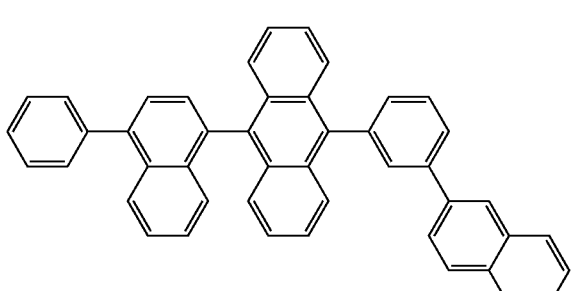
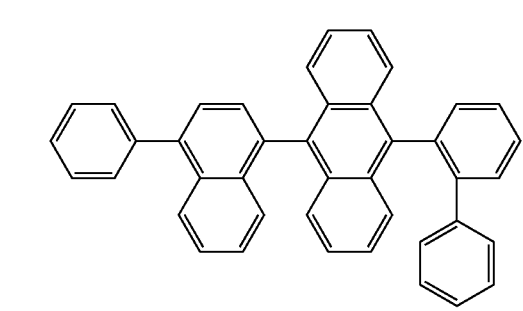
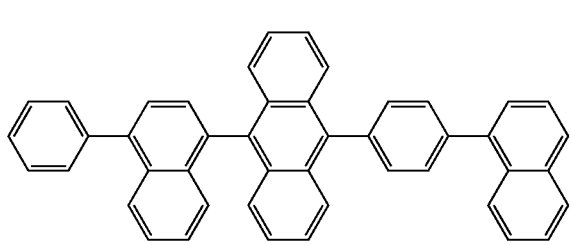
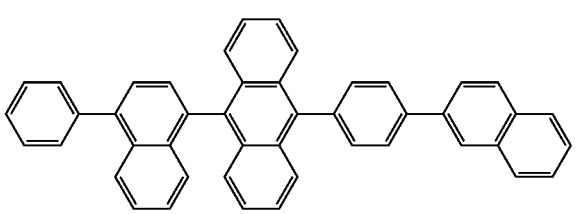
-continued
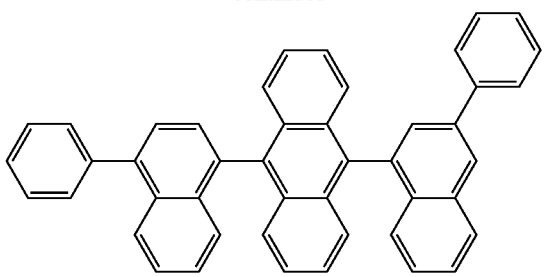

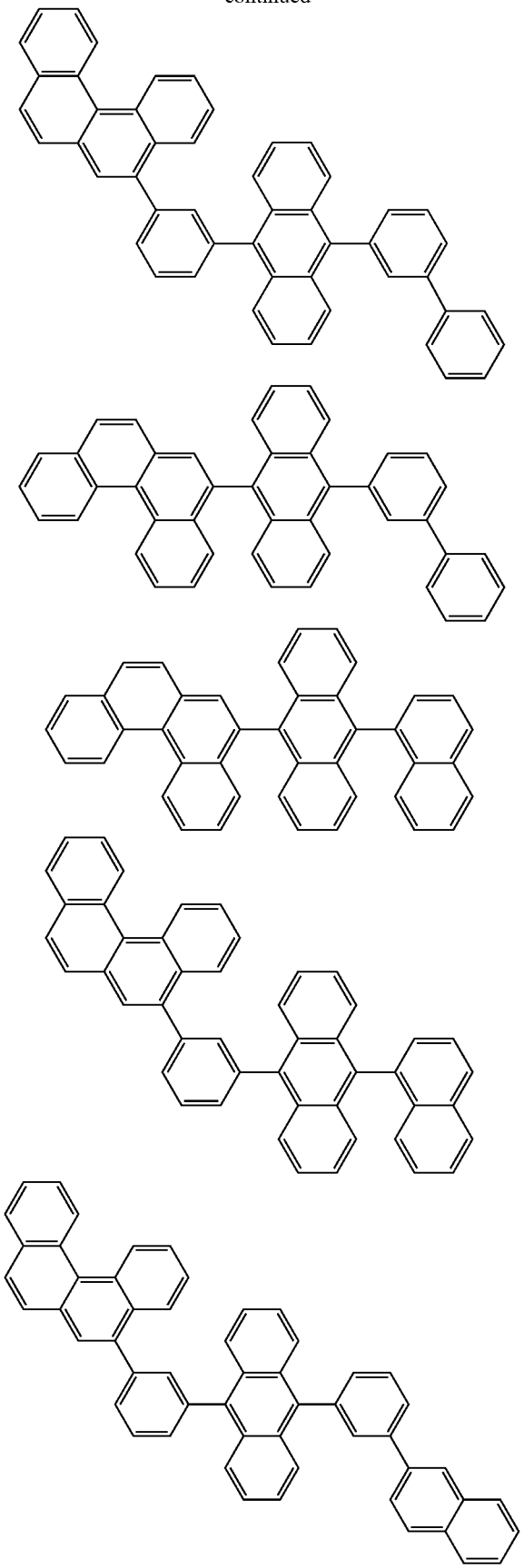
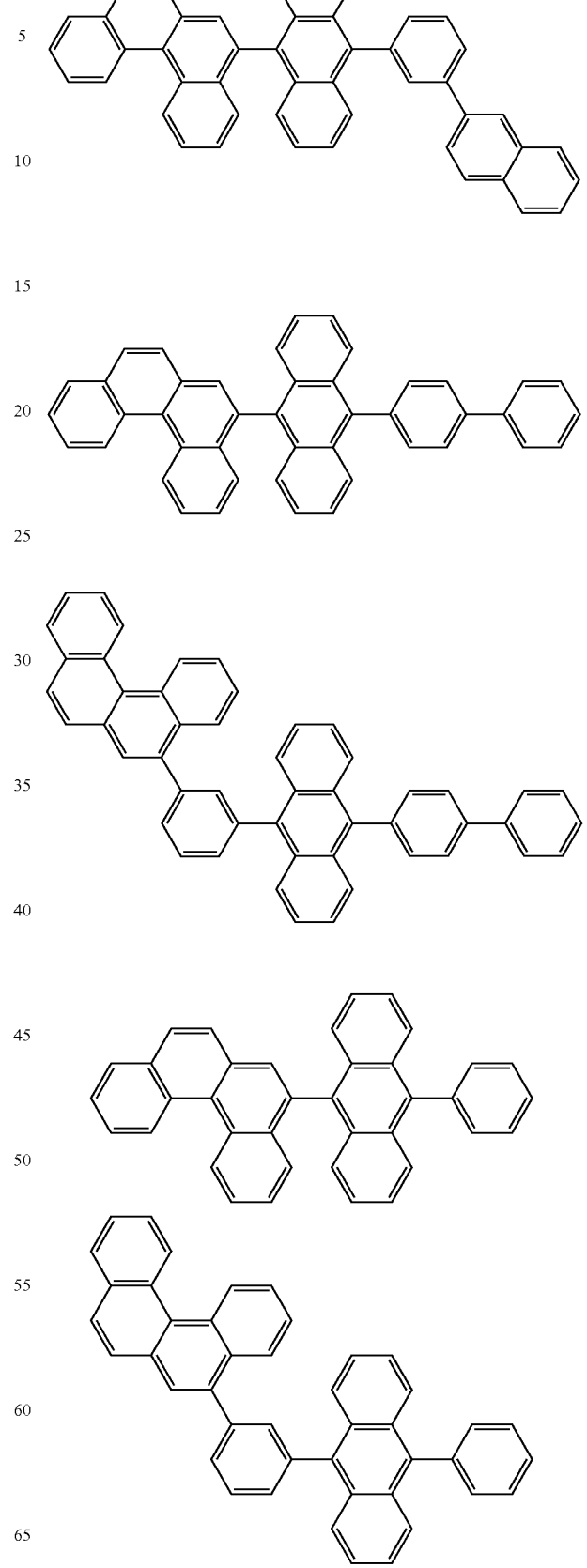

141
-continued
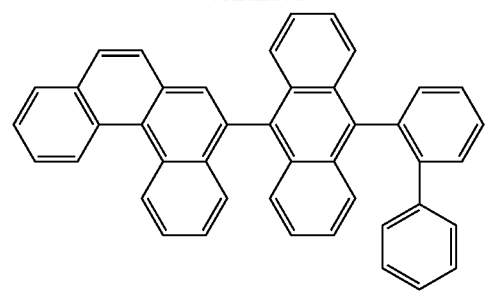
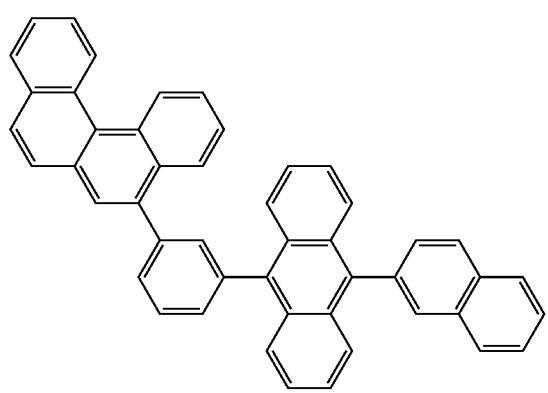
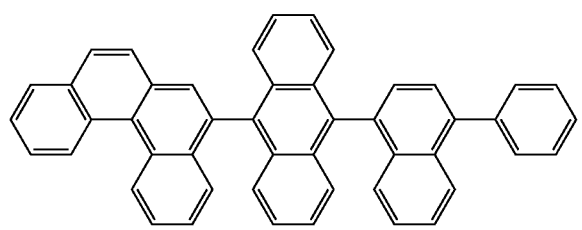
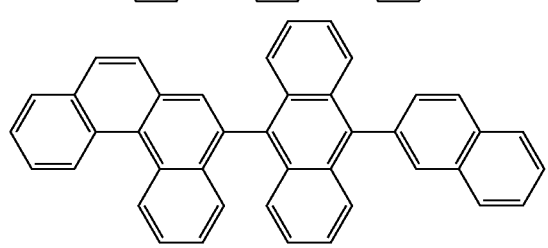
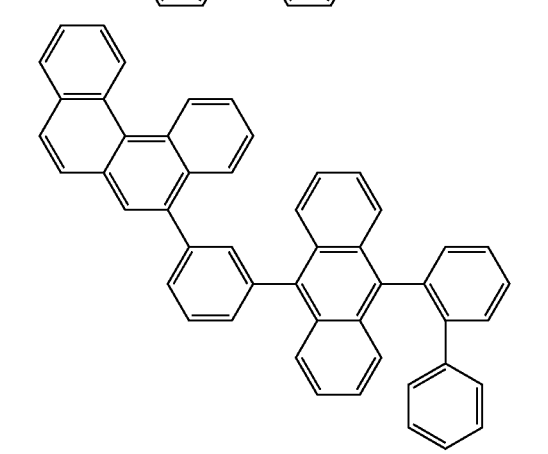
142
-continued
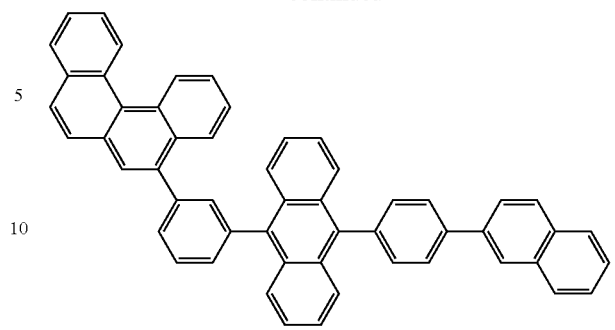
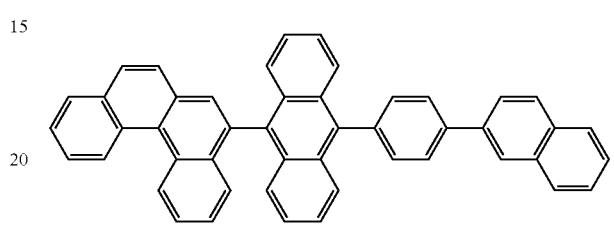
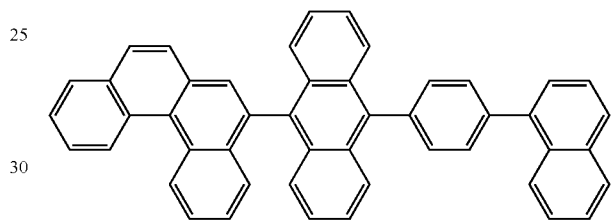
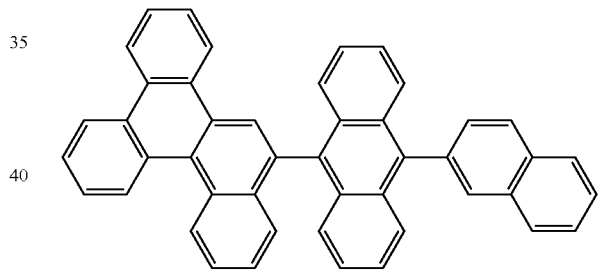
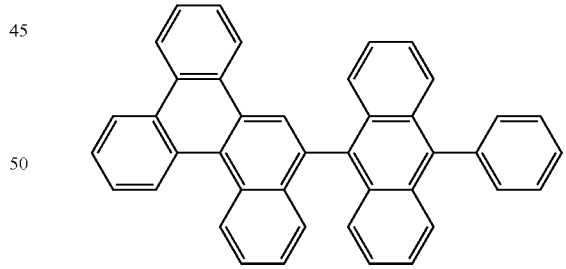
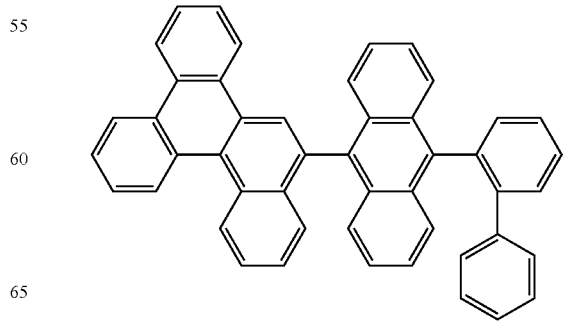

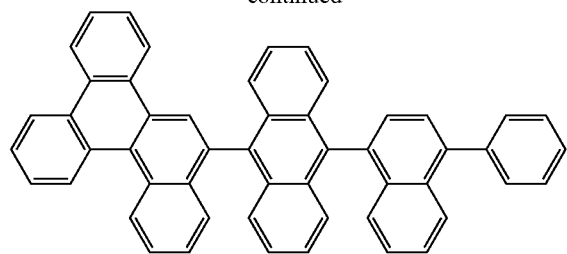
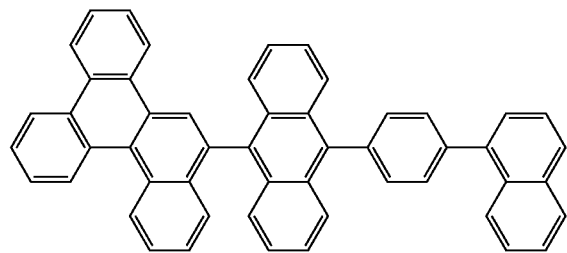
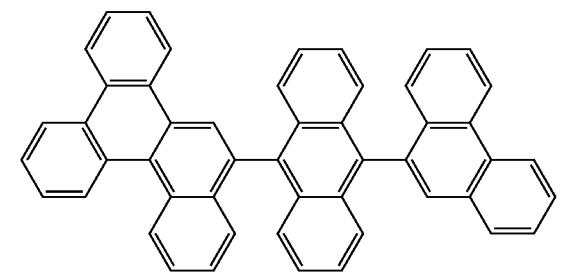
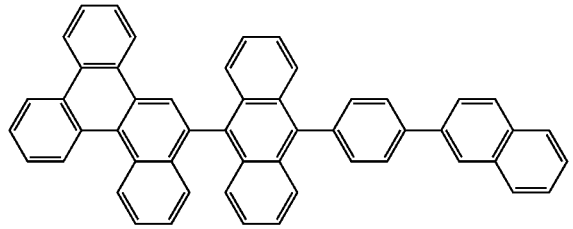
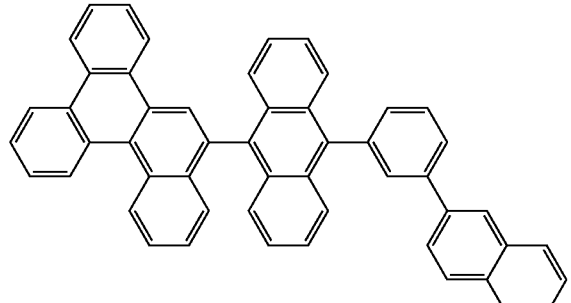
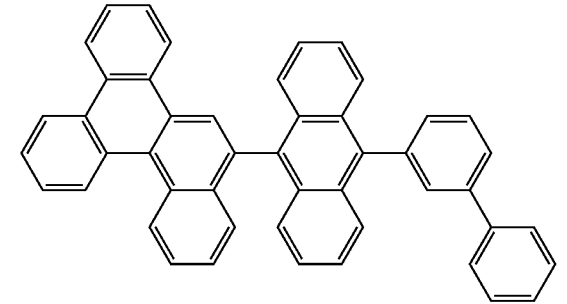
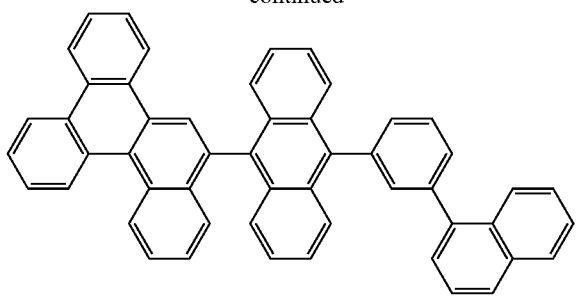
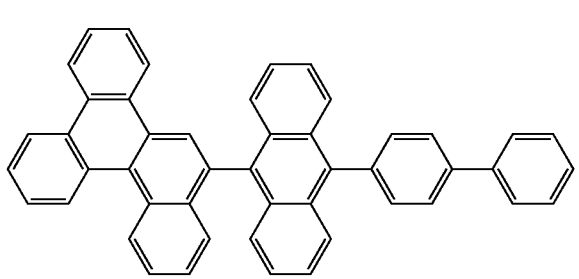
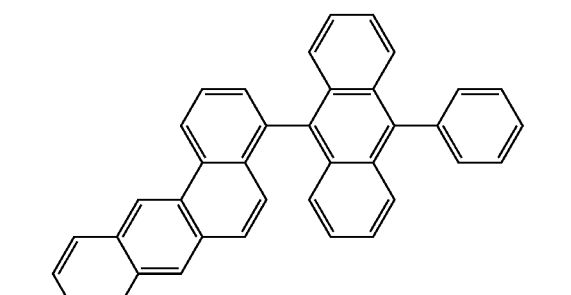
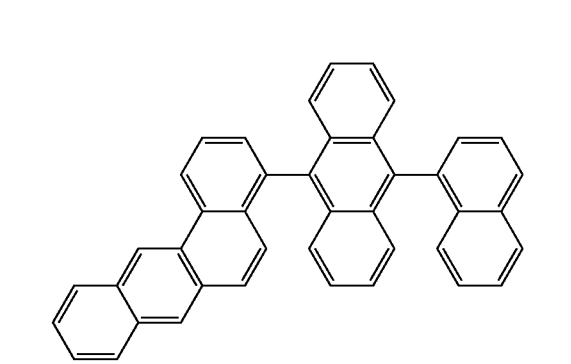
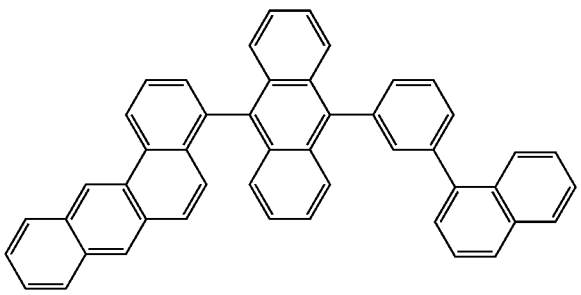

-continued
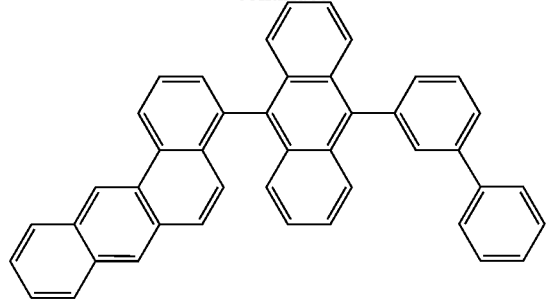
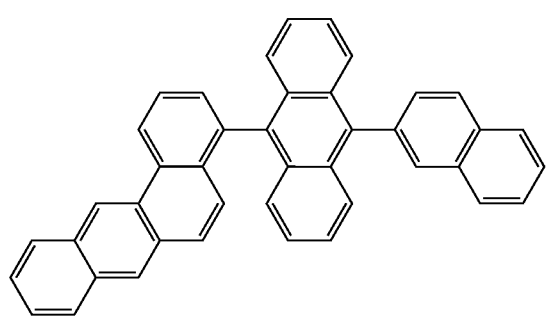
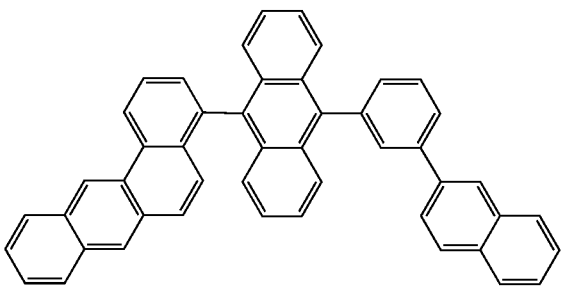
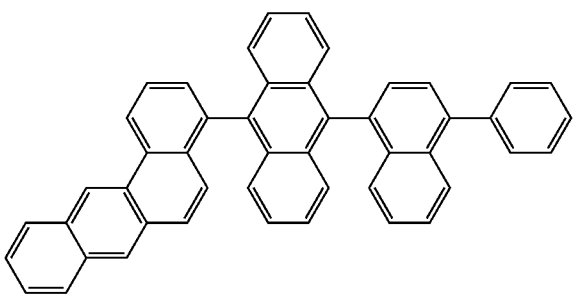
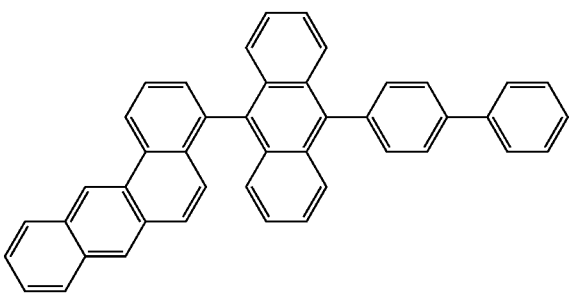
-continued
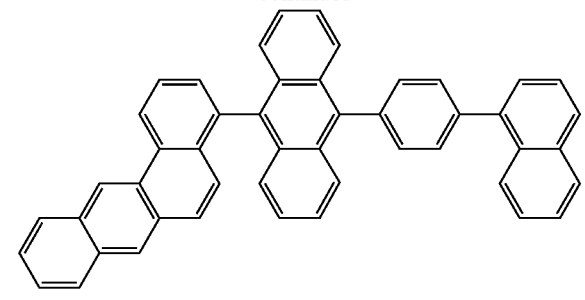
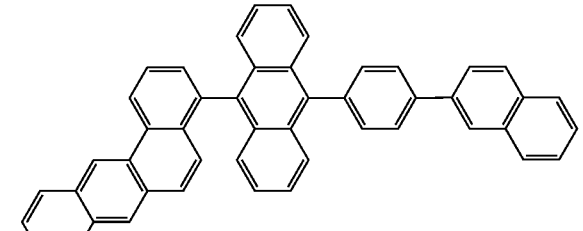
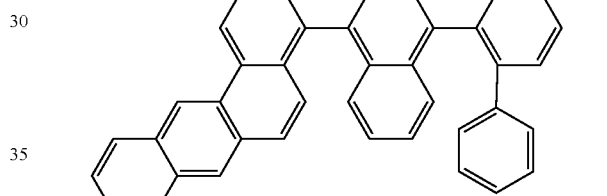
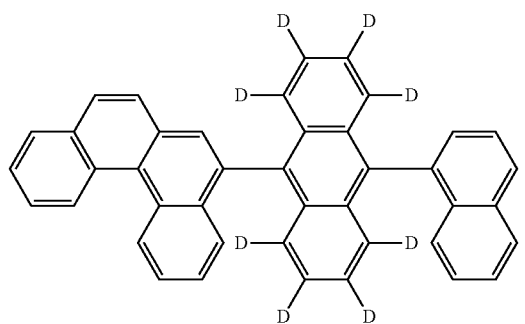
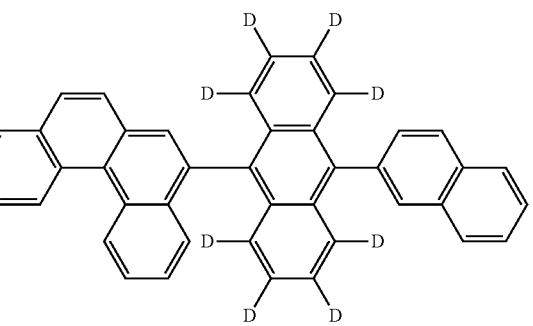

147
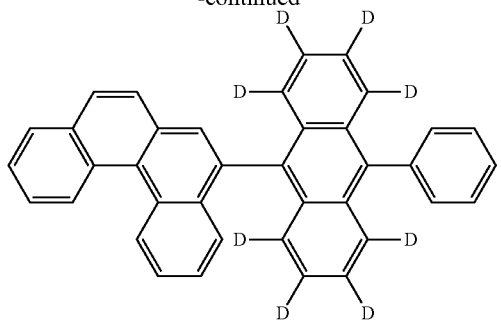
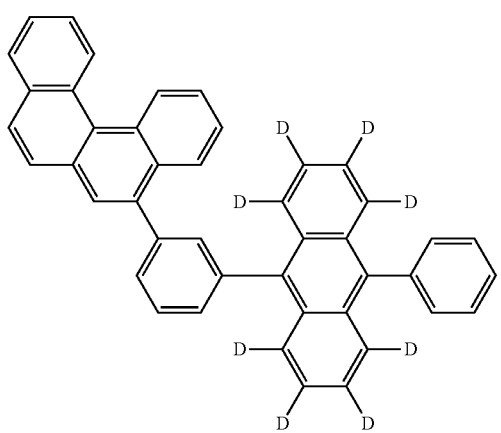
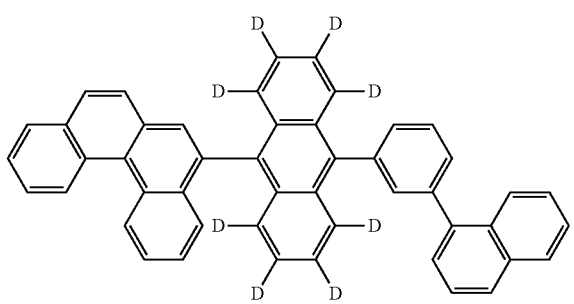
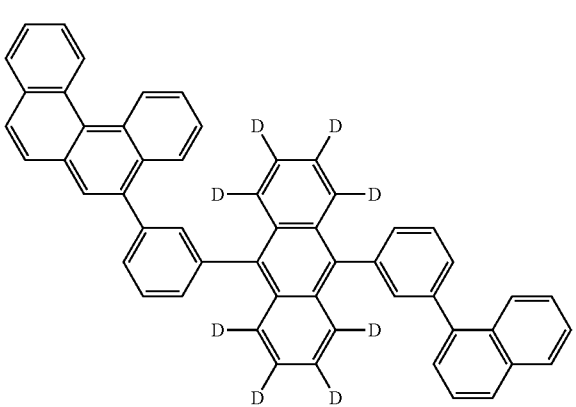
148
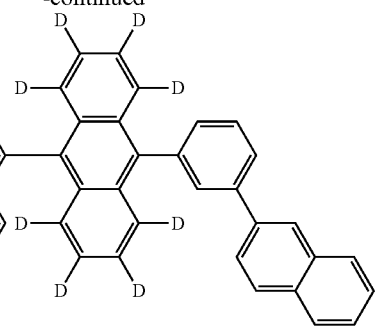
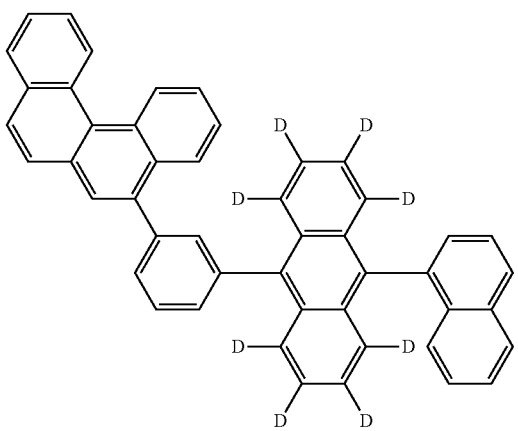
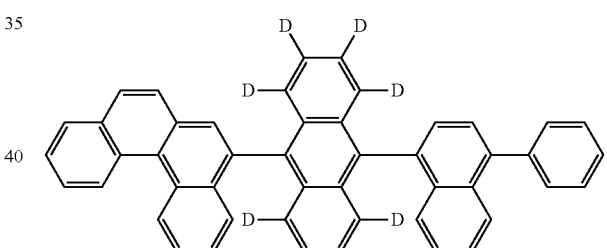

149
-continued
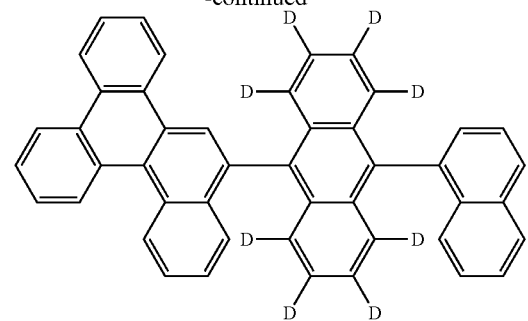
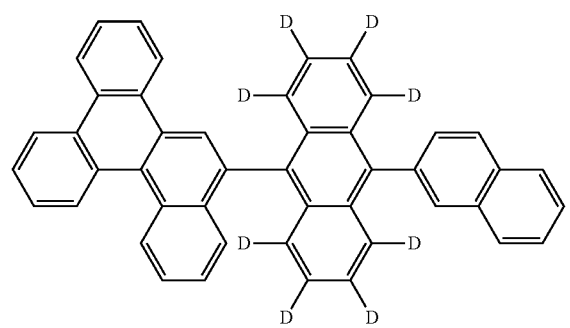
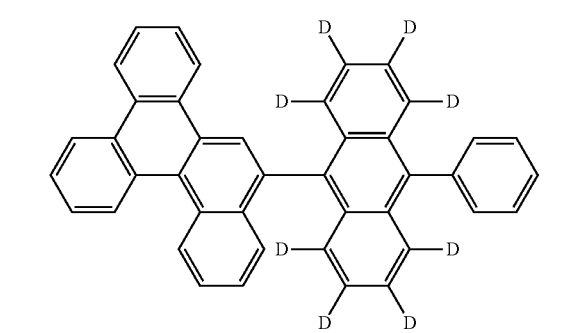
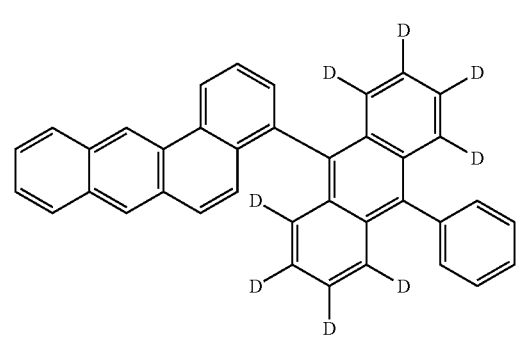
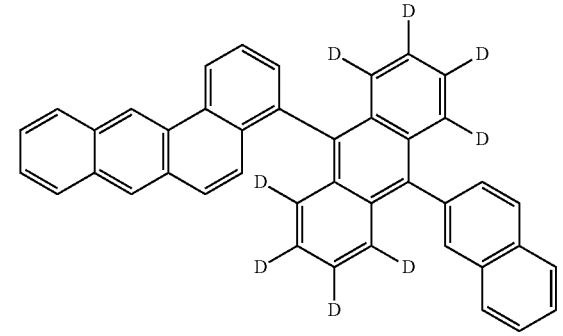
150
-continued
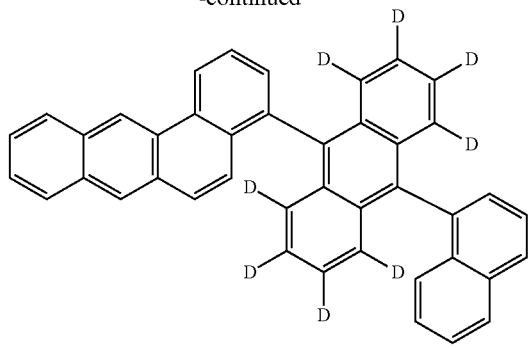
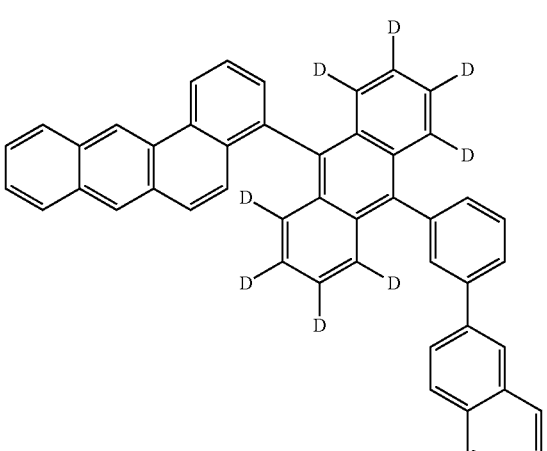
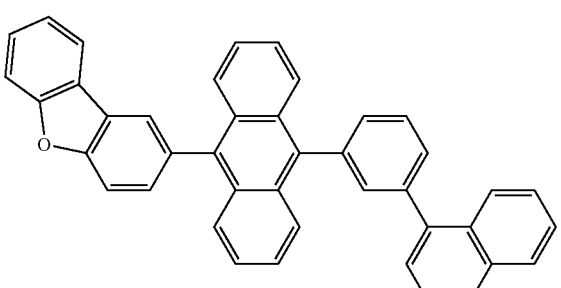
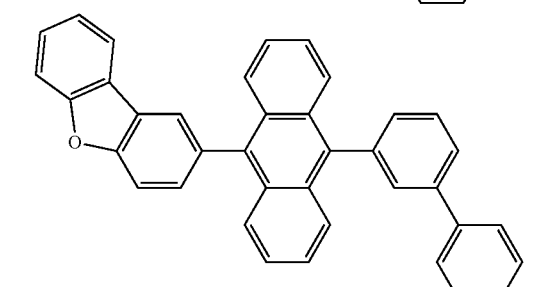
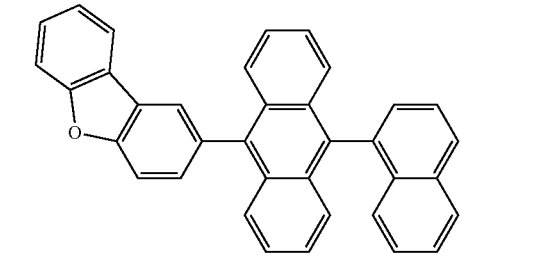

151
-continued
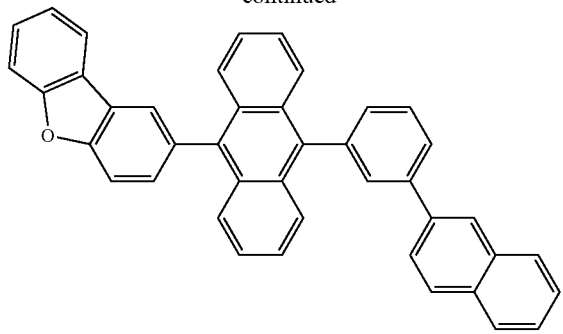
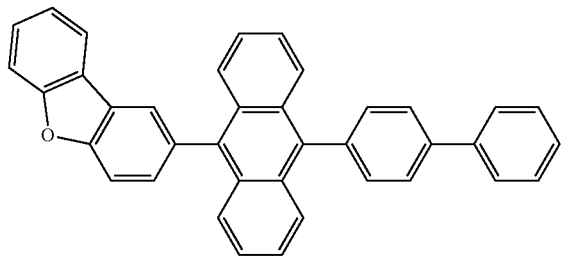
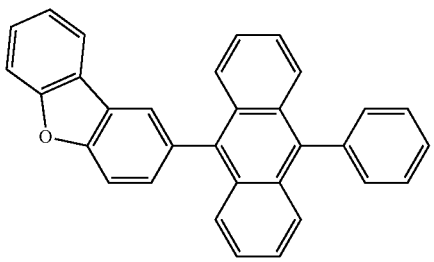
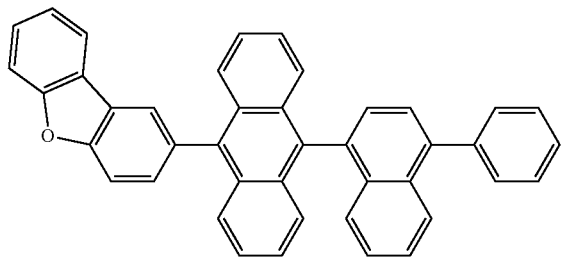
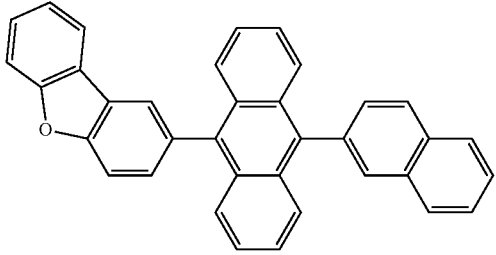
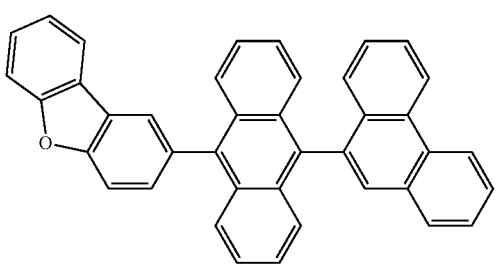
152
-continued
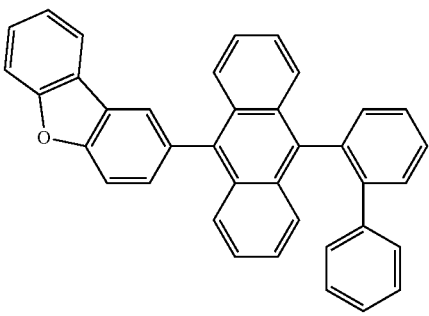
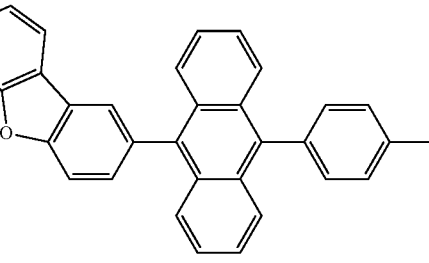
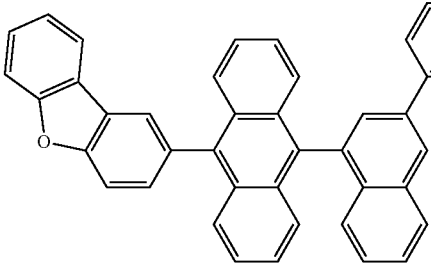
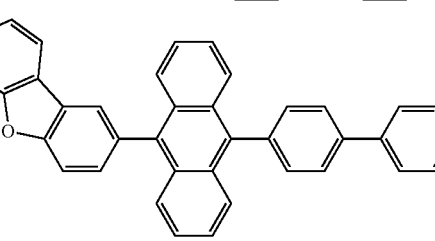
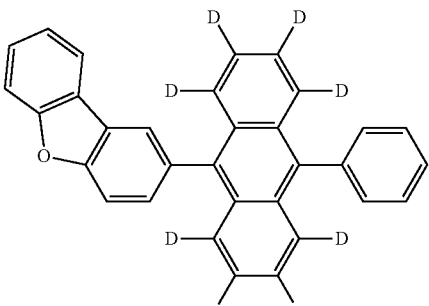
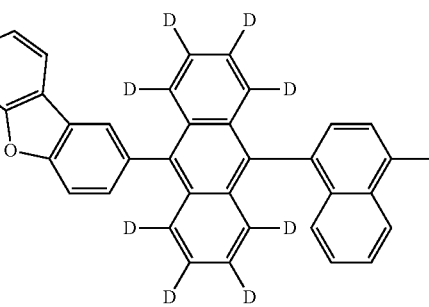

153
-continued
154
-continued
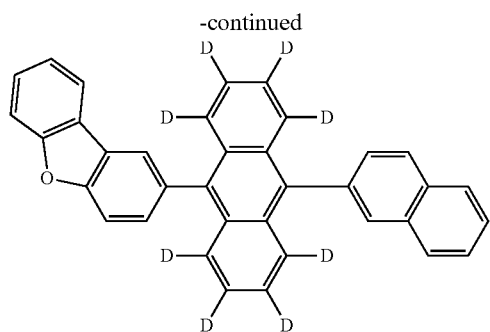
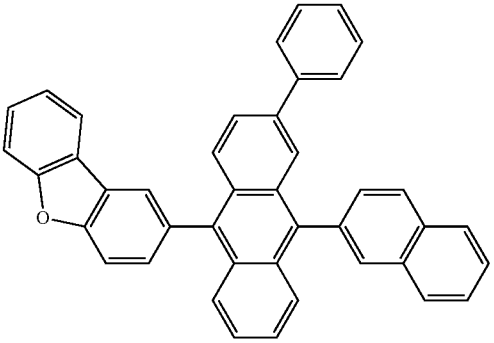
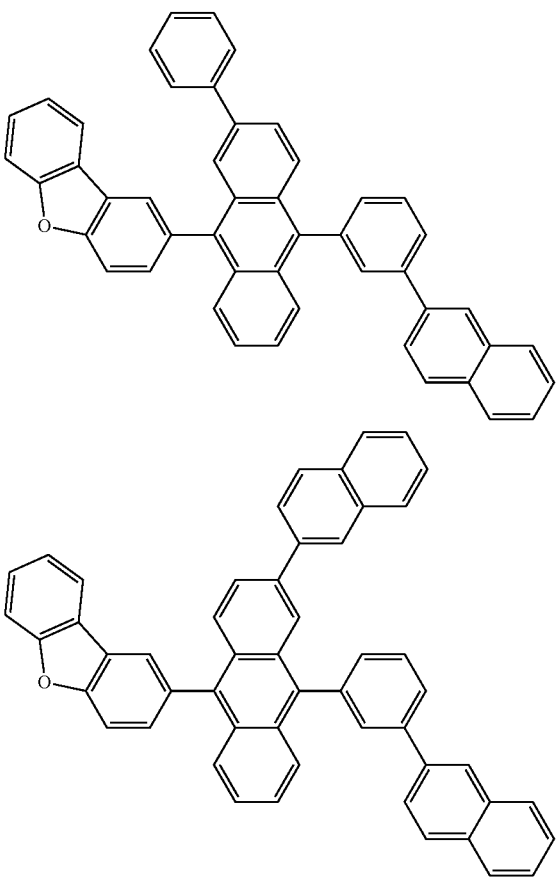

155
-continued
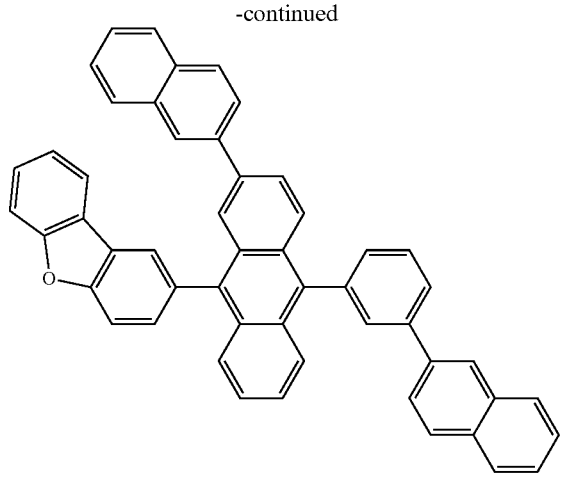
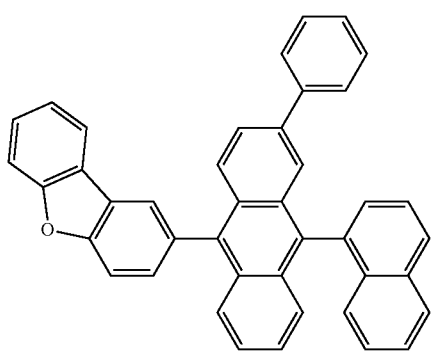
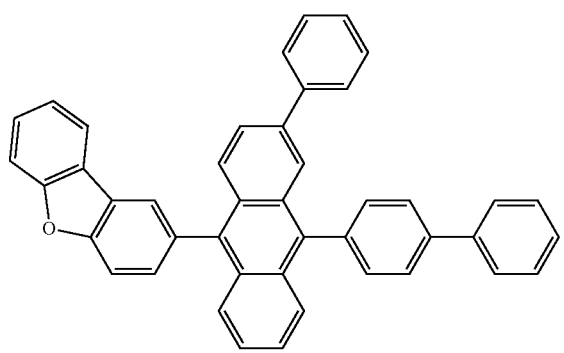
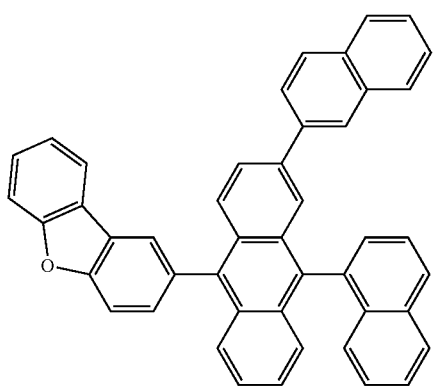
156
-continued
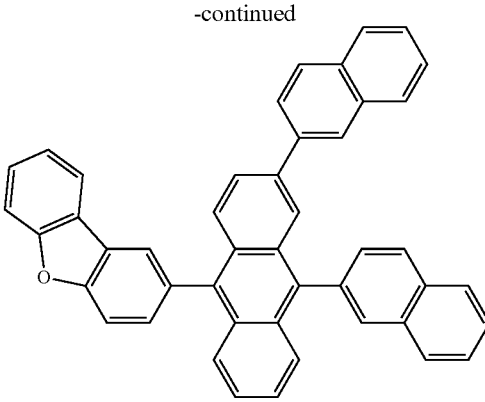
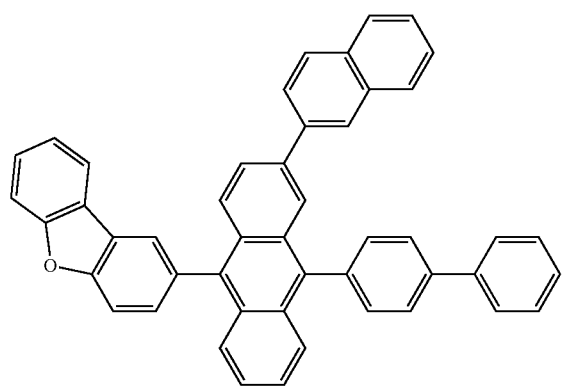
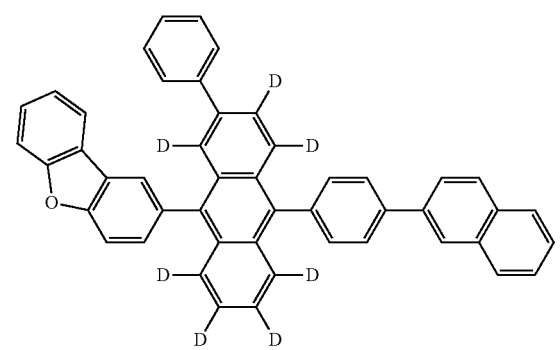
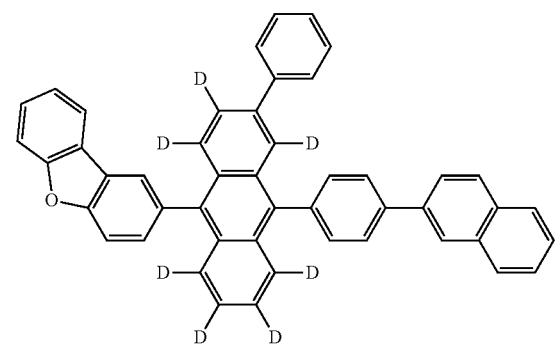

157
-continued
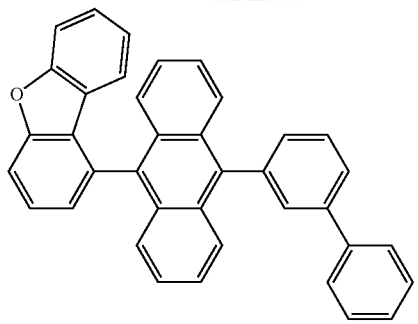
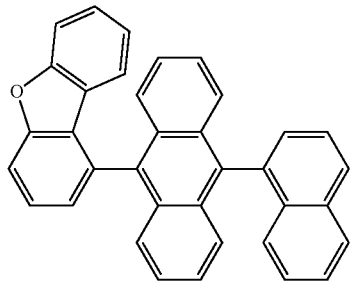
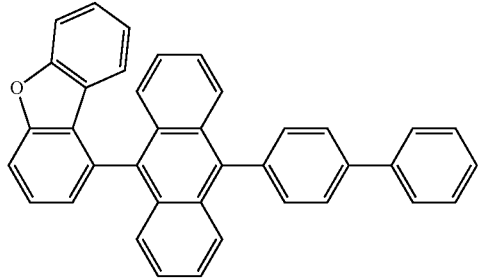
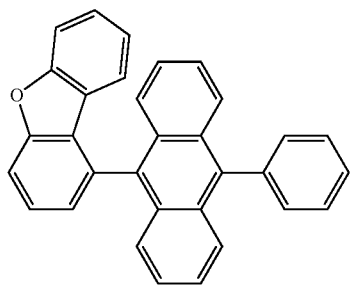
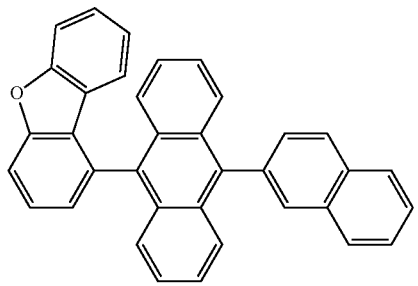
158
-continued
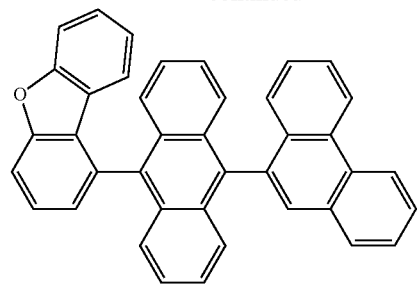
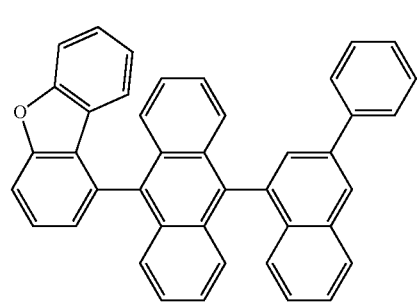
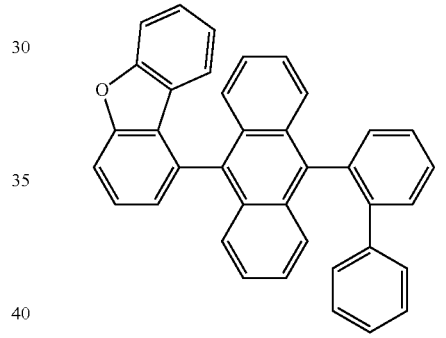
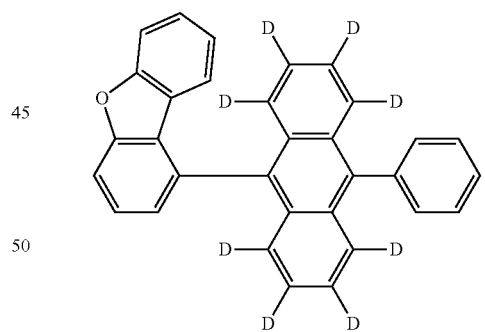
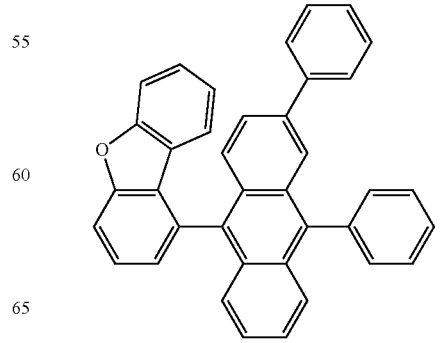

159
-continued
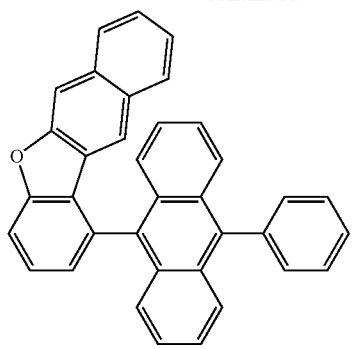
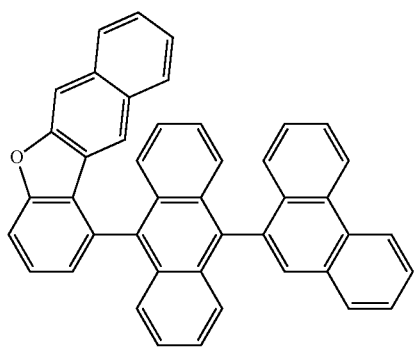
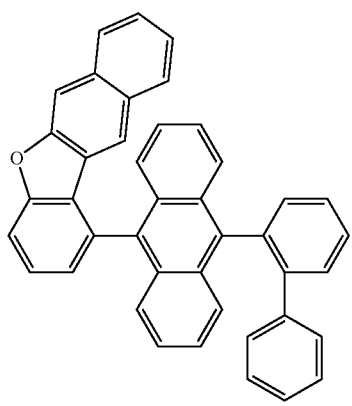
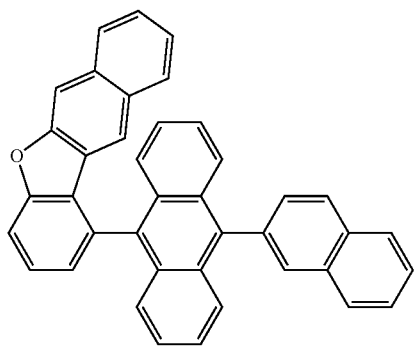
160
-continued
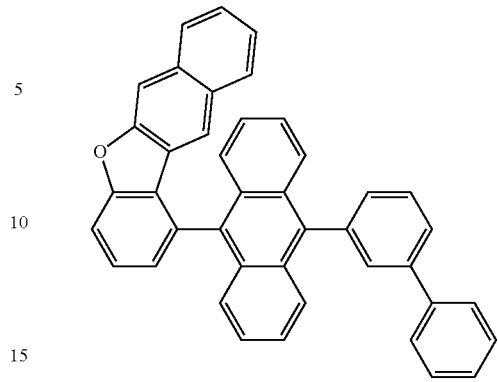
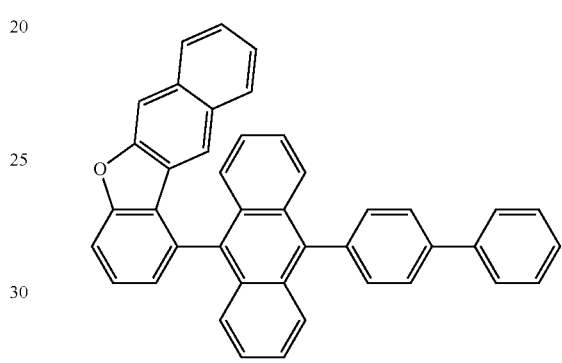
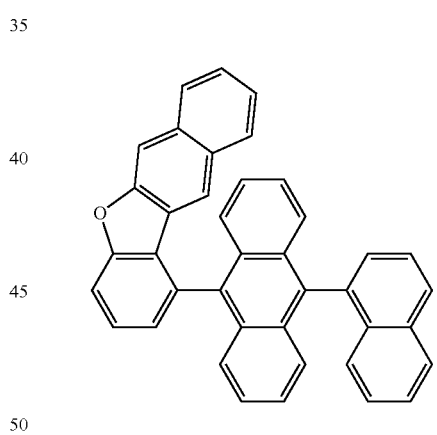
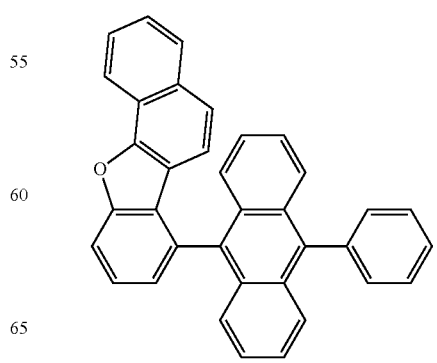

161
-continued
162
-continued
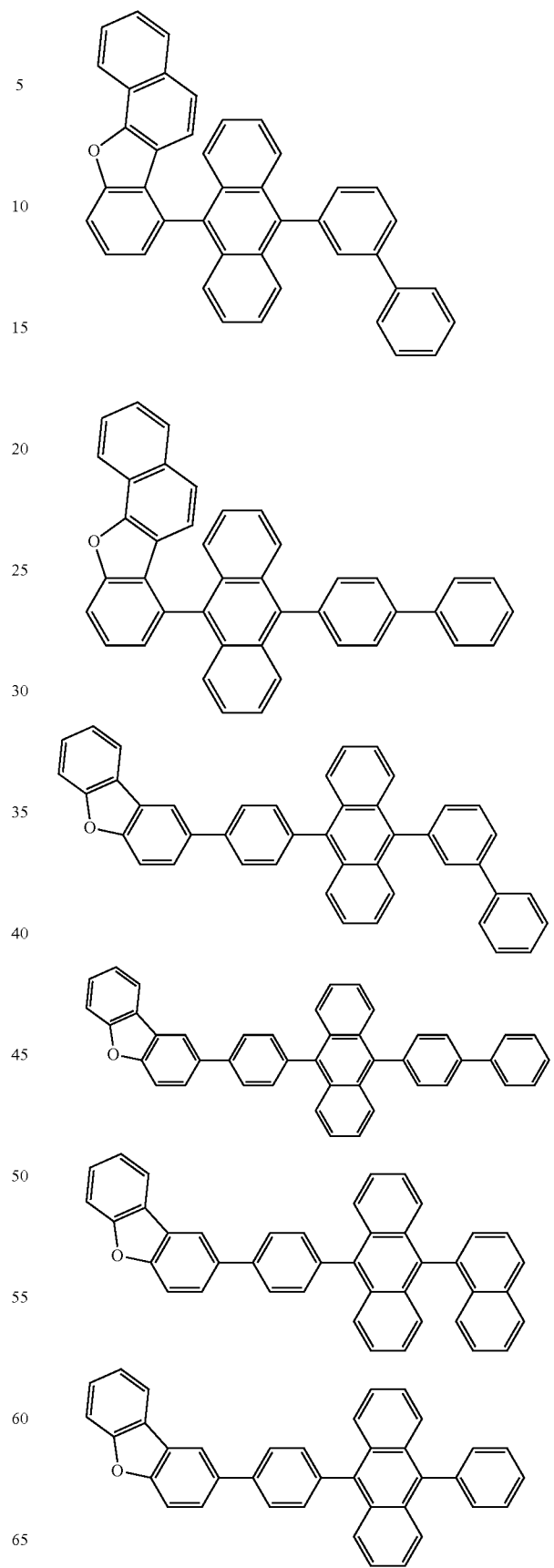

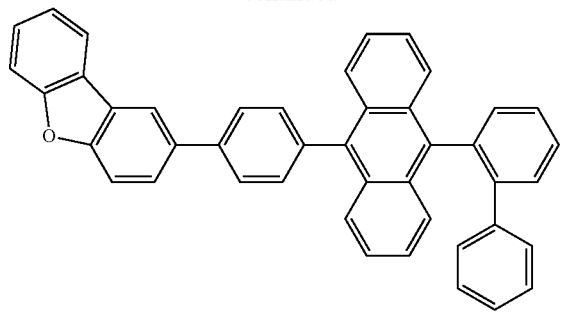
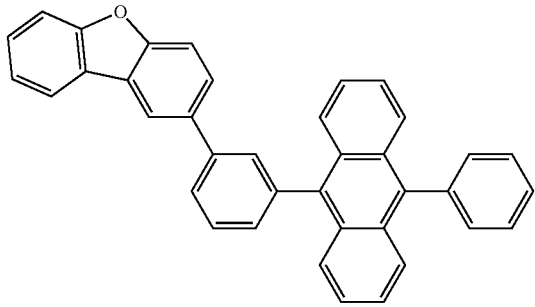
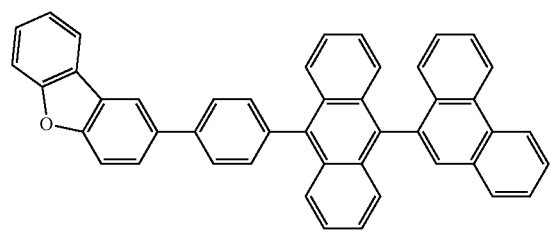
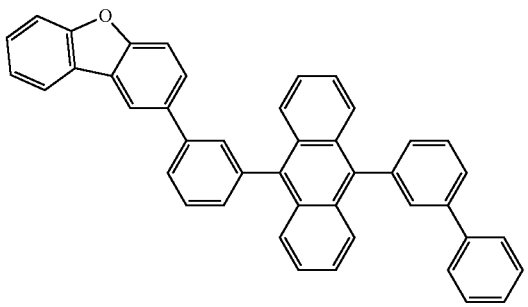
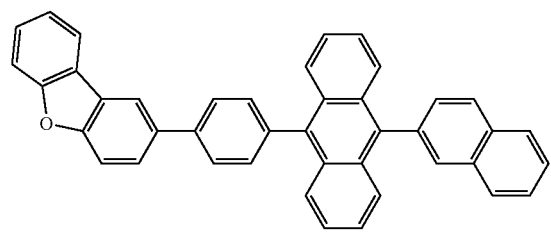
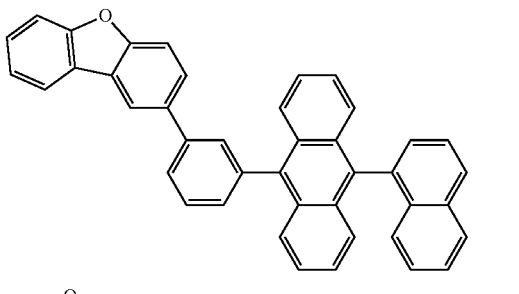
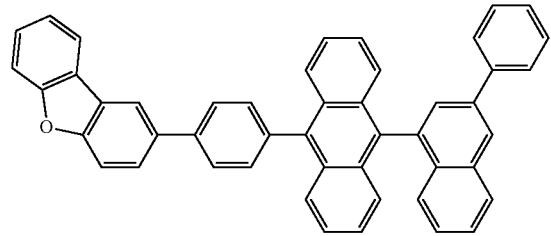
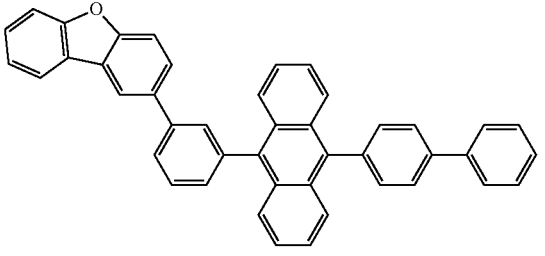
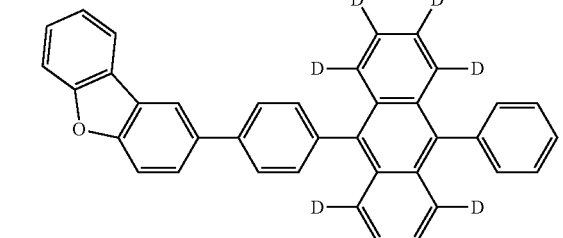
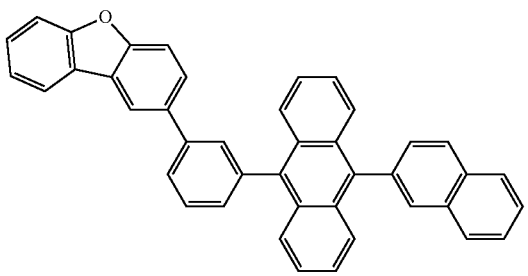
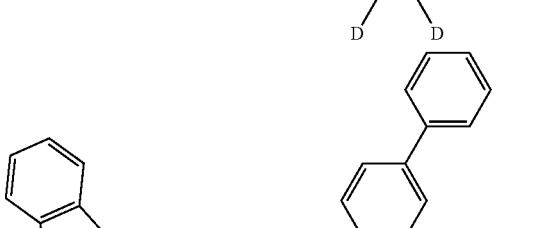
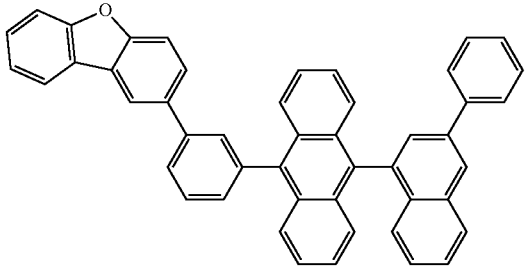
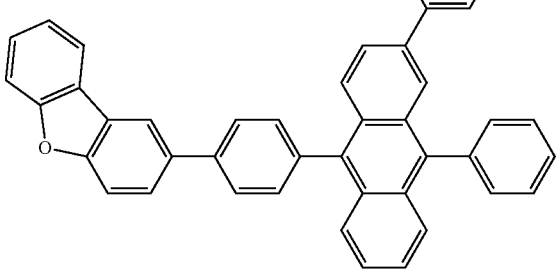

165
-continued
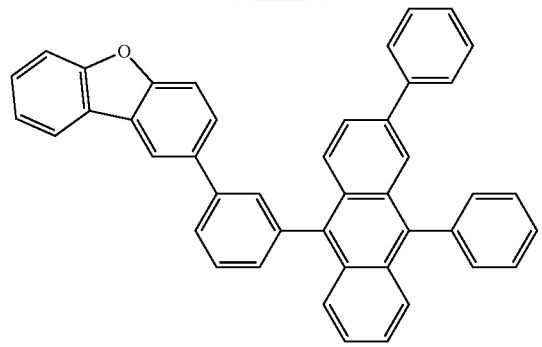
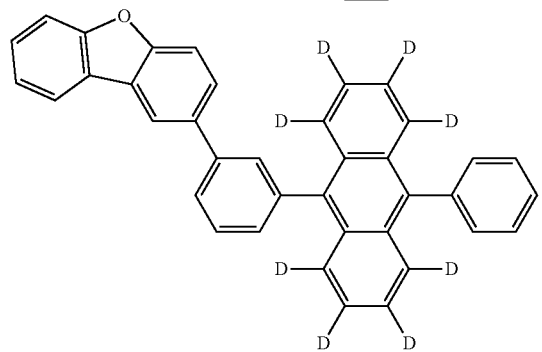
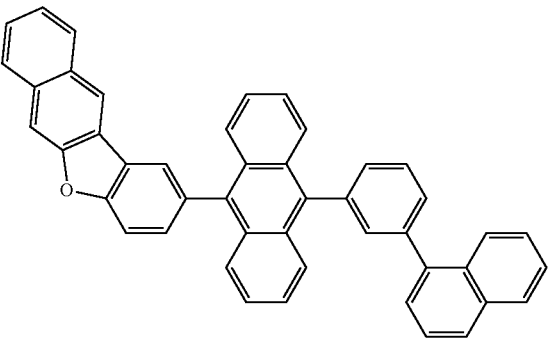
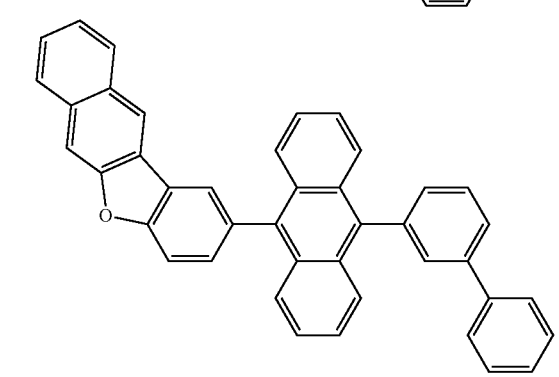
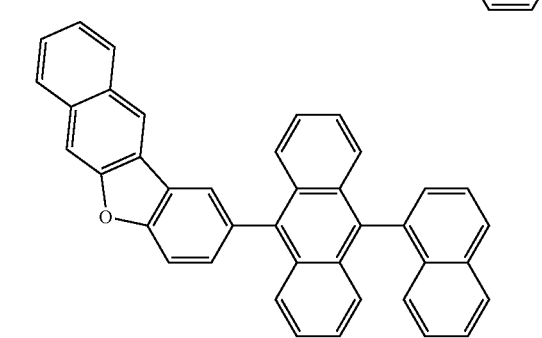
166
-continued
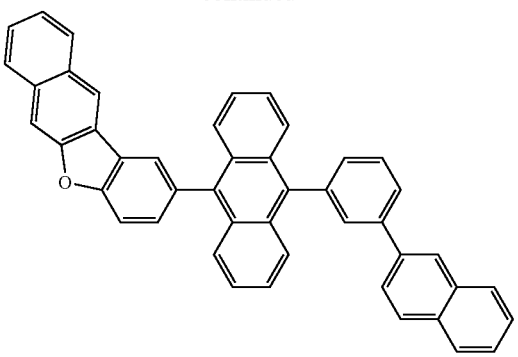
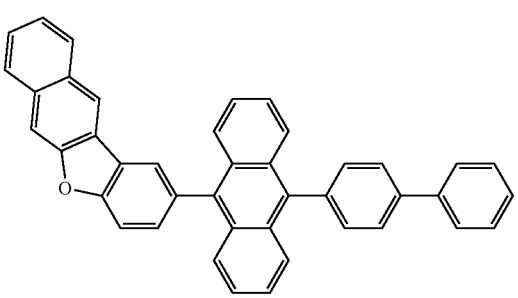
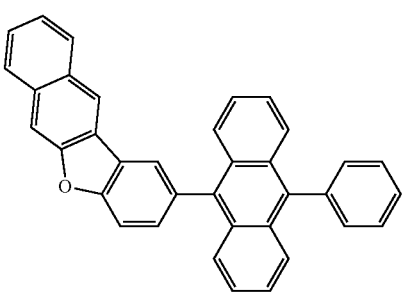
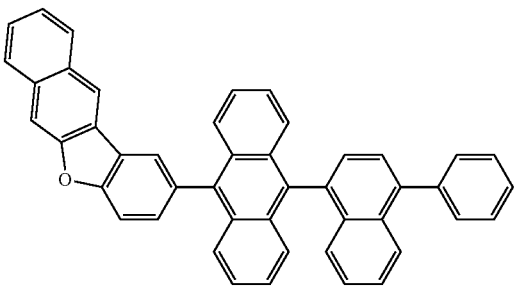
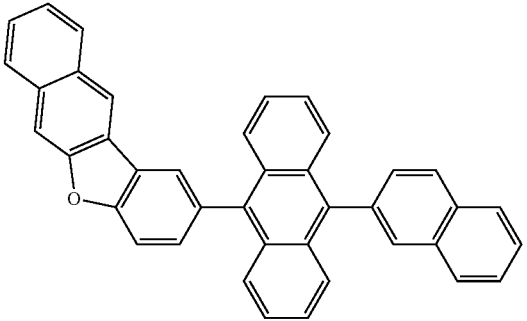

167
-continued
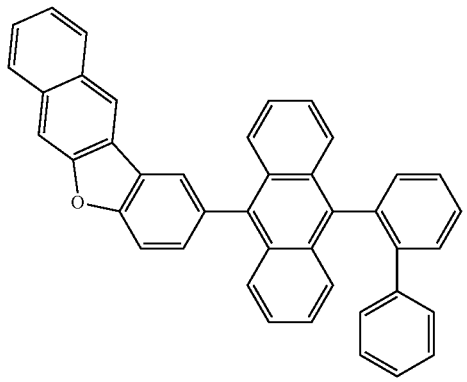
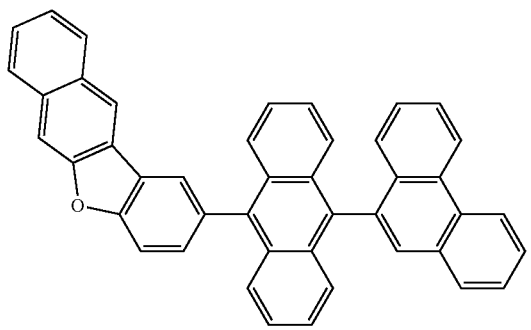
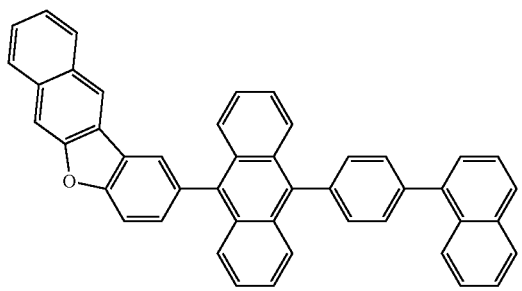
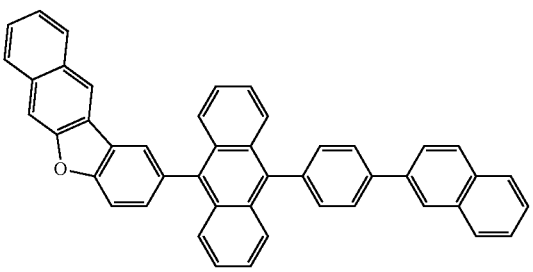
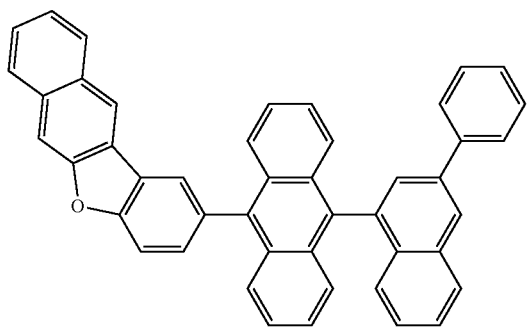
168
-continued
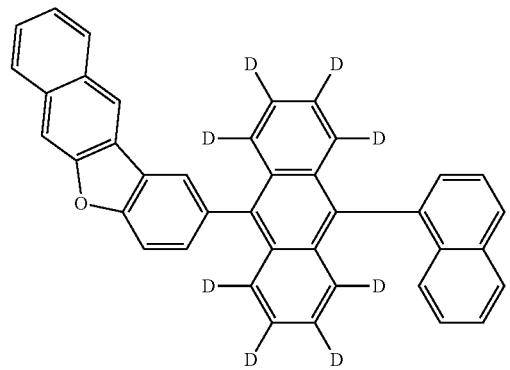
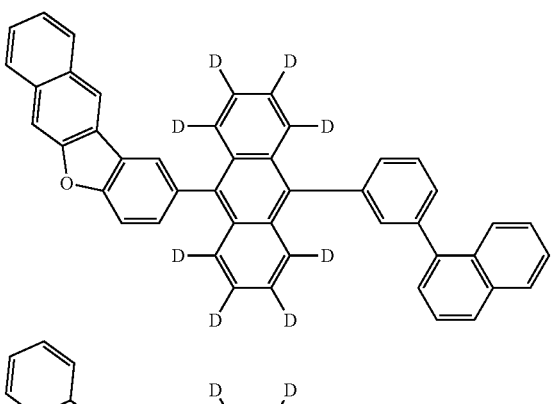
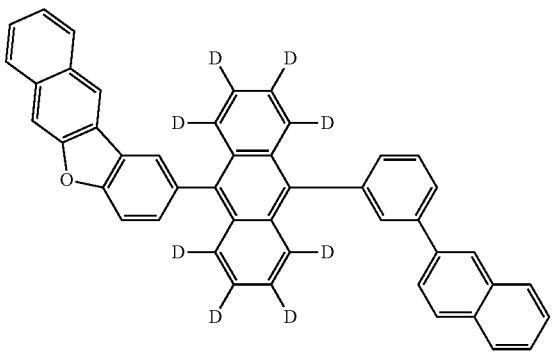
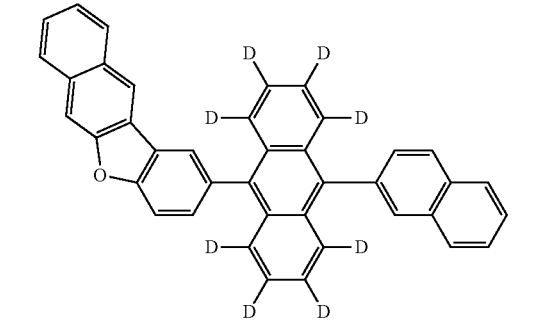
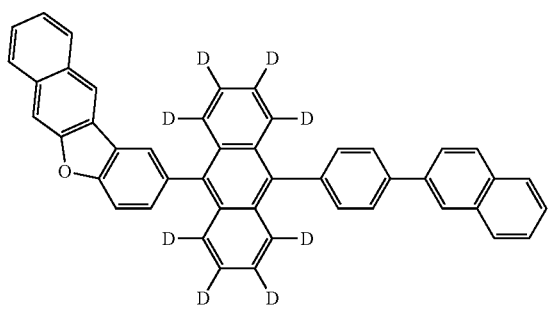

169
-continued
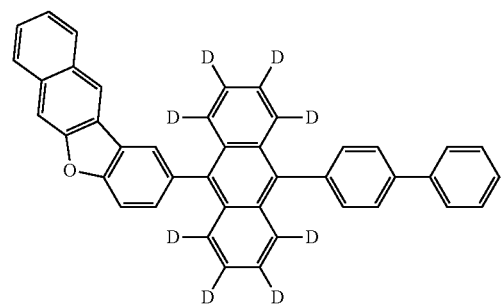
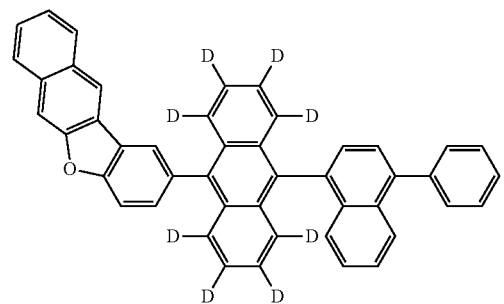
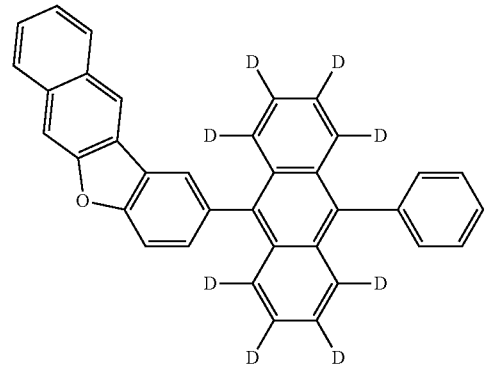
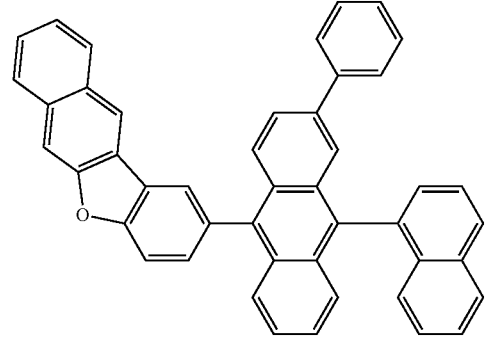
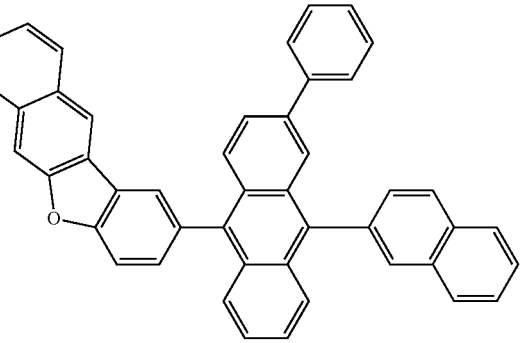
170
-continued
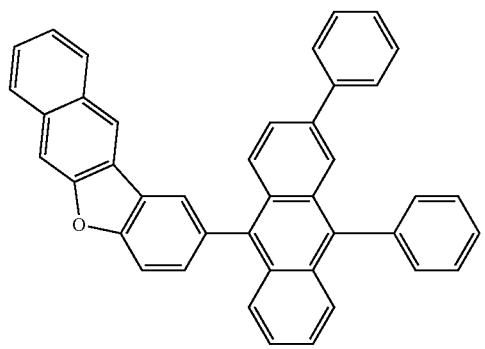
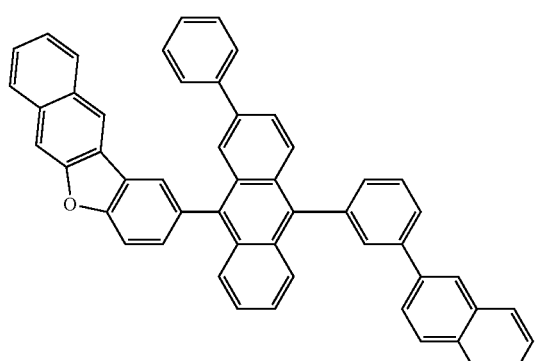
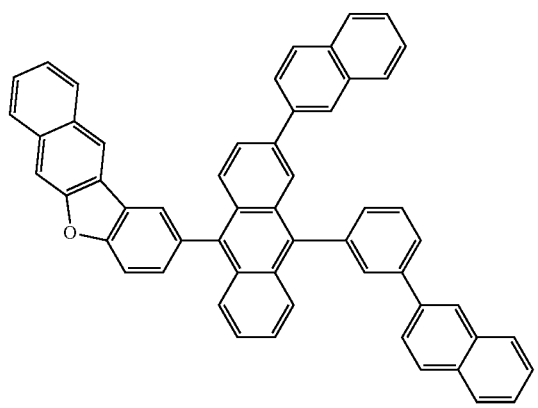
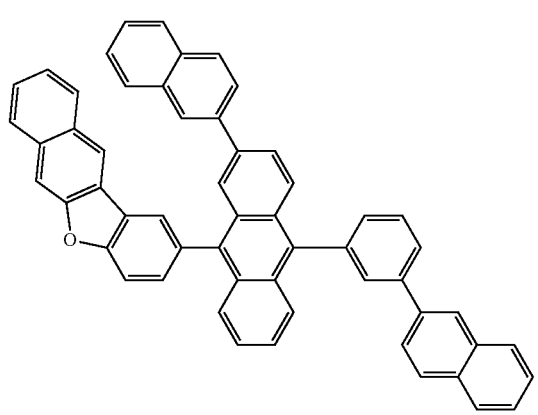

171
-continued
172
-continued
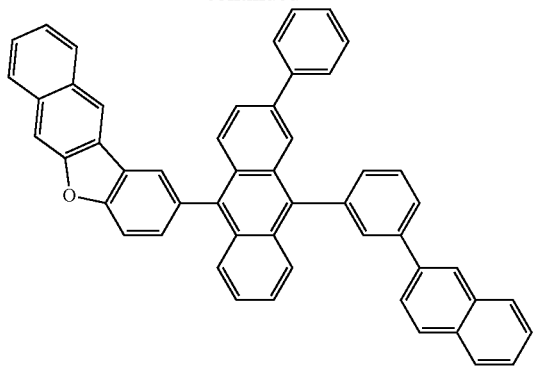
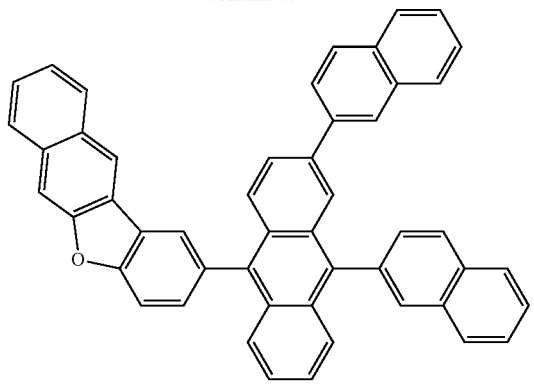
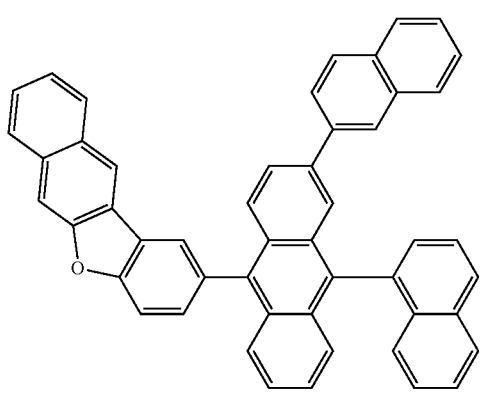
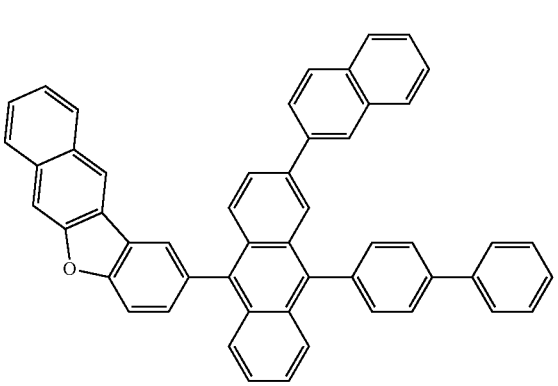
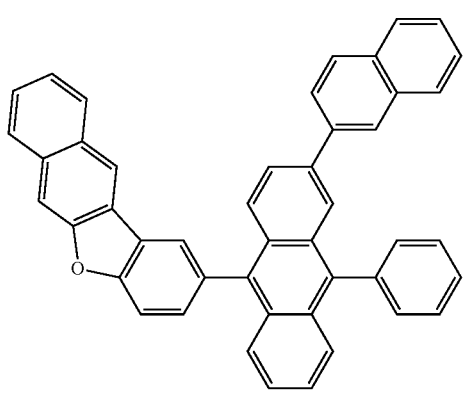
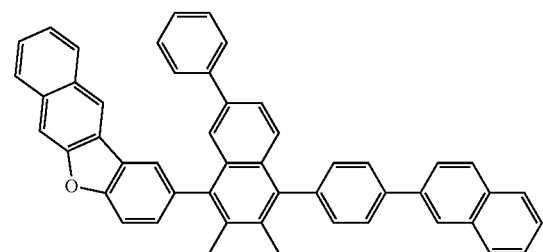
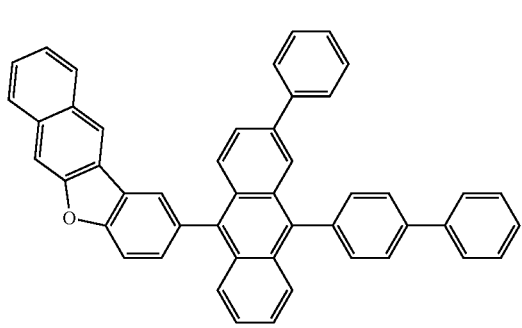
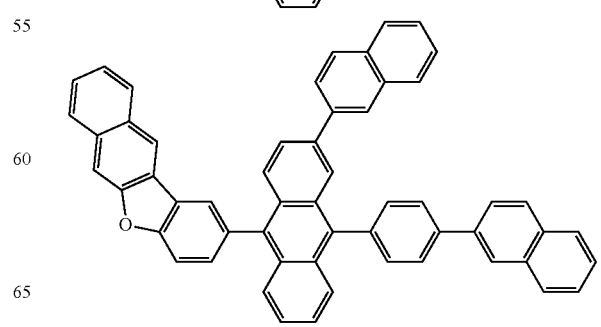

173
-continued
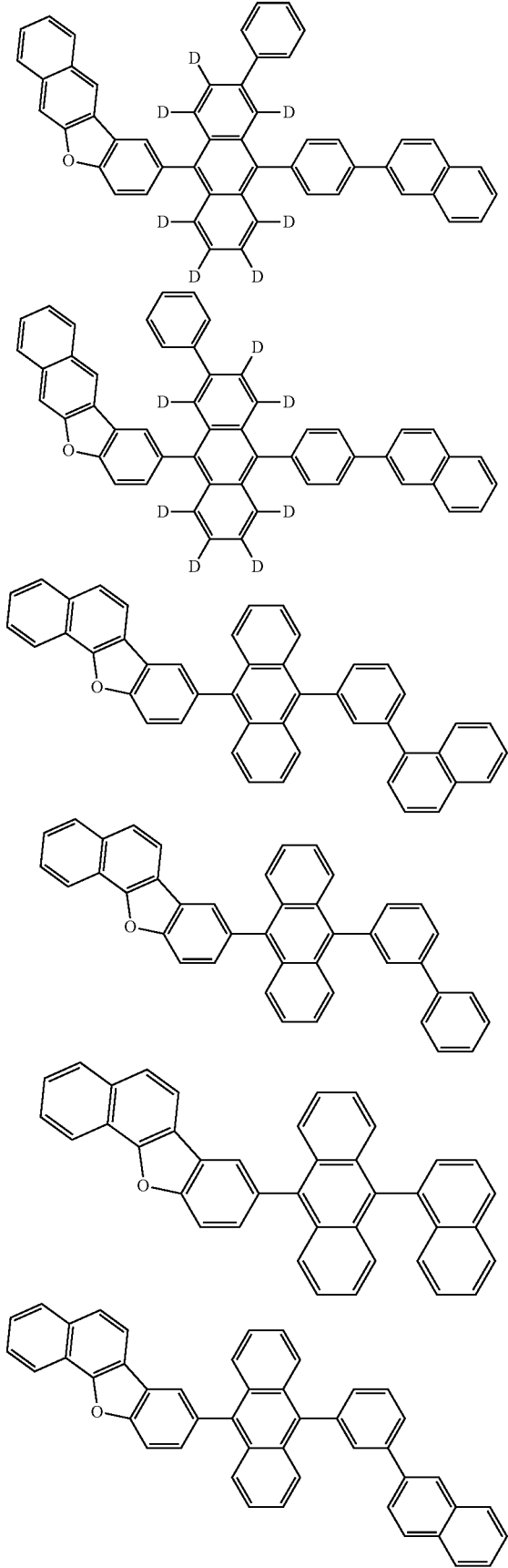
174
-continued
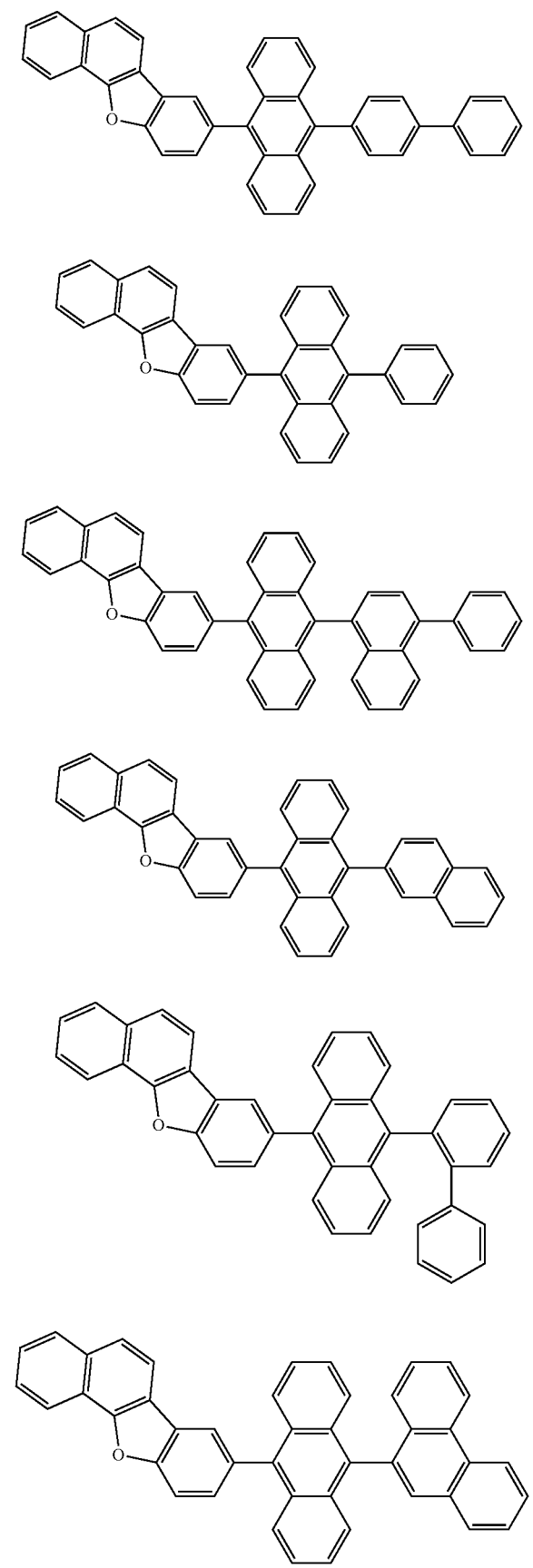

175
-continued
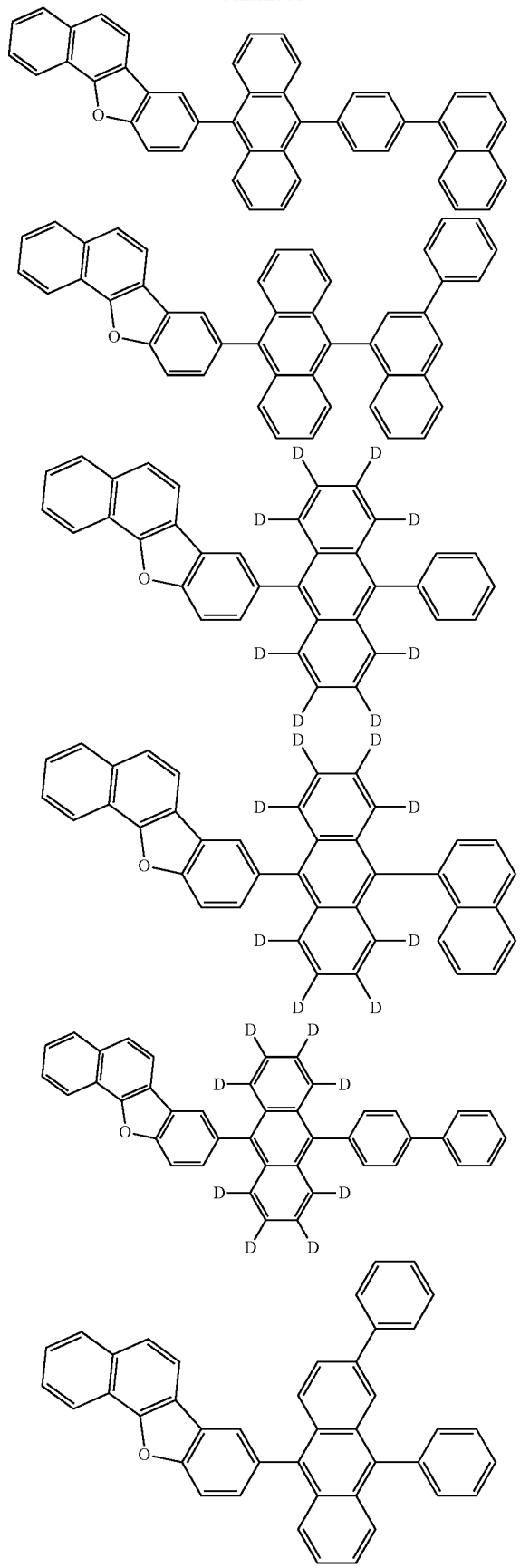
176
-continued
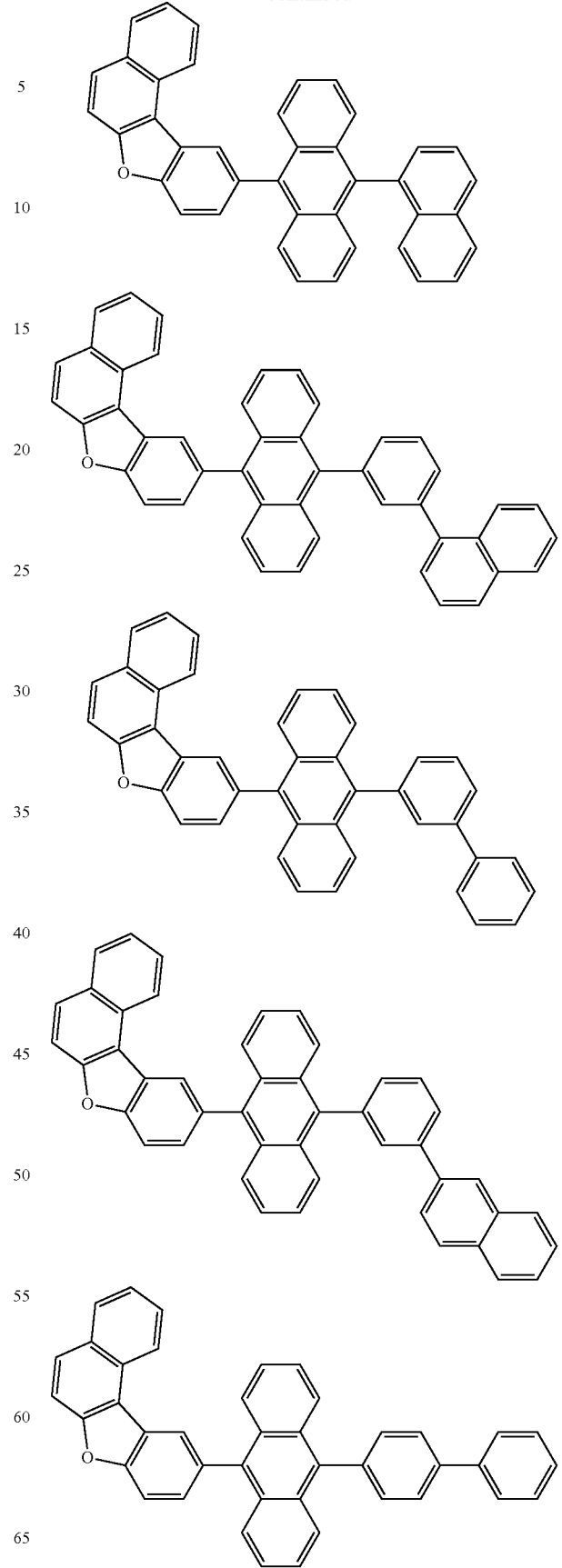

177
-continued
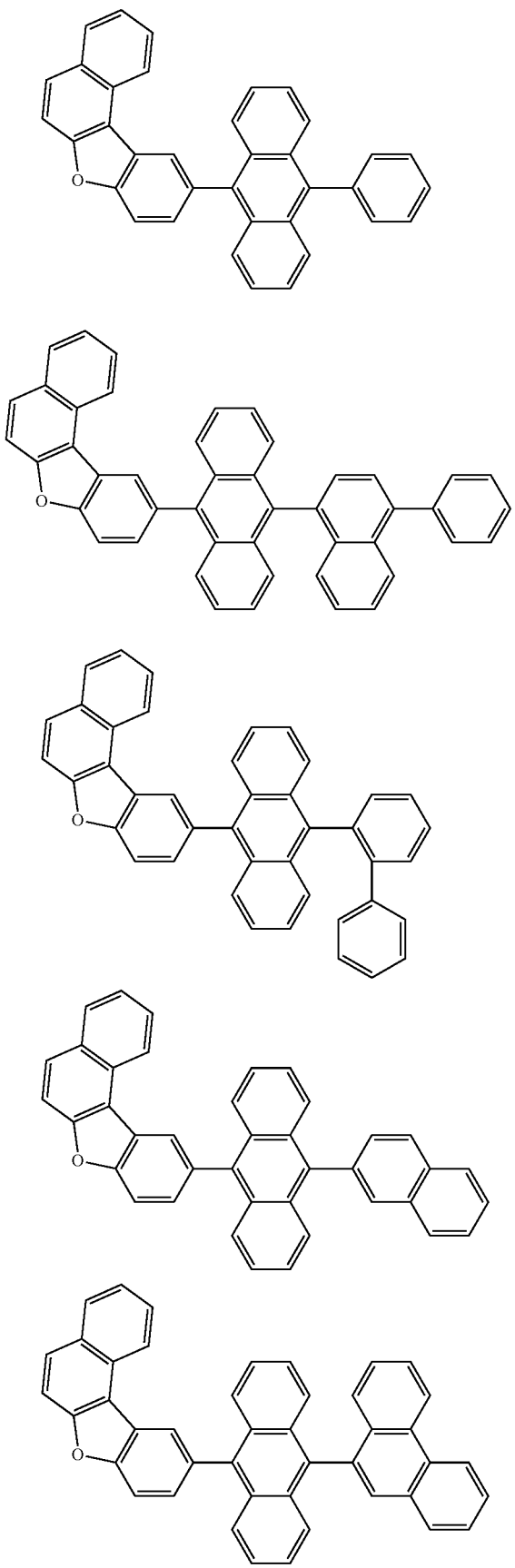
178
-continued
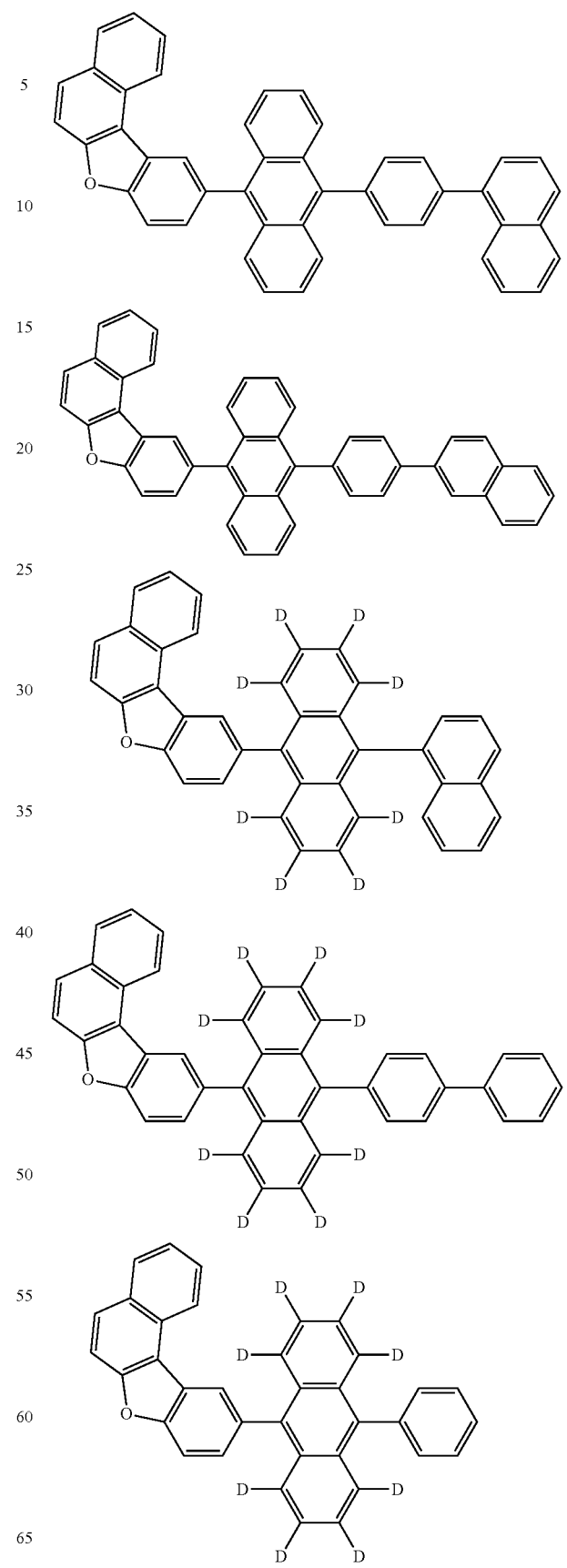

-continued
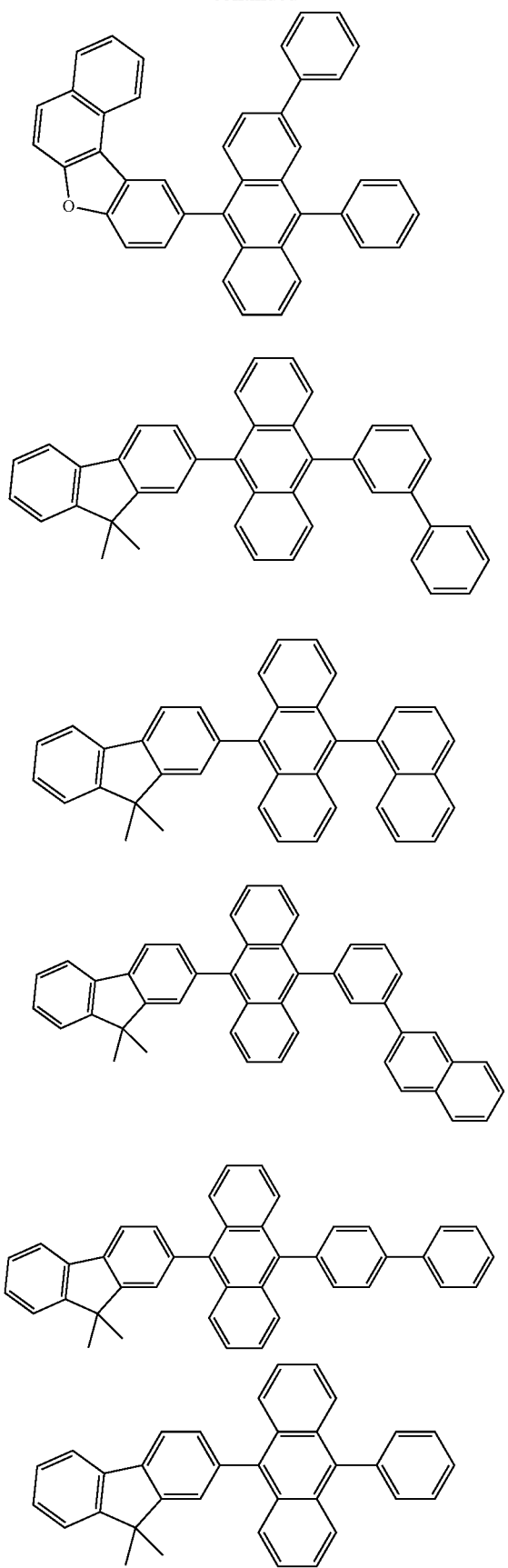
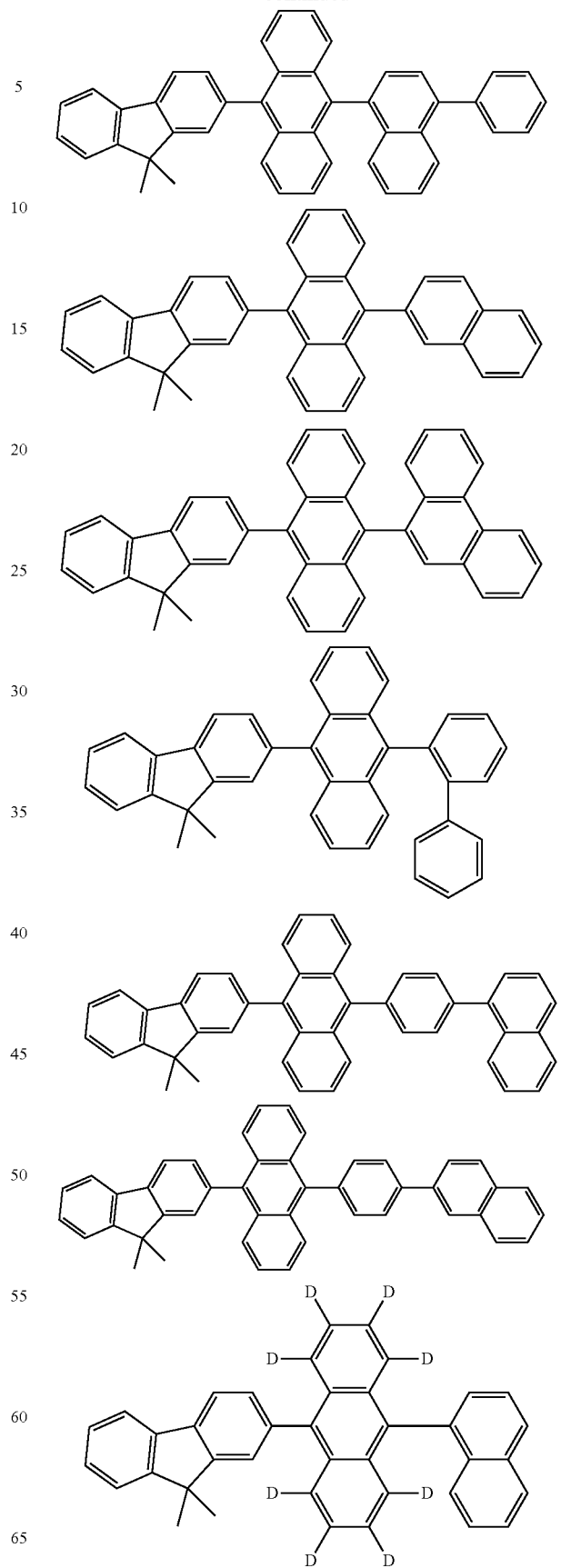

-continued
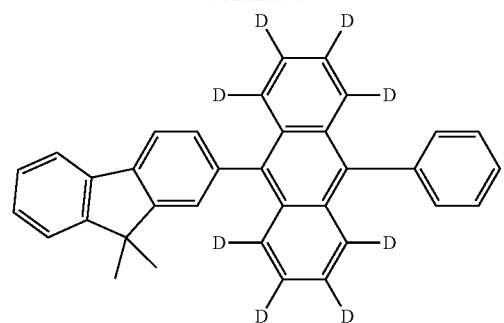
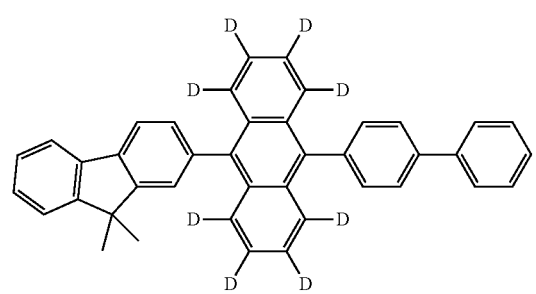
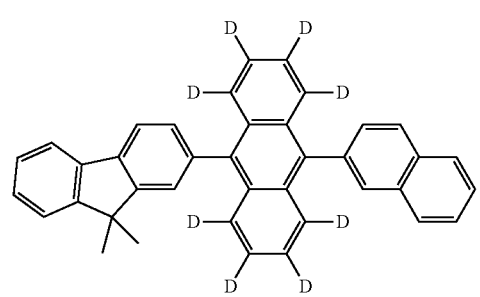
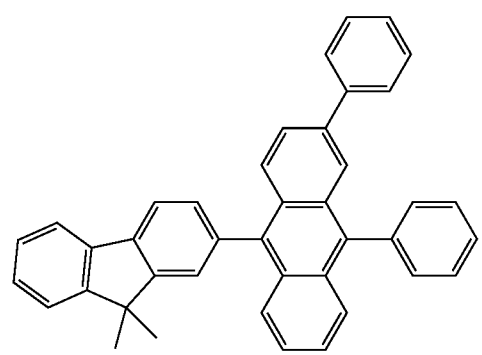
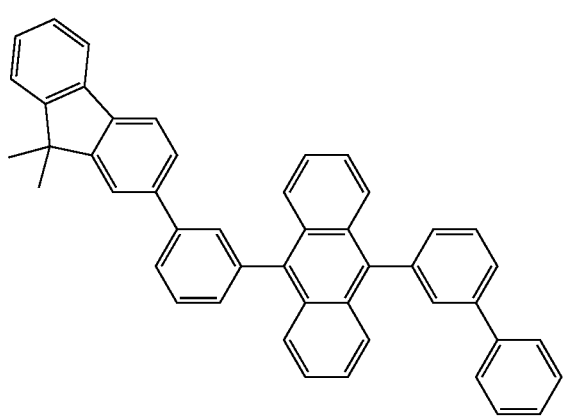
-continued
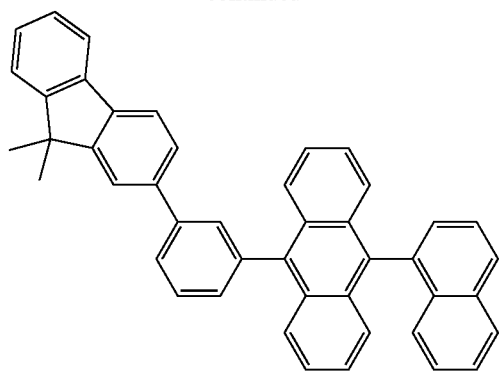
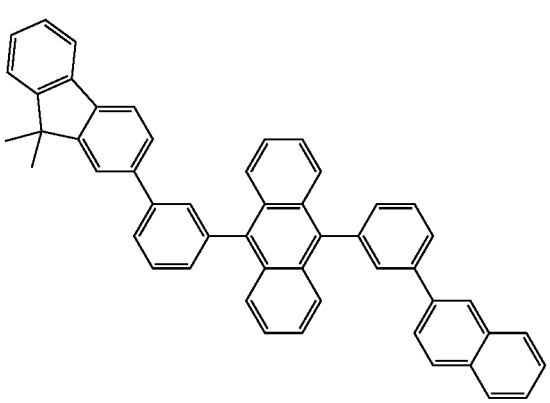
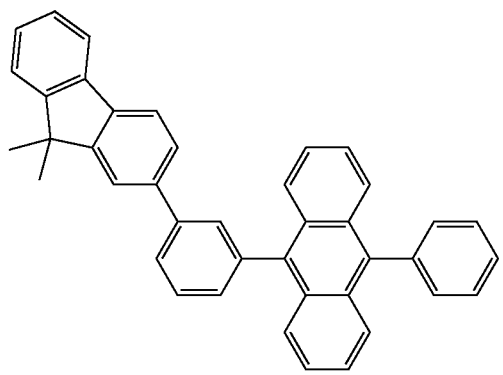
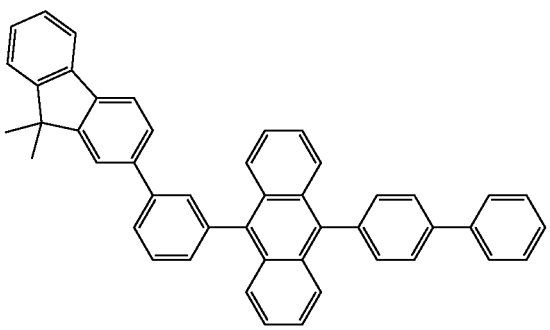

183
-continued
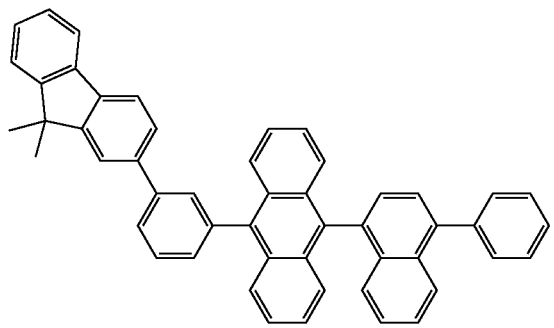
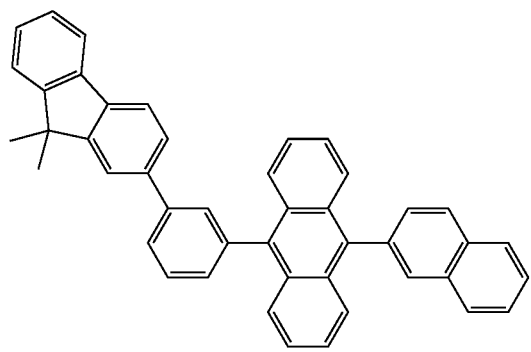
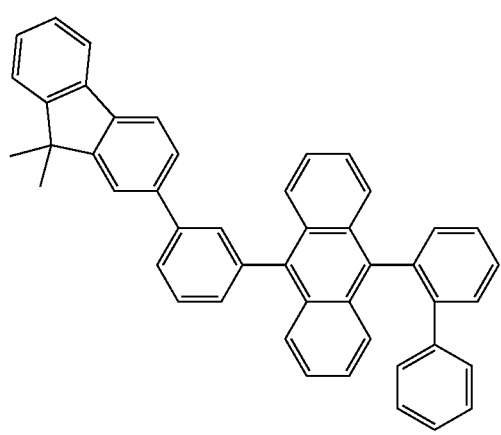
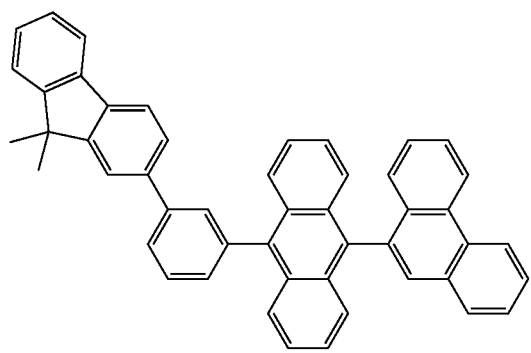
184
-continued
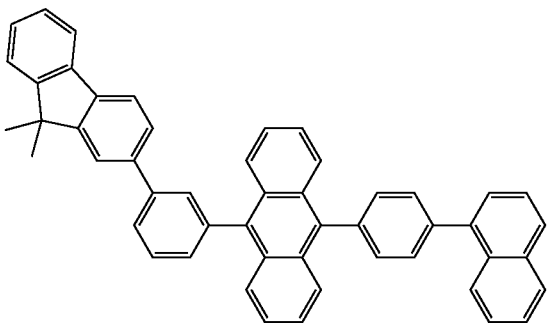
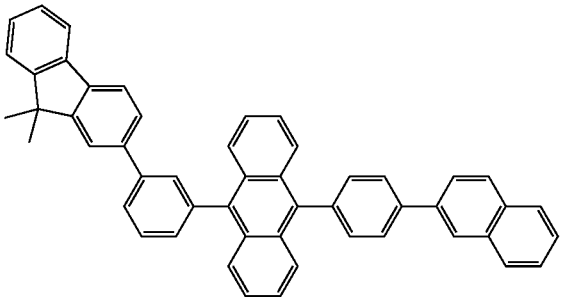
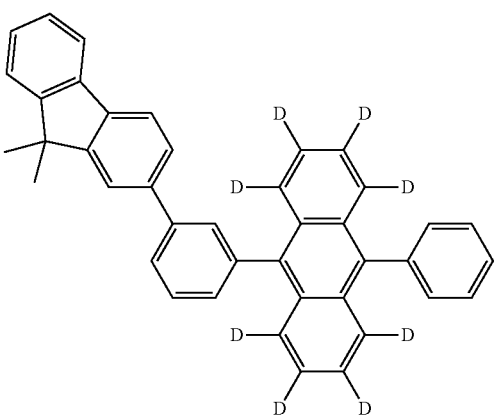
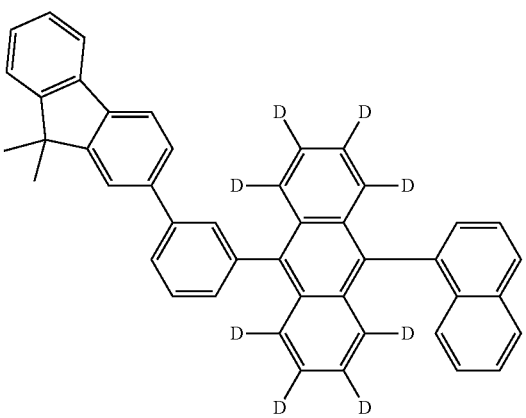

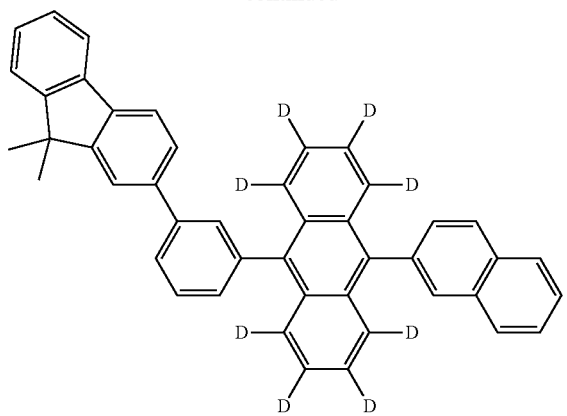
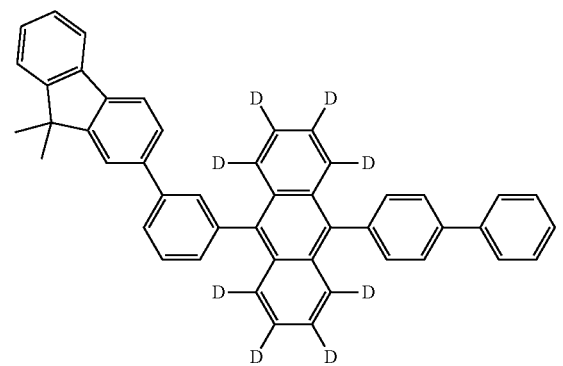
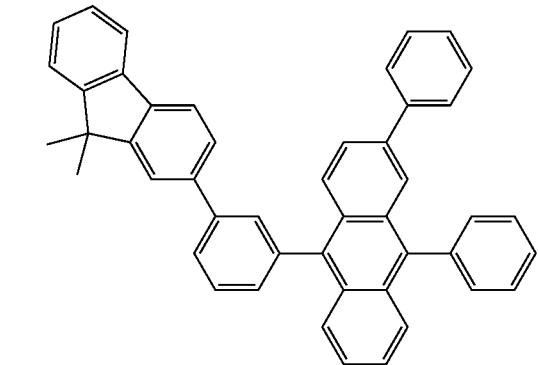
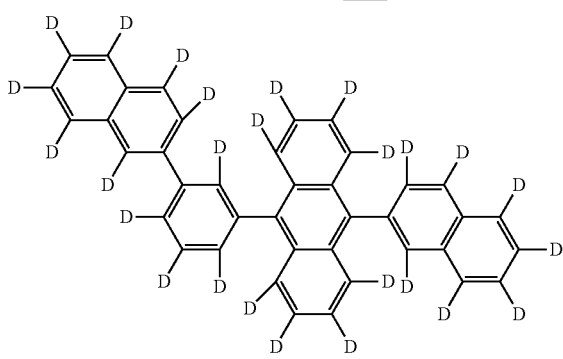
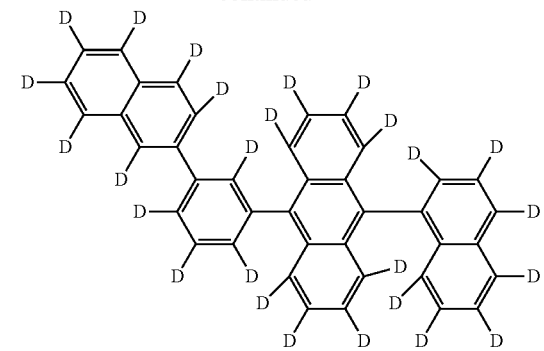

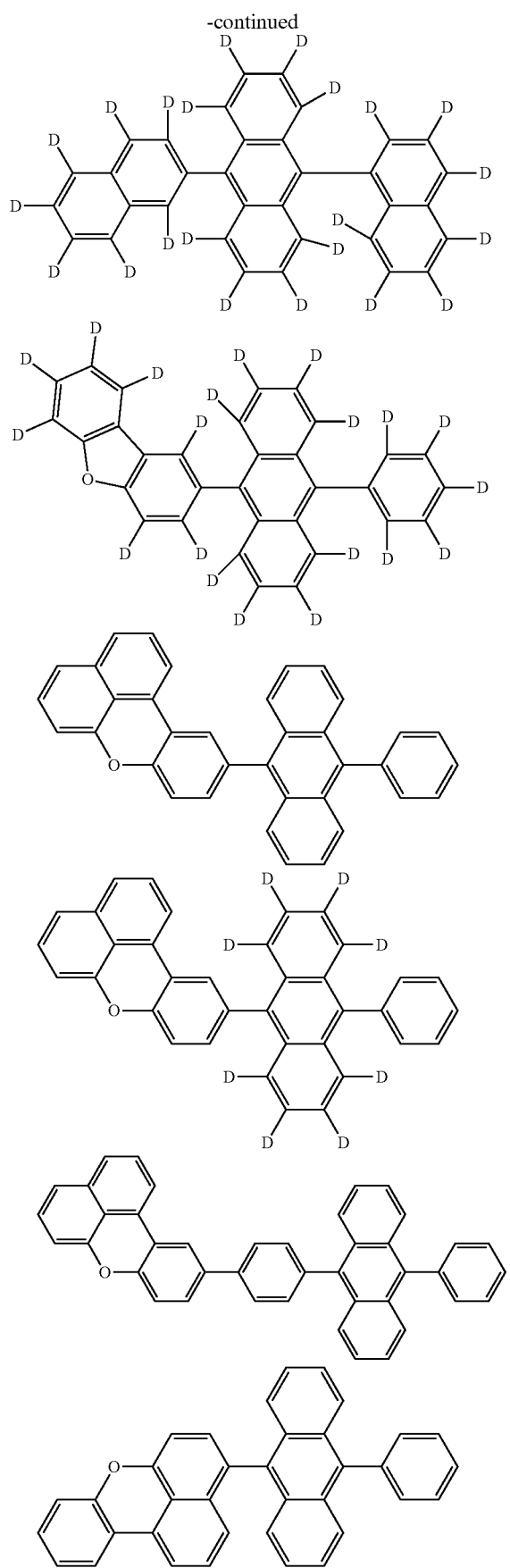
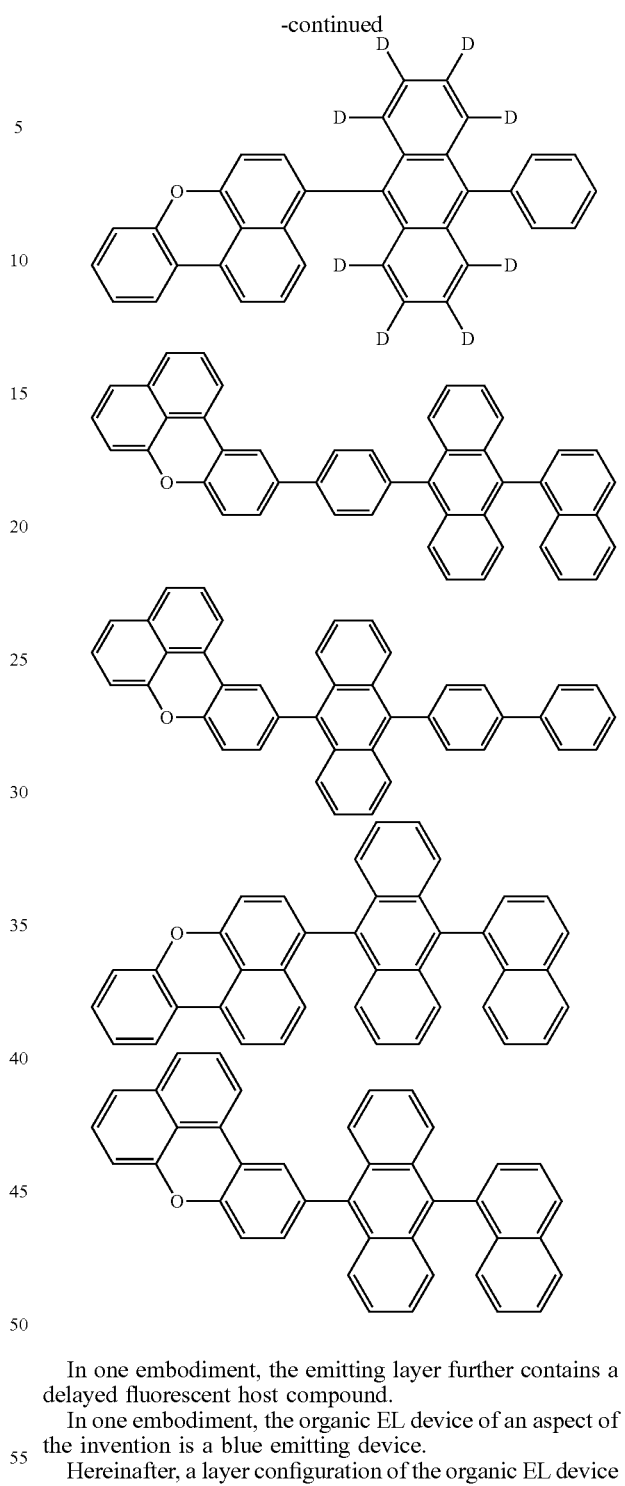

In one embodiment, the emitting layer further contains a delayed fluorescent host compound.

In one embodiment, the organic EL device of an aspect of the invention is a blue emitting device.

Hereinafter, a layer configuration of the organic EL device according to one aspect of the invention will be described.

The organic EL device according to one aspect of the invention has an organic layer between a pair of electrodes of a cathode and an anode. The organic layer includes at least one layer containing an organic compound. Alternatively, the organic layer is formed by stacking a plurality of layers containing an organic compound. The organic layer may have a layer consisting only of one or more organic compounds. The organic layer may have a layer containing an organic compound and an inorganic compound together. The organic layer EL device may have a layer consisting only of one or more inorganic compounds.

At least one of the layers included in the organic layer is an emitting layer. The organic layer may be formed, for example, as one layer of the emitting layer, or may include other layers which can be adopted in the layer configuration of an organic EL device. Layers that can be employed in the layer configuration of an organic EL device include, but are not limited to, a hole-transporting region (a hole-transporting layer, a hole-injecting layer, an electron-blocking layer, an exciton-blocking layer, etc.) provided between an anode and an emitting layer; an emitting layer; a spacing layer; an electron-transporting region (an electron-transporting layer, an electron-injecting layer, a hole-blocking layer, etc.) provided between a cathode and an emitting layer, and the like.

The organic EL device according to one aspect of the invention may be, for example, a monochromatic emitting device of a fluorescent or phosphorescent type, or a white emitting device of a fluorescent/phosphorescent hybrid type. In addition, it may be a simple type including a single light emitting unit or a tandem type including a plurality of light emitting units.

The "emitting unit" refers to the smallest unit which includes organic layers, in which at least one of the organic layers is an emitting layer, and which emits light by recombination of injected holes and electrons.

The "emitting layer" described in this specification is an organic layer having an emitting function. The emitting layer is, for example, a phosphorescent emitting layer, a fluorescent emitting layer, or the like, and may be of a single layer or a plurality of layers.

The light-emitting unit may be of a stacked type including a plurality of a phosphorescent emitting layer and a fluorescent emitting layer, and in this case, for example, may include a spacing layer between the emitting layers for preventing excitons generated in the phosphorescent emitting layer from diffusion into the fluorescent emitting layer.

The simple type organic EL device includes, for example, a device configuration such as anode/emitting unit/cathode.

Typical layer configurations of the emitting unit are shown below. The layers in parentheses are optional layers.
(a) (hole-injecting layer/) hole-transporting layer/fluorescent emitting layer (/electron-transporting layer/electron-injecting layer)
(b) (hole-injecting layer) hole-transporting layer/phosphorescent emitting layer (/electron-transporting layer/electron-injecting layer)
(c) (hole-injecting layer/) hole-transporting layer/first fluorescent emitting layer/second fluorescent emitting layer (/electron-transporting layer/electron-injecting layer)
(d) (hole-injecting layer/) hole-transporting layer/first phosphorescent emitting layer/second phosphorescent emitting layer (/electron-transporting layer/electron-injecting layer)
(e) (hole-injecting layer) hole-transporting layer/phosphorescent emitting layer/spacing layer/fluorescent emitting layer (/electron-transporting layer/electron-injecting layer)
(f) (hole-injecting layer/) hole-transporting layer/first phosphorescent emitting layer/second phosphorescent emitting layer/spacing layer/fluorescent emitting layer (/electron-transporting layer/electron-injecting layer)
(g) (hole-injecting layer) hole-transporting layer/first phosphorescent layer/spacing layer/second phosphorescent emitting layer/spacing layer/fluorescent emitting layer (/electron-transporting layer/electron-injecting layer)
(h) (hole-injecting layer/) hole-transporting layer/phosphorescent emitting layer/spacing layer/first fluorescent emitting layer/second fluorescent emitting layer (/electron-transporting layer/electron-injecting layer)
(i) (hole-injecting layer/) hole-transporting layer/electron-blocking layer/fluorescent emitting layer (/electron-transporting layer/electron-injecting layer)
(j) (hole-injecting layer/) hole-transporting layer/electron-blocking layer/phosphorescent emitting layer (/electron-transporting layer/electron-injecting layer)
(k) (hole-injecting layer/) hole-transporting layer/exciton-blocking layer/fluorescent emitting layer (/electron-transporting layer/electron-injecting layer)
(l) (hole-injecting layer/) hole-transporting layer/exciton-blocking layer/phosphorescent emitting layer (/electron-transporting layer/electron-injecting layer)
(m) (hole-injecting layer) first hole-transporting layer/second hole-transporting layer/fluorescent emitting layer (/electron-transporting layer/electron-injecting layer)
(n) (hole-injecting layer/first hole-transporting layer/second hole-transporting layer/fluorescent emitting layer (/first electron-transporting layer/second electron-transporting layer/electron-injecting layer)
(o) (hole-injecting layer) first hole-transporting layer/second hole-transporting layer/phosphorescent emitting layer (/electron-transporting layer/electron-injecting layer)
(p) (hole-injecting layer) first hole-transporting layer/second hole-transporting layer/phosphorescent emitting layer (/first electron-transporting layer/second electron-transporting layer/electron-injecting layer)
(q) (hole-injecting layer/) hole-transporting layer/fluorescent emitting layer/hole-blocking layer (/electron-transporting layer/electron-injecting layer)
(r) (hole-injecting layer/) hole-transporting layer/phosphorescent emitting layer/hole-blocking layer (/electron-transporting layer/electron-injecting layer)
(s) (hole-injecting layer/) hole-transporting layer/fluorescent emitting layer/exciton-blocking layer (/electron-transporting layer/electron-injecting layer)
(t) (hole-injecting layer/) hole-transporting layer/phosphorescent emitting layer/exciton-blocking layer (/electron-transporting layer/electron-injecting layer)

However, the layer configuration of the organic EL device according to one aspect of the invention is not limited thereto. For example, when the organic EL device has a hole-injecting layer and a hole-transporting layer, it is preferred that a hole-injecting layer be provided between the hole-transporting layer and the anode. Further, when the organic EL device has an electron-injecting layer and an electron-transporting layer, it is preferred that the electron-injecting layer be provided between the electron-transporting layer and the cathode. Further, each of the hole-injecting layer, the hole-transporting layer, the electron-transporting layer and the electron-injecting layer may be constituted of a single layer or of a plurality of layers.

The plurality of phosphorescent emitting layers, and the plurality of the phosphorescent emitting layer and the fluorescent emitting layer may be emitting layers that emit mutually different colors. For example, the emitting unit (f) may have a layer configuration of a hole-transporting layer/first phosphorescent layer (red light emission)/second phosphorescent emitting layer (green light emission)/spacing layer/fluorescent emitting layer (blue light emission)/electron-transporting layer.

An electron-blocking layer may be provided between each light emitting layer and the hole-transporting layer or the spacing layer. Further, a hole-blocking layer may be provided between each emitting layer and the electron-transporting layer. By providing the electron-blocking layer or the hole-blocking layer, it is possible to confine electrons or holes in the emitting layer, thereby to increase the recombination probability of carriers in the emitting layer, and to increase luminous efficiency.

As a representative device configuration of a tandem type organic EL device, for example, a device configuration such as anode/first emitting unit/intermediate layer/second emitting unit/cathode can be given.

The first emitting unit and the second emitting unit are independently selected from the above-mentioned emitting units, for example.

The intermediate layer is also generally referred to as an intermediate electrode, an intermediate conductive layer, a charge generating layer, an electron withdrawing layer, a connecting layer, a connector layer, or an intermediate insulating layer. The intermediate layer is a layer that supplies electrons to the first emitting unit and holes to the second emitting unit, and can be formed of known materials.

Hereinbelow, an explanation will be made on function, materials, etc. of each layer included in the organic EL device described in this specification.

(Substrate)

The substrate is used as a support of the organic EL device. The substrate preferably has a light transmittance of 50% or more in the visible light region within a wavelength of 400 to 700 nm, and a smooth substrate is preferable. Examples of the material of the substrate include soda-lime glass, aluminosilicate glass, quartz glass, plastic and the like. As the substrate, a flexible substrate can be used. The flexible substrate means a substrate that can be bent (flexible), and examples thereof include a plastic substrate and the like. Specific examples of the material for forming the plastic substrate include polycarbonate, polyallylate, polyether sulfone, polypropylene, polyester, polyvinyl fluoride, polyvinyl chloride, polyimide, polyethylene naphthalate and the like. Also, an inorganic vapor deposited film can be used.

(Anode)

As the anode, for example, it is preferable to use a metal, an alloy, a conductive compound, a mixture thereof or the like, which has a large work function (specifically, 4.0 eV or more). Specific examples of the material for the anode include indium oxide-tin oxide (ITO: Indium Tin Oxide), indium oxide-tin oxide containing silicon or silicon oxide, indium oxide-zinc oxide, indium oxide containing tungsten oxide or zinc oxide, graphene and the like. In addition, it is possible to use gold, silver, platinum, nickel, tungsten, chromium, molybdenum, iron, cobalt, copper, palladium, titanium, nitrides of these metals (e.g. titanium nitride) and the like.

The anode is normally formed by depositing these materials on the substrate by a sputtering method. For example, indium oxide-zinc oxide can be formed by a sputtering method by using a target in which 1 to 10 mass % zinc oxide is added to indium oxide. Further, indium oxide containing tungsten oxide or zinc oxide can be formed by a sputtering method by using a target in which 0.5 to 5 mass % of tungsten oxide or 0.1 to 1 mass % of zinc oxide is added to indium oxide.

As the other methods for forming the anode, for example, a vacuum deposition method, a coating method, an inkjet method, a spin coating method or the like can be given. For example, when silver paste or the like is used, it is possible to use a coating method, an inkjet method or the like.

The hole-injecting layer formed in contact with the anode is formed by using a material that allows easy hole injection regardless of the work function of the anode. For this reason, for the anode, it is possible to use a common electrode material, for example, a metal, an alloy, a conductive compound and a mixture thereof. Specifically, materials having a small work function such as alkaline metals such as lithium and cesium; magnesium; alkaline earth metals such as calcium and strontium; alloys containing these metals (for example, magnesium-silver and aluminum-lithium); rare earth metals such as europium and ytterbium; and an alloy containing a rare earth metal can also be used for the anode.

(Hole-Injecting Layer)

A hole-injecting layer is a layer that contains a substance having a high hole-injecting property and has a function of injecting holes from the anode to the organic layer. As the substance having a high hole-injecting property, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, an aromatic amine compound, an electron-attracting (acceptor) compound, a polymeric compound (oligomer, dendrimer, polymer, etc.) and the like can be given. Among these, an aromatic amine compound and an acceptor compound are preferable, with an acceptor compound being more preferable.

Specific examples of the aromatic amine compound include 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

As the acceptor compound, for example, a heterocyclic ring derivative having an electron-attracting group, a quinone derivative having an electron-attracting group, an arylborane derivative, a heteroarylborane derivative, and the like, are preferable, and specific examples include hexacyanohexaazatriphenylene, 2,3,5,6-tetrafluoro-7,7,8,8-tetracyanoquinodimethane (abbreviation: F4TCNQ), 1,2,3-tris[(cyano)(4-cyano-2,3,5,6-tetrafluorophenyl)methylene]cyclopropane, and the like.

When the acceptor compound is used, it is preferred that the hole-injecting layer further contain a matrix material. As the matrix material, materials known as the material for an organic EL device can be used. For example, an electron-donating (donor) compound is preferably used.

(Hole-Transporting Layer)

The hole-transporting layer is a layer that contains a high hole-transporting property, and has a function of transporting holes from the anode to the organic layer.

As the substance having a high hole-transporting property, a substance having a hole mobility of $10\text{-}6 \text{ cm}^2/(\text{V·s})$ or more is preferable. For example, an aromatic amine compound, a carbazole derivative, an anthracene derivative, a polymeric compound, and the like can be given.

Specific examples of the aromatic amine compound include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BAFLP), 4,4'-bis[N-(9,9-dimethylfluoren-2-yl)-N-phenylamino]biphenyl (abbreviation: DFLDPBi), 4,4',4"-tris(N,N-diphenylamino)triphenylamine (abbreviation:

TDATA), 4,4',4"-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), and the like.

Specific examples of the carbazole derivative include 4,4'-di(9-carbazolyl)biphenyl (abbreviation: CBP), 9-[4-(9-carbazolyl)phenyl]-10-phenylanthracene (abbreviation: CzPA), 9-phenyl-3-[4-(10-phenyl-9-anthryl)phenyl]-9H-carbazole (abbreviation: PCzPA) and the like.

Specific examples of the anthracene derivative include 2-t-butyl-9,10-di(2-naphthyl)anthracene (t-BuDNA), 9,10-di(2-naphthyl)anthracene (DNA), 9,10-diphenylanthracene (DPAnth), and the like.

Specific examples of the polymeric compound include poly(N-vinylcarbazole) (abbreviation: PVK), poly(4-vinyltriphenylamine) (abbreviation: PVTPA) and the like.

As long as a compound other than those mentioned above, that has a higher hole-transporting property as compared with electron-transporting property, such a compound can be used for the hole-transporting layer.

The hole-transporting layer may be a single layer or may be a stacked layer of two or more layers. In this case, it is preferred to arrange a layer that contains a substance having a larger energy gap among substances having a higher hole-transporting property, on a side nearer to the emitting layer.

(Emitting Layer)

The emitting layer is a layer containing a substance having a high emitting property (dopant material). As the dopant material, various types of material can be used. For example, a fluorescent emitting compound (fluorescent dopant), a phosphorescent emitting compound (phosphorescent dopant) or the like can be used. A fluorescent emitting compound is a compound capable of emitting light from the singlet excited state, and an emitting layer containing a fluorescent emitting compound is called as a fluorescent emitting layer. Further, a phosphorescent emitting compound is a compound capable of emitting light from the triplet excited state, and an emitting layer containing a phosphorescent emitting compound is called as a phosphorescent emitting layer.

The emitting layer normally contains a dopant material and a host material that allows the dopant material to emit light efficiently. In some literatures, a dopant material is called as a guest material, an emitter or an emitting material. In some literatures, a host material is called as a matrix material.

A single emitting layer may contain a plurality of dopant materials and a plurality of host materials. Further, a plurality of emitting layers may be provided.

In this specification, a host material combined with the fluorescent dopant is referred to as a "fluorescent host" and a host material combined with the phosphorescent dopant is referred to as the "phosphorescent host". Note that the fluorescent host and the phosphorescent host are not classified only by the molecular structure. The phosphorescent host is a material for forming a phosphorescent emitting layer containing a phosphorescent dopant, but it does not mean that it cannot be used as a material for forming a fluorescent emitting layer. The same can be applied to the fluorescent host. A compound having delayed fluorescence (thermally activated delayed fluorescence) can also be used as the fluorescent host.

The content of the dopant material in the emitting layer is not particularly limited, but from the viewpoint of adequate luminescence and concentration quenching, it is preferable, for example, to be 0.1 to 70 mass %, more preferably 0.1 to 30 mass %, more preferably 1 to 30 mass %, still more preferably 1 to 20 mass %, and particularly preferably 1 to 10 mass %.

<Fluorescent Dopant>

As the fluorescent dopant, a compound represented by the formula (1), a fused polycyclic aromatic derivative, a styrylamine derivative, a fused ring amine derivative, a boron-containing compound, a pyrrole derivative, an indole derivative, a carbazole derivative can be given, for example. Among these, a fused ring amine derivative, a boron-containing compound, and a carbazole derivative are preferable.

As the fused ring amine derivative, for example, a diaminopyrene derivative, a diaminochrysene derivative, a diaminoanthracene derivative, a diaminofluorene derivative, a diaminofluorene derivative with which one or more benzofuro skeletons are fused, and the like can be given.

As the boron-containing compound, for example, a pyrromethene derivative, a triphenylborane derivative and the like can be given.

Examples of the blue fluorescent dopant include a compound represented by the formula (1), a pyrene derivative, a styrylamine derivative, a chrysene derivative, a fluoranthene derivative, a fluorene derivative, a diamine derivative, a triarylamine derivative, and the like. Specifically, N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(10-phenyl-9-anthryl)-4'-(9-phenyl-9H-carbazol-3-yl)triphenylamine (abbreviation: PCBAPA) and the like can be given.

As the green fluorescent dopant, an aromatic amine derivative and the like can be given, for example. Specifically, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]—N-[4-(9H-carbazol-9-yl) phenyl]-N-phenylanthracene-2-amine (abbreviation: 2YGABPhA), N,N,9-triphenylanthracene-9-amine (abbreviation: DPhAPhA), and the like can be given.

As the red fluorescent dopant, a tetracene derivative, a diamine derivative and the like can be given. Specifically, N,N,N',N'-tetrakis(4-methylphenyl)tetracen-5,11-diamine (abbreviation: p-mPhTD), 7,14-diphenyl-N,N,N',N'-tetrakis(4-methylphenyl)acenaphtho[1,2-a]fluoranthen-3,10-diamine (abbreviation: p-mPhAFD) and the like can be given.

<Phosphorescent Dopant>

As the phosphorescent dopant, for example, a phosphorescent light-emitting heavy metal complex and a phosphorescent light-emitting rare earth metal complex can be given.

As the heavy metal complex, an iridium complex, an osmium complex, a platinum complex and the like can be given. As the heavy metal complex, an ortho-metalated complex of a metal selected from iridium, osmium and platinum are preferable.

As the rare earth metal complexes include, for example, a terbium complex, a europium complex and the like. Specifically, tris(acetylacetonate)(monophenanthroline)terbium (III) (abbreviation: Tb(acac)$_3$(Phen)), tris(1,3-diphenyl-1,3-propandionate)(monophenanthroline)europium (III) (abbreviation: Eu(DBM)$_3$(Phen)), tris[1-(2-thenoyl)-3,3,3-trifluoroacetonate](monophenanthroline)europium (III) (abbreviation: Eu(TTA)$_3$(Phen)) and the like can be given.

These rare earth metal complexes are preferable as phosphorescent dopants since rare earth metal ions emit light due to electronic transition between different multiplicity.

As the blue phosphorescent dopant, an iridium complex, an osmium complex, a platinum complex, and the like can be given, for example. Specific examples include bis[2-(4',6'-difluorophenyl)pyridinato-N,C2']iridium (III) tetrakis(1-pyrazolyl)borate (abbreviation: FIr6), bis[2-(4',6'-difluorophenyl)pyridinato-N,C2']iridium (III) picolinate (abbreviation: FIrpic), bis[2-(3',5'-bistrifluoromethylphenyl)pyridinato-N,C2']iridium (III) picolinate (abbreviation: Ir(CF$_3$ppy)$_2$(pic)), bis[2-(4',6'-difluorophenyl)pyridinato-N,C2']iridium (III) acetylacetonate (abbreviation: FIracac), and the like.

As the green phosphorescent dopant, an iridium complex or the like can be given, for example. Specific examples include tris(2-phenylpyridinato-N,C2')iridium (III) (abbreviation: Ir(ppy)$_3$), bis(2-phenylpyridinato-N,C2')iridium (III) acetylacetonate (abbreviation: Ir(ppy)$_2$(acac)), bis(1,2-diphenyl-1H benzimidazolate)iridium (III) acetylacetonate (abbreviation: Ir(pbi)$_2$(acac)), bis(benzo[h]quinolinato)iridium (III) acetylacetonate (abbreviation: Ir(bzq)$_2$(acac)), and the like.

As the red phosphorescent dopant, an iridium complex, a platinum complex, a terbium complex, a europium complex and the like can be given, for example. Specifically, bis[2-(2'-benzo[4,5-α] thienyl)pyridinato-N,C3']iridium (III) acetylacetonate (abbreviation: Ir(btp)$_2$(acac)), bis(1-phenylisoquinolinato-N,C2')iridium (III) acetylacetonate (abbreviation: Ir(piq)$_2$(acac)), (acetylacetonato)bis[2,3-bis(4-fluorophenyl)quinoxalinato]iridium (III) (abbreviation: Ir(Fdpq)$_2$(acac)), 2,3,7,8,12,13,17,18-octaethyl-21H,23H-porphyrin platinum (II) (abbreviation: PtOEP), and the like.

<Host Material>

As the host material, for example, metal complexes such as an aluminum complex, a beryllium complex, and a zinc complex; heterocyclic compounds such as an indole derivative, a pyridine derivative, a pyrimidine derivative, a triazine derivative, a quinoline derivative, an isoquinoline derivative, a quinazoline derivative, a dibenzofuran derivative, a dibenzothiophene derivative, an oxadiazole derivative, a benzimidazole derivative, a phenanthroline derivative; fused aromatic compounds such as a naphthalene derivative, a triphenylene derivative, a carbazole derivative, an anthracene derivative, a phenanthrene derivative, a pyrene derivative, a chrysene derivative, a naphthacene derivative, and a fluoranthene derivative; and aromatic amine compounds such as a triarylamine derivative, and a fused polycyclic aromatic amine derivative, and the like can be given. A plurality of types of host materials can be used in combination.

Specific examples of the metal complex include tris(8-quinolinolato)aluminum(II) (abbreviation: Alq), tris(4-methyl-8-quinolinolato)aluminum(III) (abbreviation: Almq3), bis(10-hydroxybenzo[h]quinolinato)beryllium(II) (abbreviation: BeBq2), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), bis[2-(2-benzothiazolyl) phenolato]zinc(II) (abbreviation: ZnBTZ), and the like.

Specific examples of the heterocyclic compound include 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-tiazole (abbreviation: TAZ), 2,2',2"-(1,3,5-benzenetriyl)tris(1-phenyl-1H-benzimidazole) (abbreviation: TPBI), bathophenanthroline (abbreviation: BPhen), bathocuproine (abbreviation: BCP), and the like.

Specific examples of the fused aromatic compound include 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3"-(benzene-1,3,5-triyl)tripyrene (abbreviation: TPB3), 9,10-diphenylanthracene (abbreviation: DPAnth), 6,12-dimethoxy-5,11-diphenylchrysene, and the like.

Specific examples of the aromatic amine compound include N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(9,9-dimethylfluoren-2-yl)-N-phenylamino]biphenyl (abbreviation: DFLDPBi), 4,4'-bis[N-(spiro-9,9'-bifluoren-2-yl)-N-phenylamino]biphenyl (abbreviation: BSPB), and the like.

As the fluorescent host, a compound having a higher singlet energy level as compared with a fluorescent dopant is preferable. For example, a heterocyclic compound, a fused aromatic compound and the like can be given. As the fused aromatic compound, for example, a compound represented by the formula (10), an anthracene derivative, a pyrene derivative, a chrysene derivative, a naphthacene derivative and the like are preferable. A compound having delayed fluorescence (thermally activated delayed fluorescence) can also be used as the fluorescent host.

As the phosphorescent host, a compound having a higher triplet energy level as compared with a phosphorescent dopant is preferable. For example, a metal complex, a heterocyclic compound, a fused aromatic compound and the like can be given. Among these, an indole derivative, a carbazole derivative, a pyridine derivative, a pyrimidine derivative, a triazine derivative, a quinoline derivative, an isoquinoline derivative, a quinazoline derivative, a dibenzofuran derivative, a dibenzothiophene derivative, a naphthalene derivative, a triphenylene derivative, a phenanthrene derivative, a fluoranthene derivative and the like are preferable, for example.

(Electron-Transporting Layer)

An electron-transporting layer is a layer that contains a substance having a high electron-transporting property. As the substance having a high electron-transporting property, a substance having an electron mobility of $10^{-6}$ cm$^2$/Vs or more is preferable. For example, a metal complex, an aromatic heterocyclic compound, an aromatic hydrocarbon compound, a polymeric compound and the like can be given.

As the metal complex, for example, an aluminum complex, a beryllium complex, a zinc complex and the like can be given. Specific examples of the metal complex include tris(8-quinolinolato)aluminum (III) (abbreviation: Alq), tris (4-methyl-8-quinolinolato)aluminum (abbreviation:

Almq3), bis(10-hydroxybenzo[h]quinolinato)beryllium (abbreviation: BeBq2), bis(2-methyl-8-quinolinolato)(4-phenylphenolato)aluminum (III) (abbreviation: BAlq), bis(8-quinolinolato)zinc (II) (abbreviation: Znq), bis[2-(2-benzoxazolyl)phenolato]zinc (II) (abbreviation: ZnPBO), bis[2-(2-benzothiazolyl) phenolato]zinc(II) (abbreviation: ZnBTZ), and the like.

As the aromatic heterocyclic compound, imidazole derivatives such as a benzimidazole derivative, an imidazopyridine derivative and a benzimidazophenanthridine derivative; azine derivatives such as a pyrimidine derivative and a triazine derivative; compounds having a nitrogen-containing 6-membered ring structure such as a quinoline derivative, an isoquinoline derivative, and a phenanthroline derivative (also including one having a phosphine oxide-based substituent on the heterocyclic ring) and the like can be given. Specifically, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), 4,4'-bis(5-methylbenzoxazol-2-yl)stilbene (abbreviation: BzOs), and the like can be given.

As the aromatic hydrocarbon compound, an anthracene derivative, a fluoranthene derivative and the like can be given, for example.

As specific examples of the polymeric compound, poly [(9,9-dihexylfluoren-2,7-diyl)-co-(pyridine-3,5-diyl)] (abbreviation: PF-Py), poly[(9,9-dioctylfluoren-2,7-diyl)-co-(2, 2'-bipyridin-6,6'-diyl)] (abbreviation: PF-BPy) and the like can be given.

A compound even other than those mentioned above, may be used in the electron-transporting layer, as long as it has a higher electron-transporting property as compared with hole-transporting property.

The electron-transporting layer may be of a single layer, or of a stacked layer of two or more layers. In this case, it is preferable to arrange a layer that contains a substance having a larger energy gap, among substances having a high electron-transporting property, on the side nearer to the emitting layer.

The electron-transporting layer may contain a metal such as an alkali metal, magnesium, an alkaline earth metal, or an alloy containing two or more of these metals; a metal compound such as an alkali metal compound such as 8-quinolinolato lithium (Liq), or an alkaline earth metal compound. When a metal such as an alkali metal, magnesium, an alkaline earth metal, or an alloy containing two or more of these metals is contained in the electron-transporting layer, the content of the metal is not particularly limited, but is preferably from 0.1 to 50 mass %, more preferably from 0.1 to 20 mass %, further preferably from 1 to 10 mass %.

When a metal compound such as an alkali metal compound or an alkaline earth metal compound is contained in the electron-transporting layer, the content of the metal compound is preferably from 1 to 99 mass %, more preferably from 10 to 90 mass %. When a plurality of electron-transporting layers are provided, the layer on the emitting layer side can be formed only of the metal compound as mentioned above.

(Electron-Injecting Layer)

The electron-injecting layer is a layer that contains a substance having a high electron-injecting property, and has the function of efficiently injecting electrons from a cathode to an emitting layer. Examples of the substance that has a high electron-injecting property include an alkali metal, magnesium, an alkaline earth metal, a compound thereof, and the like. Specific examples thereof include lithium, cesium, calcium, lithium fluoride, cesium fluoride, calcium fluoride, lithium oxide, and the like. In addition, a material in which an alkali metal, magnesium, an alkaline earth metal, or a compound thereof is incorporated to a substance having an electron-transporting property, for example, Alq incorporated with magnesium, may also be used.

Alternatively, a composite material that contains an organic compound and a donor compound may also be used in the electron-injecting layer. Such a composite material is excellent in the electron-injecting property and the electron-transporting property since the organic compound receives electrons from the donor compound.

The organic compound is preferably a substance excellent in transporting property of the received electrons, and specifically, for example, the metal complex, the aromatic heterocyclic compound, and the like, which are a substance that has a high electron-transporting property as mentioned above, can be used.

Any material capable of donating electrons to an organic compound can be used as the donor compound. Examples thereof include an alkali metal, magnesium, an alkaline earth metal, a rare earth metal and the like. Specific examples thereof include lithium, cesium, magnesium, calcium, erbium, ytterbium, and the like. Further, an alkali metal oxide and an alkaline earth metal oxide are preferred, and examples thereof include lithium oxide, calcium oxide, barium oxide, and the like. Lewis bases such as magnesium oxide can also be used. Alternatively, an organic compound such as tetrathiafulvalene (abbreviation: TTF) can be used.

(Cathode)

For the cathode, a metal, an alloy, an electrically conductive compound, and a mixture thereof, each having a small work function (specifically, a work function of 3.8 eV or lower) are preferably used. Specific examples of the material for the cathode include alkali metals such as lithium and cesium; magnesium; alkaline earth metals such as calcium, and strontium; alloys containing these metals (for example, magnesium-silver, and aluminum-lithium); rare earth metals such as europium and ytterbium; alloys containing a rare earth metal, and the like.

The cathode is usually formed by a vacuum vapor deposition or a sputtering method. Further, in the case of using a silver paste or the like, a coating method, an inkjet method, or the like can be employed.

In the case where the electron-injecting layer is provided, a cathode can be formed from a substance selected from various electrically conductive materials such as aluminum, silver, ITO, graphene, indium oxide-tin oxide containing silicon or silicon oxide, regardless of the work function value. These electrically conductive materials are made into films by using a sputtering method, an inkjet method, a spin coating method, or the like.

(Insulating layer)

In the organic EL device, pixel defects based on leakage or a short circuit are easily generated since an electric field is applied to a thin film. In order to prevent this, an insulating thin layer may be inserted between a pair of electrodes.

Examples of substances used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, vanadium oxide, and the like. A mixture thereof may be used for the insulating layer, and a stacked body of a plurality of layers that contain these substances can be also used for the insulating layer.

(Spacing Layer)

The spacing layer is a layer provided between a fluorescent emitting layer and a phosphorescent emitting layer when the fluorescent emitting layer and the phosphorescent emitting layer are stacked, in order to prevent diffusion of excitons generated in the phosphorescent emitting layer to the fluorescent emitting layer or in order to adjust the carrier balance. Further, the spacing layer can be provided between a plurality of phosphorescent emitting layers.

Since the spacing layer is provided between the emitting layers, the material used for the spacing layer is preferably a substance that has both electron-transporting property and hole-transporting property. In order to prevent diffusion of the triplet energy in adjacent phosphorescent emitting layers, it is preferred that the material used for the spacing layer have a triplet energy of 2.6 eV or more.

As the material used for the spacing layer, the same materials as those used in the above-mentioned hole-transporting layer can be given.

(Electron-Blocking Layer, Hole-Blocking Layer, Exciton-Blocking Layer)

An electron-blocking layer, a hole-blocking layer, an exciton (triplet)-blocking layer, and the like may be provided adjacent to the emitting layer.

The electron-blocking layer is a layer that has a function of preventing leakage of electrons from the emitting layer to the hole-transporting layer. The hole-blocking layer is a layer that has a function of preventing leakage of holes from the emitting layer to the electron-transporting layer. The exciton-blocking layer is a layer that has a function of preventing diffusion of excitons generated in the emitting layer to the adjacent layers, so as to confine the excitons within the emitting layer.

(Capping Layer)

The organic EL device can be provided with a capping layer above the cathode in order to adjust the intensity of the outcoupled light by the optical interference effect.

For the capping layer, for example, a polymer compound, a metal oxide, a metal fluoride, a metal boride, silicon nitride, a silicon compound (silicon oxide, etc.) and the like can be used.

Further, an aromatic amine derivative, an anthracene derivative, a pyrene derivative, a fluorene derivative, and a dibenzofuran derivative can also be used for the capping layer.

A stacked body in which layers containing these substances are stacked can also be used as a capping layer.

(Intermediate Layer)

In the tandem-type organic EL device, an intermediate layer is provided.

(Method for Forming a Layer)

The method for forming each layer of the organic EL device is not particularly limited unless otherwise specified. As the film forming method, a known film-forming method such as a dry film-forming method, a wet film-forming method or the like can be used. Specific examples of the dry film-forming method include a vacuum deposition method, a sputtering method, a plasma method, an ion plating method, and the like. Specific examples of the wet film-forming method include various coating methods such as a spin coating method, a dipping method, a flow coating method, and an inkjet method.

(Film Thickness)

The film thickness of each layer of the organic EL device is not particularly limited unless otherwise specified. If the film thickness is too small, defects such as pinholes are likely to occur to make it difficult to obtain an enough luminance. On the other hand, if the film thickness is too large, a high driving voltage is required to be applied, leading to a lowering in efficiency. In this respect, the film thickness is generally preferably 1 nm to 10 μm, and more preferably 1 nm to 0.2 μm.

[Electronic Apparatus]

The electronic apparatus according to one aspect of the invention is equipped with the above-described organic EL device according to one aspect of the invention. Examples of the electronic apparatus include display parts such as an organic EL panel module; display devices of television sets, mobile phones, smart phones, personal computers, and the like; and emitting devices of a lighting device and a vehicle lighting device.

EXAMPLES

Next, the invention will be described in more detail by referring to Examples and Comparative Examples, but the invention is not limited in any way to the description of these Examples.

<Compound>

The compounds represented by the formula (1) used for fabricating the organic EL devices of Examples 1 to 3 are shown below

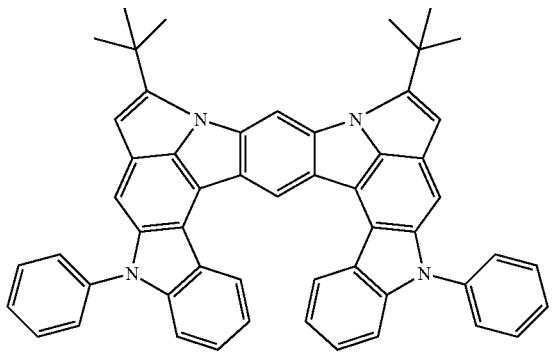

BD-1

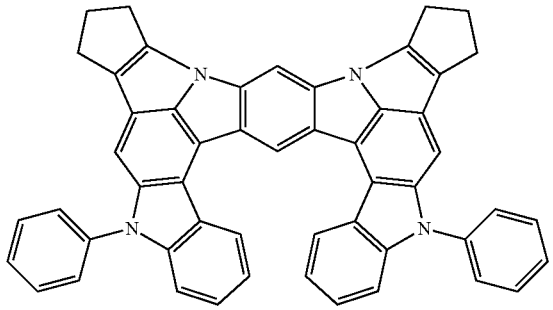

BD-2

BD-3
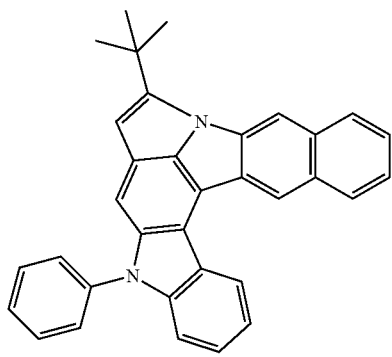
The compound used for fabricating the organic EL device of Comparative Example 1 is shown below.
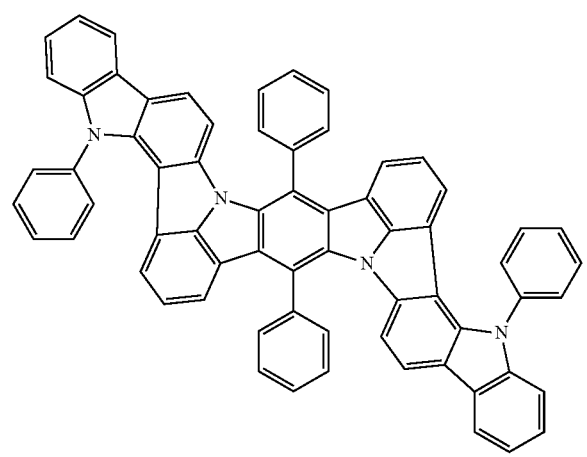 [SMILES: c1ccc(-c2c3c4cccc5c6c7c(ccc6n(c3c(-c3ccccc3)c3c6cccc8c9c%10c(ccc9n(c23)c68)c2ccccc2n%10-c2ccccc2)c45)c2ccccc2n7-c2ccccc2)cc1]
The other compounds used for fabricating the organic EL devices of Examples 1 to 3 and Comparative Example 1 are shown below
HI
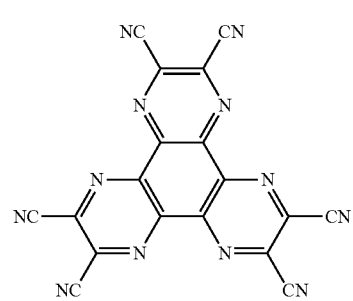
HT1
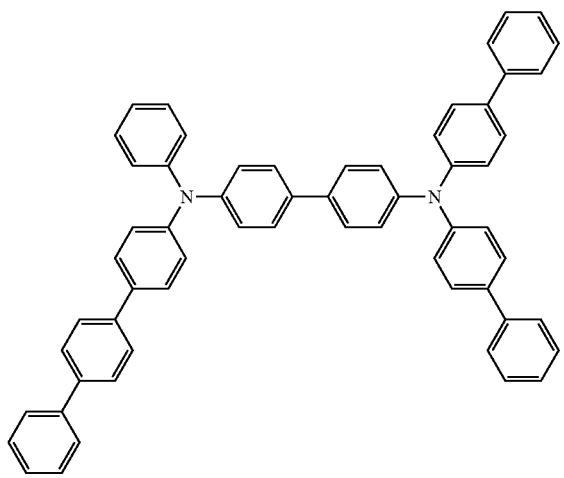
HT2
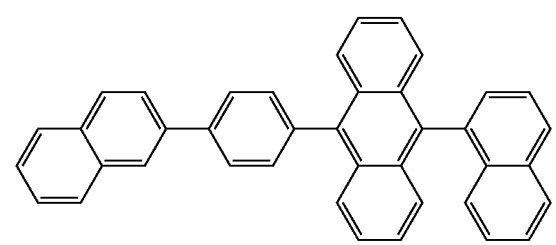
BH-1

HBL

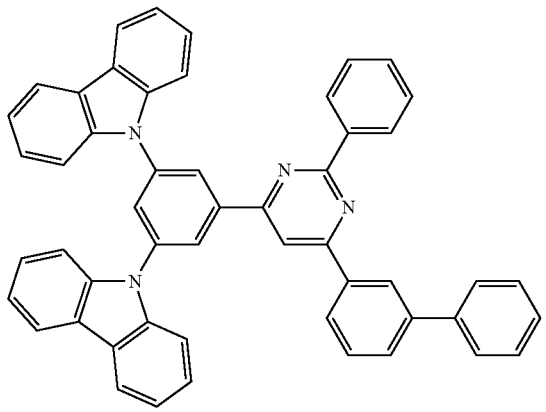

<Fabrication of Organic EL Device>
The organic EL devices were fabricated and evaluated as follows.

Example 1

A 25 mm×75 mm×1.1 mm-thick glass substrate with an ITO transparent electrode (anode) (manufactured by GEO-MATEC Co., Ltd.) was subjected to ultrasonic cleaning in isopropyl alcohol for 5 minutes, and then subjected to UV-ozone cleaning for 30 minutes. The thickness of the ITO film was 130 nm.

The glass substrate with the transparent electrode after being cleaned was mounted onto a substrate holder in a vacuum vapor deposition apparatus. First, a compound HI was deposited on a surface on the side on which the transparent electrode was formed so as to cover the transparent electrode to form a compound HI film having a thickness of 5 nm. This HI film functions as a hole-injecting layer.

Subsequent to the formation of the HI film, a compound HT1 was deposited on the HI film to form an HT1 film having a thickness of 80 nm. The HT1 film functions as a first hole-transporting layer.

Subsequent to the formation of the HT1 film, a compound HT2 was deposited on the HT1 film to form an HT2 film having a thickness of 10 nm. The HT2 film functions as a second hole-transporting layer.

A compound BH-1 (host material) and a compound BD-1 (dopant material) were co-deposited on the HT2 film to be 2% in a proportion (weight ratio) of the compound BD-1 to form an emitting layer having a thickness of 25 nm.

A compound HBL was deposited on the emitting layer to form an electron-transporting layer having a thickness of 10 nm. A compound ET as an electron-injecting material was deposited on the electron-transporting layer to form an electron-injecting layer having a thickness of 15 nm. LiF was deposited on the electron-injecting layer to form a LiF film having a thickness of 1 nm. Metal Al was deposited on the LiF film to form a metal cathode having a thickness of 80 nm.

As described above, an organic EL device was fabricated.

The layer configuration of the organic EL device of Example 1 is schematically shown as follows.

ITO(130)/HI(5)/HT1(80)/HT2(10)/BH-1:BD-1(25, 98%: 2%)/HBL(10)/ET(15)/LiF(1)/Al(80)

The numerical values in parentheses indicate the film thickness (unit: nm). Also, in parentheses, the numerical values shown in terms of the percentage (% by mass) indicate the percentages of the first compound, and the second compound in the layers.

<Evaluation of Organic EL Device>

Voltage was applied to the organic EL device to be 50 mA/cm² in current density, and the time until the luminance becomes 95% of the initial luminance was measured and indicated as LT95. The result is shown in Table 1.

Example 2 and 3, and Comparative Example 1

The organic EL devices were fabricated and evaluated in the same manner as in Example 1 except that dopant materials of the emitting layer were changed to the compounds shown in the following Table 1. The results are shown in Table 1.

TABLE 1

| | Dopant material | LT95 (hours) |
| --- | --- | --- |
| Example 1 | BD-1 | 81 |
| Example 2 | BD-2 | 85 |
| Example 3 | BD-3 | 80 |
| Comp. Ex. 1 | BD-Ref-1 | 68 |

From the results shown in Table 1, it can be seen that the organic EL devices of Examples 1 to 3 using the compound represented by the formula (1) as dopant materials have a long lifetime compared with the device of Comparative Example 1.

<Synthesis of Compounds>

Synthesis Example 1: Synthesis of the Compound BD-1

The compound BD-1 was synthesized according to the synthetic route described below.

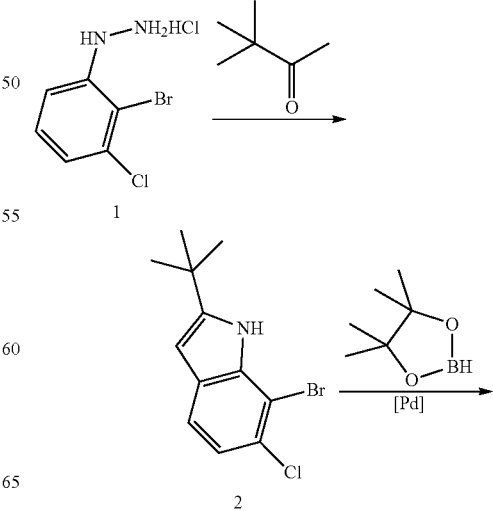

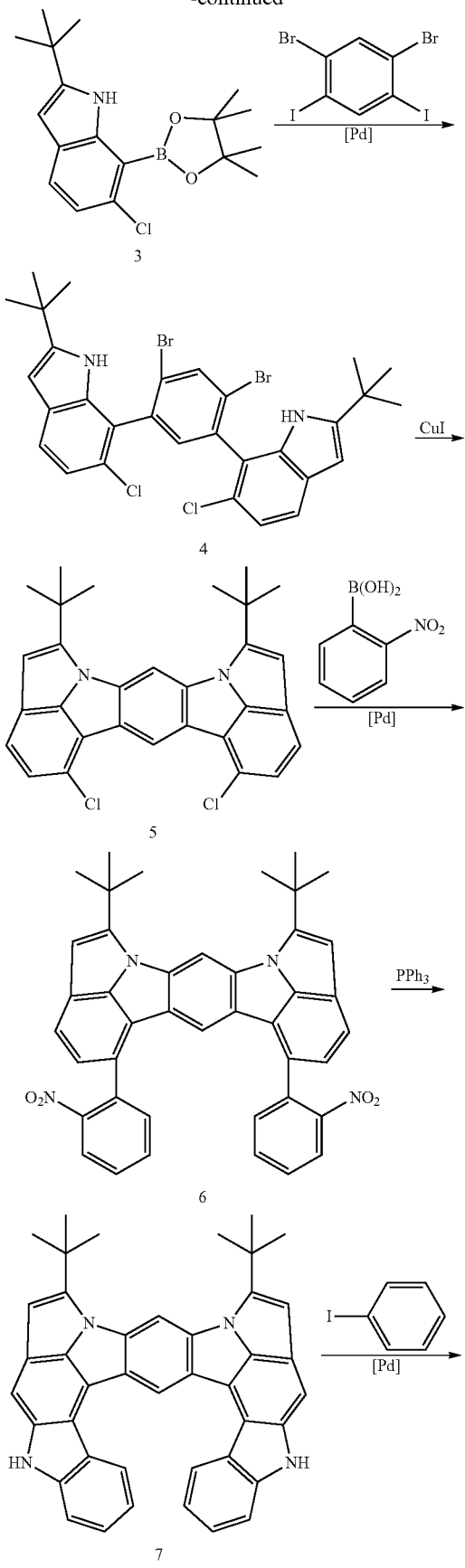
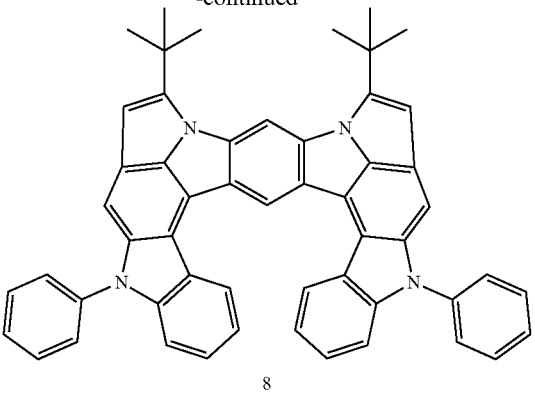

Under an argon atmosphere, 2-bromo-3-chlorophenylhydrazine hydrochloride (100 g, 388 mmol) was dissolved in methanol (1 L), t-butylmethyl ketone (78 g, 775 mmol) was added thereto, and the mixture was stirred at 70° C. for 2 days. After completion of the reaction, the solvent was concentrated and the residue was purified by column chromatography to obtain Intermediate 2 (69 g). The result of mass spectrometric analysis was: m/e=286 for a molecular weight of 287.

Under an argon atmosphere, Intermediate 2 (50 g, 174 mmol), pinacol borane (67 g, 523 mmol), dichloro[1,1′-bis(diphenylphosphino)ferrocene]palladium (PdCl$_2$ (dppf); 1.8 g, 3.5 mmol, 2% Pd) was suspended in dioxane (1 L), triethylamine (100 mL) was added thereto, and the mixture was refluxed for 7 hours. After completion of the reaction, the solvent was concentrated and the obtained residue was purified by column chromatography to obtain Intermediate 3 (41.3 g, yield: 71%). The result of mass spectrometric analysis was: m/e=334 for a molecular weight of 333.

Under an argon atmosphere, 1,5-dibromo-2,4-diiodobenzene (15.0 g, 30.8 mmol), Intermediate 3 (6.81 g, 16.8 mmol, 1.05 eq.), Pd(PPh$_3$)$_4$ (5 g, 4.31 mmol), potassium carbonate (12.7 g, 92 mmol) were suspended in 1,2-dimethoxyethane (2 L), water (500 mL) was added thereto, and the mixture was stirred for 1 day at 50° C. After completion of the reaction, the mixture was extracted using ethyl acetate and the solvent was concentrated. The obtained residue was purified by column chromatography to obtain Intermediate 4 (7.57 g, yield: 38%). The result of mass spectrometric analysis was: m/e=648 for a molecular weight of 647.

Under an argon atmosphere, Intermediate 4 (5.00 g), copper iodide (294 mg), 1,10-phenanthroline (278 mg), potassium carbonate (4.27 g) were suspended in dimethylformamide (DMF; 200 mL), and stirred with heating at 140° C. for 8 hours. After completion of the reaction, water was added to the reaction solution, and the precipitated solids were collected by filtration. The obtained solids were washed with water and methanol to obtain Intermediate 5 (2.96 g, yield: 79%). The result of mass spectrometric analysis was: m/e=486 for a molecular weight of 485.

Under an argon atmosphere, Intermediate 5 (2.5 g, 5.15 mmol), 2-nitrophenylboronic acid (10 g), bis(di-tert-butyl (4-dimethylaminophenyl)phosphine) dichloropalladium (II) (365 mg) and potassium carbonate (3.56 g) were suspended in dioxane (200 mL) and refluxed for 7 hours. After completion of the reaction, the solvent was concentrated and the obtained residue was purified by column chromatography to obtain Intermediate 6 (510 mg, yield: 15%). The result of mass spectrometric analysis was: m/e=659 for a molecular weight of 658.

Under an argon atmosphere, Intermediate 6 (500 mg, 5.15 mmol), triphenylphosphine (PPh₃; 1.2 g) was dissolved in o-dichlorobenzene (20 mL) and the mixture was stirred with heating at 190° C. for 2 days. After completion of the reaction, the precipitated solids were collected by filtration, and the obtained solids were washed with water and methanol to obtain Intermediate 7 (120 mg, yield: 27%). The result of mass spectrometric analysis was: m/e=595 for a molecular weight of 594.

Under an argon atmosphere, Intermediate 7 (120 mg), palladium acetate (4.5 mg), tri-tert-butylphosphonium tetrafluoroborate (11 mg), NaOt-Bu (58 mg) were suspended in xylene (10 mL), iodo benzene (0.2 mL) was added thereto, and the mixture was refluxed for 8 hours. After completion of the reaction, the mixture was purified by silica gel column chromatography to obtain Intended product 8 (compound BD-1) (110 mg, yield: 73%). The result of mass spectrometric analysis was: m/e=747 for a molecular weight of 746.

Synthesis Example 2: Synthesis of Compound BD-2

The compound BD-2 was synthesized in the same manner except that tert-butylmethyl ketone in the synthetic route of the compound BD-1 was changed to cyclopentanone.

Synthesis Example 3: Synthesis of Compound BD-3

The compound BD-3 was synthesized in a same manner except that 1,5-dibromo-2,4-diiodobenzene in the synthetic route of the compound BD-1 was changed to 2-chloro-3-iodonaphthalene.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification and the specification of Japanese application(s) on the basis of which the present application claims Paris convention priority are incorporated herein by reference in its entirety.

DESCRIPTION OF SYMBOLS

1 Organic EL device
2 Substrate
3 Anode
4 Organic layer
5 Emitting layer
6 Hole-transporting layer
7 Hole-injecting layer
10 Cathode

The invention claimed is:

1. A compound represented by any one of the following formulas (4C-3) to (4C-5):

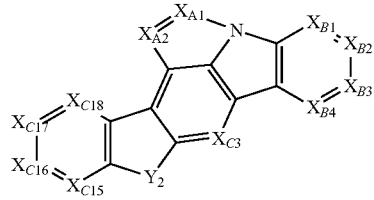

(4C-3)

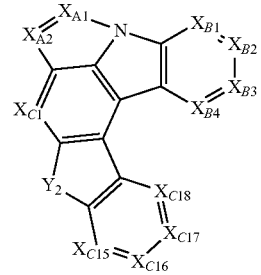

(4C-4)

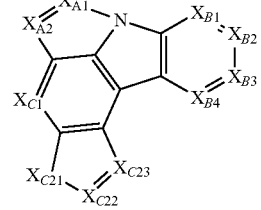

(4C-5)

wherein in the formulas (4C-3) to (4C-5), $X_{A1}$ and $X_{A2}$ are fused with a substituted or unsubstituted aliphatic hydrocarbon ring including 5 to 50 ring carbon atoms or a substituted or unsubstituted non-aromatic heterocyclic ring including 5 to 50 ring atoms, or are not fused with the ring;

$X_{A1}$ and $X_{A2}$ which are not involved in the fusion of the ring are independently
CH,
$C(R_a)$, or
N;

one or more sets of adjacent two of $X_{B1}$ to $X_{B4}$ are fused with a substituted or unsubstituted hydrocarbon ring including 5 to 50 ring carbon atoms, or a substituted or unsubstituted heterocyclic ring including 5 to 50 ring atoms;

$X_{B1}$ to $X_{B4}$ which are not involved in the fusion of the ring are independently
CH,
$C(R_a)$, or
N;

$X_{C1}$ and $X_{C3}$ are independently
CH,
$C(R_a)$, or
N;

$Y_2$ is
O,
S,
NH,
$N(R_a)$,
$CH_2$,
$CH(R_a)$, or
$C(R_a)_2$;

$X_{C15}$ to $X_{C18}$, $X_{C22}$ and $X_{C23}$ are independently
CH,

C($R_a$), or
N;
$X_{C21}$ is
NH,
N($R_a$),
$CH_2$,
CH($R_a$), or
C($R_a$)$_2$;
$R_a$ is a substituent;
when a plurality of $R_a$'s are present, the plurality of $R_a$'s may be the same as or different from each other; and
adjacent two or more $R_a$'s form a substituted or unsubstituted, saturated or unsaturated ring by bonding with each other, or do not form the ring.

2. The compound according to claim 1, wherein the compound represented by the formula (4C-4) is a compound represented by any one of the following formulas (4C-4-1) to (4C-4-4):

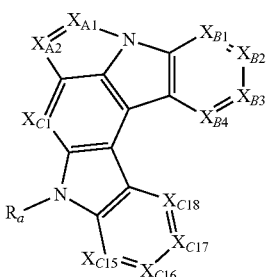
(4C-4-1)

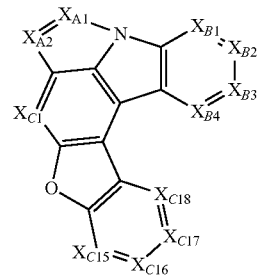
(4C-4-2)

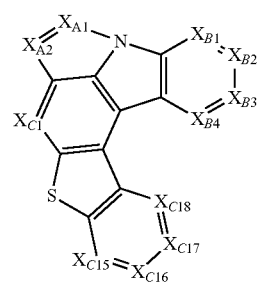
(4C-4-3)

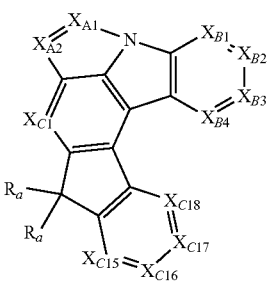
(4C-4-4)

wherein in the formulas (4C-4-1) to (4C-4-4), $X_{A1}$, $X_{A2}$, the ring $X_B$, $X_{B1}$ to $X_{B4}$, $X_{C15}$ to $X_{C18}$, and $X_{C1}$ are as defined in the formula (4C-4);
$R_a$ is a substituent;
when a plurality of $R_a$'s are present, the plurality of $R_a$'s may be the same as or different from each other; and
adjacent two or more $R_a$'s form a substituted or unsubstituted, saturated or unsaturated ring by bonding with each other, or do not form the ring.

3. The compound according to claim 1, wherein the compound represented by the formula (4C-4) is a compound represented by the following formula (1-1):

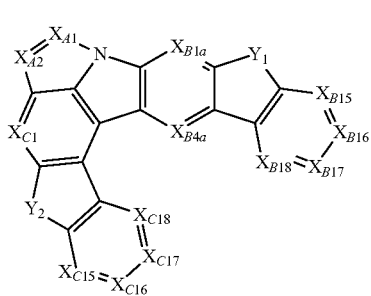
(1-1)

wherein in the formula (1-1), $X_{A1}$, $X_{A2}$, and $X_{C1}$ are as defined in the formula (4C-4);
$X_{B1a}$, $X_{B4a}$, $X_{B15}$ to $X_{B18}$, and $X_{C15}$ to $X_{C18}$ are independently
CH,
C($R_a$), or
N;
$Y_1$ and $Y_2$ are independently
O,
S,
NH,
N($R_a$),
$CH_2$,
CH($R_a$), or
C($R_a$)$_2$;
$R_a$ is a substituent;
when a plurality of $R_a$'s are present, the plurality of $R_a$'s may be the same as or different from each other; and
adjacent two or more $R_a$'s form a substituted or unsubstituted, saturated or unsaturated ring by bonding with each other, or do not form the ring.

4. The compound according to claim 3, wherein the compound represented by the formula (1-1) is a compound represented by any one of the following formulas (1-1-1) to (1-1-5):

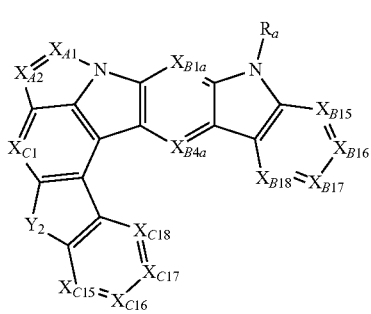
(1-1-1)

-continued

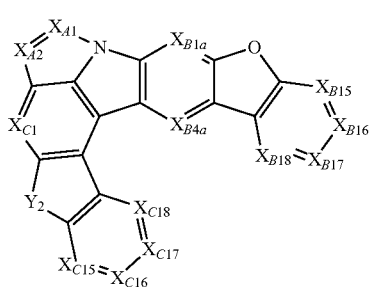

(1-1-2)

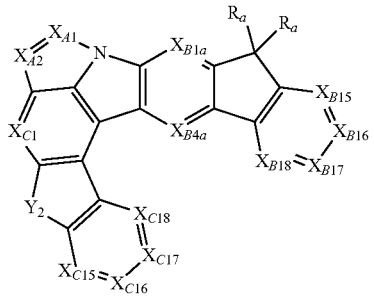

(1-1-3)

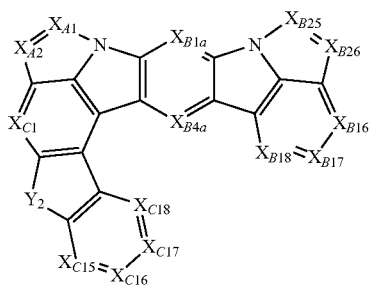

(1-1-4)

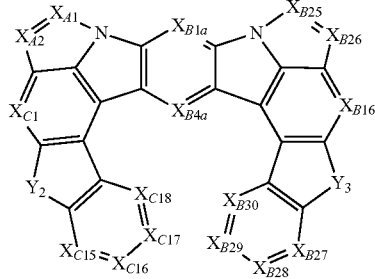

(1-1-5)

wherein in the formulas (1-1-1) to (1-1-5), $X_{A1}$, $X_{A2}$, $X_{B1a}$, $X_{B4a}$, $XB_{15}$ to $XB_{18}$, $X_{C1}$, $X_{C15}$ to $X_{C18}$, $Y_2$, and $R_a$ are as defined in the formula (1-1); and $X_{B25}$ and $X_{B26}$ are independently
CH,
$C(R_a)$, or
N.

5. The compound according to claim 4, wherein the compound represented by the formula (1-1-5) is a compound represented by the following formula (1-1-5a):

(1-1-5a)

wherein in the formula (1-1-5a), $X_{A1}$, $X_{A2}$, $X_{B1a}$, $X_{B4a}$, $X_{B16}$, $X_{C1}$, $X_{C15}$ to $X_{C18}$, $X_{B25}$, $X_{B26}$, and $Y_2$ are as defined in the formula (1-1-5);

$Y_3$ is
O,
S,
NH,
$N(R_a)$, or
$C(R_a)_2$;
$X_{B27}$ to $X_{B30}$ are independently
CH,
$C(R_a)$, or
N
$R_a$ is a substituent;
when a plurality of $R_a$'s are present, the plurality of $R_a$'s may be the same as or different from each other; and
adjacent two or more $R_a$'s form a substituted or unsubstituted, saturated or unsaturated ring by bonding with each other, or do not form the ring.

6. The compound according to claim 1, wherein the substituent $R_a$ is selected from the group consisting of
a halogen atom, a cyano group, a nitro group,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
—S—($R_{905}$),
—N($R_{906}$)($R_{907}$),
a substituted or unsubstituted aryl group including 6 to 50 ring carbon atoms, and
a substituted or unsubstituted monovalent heterocyclic group including 5 to 50 ring atoms;
$R_{901}$ to $R_{907}$ are independently
a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted monovalent heterocyclic group including 5 to 50 ring atoms; and
when two or more of each of $R_{901}$ to $R_{907}$ are present, the two or more of each of $R_{901}$ to $R_{907}$ are the same or different.

7. The compound according to claim 1, wherein the substituent $R_a$ is selected from the group consisting of
a halogen atom, a cyano group, a nitro group,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, and
a substituted or unsubstituted monovalent heterocyclic group including 5 to 50 ring atoms.

8. The compound according to claim 1, which is a material for an organic electroluminescence device.

9. A material for an organic electroluminescence device, comprising the compound according to claim 1.

10. An organic electroluminescence device comprising:
a cathode,
an anode,
one or two or more organic layers disposed between the cathode and the anode, wherein at least one of the organic layers comprises the compound according to claim 1.

11. The organic electroluminescence device according to claim 10, wherein the organic layer comprises an emitting layer, and
the emitting layer comprises the compound.

12. The organic electroluminescence device according to claim 10, wherein the organic layer comprises a second compound which is not the same as the compound.

13. The organic electroluminescence device according to claim 12, wherein the second compound is a heterocyclic compound or a fused aromatic compound.

14. The organic electroluminescence device according to claim 12, wherein the second compound is a compound selected from anthracene derivatives.

15. The organic electroluminescence device according to claim 12, wherein the second compound is a compound represented by the following formula (10):

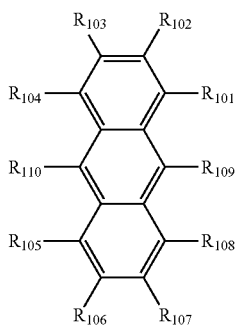

(10)

wherein in the formula (10),
one or more sets of adjacent two or more of $R_{101}$ to $R_{110}$ form a substituted or unsubstituted, saturated or unsaturated ring by bonding with each other, or do not form the substituted or unsubstituted, saturated or unsaturated ring;
$R_{101}$ to $R_{110}$ which do not form the substituted or unsubstituted, saturated or unsaturated ring are independently
a hydrogen atom,
a substituent R, or
a group represented by the following formula (11):

$-L_{101}-Ar_{101}$ (11)

wherein in the formula (11),
$L_{101}$ is
a single bond,
a substituted or unsubstituted arylene group including 6 to 50 ring carbon atoms, or
a substituted or unsubstituted divalent heterocyclic group including 5 to 50 ring atoms;
$Ar_{101}$ is
a substituted or unsubstituted aryl group including 6 to 50 ring carbon atoms, or
a substituted or unsubstituted monovalent heterocyclic group including 5 to 50 ring atoms;
the substituent R is
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms;
when two or more of the substituent R's are present, the two or more of the substituent R's may be the same as or different from each other;
$R_{901}$ to $R_{907}$ are independently
a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted monovalent heterocyclic group including 5 to 50 ring atoms;
when two or more of each of $R_{901}$ to $R_{907}$ are present, the two or more of each of $R_{901}$ to $R_{907}$ are the same or different;
provided that at least one of $R_{101}$ to $R_{110}$ which do not form the substituted or unsubstituted, saturated or unsaturated ring is a group represented by the formula (11); and
when two or more of the groups represented by the formula (11) are present, each of the two or more of the groups represented by the formula (11) may be the same or different.

16. The organic electroluminescence device according to claim 11, wherein the emitting layer further comprises a delayed fluorescent host compound.

17. The organic electroluminescence device according to claim 10, which is a blue emitting device.

18. An electronic apparatus, equipped with the organic electroluminescence device according to claim 10.

19. The compound according to claim 1, wherein at least one of $X_{A1}$ and $X_{A2}$ is C($R_a$) and, the other is CH or N.

20. The compound according to claim 1, wherein one set of $X_{B1}$ and $X_{B2}$, $X_{B2}$ and $X_{B3}$, and $X_{B3}$ and $X_{B4}$ is fused with a substituted or unsubstituted hydrocarbon ring including 5 to 50 ring carbon atoms, or a substituted or unsubstituted heterocyclic ring including 5 to 50 ring atoms.

21. The compound according to claim 1, wherein $X_{B2}$ and $X_{B3}$ are fused with a substituted or unsubstituted hydrocarbon ring including 5 to 50 ring carbon atoms, or a substituted or unsubstituted heterocyclic ring including 5 to 50 ring atoms.

* * * * *

UNITED STATES PATENT AND TRADEMARK OFFICE
CERTIFICATE OF CORRECTION

PATENT NO. : 12,098,128 B2  
APPLICATION NO. : 17/183682  
DATED : September 24, 2024  
INVENTOR(S) : Ryota Takahashi Page 1 of 1

It is certified that error appears in the above-identified patent and that said Letters Patent is hereby corrected as shown below:

In the Claims

In Claim 4, Column 211, Line 58, please delete "XB to $XB_{18}$," and replace with -- $X_{B15}$ to $X_{B18}$, --;

In Claim 5, Column 212, Line 28, please insert -- ; -- after "N".

Signed and Sealed this  
Twenty-fourth Day of December, 2024

Derrick Brent  
*Acting Director of the United States Patent and Trademark Office*